US006271253B1

(12) United States Patent
Carter et al.

(10) Patent No.: US 6,271,253 B1
(45) Date of Patent: Aug. 7, 2001

(54) SUBSTITUTED BENZOPYRAN DERIVATIVES FOR THE TREATMENT OF INFLAMMATION

(75) Inventors: Jeffery S Carter, Chesterfield; Mark G Obukowicz, Kirkwood; Balekudru Devadas, Chesterfield; John J Talley, St. Louis; David L Brown; Matthew J Graneto, both of Chesterfield, all of MO (US); Stephen R Bertenshaw, Cheshire, CT (US); Donald J Rogier, Jr.; Srinivasan Raj Nagarajan, both of Chesterfield, MO (US); Cathleen E Hanau, St. Louis, MO (US); Susan J Hartmann, Kirkwood, MO (US); Cindy L Ludwig, St. Louis, MO (US); Suzanne Metz, Chesterfield, MO (US); Donald E Korte, Mundelein, IL (US)

(73) Assignee: G.D. Searle & Co., Skokie, IL (US)

( * ) Notice: Subject to any disclaimer, the term of this patent is extended or adjusted under 35 U.S.C. 154(b) by 0 days.

(21) Appl. No.: 09/569,383

(22) Filed: May 11, 2000

Related U.S. Application Data

(63) Continuation of application No. 09/175,584, filed on Oct. 20, 1998, now Pat. No. 6,077,850, which is a continuation-in-part of application No. 09/062,537, filed on Apr. 17, 1998, now Pat. No. 6,034,256.
(60) Provisional application No. 60/044,485, filed on Apr. 21, 1997.

(51) Int. Cl.[7] .......................... A61K 31/38; A61K 31/44; C07D 215/20; C07D 335/04
(52) U.S. Cl. .......................... 514/432; 514/356; 546/170; 549/23
(58) Field of Search .................. 514/356, 432; 546/170; 549/23

(56) References Cited

U.S. PATENT DOCUMENTS

| | | |
|---|---|---|
| 4,046,778 | 9/1977 | Zinnes et al. |
| 4,609,744 | 9/1986 | Young et al. .......................... 549/402 |
| 4,665,202 | 5/1987 | Rimbault et al. ..................... 549/402 |
| 4,761,425 | 8/1988 | Girard et al. ........................ 514/456 |
| 4,814,346 | 3/1989 | Albert et al. ........................ 514/454 |
| 5,004,744 | 4/1991 | Weissmiller et al. ................ 514/247 |
| 5,082,849 | 1/1992 | Huang et al. ........................ 514/314 |
| 5,155,130 | 10/1992 | Stanton et al. ...................... 514/456 |
| 5,250,547 | 10/1993 | Lochead et al. ..................... 514/337 |
| 5,281,720 | 1/1994 | Young et al. ........................ 549/13 |
| 5,348,976 | 9/1994 | Shibata et al. ...................... 514/469 |
| 5,447,943 | 9/1995 | Lochead et al. ..................... 514/337 |
| 5,618,843 | 4/1997 | Fisher et al. ........................ 514/567 |
| 5,728,846 | 3/1998 | Vullgonda et al. .................. 549/16 |
| 5,849,798 | 12/1998 | Charpentier et al. ................ 514/456 |
| 5,869,478 | 2/1999 | Ding et al. .......................... 514/212 |
| 5,998,465 * | 12/1999 | Hellberg et al. ..................... 514/432 |
| 6,013,809 * | 1/2000 | Zimmer et al. ...................... 549/9 |
| 6,034,256 * | 3/2000 | Carter et al. ........................ 549/456 |
| 6,090,826 * | 7/2000 | Chandraratna et al. ............. 514/337 |
| 6,110,960 * | 8/2000 | Janusz et al. ....................... 514/432 |
| 6,114,349 * | 9/2000 | Kirsch et al. ....................... 514/311 |

FOREIGN PATENT DOCUMENTS

| | | |
|---|---|---|
| 412939 | 2/1991 | (EP). |
| 59-29681 | 2/1984 | (JP). |
| 2-22272 | 1/1990 | (JP). |
| 08337583 | 12/1996 | (JP). |
| WO88/04654 | 6/1988 | (WO). |
| WO94/13659 | 6/1994 | (WO). |
| WO95/07274 | 3/1995 | (WO). |
| WO96/40110 | 12/1996 | (WO). |
| WO98/34115 | 8/1998 | (WO). |
| WO98/47890 | 10/1998 | (WO). |

OTHER PUBLICATIONS

Sabbaramaiah et al., Proc. Soc. Exp. Biol. Med., 216, 201:1997.
Hida et al., Anticancer Res., 19, 775–82:1998.
Wilson, Cancer Res., 58, 2929–34:1998.
Buckman et al., Carcinogenesis, 19, 723–29:1998.
Barnes et al., Lung Biol. Health Dis., 114, 11–27:1998.
M. Tsujii et al., Cell, 93, 705–16:1998.
Bustos, J. Clin Invest., 100, 1150–58:1997.
Bagetta et al., Biochem, Biophys. Res. Commun., 244, 819–24:1998.
Sandhya et al., Brain Res., 788, 223–31:1998.
Singer et al., Gastroenterology, 115, 297–306:1998.
Nogawa et al., Proc. Natl. Acad. Sci., 95, 10966–71:1998.
Nasjletti, Hypertension, 31, 194–200:1997.
Kawamori et al., Cancer Res., 58, 409–12:1998.
Miyamoto et al., Neuro Report, 9, 2331–4:1998.
Shoup, J. Trauma: inj., Infec., Crit care, 45, 215–21:1998.
Speir et al., Circ. Res., 83, 210–16:1998.
Bosch, Curr. Med. Res. Opin., 14, 29–38:1997.

(List continued on next page.)

Primary Examiner—Deborah C. Lambkin
(74) Attorney, Agent, or Firm—James M. Warner; Joseph W. Bulock

(57) ABSTRACT

A class of benzopyrans, benzothiopyrans, dihydroquinolines, dihydronaphthalenes, and analogs thereof, is described for use in treating cyclooxygenase-2 mediated disorders. Compounds of particular interest are defined by Formula I'

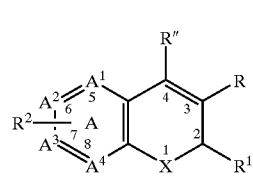

wherein X, $A^1$, $A^2$, $A^3$, $A^4$, R, R", $R^1$ and $R^2$ are as described in the specification.

14 Claims, No Drawings

OTHER PUBLICATIONS

Manrao et al., J. Indian. Counc. Chem., 12, 38–41:1996.
Loiodice et al, Tetrahdron, 6, 1001–11:1995.
Clemence et al., J. Med. Chem., 31, 1453–62:1988.
Lazer, et al., J. Med. Chem., 40, 980–89:1997.
Bunting et al., Can. J. Chem., 62, 1301–07:1984.
Ukhin et al., Izv. Akad. Nauk. Der. Khim., 5, 1222–28:1996.
Gupta et al., Indian J. Chem., 21B, 344–347:1982.
Rene and Royer, Eur. J. Med. Chem–Chim. Ther., 10, 72–78:1975.
Satoh et al., J. Med. Chem. 36, 3580–94:1993.
Bunting et al, Can.J.Chem., vo. 62, pp. 1301–1307 (1984) pp. 708, 822 (1996).

* cited by examiner

SUBSTITUTED BENZOPYRAN DERIVATIVES FOR THE TREATMENT OF INFLAMMATION

RELATED CASES

This is a continuation of a Ser. No. 09/175,584, filed Oct. 20, 1998 U.S. Pat. No. 6,077,850, which is a continuation-in-part of application Ser. No. 09/062,537 filed Apr. 17, 1998 U.S. Pat. No. 6,034,256, which claims priority of Provisional Application Ser. No. 60/044,485, filed Apr. 21, 1997.

FIELD OF THE INVENTION

This invention is in the field of anti-inflammatory pharmaceutical agents and specifically relates to compounds, compositions and methods for treating cyclooxygenase-2 mediated disorders, such as inflammation and inflammation-related disorders.

BACKGROUND OF THE INVENTION

Prostaglandins play a major role in the inflammation process and the inhibition of prostaglandin production, especially production of $PGG_2$, $PGH_2$ and $PGE_2$ has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Recently, there has been significant research into some of the roles of cyclooxygenase-2. It has been found that COX-2 is upregulated in benign and malignant tumors (K. Subbaramaiah et al., Proc. Soc. Exp. Biol. Med., 216, 201 (1997)) including lung cancer (T. Hida et al., Anticancer Res., 18, 775–82 (1998)), Barrett's esophagus (K. Wilson, Cancer Res., 58, 2929–34 (1998)) and skin cancer (S. Buckman et al., Carcinogenesis, 19, 723–29 (1998)). It is expressed in airway cells with implication in asthma (P. Barnes et al., Lung Biol. Health Dis., 114, 111–27 (1998)). Cox-2 also has a role in pre-term labor, angiogenesis (M. Tsujii et al. Cell, 93, 705–16 (1998)), vascular rejection (M. Bustos, J. Clin. Invest., 100, 1150–58 (1997)), HIV induced apoptosis (G. Bagetta et al., Biochem. Biophys. Res. Commun., 244, 819–24 (1998)), neurodegeneration (T. Sandhya et al., Brain Res., 788, 223–31 (1998)), inflammatory bowel disease, colitis, (I. Singer et al., Gastroenterology, 115, 297–306 (1998)), cerebral ischemia (S. Nogawa et al., Proc. Natl. Acad. Sci., 95, 10966–71 (1998)), hypertension (A. Nasjletti, Hypertension, 31, 194–200 (1997)), among others.

Drugs that inhibit cyclooxygenase affect colon cancer (T. Kawamori et al., Cancer Res., 58, 409–12 (1998)), allergic neuritis (K. Miyamoto et al., Neuro Report, 9, 2331–4 (1998)), dementia, burn infections (M. Shoup, J. Trauma: Inj., Infec., Crit care, 45, 215–21 (1998)), cytomegalovirus infectivity (E. Speir et al., Circ. Res., 83, 210–16 (1998)), lumbago (H. Bosch, Curr. Med. Res. Opin., 14, 29–38 (1997)), among others.

The references below that disclose antiinflammatory activity, show continuing efforts to find a safe and effective antiinflammatory agent. The novel benzopyran, dihydroquinoline, benzothiopyran and dihydronapthalene derivatives disclosed herein are such safe and also effective antiinflammatory agents furthering such efforts. The substituted benzopyran, dihydroquinoline, benzothiopyran and dihydronapthalene derivatives disclosed herein preferably selectively inhibit cyclooxygenase-2 over cyclooxygenase-1.

U.S. Pat. No. 5,618,843, to Fisher et al., generically describes acid substituted bicyclic moieties as IIb/IIIA antagonists. WO 94/13659, published Jun. 23, 1994, describes fused benzo compounds for the treatment of CNS disorders. Manrao et al. (J. Indian. Counc. Chem., 12, 38–41 (1996)) describes carboxy coumarinimide derivatives and their antifungal activity. U.S. Pat. No. 5,348,976, to Shibata et al., describes amide substituted benzopyrans as antifungals.

WO96/40110, published Dec. 19, 1996, describes benzopyran derivatives as tyrosine kinase modulators. Loiodice et al. (Tetrahedron, 6, 1001–11 (1995)) describe the preparation of 6-chloro-2,3-dihydro-4H-1-benzopyran carboxylic acids.

Clemence et al. (J. Med. Chem., 31, 1453–62, (1988)) describe 4-hydroxy-3-quinolinecarbooxylic acids as starting material in the preparation of antiinflammatories. Lazer, et al. (J. Med. Chem., 40, 980–89 (1997)) describe benzothiopyran carboxylates as starting material in the preparation of antiinflammatories.

U.S. Pat. No. 5,281,720, to Young et al., describes naphthoic acids as lipoxygenase inhibitors. U.S. Pat. No. 5,348,976, to Shibata et al., describes amide substituted benzopyrans as antifungals. U.S. Pat. No. 5,004,744, to Weissmiller et al., describes 2H-benzopyran-3-carboxylic acid as an intermediate for pesticides. U.S. Pat. No. 4,814,346, to Albert et al., describes 3-phenylbenzopyrans as 5-lipoxygenase inhibitors. U.S. Pat. No. 4,761,425, to Girard and Rokach, describes 4-oxo-benzopyrans as leukotriene antagonists. U.S. Pat. No. 4,609,744, to Young et al., describes 4-oxo-benzopyran-carboxylic acids as leukotriene antagonists. U.S. Pat. No. 5,082,849, to Huang et al., describes 4-oxo-benzopyrans as leukotriene antagonists. WO95/07274, published Mar. 16, 1996, describes 2H-benzopyran-3-carboxylic acid as intermediates. WO88/04654, published Jun. 30, 1988, describes 2H-benzopyran-3-carboxylic acid as intermediates. EP412,939, published Feb. 13, 1991, describes substituted chromenes as 5-lipoxygenase inhibitors. JP2-22272 describes benzopyran-3-carboxylic acids. JP59-29681 describes 8-methoxy-benzopyran-3-carboxylic acid as an intermediate. Bunting et al (Can. J. Chem., 62, 1301–07 (1984)) describes the synthesis of 2-hydroxy-1,2-dihydro quinolines. Ukhin et al (Izv. Akad. Nauk. Ser. Khim., 5, 1222–28 (1996)) describe the synthesis of [2-morpholino-6-nitrobenzopyran]-3-carboxylate. Gupta et al. (Indian J. Chem., 21B, 344–347 (1982)) describe chromene-3-carboxylic acid as an intermediate in the preparation of centrally acting muscle relaxants. Rene and Royer (Eur. J. Med. Chem. -Chim. Ther., 10, 72–78 (1975)) describe the preparation of chromene-3- carboxylic acid. U.S. Pat. No. 4,665,202, to Rimbault et al., describes 2-phenyl substituted flavenes and thioflavenes as 5-lipoxygenase inhibitors. U.S. Pat. No. 5,250,547, to Lochead et al., describes benzopyran derivatives as 5-lipoxygenase inhibitors. Satoh et al. [J. Med. Chem., 36, 3580–94 (1993)] describe substituted chromenes as 5-lipoxygenase inhibitors. U.S. Pat. No. 5,155,130, to Stanton et al. describes substituted chromenes as 5-lipoxygenase inhibitors, and specifically 6-benzyloxy-2H-benzopyran-3-carboxylic acid as an intermediate.

However, compounds of the current invention have not been described as antiinflammatory cyclooxygenase inhibitors.

DESCRIPTION OF THE INVENTION

A class of compounds useful in treating cyclooxygenase-2 medicated disorders is defined by Formula I":

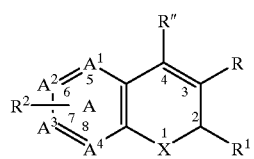

wherein X is selected from O, S, $CR^cR^b$ and $NR^a$;

wherein $R^a$ is selected from hydrido, $C_1$–$C_3$-alkyl, (optionally substituted phenyl)-$C_1$–$C_3$-alkyl, acyl and carboxy-$C_1$–$C_6$-alkyl;

wherein each of $R^b$ and $R^c$ is independently selected from hydrido, $C_1$–$C_3$-alkyl, phenyl-$C_1$–$C_3$-alkyl, $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; or wherein $CR^bR^c$ forms a 3–6 membered cycloalkyl ring;

wherein R is selected from carboxyl, aminocarbonyl, $C_1$–$C_6$-alkylsulfonylaminocarbonyl and $C_1$–$C_6$-alkoxycarbonyl;

wherein R" is selected from hydrido, phenyl, thienyl, $C_1$–$C_6$-alkyl and $C_2$–$C_6$-alkenyl;

wherein $R^1$ is selected from $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl;

wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkyloxy, heteroaryl-$C_1$–$C_6$-alkyloxy, aryl-$C_1$–$C_6$-alkoxy-$C_{11}$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are independently selected from carbon and nitrogen with the proviso that at least two of $A^1$, $A^2$, $A^3$ and $A^4$ are carbon;

or wherein $R^2$ together with ring A forms a radical selected from naphthyl, quinolyl, isoquinolyl, quinolizinyl, quinoxalinyl and dibenzofuryl;

or an isomer or pharmaceutically acceptable salt thereof.

A related class of compounds useful in treating cyclooxygenase-2 medicated disorders is defined by Formula I':

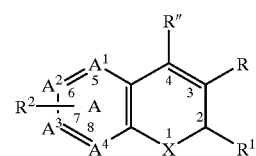

wherein X is selected from O, S, $CR^cR^b$ and $NR^a$;

wherein $R^a$ is selected from hydrido, $C_1$–$C_3$-alkyl, (optionally substituted phenyl)-$C_1$–$C_3$-alkyl, alkylsulfonyl, phenylsulfonyl, benzylsulfonyl, acyl and carboxy-$C_1$–$C_6$-alkyl;

wherein each of $R^b$ and $R^c$ is independently selected from hydrido, $C_1$–$C_3$-alkyl, phenyl-$C_1$–$C_3$-alkyl, $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl;

or wherein $CR^cR^b$ form a cyclopropyl ring;

wherein R is selected from carboxyl, aminocarbonyl, $C_1$–$C_6$-alkylsulfonylaminocarbonyl and $C_1$–$C_6$-alkoxycarbonyl;

wherein R" is selected from hydrido, phenyl, thienyl, $C_2$–$C_6$-alkynyl and $C_2$–$C_6$-alkenyl;

wherein $R^1$ is selected from $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl;

wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, —O(CF_2)_2O—, aryloxy, arylthio, arylsulfinyl, heteroaryloxy, $C_1$–$C_6$-alkoxy-$C_1$–$C_6$-alkyl, aryl-$C_1$–$C_6$-alkyloxy, heteroaryl-$C_1$–$C_6$-alkyloxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are independently selected from carbon and nitrogen with the proviso that at least two of $A^1$, $A^2$, $A^3$ and $A^4$ are carbon;

or wherein R² together with ring A forms a radical selected from naphthyl, quinolyl, isoquinolyl, quinolizinyl, quinoxalinyl and dibenzofuryl;

or an isomer or pharmaceutically acceptable salt thereof.

A related class of compounds useful in treating cyclooxygenase-2 medicated disorders is defined by Formula I:

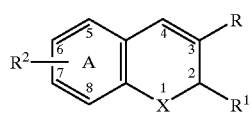

wherein X is selected from O or S or NR$^a$;

wherein R$^a$ is alkyl;

wherein R is selected from carboxyl, aminocarbonyl, alkylsulfonylaminocarbonyl and alkoxycarbonyl;

wherein R¹ is selected from haloalkyl, alkyl, aralkyl, cycloalkyl and aryl optionally substituted with one or more radicals selected from alkylthio, nitro and alkylsulfonyl; and wherein R² is one or more radicals selected from hydrido, halo, alkyl, aralkyl, alkoxy, aryloxy, heteroaryloxy, aralkyloxy, heteroaralkyloxy, haloalkyl, haloalkoxy, alkylamino, arylamino, aralkylamino, heteroarylamino, heteroarylalkylamino, nitro, amino, aminosulfonyl, alkylaminosulfonyl, arylaminosulfonyl, heteroarylaminosulfonyl, aralkylaminosulfonyl, heteroaralkylaminosulfonyl, heterocyclosulfonyl, alkylsulfonyl, optionally substituted aryl, optionally substituted heteroaryl, aralkylcarbonyl, heteroarylcarbonyl, arylcarbonyl, aminocarbonyl, and alkylcarbonyl;

or wherein R² together with ring A forms a naphthyl radical;

or an isomer or pharmaceutically acceptable salt thereof.

Compounds of the present invention would be useful for, but not limited to, the treatment of inflammation in a subject, and for treatment of other cyclooxygenase-2 mediated disorders, such as, as an analgesic in the treatment of pain and headaches, or as an antipyretic for the treatment of fever. For example, compounds of the invention would be useful to treat arthritis, including but not limited to rheumatoid arthritis, spondyloarthropathies, gouty arthritis, osteoarthritis, systemic lupus erythematosus and juvenile arthritis. Such compounds of the invention would be useful in the treatment of asthma, bronchitis, menstrual cramps, preterm labor, tendinitis, bursitis, allergic neuritis, cytomegalovirus infectivity, apoptosis including HIV induced apoptosis, lumbago, liver disease including hepatitis, skin-related conditions such as psoriasis, eczema, acne, UV damage, burns and dermatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. The compounds would also be useful in the treatment of ophthalmic diseases, such as retinitis, conjunctivitis, retinopathies, uveitis, ocular photophobia, and of acute injury to the eye tissue. The compounds would also be useful in the treatment of pulmonary inflammation, such as that associated with viral infections and cystic fibrosis, and in bone reorption such as associated with osteoporosis.

The compounds would also be useful for the treatment of certain central nervous system disorders, such as cortical dementias including Alzheimer's disease, neurodegeneration, and central nervous system damage resulting from stroke, ischemia and trauma. The term "treatment" includes partial or total inhibition of the dementia, including Alzheimer's disease, vascular dementia, multi-infarct dementia, pre-senile dementia, alcoholic dementia, and senile dementia.

The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and liver disease. The compounds would also be useful in the treatment of pain, but not limited to postoperative pain, dental pain, muscular pain, and pain resulting from cancer.

The method above would be useful for, but not limited to, treating and preventing inflammation-related cardiovascular disorders in a subject. The method would be useful for treatment and prevention of vascular diseases, coronary artery disease, aneurysm, vascular rejection, arteriosclerosis, atherosclerosis including cardiac transplant atherosclerosis, myocardial infarction, embolism, stroke, thrombosis, including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

The compounds would be useful for, but not limited to, the treatment of angiogenesis-related disorders in a subject. According to the present invention, the compounds can be administered to a subject in need of angiogenesis inhibition. The method would be useful for treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including invantile hemaginomas, angiofibroma of the nasopharynx and avascular necrosis of bone; and disorders of the female reproductive system such as endometriosis.

Compounds of the invention would be useful for the prevention or treatment of benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body. Preferably, neoplasia is selected from gastrointestinal cancer, Barrett's esophagus, liver cancer, bladder cancer, pancreas cancer, ovary cancer, prostate cancer, cervical cancer, lung cancer, breast cancer and skin cancer, such as squamus cell and basal cell cancers. The compounds can also be used to treat the fibrosis which occurs with radiation therapy. The method can be used to treat subjects having adenomatous polyps, including those with familial adenomatous polyposis (FAP). Additionally, the method can be used to prevent polyps from forming in patients at risk of FAP.

The administration of compounds of the present invention may be used alone or in conjunction with additional therapies known to those skilled in the art in the prevention or treatment of neoplasia. Alternatively, the compounds described herein may be used in conjunctive therapy. By way of example, the compounds may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallo-matrix proteases (MMP), SOD mimics or $\alpha_v\beta_3$ inhibitors may be used.

A first family of antineoplastic agents which may be used in combination with compounds of the present invention consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimeterxate, tyrosine kinase inhibitors, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, -SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in combination with compounds of the present invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in addition to other antiinflammatories, such as together with steroids, NSAIDs, iNOS inhibitors, p-38 inhibitors, TNF inhibitors, 5-lipoxygenase inhibitors, $LTB_4$ receptor antagonists and $LTA_4$ hydrolase inhibitors.

Suitable $LTA_4$ hydrolase inhibitors include RP-64966, (S,S)-3-amino-4-(4-benzyloxyphenyl)- 2-hydroxybutyric acid benzyl ester (Scripps Res. Inst.), N-(2(R)-(cyclohexylmethyl)-3-(hydroxycarbamoyl)propionyl)-L-alanine (Searle), 7-(4-(4-ureidobenzyl)phenyl)heptanoic acid (Rhone-Poulenc Rorer), and 3-(3-(1E,3E-tetradecadienyl)-2-oxiranyl)benzoic acid lithium salt (Searle).

Suitable $LTB_4$ receptor antagonists include, among others, ebselen, linazolast, ontazolast, Bayer Bay-x-1005, Ciba Geigy compound CGS-25019C, Leo Denmark compound ETH-615, Merck compound MAFP, Terumo compound TMK-688, Tanabe compound T-0757, Lilly compounds LY-213024, LY-210073, LY223982, LY233469, and LY255283, LY-293111, 264086 and 292728, ONO compounds ONO-LB457, ONO-4057, and ONO-LB-448, Shionogi compound S-2474, calcitrol, Lilly compounds Searle compounds SC-53228, SC-41930, SC-50605 and SC-51146, Warner Lambert compound BPC 15, SmithKline Beecham compound SB-209247 and SK&F compound SKF-104493. Preferably, the $LTB_4$ receptor antagonists are selected from calcitrol, ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, Abbott compounds A-76745, 78773 and ABT761, Bayer Bay-x-1005, Cytomed CMI-392, Eisai E-3040, Scotia Pharmaceutica EF-40, Fujirebio F-1322, Merckle ML-3000, Purdue Frederick PF-5901, 3M Pharmaceuticals R-840, rilopirox, flobufen, linasolast, lonapolene, masoprocol, ontasolast, tenidap, zileuton, pranlukast, tepoxalin, rilopirox, flezelastine hydrochloride, enazadrem phosphate, and bunaprolast.

The present compounds may also be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. More preferred would be combinations with compounds selected from morphine, meperidine, codeine, pentazocine, buprenorphine, butorphanol, dezocine, meptazinol, hydrocodone, oxycodone, methadone, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirfentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

The compounds can be used in co-therapies, in place of other conventional antiinflammatories, in combination with one or more antihistamines, decongestants, diuretics, antitussive agents or with other agents previously known to be effective in combination with antiinflammatory agents.

The term "prevention" includes either preventing the onset of clinically evident cardiovascular disorders altogether or preventing the onset of a preclinically evident stage of cardiovascular disorder in individuals. This includes prophylactic treatment of those at risk of developing a disease, such as a cardiovascular disorder, dementia or cancer, for example.

The phrase "therapeutically-effective" is intended to qualify the amount of each agent which will achieve the goal of improvement in disorder severity and the frequency of incidence over treatment of each agent by itself, while avoiding adverse side effects typically associated with alternative therapies.

The present invention preferably includes compounds which selectively inhibit cyclooxygenase-2 over cyclooxygenase-1. Preferably, the compounds have a cyclooxygenase-2 $IC_{50}$ of less than about 0.5 $\mu M$, and also have a selectivity ratio of cyclooxygenase-2 inhibition over cyclooxygenase-1 inhibition of at least 50, and more preferably of at least 100. Even more preferably, the compounds have a cyclooxygenase-1 IC$_{50}$ of greater than about 5 μM. Such preferred selectivity may indicate an ability to reduce the incidence of common NSAID-induced side effects.

A preferred class of compounds consists of those compounds of Formula I wherein X is oxygen or sulfur; wherein R is selected from carboxyl, lower alkyl, lower aralkyl and lower alkoxycarbonyl; wherein $R^1$ is selected from lower haloalkyl, lower cycloalkyl and phenyl; and wherein $R^2$ is one or more radicals selected from hydrido, halo, lower alkyl, lower alkoxy, lower haloalkyl, lower haloalkoxy, lower alkylamino, nitro, amino, aminosulfonyl, lower alkylaminosulfonyl, 5- or 6-membered heteroarylalkylaminosulfonyl, lower aralkylaminosulfonyl, 5- or 6-membered nitrogen containing heterocyclosulfonyl, lower alkylsulfonyl, optionally substituted phenyl, lower aralkylcarbonyl, and lower alkylcarbonyl; or wherein $R^2$ together with ring A forms a naphthyl radical; or an isomer or pharmaceutically acceptable salt thereof.

A more preferred class of compounds consists of those compounds of Formula I wherein X is oxygen or sulfur; wherein R is selected from carboxyl; wherein $R^1$ is selected from lower haloalkyl; and wherein $R^2$ is one or more radicals selected from hydrido, halo, lower alkyl, lower haloalkyl, lower haloalkoxy, lower alkylamino, amino, aminosulfonyl, lower alkylaminosulfonyl, 5- or 6-membered heteroarylalkylaminosulfonyl, lower aralkylaminosulfonyl, lower alkylsulfonyl, 6-membered nitrogen containing heterocyclosulfonyl, optionally substituted phenyl, lower aralkylcarbonyl, and lower alkylcarbonyl; or wherein $R^2$ together with ring A forms a naphthyl radical; or an isomer or pharmaceutically acceptable salt thereof.

An even more preferred class of compounds consists of those compounds of Formula I wherein R is carboxyl; wherein $R^1$ is selected from fluoromethyl, chloromethyl, dichloromethyl, trichloromethyl, pentafluoroethyl, heptafluoropropyl, difluoroethyl, difluoropropyl, dichloroethyl, dichloropropyl, difluoromethyl, and trifluoromethyl; and wherein $R^2$ is one or more radicals selected from hydrido, chloro, fluoro, bromo, iodo, methyl, ethyl, isopropyl, tert-butyl, butyl, isobutyl, pentyl, hexyl, methoxy, ethoxy, isopropyloxy, tertbutyloxy, trifluoromethyl, difluoromethyl, trifluoromethoxy, amino, N,N-dimethylamino, N,N-diethylamino, N-phenylmethylaminosulfonyl, N-phenylethylaminosulfonyl, N-(2-furylmethyl)aminosulfonyl, nitro, N,N-dimethylaminosulfonyl, aminosulfonyl, N-methylaminosulfonyl, N-ethylsulfonyl, 2,2-dimethylethylaminosulfonyl, N,N-dimethylaminosulfonyl, N-(2-methylpropyl)aminosulfonyl, N-morpholinosulfonyl, methylsulfonyl, benzylcarbonyl, 2,2-dimethylpropylcarbonyl, phenylacetyl and phenyl; or wherein $R^2$ together with ring A forms a naphthyl radical; or an isomer or pharmaceutically acceptable salt thereof.

An even more preferred class of compounds consists of those compounds of Formula I wherein R is carboxyl; wherein $R^1$ is trifluoromethyl or pentafluorethyl; and wherein $R^2$ is selected from one or more radicals hydrido, chloro, fluoro, bromo, iodo, methyl, ethyl, isopropyl, tertbutyl, methoxy, trifluoromethyl, trifluoromethoxy, N-phenylmethylaminosulfonyl, N-phenylethylaminosulfonyl, N-(2-furylmethyl)aminosulfonyl, N,N-dimethylaminosulfonyl, N-methylaminosulfonyl, N-(2,2-dimethylethyl)aminosulfonyl, dimethylaminosulfonyl, 2-methylpropylaminosulfonyl, N-morpholinosulfonyl, methylsulfonyl, benzylcarbonyl, and phenyl; or wherein $R^2$ together with ring A forms a naphthyl radical; or an isomer or pharmaceutically acceptable salt thereof.

A preferred class of compounds consists of those compounds of Formula I' wherein X is selected from O, S, $CR^cR^b$ and $NR^a$; wherein $R^a$ is selected from hydrido, $C_1$–$C_3$-alkyl, (optionally substituted phenyl)-$C_1$–$C_3$-alkyl, acyl and carboxy-$C_1$–$C_6$-alkyl; wherein each of $R^b$ and $R^b$ is independently selected from hydrido, $C_1$–$C_3$-alkyl, phenyl-$C_{11}$–$C_3$-alkyl, $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; wherein R is selected from carboxyl, aminocarbonyl, $C_1$–$C_6$-alkylsulfonylaminocarbonyl and $C_1$–$C_6$-alkoxycarbonyl; wherein R' is selected from hydrido, phenyl, thienyl and $C_2$–$C_6$-alkenyl; wherein $R^1$ is selected from $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkyloxy, heteroaryl-$C_1$–$C_6$-alkyloxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl or quinolyl radical; or an isomer or pharmaceutically acceptable salt thereof.

A more preferred class of compounds consists of those compounds of Formula I' wherein X is selected from O, S and $NR^a$; wherein $R^a$ is selected from hydrido, $C_1$–$C_3$-alkyl and (optionally substituted phenyl)methyl; wherein R' is selected from hydrido and $C_2$–$C_6$-alkenyl; wherein R is carboxyl; wherein $R^1$ is selected from $C_1$–$C_3$-perfluoroalkyl; wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, phenyl-$C_1$–$C_6$-alkyl, phenyl-$C_2$–$C_6$-alkynyl, phenyl-$C_2$–$C_6$-alkenyl, $C_1$–$C_3$-alkoxy, methylenedioxy, $C_1$–$C_3$-alkoxy-$C_1$–$C_3$-alkyl, $C_1$–$C_3$-alkylthio, $C_1$–$C_3$-alkylsulfinyl, phenyloxy, phenylthio, phenylsulfinyl, $C_1$–$C_3$-haloalkyl-$C_1$–$C_3$-hydroxyalkyl, phenyl-$C_1$–$C_3$-alkyloxy-$C_1$–$C_3$-alkyl, $C_1$–$C_3$-haloalkyl, $C_1$–$C_3$-haloalkoxy, $C_1$–$C_3$-haloalkylthio, $C_1$–$C_3$-hydroxyalkyl, $C_1$–$C_3$-alkoxy-$C_1$–$C_3$-alkyl, hydroxyimino-$C_1$–$C_3$-alkyl, $C_1$–$C_6$-alkylamino, nitro, cyano, amino, aminosulfonyl, N-alkylaminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, phenyl-$C_1$–$C_3$-alkylsulfonyl, 5- to 8-membered heterocyclylsulfonyl, $C_1$–$C_6$-alkylsulfonyl, optionally substituted phenyl, optionally substituted 5- to 9-membered heteroaryl, phenyl-$C_1$–$C_6$-alkylcarbonyl, phenylcarbonyl, 4-chlorophenylcarbonyl, 4-hydroxyphenylcarbonyl, 4-trifluoromethylphenylcarbonyl, 4-methoxyphenylcarbonyl, aminocarbonyl, formyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, benzofurylphenyl, or quinolyl radical; or an isomer or pharmaceutically acceptable salt thereof.

An even more preferred class of compounds consists of those compounds of Formula I' wherein X is selected from O, S and $NR^a$; wherein $R^a$ is selected from hydrido, methyl, ethyl, (4-trifluoromethyl)benzyl, (4-chloromethyl)benzyl, (4-methoxy)benzyl, and (4-cyano)benzyl, (4-nitro)benzyl; wherein R is carboxyl; wherein R' is selected from hydrido and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, optionally substituted phenylcarbonyl, aminocarbonyl, formyl and methylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, or quinolyl radical; or an isomer or pharmaceutically acceptable salt thereof.

Within Formula I' there is a subclass of chromene compounds wherein X is O; wherein R is carboxyl; wherein R" is selected from hydrido and $C_2$–$C_6$-alkenyl; wherein $R^1$ is selected from $C_1$–$C_3$-perfluoroalkyl; wherein $R^2$ is one or more radicals independently selected from hydrido, halo, $C_1$–$C_6$-alkyl, phenyl-$C_1$–$C_6$-alkyl, phenyl-$C_1$–$C_6$-alkynyl, phenyl-$C_2$–$C_6$-alkenyl, $C_1$–$C_6$-alkoxy, phenyloxy, 5- or 6-membered heteroaryloxy, phenyl-$C_1$–$C_6$-alkyloxy, 5- or 6-membered heteroaryl-$C_1$–$C_6$-alkyloxy, $C_1$–$C_6$-haloalkyl, $C_1$–$C_6$-haloalkoxy, N-($C_1$–$C_6$-alkyl)amino, N,N-di-($C_1$–$C_6$-alkyl) amino, N-phenylamino, N-(phenyl-$C_1$–$C_6$-alkyl) amino, N-heteroarylamino, N-(heteroaryl-$C_1$–$C_6$-alkylamino, nitro, amino, aminosulfonyl, N-($C_1$–$C_6$-alkyl) aminosulfonyl, N,N-di-($C_1$–$C_6$-alkyl)aminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, 5- to 8-membered heterocyclylsulfonyl, $C_1$–$C_6$-alkylsulfonyl, optionally substituted phenyl, optionally substituted 5- or 6-membered heteroaryl, phenyl-$C_1$–$C_6$-alkylcarbonyl, heteroarylcarbonyl, phenylcarbonyl, aminocarbonyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or an isomer or pharmaceutically acceptable salt thereof.

An even more preferred class of compounds consists of those compounds of Formula I' wherein X is O; wherein R is carboxyl; wherein R" is selected from hydrido and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, pyridyloxy, thienyloxy, furyloxy, phenylmethoxy, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, N-phenylamino, N-(benzyl)amino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, furylcarbonyl, phenylcarbonyl, aminocarbonyl, formyl, and methylcarbonyl; and wherein one of the A ring atoms $A^1$, $A^2$, $A^3$ and $A^4$ is nitrogen and the other three are carbon; or an isomer or pharmaceutically acceptable salt thereof.

Another even more preferred class of compounds consists of those compounds of Formula I' wherein X is O; wherein R is carboxyl; wherein R" is selected from hydrido and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, pyridyloxy, thienyloxy, furyloxy, phenylmethoxy, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, N-phenylamino, N-(benzyl)amino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, furylcarbonyl, phenylcarbonyl, aminocarbonyl, formyl, and methylcarbonyl; wherein the A ring atoms $A^1$, $A^2$, $A^3$ and $A^4$ are carbon; or an isomer or pharmaceutically acceptable salt thereof.

Within Formula I' there is another subclass of benzothiopyran compounds wherein X is S; wherein R is carboxyl;

wherein $R^1$ is selected from $C_1$–$C_3$-perfluoroalkyl; wherein $R^2$ is one or more radicals independently selected from hydrido, halo, $C_1$–$C_6$-alkyl, phenyl-$C_1$–$C_6$-alkyl, phenyl-$C_2$–$C_6$-alkynyl, phenyl-$C_2$–$C_6$-alkenyl, $C_1$–$C_6$-alkoxy, phenyloxy, 5- or 6-membered heteroaryloxy, phenyl-$C_1$–$C_6$-alkyloxy, 5- or 6-membered heteroaryl-$C_1$–$C_6$-alkyloxy, $C_1$–$C_6$-haloalkyl, $C_1$–$C_6$-haloalkoxy, $C_1$–$C_6$-alkylamino, N-phenylamino, N-(phenyl-$C_1$–$C_6$-alkyl)amino, N-heteroarylamino, N-(heteroaryl-$C_1$–$C_6$-alkylamino, nitro, amino, aminosulfonyl, N-alkylaminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, 5- to 8-membered heterocyclylsulfonyl, $C_1$–$C_6$-alkylsulfonyl, optionally substituted phenyl, optionally substituted 5- or 6-membered heteroaryl, phenyl-$C_1$–$C_6$-alkylcarbonyl, heteroarylcarbonyl, phenylcarbonyl, aminocarbonyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or an isomer or pharmaceutically acceptable salt thereof.

An even more preferred class of compounds consists of those compounds of Formula I' wherein X is S; wherein R is carboxyl; wherein R" is selected from hydrido and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, pyridyloxy, thienyloxy, furyloxy, phenylmethoxy, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, N-phenylamino, N-(benzyl)amino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, furylcarbonyl, phenylcarbonyl, aminocarbonyl, formyl, and methylcarbonyl; wherein the A ring atoms $A^1$, $A^2$, $A^3$ and $A^4$ are carbon; or an isomer or pharmaceutically acceptable salt thereof.

Within Formula I' there is a third subclass of dihydroquinoline compounds wherein X is $NR^a$; wherein $R^a$ is selected from hydrido, $C_1$–$C_3$-alkyl, phenyl-$C_1$–$C_3$-alkyl, acyl and carboxy-$C_1$–$C_3$-alkyl; wherein R is carboxyl; wherein $R^1$ is selected from $C_1$–$C_3$-perfluoroalkyl; wherein $R^2$ is one or more radicals independently selected from hydrido, halo, $C_1$–$C_6$-alkyl, phenyl-$C_1$–$C_6$-alkyl, phenyl-$C_2$–$C_6$-alkynyl, phenyl-$C_2$–$C_6$-alkenyl, $C_1$–$C_6$-alkoxy, phenyloxy, 5- or 6-membered heteroaryloxy, phenyl-$C_1$–$C_6$-alkyloxy, 5- or 6-membered heteroaryl-$C_1$–$C_6$-alkyloxy, $C_1$–$C_6$-haloalkyl, $C_1$–$C_6$-haloalkoxy, $C_1$–$C_6$-alkylamino, N-phenylamino, N-(phenyl-$C_1$–$C_6$-alkyl)amino, N-heteroarylamino, N-(heteroaryl-$C_1$–$C_6$-alkylamino, nitro, amino, aminosulfonyl, N-alkylaminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, 5- to 8-membered heterocyclylsulfonyl, $C_1$–$C_6$-alkylsulfonyl, optionally substituted phenyl, optionally substituted 5- or 6-membered heteroaryl, phenyl-$C_1$–$C_6$-alkylcarbonyl, heteroarylcarbonyl, phenylcarbonyl, aminocarbonyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or an isomer or pharmaceutically acceptable salt thereof.

An even more preferred class of compounds consists of those compounds of Formula I' wherein X is $NR^a$; wherein $R^a$ is selected from hydrido, methyl, ethyl, (4-trifluoromethyl)benzyl, (4-chloromethyl)benzyl, (4-methoxy)benzyl, (4-cyano)benzyl, and (4-nitro)benzyl; wherein R is carboxyl; wherein R" is selected from hydrido and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, pyridyloxy, thienyloxy, furyloxy, phenylmethoxy, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, N-phenylamino, N-(benzyl)amino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, furylcarbonyl, phenylcarbonyl, aminocarbonyl, formyl, and methylcarbonyl; wherein the A ring atoms $A^1$, $A^2$, $A^3$ and $A^4$ are carbon; or an isomer or pharmaceutically acceptable salt thereof.

Within Formula I' there is a fourth subclass of compounds wherein X is selected from O, S and $NR^a$; wherein $R^a$ is selected from hydrido, $C_1$–$C_3$-alkyl, phenyl-$C_1$–$C_3$-alkyl, acyl and carboxy-$C_1$–$C_3$-alkyl; wherein R is selected from carboxyl; wherein $R^1$ is selected from $C_1$–$C_3$-perfluoroalkyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; and wherein $R^2$ together with ring A forms a naphthyl or quinolyl radical; or an isomer or pharmaceutically acceptable salt thereof.

An even more preferred class of compounds consists of those compounds of Formula I' wherein X is selected from O, S and $NR^a$; wherein $R^a$ is selected from hydrido, methyl, ethyl, (4-trifluoromethyl)benzyl, (4-chloromethyl)benzyl, (4-methoxy)benzyl, and (4-cyano)benzyl, (4-nitro)benzyl; wherein R is carboxyl; wherein R' is selected from hydrido and ethenyl; wherein $R^1$ is selected from trifluoromethyl and pentafluoroethyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, or quinolyl radical; or an isomer or pharmaceutically acceptable salt thereof.

A preferred class of compounds consists of those compounds of Formula I" wherein X is selected from O, S, $CR^cR^b$ and $NR^a$; wherein $R^a$ is selected from hydrido, $C_1-C_3$-alkyl, (optionally substituted phenyl)-$C_1-C_3$-alkyl, acyl and carboxy-$C_1-C_6$-alkyl; wherein each of $R^b$ and $R^c$ is independently selected from hydrido, $C_1-C_3$-alkyl, phenyl-$C_1-C_3$-alkyl, $C_1-C_3$-perfluoroalkyl, chloro, $C_1-C_6$-alkylthio, $C_1-C_6$-alkoxy, nitro, cyano and cyano-$C_1-C_3$-alkyl; or wherein $CR^bR^c$ forms a cyclopropyl ring; wherein R is selected from carboxyl, aminocarbonyl, $C_1-C_6$-alkylsulfonylaminocarbonyl and $C_1-C_6$-alkoxycarbonyl; wherein R" is selected from hydrido, phenyl, thienyl, $C_1-C_4$-alkyl and $C_2-C_4$-alkenyl; wherein $R^1$ is selected from $C_1-C_3$-perfluoroalkyl, chloro, $C_1-C_6$-alkylthio, $C_1-C_6$-alkoxy, nitro, cyano and cyano-$C_1-C_3$-alkyl; wherein $R^2$ is one or more radicals independently selected from hydrido, halo, $C_1-C_6$-alkyl, $C_2-C_6$-alkenyl, $C_2-C_6$-alkynyl, halo-$C_2-C_6$-alkynyl, aryl-$C_1-C_3$-alkyl, aryl-$C_2-C_6$-alkynyl, aryl-$C_2-C_6$-alkenyl, $C_1-C_6$-alkoxy, methylenedioxy, $C_1-C_6$-alkylthio, $C_1-C_6$-alkylsulfinyl, aryloxy, arylthio, arylsulfinyl, heteroaryloxy, $C_1-C_6$-alkoxy-$C_1-C_6$-alkyl, aryl-$C_1-C_6$-alkyloxy, heteroaryl-$C_1-C_6$-alkyloxy, aryl-$C_1-C_6$-alkoxy-$C_1-C_6$-alkyl, $C_1-C_6$-haloalkyl, $C_1-C_6$-haloalkoxy, $C_1-C_6$-haloalkylthio, $C_1-C_6$-haloalkylsulfinyl, $C_1-C_6$-haloalkylsulfonyl, $C_1-C_3$-(haloalkyl-$C_1-C_3$-hydroxyalkyl, $C_1-C_6$-hydroxyalkyl, hydroxyimino-$C_1-C_6$-alkyl, $C_1-C_6$-alkylamino, arylamino, aryl-$C_1-C_6$-alkylamino, heteroarylamino, heteroaryl-$C_1-C_6$-alkylamino, nitro, cyano, amino, aminosulfonyl, $C_1-C_6$-alkylaminosulfonyl, arylaminosulfonyl, heteroarylaminosulfonyl, aryl-$C_1-C_6$-alkylaminosulfonyl, heteroaryl-$C_1-C_6$-alkylaminosulfonyl, heterocyclylsulfonyl, $C_1-C_6$-alkylsulfonyl, aryl-$C_1-C_6$-alkylsulfonyl, optionally substituted aryl, optionally substituted heteroaryl, aryl-$C_1-C_6$-alkylcarbonyl, heteroaryl-$C_1-C_6$-alkylcarbonyl, heteroarylcarbonyl, arylcarbonyl, aminocarbonyl, $C_1-C_6$-alkoxycarbonyl, formyl, $C_1-C_6$-haloalkylcarbonyl and $C_1-C_6$-alkylcarbonyl; and wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl or quinolyl radical; or an isomer or pharmaceutically acceptable salt thereof.

A more preferred class of compounds of Formula I" consists of compounds wherein X is selected from O, S and $NR^a$; wherein $R^a$ is selected from hydrido, $C_1-C_3$-alkyl and (optionally substituted phenyl)methyl; wherein R is carboxyl; wherein R" is selected from hydrido, $C_1-C_3$-alkyl and $C_2-C_3$-alkenyl; wherein $R^1$ is selected from $C_1-C_3$-perfluoroalkyl; wherein $R^2$ is one or more radicals independently selected from hydrido, halo, $C_1-C_6$-alkyl, $C_2-C_6$-alkenyl, $C_2-C_6$-alkynyl, halo-$C_2-C_6$-alkynyl, optionally substituted phenyl-$C_1-C_6$-alkyl, optionally substituted phenyl-$C_2-C_6$-alkynyl, phenyl-$C_2-C_6$-alkenyl, $C_1-C_3$-alkoxy, methylenedioxy, $C_1-C_3$-alkoxy-$C_1-C_3$-alkyl, $C_1-C_3$-alkylthio, $C_1-C_3$-alkylsulfinyl, optionally substituted phenyloxy, optionally substituted phenylthio, optionally substituted phenylsulfinyl, $C_1-C_3$-haloalkyl-$C_1-C_3$-hydroxyalkyl, phenyl-$C_1-C_3$-alkyloxy-$C_1-C_3$-alkyl, $C_1-C_3$-haloalkyl, $C_1-C_3$-haloalkoxy, $C_1-C_3$-haloalkylthio, $C_1-C_3$-hydroxyalkyl, $C_1-C_3$-alkoxy-$C_1-C_3$-alkyl, hydroxyimino-$C_1-C_3$-alkyl, $C_1-C_6$-alkylamino, nitro, cyano, amino, aminosulfonyl, N-alkylaminosulfonyl, N-arylaminosulfonyl, N-heteroarylaminosulfonyl, N-(phenyl-$C_1-C_6$-alkyl)aminosulfonyl, N-(heteroaryl-$C_1-C_6$-alkyl)aminosulfonyl, phenyl-$C_1-C_3$-alkylsulfonyl, 5- to 8-membered heterocyclylsulfonyl, $C_1-C_6$-alkylsulfonyl, optionally substituted phenyl, optionally substituted 5- to 9-membered heteroaryl, phenyl-$C_1-C_6$-alkylcarbonyl, phenylcarbonyl, 4-chlorophenylcarbonyl, 4-hydroxyphenylcarbonyl, 4-trifluoromethylphenylcarbonyl, 4-methoxyphenylcarbonyl, aminocarbonyl, formyl, and $C_1-C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, benzofurylphenyl, or quinolyl radical; or an isomer or pharmaceutically acceptable salt thereof.

An even more preferred class of compounds of Formula I" consists of compounds wherein X is selected from O, S and $NR^a$; wherein $R^a$ is selected from hydrido, methyl, ethyl, (4-trifluoromethyl)benzyl, (4-chloromethyl)benzyl, (4-methoxy)benzyl, and (4-cyano)benzyl, (4-nitro)benzyl; wherein R is carboxyl; wherein R" is selected from hydrido, ethyl and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, nitro, cyano, amino, aminosulfonyl, N-methylaminosulfonyl, N-phenylaminosulfonyl, N-furylaminosulfonyl, N-(benzyl) aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, optionally substituted phenylcarbonyl, aminocarbonyl, formyl and methylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, or quinolyl radical; or an isomer or pharmaceutically acceptable salt thereof.

Within Formula I there is a subclass of compounds of high interest represented by Formula II:

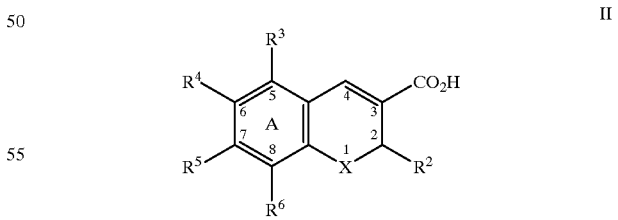

II wherein X is selected from O, $NR^a$ and S;
wherein $R^2$ is lower haloalkyl;
wherein $R^3$ is selected from hydrido, and halo;
wherein $R^4$ is selected from hydrido, halo, lower alkyl, lower haloalkoxy, lower alkoxy, lower aralkylcarbonyl, lower dialkylaminosulfonyl, lower alkynyl, phenyl-lower alkynyl, lower alkylaminosulfonyl, lower aralkylaminosulfonyl, lower heteroaralkylaminosulfonyl, and 5- or 6-membered nitrogen containing heterocyclosulfonyl;

wherein $R^5$ is selected from hydrido, lower alkyl, lower hydroxyalkyl, halo, lower alkenyl, lower alkynyl, lower alkoxy, phenyloxy, and aryl; and wherein $R^6$ is selected from hydrido, halo, lower alkyl, lower alkoxy, and aryl;

or an isomer or pharmaceutically acceptable salt thereof.

A class of compounds of particular interest consists of those compounds of Formula II wherein $R^2$ is trifluoromethyl or pentafluoroethyl; wherein $R^3$ is selected from hydrido, chloro, and fluoro; wherein $R^4$ is selected from hydrido, chloro, bromo, fluoro, iodo, methyl, tert-butyl, trifluoromethoxy, methoxy, ethynyl, phenylethynyl, benzylcarbonyl, dimethylaminosulfonyl, isopropylaminosulfonyl, methylaminosulfonyl, benzylaminosulfonyl, phenylethylaminosulfonyl, methylpropylaminosulfonyl, methylsulfonyl, and morpholinosulfonyl; wherein $R^5$ is selected from hydrido, methyl, ethyl, isopropyl, tert-butyl, chloro, methoxy, diethylamino, ethynyl, ethenyl, 2-hydroxy-1,1-dimethylethyl, phenyloxy and phenyl; and wherein $R^6$ is selected from hydrido, chloro, bromo, fluoro, methyl, ethyl, tert-butyl, methoxy, and phenyl; or an isomer or pharmaceutically acceptable salt thereof.

Within Formula I there is a subclass of compounds of high interest represented by Formula IIa:

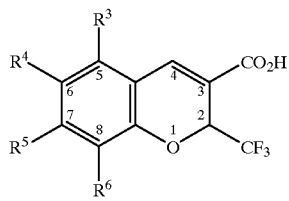

IIa wherein $R^4$ is selected from hydrido, $C_1$–$C_3$-alkyl, $C_1$–$C_3$-hydroxyalkyl, $C_1$–$C_3$-alkoxy and halo;

wherein $R^4$ is selected from hydrido, halo, $C_1$–$C_4$-alkyl, $C_1$–$C_3$-alkylthio, $C_1$–$C_3$-haloalkyl, amino, aminosulfonyl, $C_1$–$C_3$-alkylsulfonyl, $C_1$–$C_3$-alkylsulfinyl, $C_1$–$C_3$-alkoxy-$C_1$–$C_3$-alkyl, $C_1$–$C_3$-alkylcarbonyl, formyl, cyano, $C_1$–$C_3$-haloalkylthio, substituted or unsubstituted phenylcarbonyl, $C_1$–$C_3$-haloalkoxy, $C_1$–$C_3$-alkoxy, aryl-$C_1$–$C_3$-alkylcarbonyl, di-$C_1$–$C_3$-alkylaminosulfonyl, $C_1$–$C_3$-alkylaminosulfonyl, aryl-$C_1$–$C_3$-alkylaminosulfonyl, 5- or 6-heteroaryl-$C_1$–$C_3$-alkylaminosulfonyl, 5- or 6-membered heteroaryl, $C_1$–$C_3$-hydroxyalkyl, substituted or unsubstituted phenyl and 5- or 6-membered nitrogen-containing heterocyclosulfonyl; wherein $R^5$ is selected from hydrido, $C_1$–$C_3$-alkyl, halo, $C_1$–$C_3$-haloalkyl, $C_1$–$C_4$-hydroxyalkyl, $C_2$–$C_3$-alkynyl, $C_2$–$C_3$-alkenyl, $C_1$–$C_3$-alkoxy, phenoxy, phenoxy independently substituted with one or more radicals selected from $C_1$–$C_3$-haloalkyl, nitro, carboxy, $C_1$–$C_3$-haloalkoxy, $C_1$–$C_3$-alkoxy, cyano, $C_1$–$C_3$-alkyl and halo, naphthyloxy, naphthyloxy substituted with one or more halo radicals, phenylthio, phenylthio substituted with one or more halo radicals, phenylsulfinyl, phenylsulfinyl substituted with one or more halo radicals, phenylsulfonyl, phenylsulfonyl substituted with one or more halo radicals, pyridinyloxy, pyridinyloxy substituted with one or more halo radicals, and phenyl; and wherein $R^6$ is selected from hydrido, halo, cyano, hydroxyiminomethyl, $C_1$–$C_3$-hydroxyalkyl, $C_2$–$C_3$-alkynyl, phenyl-$C_2$–$C_3$-alkynyl, $C_1$–$C_3$-alkyl, $C_1$–$C_3$-alkoxy, formyl and phenyl;

or an isomer or pharmaceutically acceptable salt thereof.

A class of compounds of particular interest consists of those compounds of Formula IIa wherein $R^3$ is selected from hydrido, and chloro; wherein $R^4$ is selected from chloro, methyl, tert-butyl, methylthio, trifluoromethyl, difluoromethyl, pentafluoromethyl, trifluoromethylthio, trifluoromethoxy, cyano, substituted or unsubstituted phenylcarbonyl, and substituted or unsubstituted phenyl; wherein $R^5$ is selected from hydrido, methyl, tert-butyl, 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, (2-pyridinyl)oxy, iodo, ethenyl, ethynyl, chloro; and wherein $R^6$ is selected from hydrido, chloro, thienyl, hydroxyiminomethyl, substituted or unsubstituted phenylethynyl, and substituted or unsubstituted phenyl; or an isomer or pharmaceutically acceptable salt thereof.

A class of compounds of more particular interest consists of those compounds of Formula IIa wherein $R^3$ is hydrido; wherein $R^4$ is chloro or hydrido; and wherein $R^6$ is hydrido; or an isomer or pharmaceutically acceptable salt thereof.

An even more preferred class of compounds of Formula IIa consists of compounds wherein $R^5$ is selected from 2,2,2-trifluoroethoxy, 2-hydroxy-1,1-dimethylethyl, phenoxy, 4-methoxyphenoxy, 4-chlorophenoxy, 3-chlorophenoxy, 2-chlorophenoxy, 4-cyanophenoxy, 2,6-dimethylphenoxy, 2,4-dichlorophenoxy, 3,4-difluorophenoxy, 4-chloro-3-fluorophenoxy, 4-(trifluoromethyl)phenoxy, 4-nitrophenoxy, 4-carboxyphenoxy, 3-carboxyphenoxy, 2-chloro-4-carboxyphenoxy, 4-(trifluoromethoxy)phenoxy, 2-bromo-4-chlorophenoxy, (6-bromo-2-naphthalenyl)oxy, phenylthio, (4-methoxyphenyl)thio, (4-chlorophenyl)thio, (4-chlorophenyl)sulfinyl, (4-chlorophenyl)sulfonyl, (6-chloro-2-pyridinyl)oxy, (2-chloro-3-pyridinyl)oxy, (3-pyridinyl)oxy, and (2-pyridinyl)oxy; or an isomer or pharmaceutically acceptable salt thereof.

Within Formula I there is a subclass of compounds of high interest represented by Formula IIb

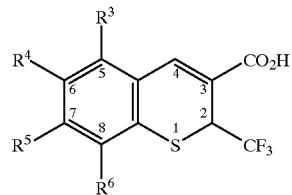

IIb wherein $R^3$ is selected from hydrido, lower alkyl, lower hydroxyalkyl, lower alkoxy and halo;

wherein $R^4$ is selected from hydrido, halo, lower. alkyl, lower alkylthio, lower haloalkyl, amino, aminosulfonyl, lower alkylsulfonyl, lower alkylsulfinyl, lower alkoxyalkyl, lower alkylcarbonyl, formyl, cyano, lower haloalkylthio, substituted or unsubstituted phenylcarbonyl, lower haloalkoxy, lower alkoxy, lower aralkylcarbonyl, lower dialkylaminosulfonyl, lower alkylaminosulfonyl, lower aralkylaminosulfonyl, lower heteroaralkylaminosulfonyl, 5- or 6-membered heteroaryl, lower hydrooxyalkyl, optionally substituted phenyl and 5- or 6-membered nitrogen containing heterocyclosulfonyl;

wherein $R^5$ is selected from hydrido, lower alkyl, halo, lower haloalkyl, lower alkoxy, and phenyl; and wherein $R^6$ is selected from hydrido, halo, cyano, hydrooxyiminomethyl, lower hydroxyalkyl, lower alkynyl, phenylalkynyl, lower alkyl, lower alkoxy, formyl and phenyl;

or an isomer or pharmaceutically acceptable salt thereof.

A class of compounds of particular interest consists of those compounds of Formula IIb wherein $R^3$ is selected from hydrido, and chloro; wherein $R^4$ is selected from chloro, methyl, tert-butyl, methylthio, trifluoromethyl, difluoromethyl, pentafluoromethyl, trifluoromethylsulfide, trifluoromethooxy, cyano, substituted or unsubstituted phenylcarbonyl, and substituted or unsubstituted phenyl; wherein $R^5$ is selected from hydrido, methyl, tert-butyl, chloro; and wherein $R^6$ is selected from hydrido, chloro, thienyl, hydroxyiminomethyl, substituted or unsubstituted phenylethynyl, and substituted or unsubstituted phenyl; or an isomer or pharmaceutically acceptable salt thereof.

Within Formula I there is a subclass of compounds of high interest represented by Formula IIc:

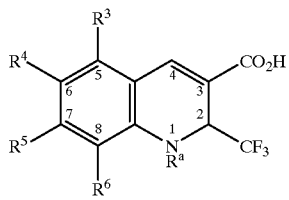

wherein $R^a$ is selected from hydrido and lower aralkyl;
wherein $R^3$ is selected from hydrido, lower alkyl, lower hydroxyalkyl, lower alkoxy and halo;
wherein $R^4$ is selected from hydrido, halo, lower alkyl, lower alkylthio, lower haloalkyl, amino, aminosulfonyl, lower alkylsulfonyl, lower alkylsulfinyl, lower alkoxyalkyl, lower alkylcarbonyl, formyl, cyano, lower haloalkylthio, substituted or unsubstituted phenylcarbonyl, lower haloalkoxy, lower alkoxy, lower alkynyl, phenyl-lower alkynyl, lower aralkylcarbonyl, lower dialkylaminosulfonyl, lower alkylaminosulfonyl, lower aralkylaminosulfonyl, lower heteroaralkylaminosulfonyl, 5- or 6-membered heteroaryl, lower hydroxyalkyl, optionally substituted phenyl and 5- or 6-membered nitrogen containing heterocyclosulfonyl;
wherein $R^5$ is selected from hydrido, lower alkyl, halo, lower haloalkyl, lower alkoxy, and phenyl; and
wherein $R^6$ is selected from hydrido, halo, cyano, hydroxyiminomethyl, lower hydroxyalkyl, lower alkynyl, phenylalkynyl, lower alkyl, lower alkoxy, formyl and phenyl;
or an isomer or pharmaceutically acceptable salt thereof.

A class of compounds of particular interest consists of those compounds of Formula IIc wherein $R^3$ is selected from hydrido, and chloro; wherein $R^4$ is selected from chloro, methyl, tert-butyl, methylthio, trifluoromethyl, difluoromethyl, pentafluoromethyl, trifluoromethylsulfide, trifluoromethoxy, ethynyl, phenylethynyl, substituted or unsubstituted phenylcarbonyl, and substituted or unsubstituted phenyl; wherein $R^5$ is selected from hydrido, methyl, tert-butyl, chloro; and wherein $R^6$ is selected from hydrido, chloro, thienyl, hydroxyiminomethyl, substituted or unsubstituted phenylethynyl, and substituted or unsubstituted phenyl; or an isomer or pharmaceutically acceptable salt thereof.

A class of compounds of more particular interest consists of those compounds of Formula IIc wherein $R^3$ is hydrido or chloro; wherein $R^4$ is selected from ethynyl, and optionally substituted phenylethynyl; or an isomer or pharmaceutically acceptable salt thereof.

A family of specific compounds of particular interest within Formula I consists of compounds and pharmaceutically-acceptable salts thereof as follows:

6-chloro-7-[(2-pyridyl-N-oxide)thio]-2-(trifluoromethyl)-2H-1-benzopyran-3-carboxylic acid;
6-chloro-7-[(3-chloro-2-pyridyl-{N-oxide})thio]-2-(trifluoromethyl)-2H-1-benzopyran-3-carboxylic acid;
6-chloro-1,2-dihydro-7-[(2-pyridyl-N-oxide)oxy]-2-(trifluoromethyl)-2H-quinoline-3-carboxylic acid;
6-chloro-7-[(3-chloro-2-pyridyl-{N-oxide})oxy]-1,2-dihydro-2-(trifluoromethyl)-2H-quinoline-3-carboxylic acid;
6-chloro-1,2-dihydro-7-[(2-pyridyl-N-oxide)thio]-2-(trifluoromethyl)-2H-quinoline-3-carboxylic acid;
6-chloro-7-[(3-chloro-2-pyridyl-{N-oxide})thio]-1,2-dihydro-2-(trifluoromethyl)-2H-quinoline-3-carboxylic acid;
6-chloro-7-[(2-pyridyl-N-oxide)oxy]-2-(trifluoromethyl)-2H-1-benzothiopyran-3-carboxylic acid;
6-chloro-7-[(3-chloro-2-pyridyl-{N-oxide})oxy]-2-(trifluoromethyl)-2H-1-benzothiopyran-3-carboxylic acid;
6-chloro-7-[(2-pyridyl-N-oxide)thio]-2-(trifluoromethyl)-2H-1-benzothiopyran-3-carboxylic acid;
6-chloro-7-[(3-chloro-2-pyridyl-{N-oxide})thio]-2-(trifluoromethyl)-2H-1-benzothiopyran-3-carboxylic acid;
6-chloro-7-(3,4-dichlorophenoxy)2-(trifluoromethyl)-2H-1-benzopyran-3-carboxylic acid;
6-chloro-7-(3-bromo-4-chlorophenoxy)2-(trifluoromethyl)-2H-1-benzopyran-3-carboxylic acid;
6-chloro-7-(4-bromo-3-chlorophenoxy)2-(trifluoromethyl)-2H-1-benzopyran-3-carboxylic acid;
6-chloro-7-(3,4-dibromophenoxy)2-(trifluoromethyl)-2H-1-benzopyran-3-carboxylic acid;
6-chloro-7-[4-chloro-3-(trifluoromethyl)phenoxy]-2-(trifluoromethyl)-2H-1-benzopyran-3-carboxylic acid;
6-chloro-7-[3-chloro-4-(trifluoromethyl)phenoxy]-2-(trifluoromethyl)-2H-1-benzopyran-3-carboxylic acid;
6-chloro-7-(2,6-dichlorophenoxy)2-(trifluoromethyl)-2H-1-benzopyran-3-carboxylic acid;
6-chloro-7-(2,6-dibromophenoxy)2-(trifluoromethyl)-2H-1-benzopyran-3-carboxylic acid;
6-chloro-7-(2,6-difluorophenoxy)2-(trifluoromethyl)-2H-1-benzopyran-3-carboxylic acid;
6-chloro-7-(2,5-dichlorophenoxy)2-(trifluoromethyl)-2H-1-benzopyran-3-carboxylic acid;
6-chloro-7-(2,5-dibromophenoxy)2-(trifluoromethyl)-2H-1-benzopyran-3-carboxylic acid;

6-chloro-7-(2,5-difluorophenoxy)2-(trifluoromethyl)-2H-1-benzopyran-3-carboxylic acid;
6-chloro-7-(2,3-dichlorophenoxy)2-(trifluoromethyl)-2H-1-benzopyran-3-carboxylic acid;
6-chloro-7-(2,3-dibromophenoxy)2-(trifluoromethyl)-2H-1-benzopyran-3-carboxylic acid;
6-chloro-7-(2,3-difluorophenoxy)2-(trifluoromethyl)-2H-1-benzopyran-3-carboxylic acid;
6-chloro-7-(4-chloro-3-cyanophenoxy)2-(trifluoromethyl)-2H-1-benzopyran-3-carboxylic acid;
6-chloro-7-(3-tert-butylphenoxy)2-(trifluoromethyl)-2H-1-benzopyran-3-carboxylic acid;
6-chloro-7-(2-tert-butylphenoxy)2-(trifluoromethyl)-2H-1-benzopyran-3-carboxylic acid;
6-chloro-7-(4-chloro-3-tert-butylphenoxy)2-(trifluoromethyl)-2H-1-benzopyran-3-carboxylic acid;
6-chloro-7-(4-chloro-2-tert-butylphenoxy)2-(trifluoromethyl)-2H-1-benzopyran-3-carboxylic acid;
6-chloro-7-(2-chloro-3-tert-butyl phenoxy)2-(trifluoromethyl)-2H-1-benzopyran-3-carboxylic acid;
7-phenoxy-2-(trifluoromethyl)-2H-1-benzopyran-3-carboxylic acid;
6-chloro-7-phenoxy-2-(trifluoromethyl)-2H-1-benzopyran-3-carboxylic acid;
6-chloro-7-(2-hydroxy-1,1-dimethylethyl)-2-(trifluoromethyl)-2H-1-benzopyran-3-carboxylic acid;
7-(2-hydroxy-1,1-dimethylethyl)-2-(trifluoromethyl)-2H-1-benzopyran-3-carboxylic;
6-chloro-7-iodo-2-(trifluoromethyl)-2H-1-benzopyran-3-carboxylic acid;
6-chloro-7-ethynyl-2-(trifluoromethyl)-2H-1-benzopyran-3-carboxylic acid;
6-chloro-7-ethenyl-2-(trifluoromethyl)-2H-1-benzopyran-3-carboxylic acid;
6-chloro-7-(4-methoxyphenoxy)-2-(trifluoromethyl)-2H-1-benzopyran-3-carboxylic acid;
6-chloro-7-(4-chlorophenoxy)-2-(trifluoromethyl)-2H-1-benzopyran-3-carboxylic acid;
6-chloro-7-(4-chlorophenoxy)-2-(trifluoromethyl)-2H-1-benzopyran-3-carboxylic acid;
6-chloro-7-(4-cyanophenoxy)-2-(trifluoromethyl)-2H-1-benzopyran-3-carboxylic acid;
6-chloro-7-[4-(trifluoromethyl)phenoxy]-2-(trifluoromethyl)-2H-1-benzopyran-3-carboxylic acid;
6-chloro-7-[4-(trifluoromethoxy)phenoxy]-2-(trifluoromethyl)-2H-1-benzopyran-3-carboxylic acid;
6-chloro-7-(2-bromo-4-chlorophenoxy)-2-(trifluoromethyl)-2H-1-benzopyran-3-carboxylic acid;
6-chloro-7-[(6-bromo-2-naphthyl)oxy-2-(trifluoromethyl)-2H-1-benzopyran-3-carboxylic acid;
6-chloro-7-(2,6-dimethylphenoxy)-2-(trifluoromethyl)-2H-1-benzopyran-3-carboxylic acid;
6-chloro-7-[(4-methoxyphenyl)thio]-2-(trifluoromethyl)-2H-1-benzopyran-3-carboxylic acid;
6-chloro-7-[(4-chlorophenyl)thio]-2-(trifluoromethyl)-2H-1-benzopyran-3-carboxylic acid;
6-chloro-7-[(4-chlorophenyl)sulfinyl]-2-(trifluoromethyl)-2H-1-benzopyran-3-carboxylic acid;
6-chloro-7-[(4-chlorophenyl)sulfonyl]-2-(trifluoromethyl)-2H-1-benzopyran-3-carboxylic acid;
6-chloro-7-phenylthio-2-(trifluoromethyl)-2H-1-benzopyran-3-carboxylic acid;
6-chloro-7-(3-chlorophenoxy)-2-(trifluoromethyl)-2H-1-benzopyran-3-carboxylic acid;
6-chloro-7-(2,4-dichlorophenoxy)-2-(trifluoromethyl)-2H-1-benzopyran-3-carboxylic acid;
6-chloro-7-(3,4-difluorophenoxy)-2-(trifluoromethyl)-2H-1-benzopyran-3-carboxylic acid;
6-chloro-7-[(6-chloro-2-pyridinyl)oxy]-2-(trifluoromethyl)-2H-1-benzopyran-3-carboxylic acid;
6-chloro-7-[(2-chloro-3-pyridinyl)oxy]-2-(trifluoromethyl)-2H-1-benzopyran-3-carboxylic acid;
6-chloro-7-[(3-pyridinyl)oxy]-2-(trifluoromethyl)-2H-1-benzopyran-3-carboxylic acid;
6-chloro-7-[(2-pyridinyl)oxy]-2-(trifluoromethyl)-2H-1-benzopyran-3-carboxylic acid;
6-chloro-7-(4-nitrophenoxy)-2-(trifluoromethyl)-2H-1-benzopyran-3-carboxylic acid;
6-chloro-7-(2-chlorophenoxy)-2-(trifluoromethyl)-2H-1-benzopyran-3-carboxylic acid;
6-chloro-7-(4-chloro-3-fluorophenoxy)-2-(trifluoromethyl)-2H-1-benzopyran-3-carboxylic acid;
6-chloro-7-(4-carboxyphenoxy)-2-(trifluoromethyl)-2H-1-benzopyran-3-carboxylic acid;
6-chloro-7-(2-chloro-4-carboxyphenoxy)-2-(trifluoromethyl)-2H-1-benzopyran-3-carboxylic acid;
6-chloro-7-(3-carboxyphenoxy)-2-(trifluoromethyl)-2H-1-benzopyran-3-carboxylic acid;
6-chloro-7-(2,2,2-trifluoroethoxy)-2-(trifluoromethyl)-2H-1-benzopyran-3-carboxylic acid;
6-chloro-1,2-dihydro-8-methyl-2-(trifluoromethyl)-3-quinolinecarboxylic acid;
1,2-dihydro-5-methyl-2-(trifluoromethyl)-3-quinolinecarboxylic acid;
1,2-dihydro-6-(4-fluorophenyl)-2-(trifluoromethyl)-3-quinolinecarboxylic acid;
1,2-dihydro-6-ethynyl-2-(trifluoromethyl)-3-quinolinecarboxylic acid;
8-bromo-1,2-dihydro-6-methyl-2-(trifluoromethyl)-3-quinolinecarboxylic acid;
1,2-dihydro-6-phenylethynyl-2-(trifluoromethyl)-3-quinolinecarboxylic acid;
6-chloro-7-[(3-pyridyl-N-oxide)oxy]-2-(trifluoromethyl)-2H-1-benzopyran-3-carboxylic acid;
6-chloro-7-[(2-pyridyl-N-oxide)oxy]-2-(trifluoromethyl)-2H-1-benzopyran-3-carboxylic acid;
6-chloro-7-[(3-chloro-2-pyridyl-{N-oxide})oxy]-2-(trifluoromethyl)-2H-1-benzopyran-3-carboxylic acid;
6-chloro-7-[(4-chloro-2-pyridyl-{N-oxide})oxy]-2-(trifluoromethyl)-2H-1-benzopyran-3-carboxylic acid;
6-chloro-7-[(5-chloro-2-pyridyl-{N-oxide})oxy]-2-(trifluoromethyl)-2H-1-benzopyran-3-carboxylic acid;
6-chloro-7-[(6-chloro-2-pyridyl-{N-oxide})oxy]-2-(trifluoromethyl)-2H-1-benzopyran-3-carboxylic acid;
6-chloro-2-trifluoromethyl-2H-1-benzopyran-3-carboxylic acid;
7-ethyl-2-trifluoromethyl-2H-1-benzopyran-3-carboxylic acid;
7-methyl-2-trifluoromethyl-2H-1-benzopyran-3-carboxylic acid;
2,7-bis(trifluoromethyl)-2H-1-benzopyran-3-carboxylic acid;
7-bromo-2-trifluoromethyl-2H-1-benzopyran-3-carboxylic acid;
6-chloro-7-methyl-2-trifluoromethyl-2H-1-benzopyran-3-carboxylic acid;
8-(1-methylethyl)-2-trifluoromethyl-2H-1-benzopyran-3-carboxylic acid;
6-chloro-7-(1,1-dimethylethyl)-2-trifluoromethyl-2H-1-benzopyran-3-carboxylic acid;
6-chloro-8-(1-methylethyl)-2-trifluoromethyl-2H-1-benzopyran-3-carboxylic acid;
2-trifluoromethyl-2H-1-benzopyran-3-carboxylic acid;
8-ethoxy-2-trifluoromethyl-2H-1-benzopyran-3-carboxylic acid;

7-(1,1-dimethylethyl)-2-trifluoromethyl-2H-1-benzopyran-3-carboxylic acid;
6-bromo-2-trifluoromethyl-2H-1-benzopyran-3-carboxylic acid;
8-chloro-2-trifluoromethyl-2H-1-benzopyran-3-carboxylic acid;
8-bromo-6-chloro-2-trifluoromethyl-2H-1-benzopyran-3-carboxylic acid;
6-trifluoromethoxy-2-trifluoromethyl-2H-1-benzopyran-3-carboxylic acid;
8-fluoro-2-trifluoromethyl-2H-1-benzopyran-3-carboxylic acid;
5,7-dichloro-2-trifluoromethyl-2H-1-benzopyran-3-carboxylic acid;
7,8-dichloro-2-trifluoromethyl-2H-1-benzopyran-3-carboxylic acid;
7-isopropyloxy-2-trifluoromethyl-2H-1-benzopyran-3-carboxylic acid;
8-phenyl-2-trifluoromethyl-2H-1-benzopyran-3-carboxylic acid;
7,8-dimethyl-2-trifluoromethyl-2H-1-benzopyran-3-carboxylic acid;
6,8-bis(1,1-dimethylethyl)-2-trifluoromethyl-2H-1-benzopyran-3-carboxylic acid;
7-chloro-2-trifluoromethyl-2H-1-benzopyran-3-carboxylic acid;
7-(1-methylethyl)-2-trifluoromethyl-2H-1-benzopyran-3-carboxylic acid;
7-phenyl-2-trifluoromethyl-2H-1-benzopyran-3-carboxylic acid;
6-chloro-7-ethyl-2-trifluoromethyl-2H-1-benzopyran-3-carboxylic acid;
8-ethyl-2-trifluoromethyl-2H-1-benzopyran-3-carboxylic acid;
6-chloro-8-ethyl-2-trifluoromethyl-2H-1-benzopyran-3-carboxylic acid;
6-chloro-7-phenyl-2-trifluoromethyl-2H-1-benzopyran-3-carboxylic acid;
6,7-dichloro-2-trifluoromethyl-2H-1-benzopyran-3-carboxylic acid;
6,8-dichloro-2-trifluoromethyl-2H-1-benzopyran-3-carboxylic acid;
6,8-dibromo-2-trifluoromethyl-2H-1-benzopyran-3-carboxylic acid;
6,8-dimethoxy-2-trifluoromethyl-2H-1-benzopyran-3-carboxylic acid;
6-nitro-2-trifluoromethyl-2H-1-benzopyran-3-carboxylic acid;
6-amino-2-trifluoromethyl-2H-1-benzopyran-3-carboxylic acid;
ethyl 6-amino-2-trifluoromethyl-2H-1-benzopyran-3-carboxylate;
6-chloro-8-methyl-2-trifluoromethyl-2H-1-benzopyran-3-carboxylic acid;
8-chloro-6-methyl-2-trifluoromethyl-2H-1-benzopyran-3-carboxylic acid;
8-chloro-6-methoxy-2-trifluoromethyl-2H-1-benzopyran-3-carboxylic acid;
6,8-difluoro-2-trifluoromethyl-2H-1-benzopyran-3-carboxylic acid;
6-bromo-8-chloro-2-trifluoromethyl-2H-1-benzopyran-3-carboxylic acid;
8-bromo-6-fluoro-2-trifluoromethyl-2H-1-benzopyran-3-carboxylic acid;
8-bromo-6-methyl-2-trifluoromethyl-2H-1-benzopyran-3-carboxylic acid;
8-bromo-5-fluoro-2-trifluoromethyl-2H-1-benzopyran-3-carboxylic acid;
6-chloro-8-fluoro-2-trifluoromethyl-2H-1-benzopyran-3-carboxylic acid;
6-bromo-8-methoxy-2-trifluoromethyl-2H-1-benzopyran-3-carboxylic acid;
7-(N,N-diethylamino)-2-trifluoromethyl-2H-1-benzopyran-3-carboxylic acid;
6-[[(phenylmethyl)amino]sulfonyl]-2-trifluoromethyl-2H-1-benzopyran-3-carboxylic acid;
6-[(dimethylamino)sulfonyl]-2-trifluoromethyl-2H-1-benzopyran-3-carboxylic acid;
6-aminosulfonyl-2-trifluoromethyl-2H-1-benzopyran-3-carboxylic acid;
6-(methylamino)sulfonyl-2-trifluoromethyl-2H-1-benzopyran-3-carboxylic acid;
6-[(4-morpholino)sulfonyl]-2-trifluoromethyl-2H-1-benzopyran-3-carboxylic acid;
6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-N,N-diethylaminosulfonyl-2-trifluoromethyl-2H-1-benzopyran-3-carboxylic acid;
6-phenylacetyl-2-trifluoromethyl-2H-1-benzopyran-3-carboxylic acid;
6-(2,2-dimethylpropylcarbonyl)-2-trifluoromethyl-2H-1-benzopyran-3-carboxylic acid;
6,8-dichloro-7-methoxy-2-trifluoromethyl-2H-1-benzopyran-3-carboxylic acid;
6-chloro-2-trifluoromethyl-2H-1-benzothiopyran-3-carboxylic acid;
6-[[(2-furanylmethyl)amino]sulfonyl]-2-(trifluoromethyl)-2H-1-benzopyran-3-carboxylic acid;
6-[(phenylmethyl)sulfonyl]-2-(trifluoromethyl)-2H-1-benzopyran-3-carboxylic acid;
6-[[(phenylethyl)amino]sulfonyl]-2-(trifluoromethyl)-2H-1-benzopyran-3-carboxylic acid;
6-iodo-2-trifluoromethyl-2H-1-benzopyran-3-carboxylic acid;
6-chloro-8-iodo-2-(trifluoromethyl)-2H-1-benzopyran-3-carboxylic acid;
8-bromo-6-chloro-2-trifluoromethyl-2H-1-benzopyran-3-carboxylic acid;
6-formyl-2-(trifluoromethyl)-2H-1-benzopyran-3-carboxylic acid;
6-chloro-8-formyl-2-(trifluoromethyl)-2H-1-benzopyran-3-carboxylic acid;
6-bromo-7-(1,1-dimethylethyl)-2-(trifluoromethyl)-2H-1-benzopyran-3-carboxylic acid;
5,6-dichloro-2-(trifluoromethyl)-2H-1-benzopyran-3-carboxylic acid;
6-cyano-2-(trifluoromethyl)-2H-1-benzopyran-3-carboxylic acid;
6-hydroxymethyl-2-(trifluoromethyl)-2H-1-benzopyran-3-carboxylic acid;
6-(difluoromethyl)-2-(trifluoromethyl)-2H-1-benzopyran-3-carboxylic acid;
2,6-bis(trifluoromethyl)-2H-1-benzopyran-3-carboxylic acid;
5,6,7-trichloro-2-(trifluoromethyl)-2H-1-benzopyran-3-carboxylic acid;
6,7,8-trichloro-2-(trifluoromethyl)-2H-1-benzopyran-3-carboxylic acid;
6-(methylthio)-2-(trifluoromethyl)-2H-1-benzopyran-3-carboxylic acid;

6-(methylsulfinyl)-2-(trifluoromethyl)-2H-1-benzopyran-3-carboxylic acid;
5,8-dichloro-2-(trifluoromethyl)-2H-1-benzopyran-3-carboxylic acid;
6-(pentafluoroethyl)-2-(trifluoromethyl)-2H-1-benzopyran-3-carboxylic acid;
6-(1,1-dimethylethyl)-2-(trifluoromethyl)-2H-1-benzopyran-3-carboxylic acid;
2-(trifluoromethyl)-6-[(trifluoromethyl)thio]-2H-1-benzopyran-3-carboxylic acid;
6,8-dichloro-7-methyl-2-(trifluoromethyl)-2H-1-benzopyran-3-carboxylic acid;
6-chloro-2,7-bis(trifluoromethyl)-2H-1-benzopyran-3-carboxylic acid;
5-methoxy-2-(trifluoromethyl)-2H-1-benzopyran-3-carboxylic acid;
6-benzoyl-2-(trifluoromethyl)-2H-1-benzopyran-3-carboxylic acid;
6-(4-chlorobenzoyl)-2-(trifluoromethyl)-2H-1-benzopyran-3-carboxylic acid;
6-(4-hydroxybenzoyl)-2-(trifluoromethyl)-2H-1-benzopyran-3-carboxylic acid;
6-phenoxy-2-(trifluoromethyl)-2H-1-benzopyran-3-carboxylic acid;
8-chloro-6-(4-chlorophenoxy)-2-trifluoromethyl-2H-1-benzopyran-3-carboxylic acid;
2-(trifluoromethyl)-6-[4-(trifluoromethyl)phenoxy]-2H-1-benzopyran-3-carboxylic acid;
6-(4-methoxyphenoxy)-2-(trifluoromethyl)-2H-1-benzopyran-3-carboxylic acid;
6-(3-chloro-4-methoxyphenoxy)-2-(trifluoromethyl)-2H-1-benzopyran-3-carboxylic acid;
6-(4-chlorophenoxy)-2-(trifluoromethyl)-2H-1-benzopyran-3-carboxylic acid;
8-chloro-2-(trifluoromethyl)-6-[4-(trifluoromethyl)phenoxy]-2H-1-benzopyran-3-carboxylic acid;
6-chloro-8-cyano-2-(trifluoromethyl)-2H-1-benzopyran-3-carboxylic acid;
6-chloro-8-[(hydroxyimino)methyl]-2-(trifluoromethyl)-2H-1-benzopyran-3-carboxylic acid;
6-chloro-8-(hydroxymethyl)-2-(trifluoromethyl)-2H-1-benzopyran-3-carboxylic acid;
8-(1H-benzimidazol-2-yl)-6-chloro-2-(trifluoromethyl)-2H-1-benzopyran-3-carboxylic acid;
7-(1,1-dimethylethyl)-2-(pentafluoroethyl)-2H-1-benzopyran-3-carboxylic acid;
6-chloro-8-(methoxymethyl)-2-(trifluoromethyl)-2H-1-benzopyran-3-carboxylic acid;
6-chloro-8-(benzyloxymethyl)-2-(trifluoromethyl)-2H-1-benzopyran-3-carboxylic acid;
6-chloro-8-ethenyl-2-(trifluoromethyl)-2H-1-benzopyran-3-carboxylic acid;
6-chloro-8-ethynyl-2-(trifluoromethyl)-2H-1-benzopyran-3-carboxylic acid;
6-chloro-8-(2-thienyl)-2-(trifluoromethyl)-2H-1-benzopyran-3-carboxylic acid;
6-chloro-8-(2-furanyl)-2-(trifluoromethyl)-2H-1-benzopyran-3-carboxylic acid;
6-chloro-8-(5-chloro-1-pentynyl)-2-(trifluoromethyl)-2H-1-benzopyran-3-carboxylic acid;
6-chloro-8-(1-pentynyl)-2-(trifluoromethyl)-2H-1-benzopyran-3-carboxylic acid;
6-chloro-8-(phenylethynyl)-2-(trifluoromethyl)-2H-1-benzopyran-3-carboxylic acid;
6-chloro-8-(3,3-dimethyl-1-butynyl)-2-(trifluoromethyl)-2H-1-benzopyran-3-carboxylic acid;
6-chloro-8-[(4-chlorophenyl)ethynyl]-2-(trifluoromethyl)-2H-1-benzopyran-3-carboxylic acid;
6-chloro-8-[(4-methoxyphenyl)ethynyl]-2-(trifluoromethyl)-2H-1-benzopyran-3-carboxylic acid;
6-(phenylethynyl)-2-(trifluoromethyl)-2H-1-benzopyran-3-carboxylic acid;
6-chloro-8-(4-chlorophenyl)-2-(trifluoromethyl)-2H-1-benzopyran-3-carboxylic acid;
6-chloro-8-(3-methoxyphenyl)-2-(trifluoromethyl)-2H-1-benzopyran-3-carboxylic acid;
6-chloro-8-[(4-methylthio)phenyl]-2-(trifluoromethyl)-2H-1-benzopyran-3-carboxylic acid;
6-chloro-8-[(4-methylsulfonyl)phenyl]-2-(trifluoromethyl)-2H-1-benzopyran-3-carboxylic acid;
6-chloro-8-phenyl-2-(trifluoromethyl)-2H-1-benzopyran-3-carboxylic acid;
6-bromo-8-fluoro-2-(trifluoromethyl)-2H-1-benzopyran-3-carboxylic acid;
6-(4-fluorophenyl)-2-(trifluoromethyl)-2H-1-benzopyran-3-carboxylic acid;
6-phenyl-2-(trifluoromethyl)-2H-1-benzopyran-3-carboxylic acid;
8-chloro-6-fluoro-2-(trifluoromethyl)-2H-1-benzopyran-3-carboxylic acid;
6,8-diiodo-2-(trifluoromethyl)-2H-1-benzopyran-3-carboxylic acid;
6-(5-chloro-2-thienyl)-2-(trifluoromethyl)-2H-1-benzopyran-3-carboxylic acid;
6-(2-thienyl)-2-(trifluoromethyl)-2H-1-benzopyran-3-carboxylic acid;
6-(4-chlorophenyl)-2-(trifluoromethyl)-2H-1-benzopyran-3-carboxylic acid;
6-(4-bromophenyl)-2-(trifluoromethyl)-2H-1-benzopyran-3-carboxylic acid;
6-(ethynyl)-2-(trifluoromethyl)-2H-1-benzopyran-3-carboxylic acid;
6-methyl-2-(trifluoromethyl)-2H-1-benzopyran-3-carboxylic acid;
6-chloro-8-(4-methoxyphenyl)-2-trifluoromethyl-2H-1-benzopyran-3-carboxylic acid;
6-chloro-2-(trifluoromethyl)-4-ethenyl-2H-1-benzopyran-3-carboxylic acid;
6-chloro-2-(trifluoromethyl)-4-phenyl-2H-1-benzopyran-3-carboxylic acid;
6-chloro-4-(2-thienyl)-2-(trifluoromethyl)-2H-1-benzopyran-3-carboxylic acid;
6-(2,2,2-trifluoro-1-hydroxyethyl)-2-(trifluoromethyl)-2H-1-benzopyran-3-carboxylic acid;
6-methyl-2-(trifluoromethyl)-2H-1-benzothiopyran-3-carboxylic acid;
6,8-dimethyl-2-(trifluoromethyl)-2H-1-benzothiopyran-3-carboxylic acid;
6-(1,1-dimethylethyl)-2-(trifluoromethyl)-2H-1-benzothiopyran-3-carboxylic acid;
7-methyl-2-(trifluoromethyl)-2H-1-benzothiopyran-3-carboxylic acid;
6,7-dimethyl-2-(trifluoromethyl)-2H-1-benzothiopyran-3-carboxylic acid;
8-methyl-2-(trifluoromethyl)-2H-1-benzothiopyran-3-carboxylic acid;
2-(trifluoromethyl)-2H-1-benzothiopyran-3-carboxylic acid;
6-chloro-7-methyl-2-(trifluoromethyl)-2H-1-benzothiopyran-3-carboxylic acid;
7-chloro-2-(trifluoromethyl)-2H-1-benzothiopyran-3-carboxylic acid;
6,7-dichloro-2-(trifluoromethyl)-2H-1-benzothiopyran-3-carboxylic acid;
2-(trifluoromethyl)-6-[(trifluoromethyl)thio]-2H-1-benzothiopyran-3-carboxylic acid;

6,8-dichloro-2-trifluoromethyl-2H-1-benzothiopyran-3-carboxylic acid;
6-chloro-1,2-dihydro-2-(trifluoromethyl)-3-quinolinecarboxylic acid;
6,8-dichloro-1,2-dihydro-2-(trifluoromethyl)-3-quinolinecarboxylic acid;
6,7-difluoro-1,2-dihydro-2-(trifluoromethyl)-3-quinolinecarboxylic acid;
6-iodo-1,2-dihydro-2-(trifluoromethyl)-3-quinolinecarboxylic acid;
6-bromo-1,2-dihydro-2-(trifluoromethyl)-3-quinolinecarboxylic acid;
1,2-dihydro-6-(trifluoromethoxy)-2-(trifluoromethyl)-3-quinolinecarboxylic acid;
6-(trifluoromethyl)-1,2-dihydro-2-(trifluoromethyl)-3-quinolinecarboxylic acid;
6-cyano-1,2-dihydro-2-(trifluoromethyl)-3-quinolinecarboxylic acid;
6-chloro-1,2-dihydro-1-methyl-2-(trifluoromethyl)-3-quinolinecarboxylic acid;
6-chloro-1,2-dihydro-2-(trifluoromethyl)-1-[[4-(trifluoromethyl)phenyl]methyl]-3-quinolinecarboxylic acid;
6-chloro-1-[(4-chlorophenyl)methyl]-1,2-dihydro-2-(trifluoromethyl)-3-quinolinecarboxylic acid;
6-chloro-1,2-dihydro-2-(trifluoromethyl)-1-[[4-(methoxy)phenyl]methyl]-3-quinolinecarboxylic acid;
6-chloro-1-[(4-cyanophenyl)methyl]-1,2-dihydro-2-(trifluoromethyl)-3-quinolinecarboxylic acid;
6-chloro-1,2-dihydro-1-[(4-nitrophenyl)methyl]-2-(trifluoromethyl)-3-quinolinecarboxylic acid;
6-chloro-1,2-dihydro-1-ethyl-2-(trifluoromethyl)-3-quinolinecarboxylic acid;
6-chloro-2-(triflouromethyl)-1,2-dihydro[1,8]napthyridine-3-carboxylic acid;
6-chloro-7-[(3-pyridyl-N-oxide)oxy]-2-(trifluoromethyl)-2H-1-benzopyran-3-carboxylic acid;
6-chloro-7-[(2-pyridyl-N-oxide)oxy]-2-(trifluoromethyl)-2H-1-benzopyran-3-carboxylic acid;
6-chloro-7-[(3-chloro-2-pyridyl-{N-oxide})oxy]-2-(trifluoromethyl)-2H-1-benzopyran-3-carboxylic acid;
6-chloro-7-[(4-chloro-2-pyridyl-{N-oxide})oxy]-2-(trifluoromethyl)-2H-1-benzopyran-3-carboxylic acid;
6-chloro-7-[(5-chloro-2-pyridyl-{N-oxide})oxy]-2-(trifluoromethyl)-2H-1-benzopyran-3-carboxylic acid;
6-chloro-7-[(6-chloro-2-pyridyl-{N-oxide})oxy]-2-(trifluoromethyl)-2H-1-benzopyran-3-carboxylic acid;
6-chloro-7-[(2-pyridyl-N-oxide)thio]-2-(trifluoromethyl)-2H-1-benzopyran-3-carboxylic acid;
6-chloro-7-[(3-chloro-2-pyridyl-{N-oxide})thio]-2-(trifluoromethyl)-2H-1-benzopyran-3-carboxylic acid;
6-chloro-7-[(2-pyridyl-N-oxide)oxy]-2-(trifluoromethyl)-2H-1-dihydroquinoline-3-carboxylic acid;
6-chloro-7-[(3-chloro-2-pyridyl-{N-oxide})oxy]-2-(trifluoromethyl)-2H-1-dihydroquinoline-3-carboxylic acid;
6-chloro-7-[(2-pyridyl-N-oxide)thio]-2-(trifluoromethyl)-2H-1-dihydroquinoline-3-carboxylic acid;
6-chloro-7-[(3-chloro-2-pyridyl-{N-oxide})thio]-2-(trifluoromethyl)-2H-1-dihydroquinoline-3-carboxylic acid;
6-chloro-7-[(2-pyridyl-N-oxide)oxy]-2-(trifluoromethyl)-2H-1-benzothiopyran-3-carboxylic acid;
6-chloro-7-[(3-chloro-2-pyridyl-{N-oxide})oxy]-2-(trifluoromethyl)-2H-1-benzothiopyran-3-carboxylic acid;
6-chloro-7-[(2-pyridyl-N-oxide)thio]-2-(trifluoromethyl)-2H-1-benzothiopyran-3-carboxylic acid;
6-chloro-7-[(3-chloro-2-pyridyl-{N-oxide})thio]-2-(trifluoromethyl)-2H-1-benzothiopyran-3-carboxylic acid;
7-phenoxy-2-(trifluoromethyl)-2H-1-benzopyran-3-carboxylic acid;
6-chloro-7-phenoxy-2-(trifluoromethyl)-2H-1-benzopyran-3-carboxylic acid;
6-chloro-7-(2-hydroxy-1,1-dimethylethyl)-2-(trifluoromethyl)-2H-1-benzopyran-3-carboxylic acid;
7-(2-hydroxy-1,1-dimethylethyl)-2-(trifluoromethyl)-2H-1-benzopyran-3-carboxylic;
6-chloro-7-iodo-2-(trifluoromethyl)-2H-1-benzopyran-3-carboxylic acid;
6-chloro-7-ethynyl-2-(trifluoromethyl)-2H-1-benzopyran-3-carboxylic acid;
6-chloro-7-ethenyl-2-(trifluoromethyl)-2H-1-benzopyran-3-carboxylic acid;
6-chloro-7-(4-methoxyphenoxy)-2-(trifluoromethyl)-2H-1-benzopyran-3-carboxylic acid;
6-chloro-7-(4-chlorophenoxy)-2-(trifluoromethyl)-2H-1-benzopyran-3-carboxylic acid;
6-chloro-7-(4-chlorophenoxy)-2-(trifluoromethyl)-2H-1-benzopyran-3-carboxylic acid;
6-chloro-7-(4-cyanophenoxy)-2-(trifluoromethyl)-2H-1-benzopyran-3-carboxylic acid;
6-chloro-7-[4-(trifluoromethyl)phenoxy]-2-(trifluoromethyl)-2H-1-benzopyran-3-carboxylic acid;
6-chloro-7-[4-(trifluoromethoxy)phenoxy]-2-(trifluoromethyl)-2H-1-benzopyran-3-carboxylic acid;
6-chloro-7-(2-bromo-4-chlorophenoxy)-2-(trifluoromethyl)-2H-1-benzopyran-3-carboxylic acid;
6-chloro-7-[(6-bromo-2-naphthyl)oxy]-2-(trifluoromethyl)-2H-1-benzopyran-3-carboxylic acid;
6-chloro-7-(2,6-dimethylphenoxy)-2-(trifluoromethyl)-2H-1-benzopyran-3-carboxylic acid;
6-chloro-7-[(4-methoxyphenyl)thio]-2-(trifluoromethyl)-2H-1-benzopyran-3-carboxylic acid;
6-chloro-7-[(4-chlorophenyl)thio]-2-(trifluoromethyl)-2H-1-benzopyran-3-carboxylic acid;
6-chloro-7-[(4-chlorophenyl)sulfinyl]-2-(trifluoromethyl)-2H-1-benzopyran-3-carboxylic acid;
6-chloro-7-[(4-chlorophenyl)sulfonyl]-2-(trifluoromethyl)-2H-1-benzopyran-3-carboxylic acid;
6-chloro-7-phenylthio-2-(trifluoromethyl)-2H-1-benzopyran-3-carboxylic acid;
6-chloro-7-(3-chlorophenoxy)-2-(trifluoromethyl)-2H-1-benzopyran-3-carboxylic acid;
6-chloro-7-(2,4-dichlorophenoxy)-2-(trifluoromethyl)-2H-1-benzopyran-3-carboxylic acid;
6-chloro-7-(3,4-difluorophenoxy)-2-(trifluoromethyl)-2H-1-benzopyran-3-carboxylic acid;
6-chloro-7-[(6-chloro-2-pyridinyl)oxy]-2-(trifluoromethyl)-2H-1-benzopyran-3-carboxylic acid;
6-chloro-7-[(2-chloro-3-pyridinyl)oxy]-2-(trifluoromethyl)-2H-1-benzopyran-3-carboxylic acid;
6-chloro-7-[(3-pyridinyl)oxy]-2-(trifluoromethyl)-2H-1-benzopyran-3-carboxylic acid;
6-chloro-7-[(2-pyridinyl)oxy]-2-(trifluoromethyl)-2H-1-benzopyran-3-carboxylic acid;
6-chloro-7-(4-nitrophenoxy)-2-(trifluoromethyl)-2H-1-benzopyran-3-carboxylic acid;
6-chloro-7-(2-chlorophenoxy)-2-(trifluoromethyl)-2H-1-benzopyran-3-carboxylic acid;
6-chloro-7-(4-chloro-3-fluorophenoxy)-2-(trifluoromethyl)-2H-1-benzopyran-3-carboxylic acid;
6-chloro-7-(4-carboxyphenoxy)-2-(trifluoromethyl)-2H-1-benzopyran-3-carboxylic acid;

6-chloro-7-(2-chloro-4-carboxyphenoxy)-2-(trifluoromethyl)-2H-1-benzopyran-3-carboxylic acid;
6-chloro-7-(3-carboxyphenoxy)-2-(trifluoromethyl)-2H-1-benzopyran-3-carboxylic acid;
6-chloro-7-(2,2,2-trifluoroethoxy)-2-(trifluoromethyl)-2H-1-benzopyran-3-carboxylic acid;
1,2-dihydro-6-ethynyl-2-(trifluoromethyl)-3-quinolinecarboxylic acid;
1,2-dihydro-6-phenylethynyl-2-(trifluoromethyl)-3-quinolinecarboxylic acid;
6-chloro-7-(3,4-dichlorophenoxy)2-(trifluoromethyl)-2H-1-benzopyran-3-carboxylic acid;
6-chloro-7-(3-bromo-4-chlorophenoxy)2-(trifluoromethyl)-2H-1-benzopyran-3-carboxylic acid;
6-chloro-7-(4-bromo-3-chlorophenoxy)2-(trifluoromethyl)-2H-1-benzopyran-3-carboxylic acid;
6-chloro-7-(3,4-dibromophenoxy)2-(trifluoromethyl)-2H-1-benzopyran-3-carboxylic acid;
6-chloro-7-[4-chloro-3-(trifluoromethyl)phenoxy]-2-(trifluoromethyl)-2H-1-benzopyran-3-carboxylic acid;
6-chloro-7-[3-chloro-4-(trifluoromethyl)phenoxy]-2-(trifluoromethyl)-2H-1-benzopyran-3-carboxylic acid;
6-chloro-7-(2,6-dichlorophenoxy)2-(trifluoromethyl)-2H-1-benzopyran-3-carboxylic acid;
6-chloro-7-(2,6-dibromophenoxy)2-(trifluoromethyl)-2H-1-benzopyran-3-carboxylic acid;
6-chloro-7-(2,6-difluorophenoxy)2-(trifluoromethyl)-2H-1-benzopyran-3-carboxylic acid;
6-chloro-7-(2,5-dichlorophenoxy)2-(trifluoromethyl)-2H-1-benzopyran-3-carboxylic acid;
6-chloro-7-(2,5-dibromophenoxy)2-(trifluoromethyl)-2H-1-benzopyran-3-carboxylic acid;
6-chloro-7-(2,5-difluorophenoxy)2-(trifluoromethyl)-2H-1-benzopyran-3-carboxylic acid;
6-chloro-7-(2,3-dichlorophenoxy)2-(trifluoromethyl)-2H-1-benzopyran-3-carboxylic acid;
6-chloro-7-(2,3-dibromophenoxy)2-(trifluoromethyl)-2H-1-benzopyran-3-carboxylic acid;
6-chloro-7-(2,3-difluorophenoxy)2-(trifluoromethyl)-2H-1-benzopyran-3-carboxylic acid;
6-chloro-7-(4-chloro-3-cyanophenoxy)2-(trifluoromethyl)-2H-1-benzopyran-3-carboxylic acid;
6-chloro-7-(3-tert-butylphenoxy)2-(trifluoromethyl)-2H-1-benzopyran-3-carboxylic acid;
6-chloro-7-(2-tert-butylphenoxy)2-(trifluoromethyl)-2H-1-benzopyran-3-carboxylic acid;
6-chloro-7-(4-chloro-3-tert-butylphenoxy)2-(trifluoromethyl)-2H-1-benzopyran-3-carboxylic acid;
6-chloro-7-(4-chloro-2-tert-butylphenoxy)2-(trifluoromethyl)-2H-1-benzopyran-3-carboxylic acid;
6-chloro-7-(2-chloro-3-tert-butyl phenoxy)2-(trifluoromethyl)-2H-1-benzopyran-3-carboxylic acid;
6-chloro-7-(3-chloro-2-tert-butyl phenoxy)2-(trifluoromethyl)-2H-1-benzopyran-3-carboxylic acid;
6-chloro-7-(3-thienyloxy)-2-(trifluoromethyl)-2H-1-benzopyran-3-carboxylic acid;
6-chloro-7-(2-chloro-3-thienyloxy)-2-(trifluoromethyl)-2H-1-benzopyran-3-carboxylic acid;
6-chloro-7-(4-chloro-3-thienyloxy)-2-(trifluoromethyl)-2H-1-benzopyran-3-carboxylic acid;
6-chloro-7-(5-chloro-3-thienyloxy)-2-(trifluoromethyl)-2H-1-benzopyran-3-carboxylic acid;
6-chloro-7-(2,5-dichloro-3-thienyloxy)-2-(trifluoromethyl)-2H-1-benzopyran-3-carboxylic acid;
6-chloro-7-(2,4-dichloro-3-thienyloxy)-2-(trifluoromethyl)-2H-1-benzopyran-3-carboxylic acid;
6-chloro-7-[(3-chloro-2-pyridyl)oxy]-2-(trifluoromethyl)-2H-1-benzopyran-3-carboxylic acid;
6-chloro-7-[(4-chloro-2-pyridyl)oxy]-2-(trifluoromethyl)-2H-1-benzopyran-3-carboxylic acid;
6-chloro-7-[(3-chloro-2-pyridyl)oxy]-2-(trifluoromethyl)-2H-1-benzopyran-3-carboxylic acid;
6-chloro-7-[(5-chloro-2-pyridyl)oxy]-2-(trifluoromethyl)-2H-1-benzopyran-3-carboxylic acid;
6-chloro-7-[(6-chloro-2-pyridyl)oxy]-2-(trifluoromethyl)-2H-1-benzopyran-3-carboxylic acid;
6-chloro-7-[(5,6-dichloro-2-pyridyl)oxy]-2-(trifluoromethyl)-2H-1-benzopyran-3-carboxylic acid;
6-chloro-7-[(3,4-dichloro-2-pyridyl)oxy]-2-(trifluoromethyl)-2H-1-benzopyran-3-carboxylic acid;
6-chloro-7-[(4,5-dichloro-2-pyridyl)oxy]-2-(trifluoromethyl)-2H-1-benzopyran-3-carboxylic acid;
6-chloro-7-[(3,5-dichloro-2-pyridyl)oxy]-2-(trifluoromethyl)-2H-1-benzopyran-3-carboxylic acid;
6-chloro-7-[(3,6-dichloro-2-pyridyl)oxy]-2-(trifluoromethyl)-2H-1-benzopyran-3-carboxylic acid;
6-chloro-7-[(4,5-dichloro-2-pyridyl)oxy]-2-(trifluoromethyl)-2H-1-benzopyran-3-carboxylic acid;
6-chloro-7-[(4,6-dichloro-2-pyridyl)oxy]-2-(trifluoromethyl)-2H-1-benzopyran-3-carboxylic acid;
6-chloro-7-[(5,6-dichloro-2-pyridyl)oxy]-2-(trifluoromethyl)-2H-1-benzopyran-3-carboxylic acid;
6-chloro-7-[(2-quinolyl)oxy]-2-(trifluoromethyl)-2H-1-benzopyran-3-carboxylic acid;
2-trifluoromethyl-2H-naphtho[1,2-b]pyran-3-carboxylic acid;
2-trifluoromethyl-3H-naphtho[2,1-b]pyran-3-carboxylic acid;
2-trifluoromethyl-2H-naphtho[2,3-b]pyran-3-carboxylic acid;
5-(hydroxymethyl)-8-methyl-2-(trifluoromethyl)-2H-pyrano[2,3-c]pyridine-3-carboxylic acid;
6-(trifluoromethyl)-6h-1,3-dioxolo[4,5-g][1]benzopyran-7-carboxylic acid; and
3-(trifluoromethyl)-3H-benzofuro[3,2-f][1]benzopyran-2-carboxylic acid.

A preferred family of specific compounds of particular interest within Formulas I–I" consists of compounds as follows:
(S)-7-phenoxy-2-(trifluoromethyl)-2H-1-benzopyran-3-carboxylic acid;
(S)-6-chloro-7-phenoxy-2-(trifluoromethyl)-2H-1-benzopyran-3-carboxylic acid;
(S)-6-chloro-7-(2-hydroxy-1,1-dimethylethyl)-2-(trifluoromethyl)-2H-1-benzopyran-3-carboxylic acid;
(S)-7-(2-hydroxy-1,1-dimethylethyl)-2-(trifluoromethyl)-2H-1-benzopyran-3-carboxylic;
(S)-6-chloro-7-iodo-2-(trifluoromethyl)-2H-1-benzopyran-3-carboxylic acid;
(S)-6-chloro-7-ethynyl-2-(trifluoromethyl)-2H-1-benzopyran-3-carboxylic acid;
(S)-6-chloro-7-ethenyl-2-(trifluoromethyl)-2H-1-benzopyran-3-carboxylic acid;
(S)-6-chloro-7-(4-methoxyphenoxy)-2-(trifluoromethyl)-2H-1-benzopyran-3-carboxylic acid;
(S)-6-chloro-7-(4-chlorophenoxy)-2-(trifluoromethyl)-2H-1-benzopyran-3-carboxylic acid;
(S)-6-chloro-7-(4-chlorophenoxy)-2-(trifluoromethyl)-2H-1-benzopyran-3-carboxylic acid;
(S)-6-chloro-7-(4-cyanophenoxy)-2-(trifluoromethyl)-2H-1-benzopyran-3-carboxylic acid;
(S)-6-chloro-7-[4-(trifluoromethyl)phenoxy]-2-(trifluoromethyl)-2H-1-benzopyran-3-carboxylic acid;
(S)-6-chloro-7-[4-(trifluoromethoxy)phenoxy]-2-(trifluoromethyl)-2H-1-benzopyran-3-carboxylic acid;

(S)-6-chloro-7-(2-bromo-4-chlorophenoxy)-2-(trifluoromethyl)-2H-1-benzopyran-3-carboxylic acid;

(S)-6-chloro-7-[(6-bromo-2-naphthyl)oxy]-2-(trifluoromethyl)-2H-1-benzopyran-3-carboxylic acid;

(S)-6-chloro-7-(2,6-dimethylphenoxy)-2-(trifluoromethyl)-2H-1-benzopyran-3-carboxylic acid;

(S)-6-chloro-7-[(4-methoxyphenyl)thio]-2-(trifluoromethyl)-2H-1-benzopyran-3-carboxylic acid;

(S)-6-chloro-7-[(4-chlorophenyl)thio]-2-(trifluoromethyl)-2H-1-benzopyran-3-carboxylic acid;

(S)-6-chloro-7-[(4-chlorophenyl)sulfinyl]-2-(trifluoromethyl)-2H-1-benzopyran-3-carboxylic acid;

(S)-6-chloro-7-[(4-chlorophenyl)sulfonyl]-2-(trifluoromethyl)-2H-1-benzopyran-3-carboxylic acid;

(S)-6-chloro-7-phenylthio-2-(trifluoromethyl)-2H-1-benzopyran-3-carboxylic acid;

(S)-6-chloro-7-(3-chlorophenoxy)-2-(trifluoromethyl)-2H-1-benzopyran-3-carboxylic acid;

(S)-6-chloro-7-(2,4-dichlorophenoxy)-2-(trifluoromethyl)-2H-1-benzopyran-3-carboxylic acid;

(S)-6-chloro-7-(3,4-difluorophenoxy)-2-(trifluoromethyl)-2H-1-benzopyran-3-carboxylic acid;

(S)-6-chloro-7-[(6-chloro-2-pyridinyl)oxy]-2-(trifluoromethyl)-2H-1-benzopyran-3-carboxylic acid;

(S)-6-chloro-7-[(2-chloro-3-pyridinyl)oxy]-2-(trifluoromethyl)-2H-1-benzopyran-3-carboxylic acid;

(S)-6-chloro-7-[(3-pyridinyl)oxy]-2-(trifluoromethyl)-2H-1-benzopyran-3-carboxylic acid;

(S)-6-chloro-7-[(2-pyridinyl)oxy]-2-(trifluoromethyl)-2H-1-benzopyran-3-carboxylic acid;

(S)-6-chloro-7-(4-nitrophenoxy)-2-(trifluoromethyl)-2H-1-benzopyran-3-carboxylic acid;

(S)-6-chloro-7-(2-chlorophenoxy)-2-(trifluoromethyl)-2H-1-benzopyran-3-carboxylic acid;

(S)-6-chloro-7-(4-chloro-3-fluorophenoxy)-2-(trifluoromethyl)-2H-1-benzopyran-3-carboxylic acid;

(S)-6-chloro-7-(4-carboxyphenoxy)-2-(trifluoromethyl)-2H-1-benzopyran-3-carboxylic acid;

(S)-6-chloro-7-(2-chloro-4-carboxyphenoxy)-2-(trifluoromethyl)-2H-1-benzopyran-3-carboxylic acid;

(S)-6-chloro-7-(3-carboxyphenoxy)-2-(trifluoromethyl)-2H-1-benzopyran-3-carboxylic acid;

(S)-6-chloro-7-(2,2,2-trifluoroethoxy)-2-(trifluoromethyl)-2H-1-benzopyran-3-carboxylic acid;

(S)-6-chloro-1,2-dihydro-8-methyl-2-(trifluoromethyl)-3-quinolinecarboxylic acid;

(S)-1,2-dihydro-5-methyl-2-(trifluoromethyl)-3-quinolinecarboxylic acid;

(S)-1,2-dihydro-6-(4-fluorophenyl)-2-(trifluoromethyl)-3-quinolinecarboxylic acid;

(S)-1,2-dihydro-6-ethynyl-2-(trifluoromethyl)-3-quinolinecarboxylic acid;

(S)-8-bromo-1,2-dihydro-6-methyl-2-(trifluoromethyl)-3-quinolinecarboxylic acid;

(S)-1,2-dihydro-6-phenylethynyl-2-(trifluoromethyl)-3-quinolinecarboxylic acid;

(S)-6-chloro-2-trifluoromethyl-2H-1-benzopyran-3-carboxylic acid;

(S)-7-ethyl-2-trifluoromethyl-2H-1-benzopyran-3-carboxylic acid;

(S)-7-methyl-2-trifluoromethyl-2H-1-benzopyran-3-carboxylic acid;

(S)-2,7-bis(trifluoromethyl)-2H-1-benzopyran-3-carboxylic acid;

(S)-7-bromo-2-trifluoromethyl-2H-1-benzopyran-3-carboxylic acid;

(S)-6-chloro-7-methyl-2-trifluoromethyl-2H-1-benzopyran-3-carboxylic acid;

(S)-8-(1-methylethyl)-2-trifluoromethyl-2H-1-benzopyran-3-carboxylic acid;

(S)-6-chloro-7-(1,1-dimethylethyl)-2-trifluoromethyl-2H-1-benzopyran-3-carboxylic acid;

(S)-6-chloro-8-(1-methylethyl)-2-trifluoromethyl-2H-1-benzopyran-3-carboxylic acid;

(S)-2-trifluoromethyl-2H-1-benzopyran-3-carboxylic acid;

(S)-8-ethoxy-2-trifluoromethyl-2H-1-benzopyran-3-carboxylic acid;

(S)-7-(1,1-dimethylethyl)-2-trifluoromethyl-2H-1-benzopyran-3-carboxylic acid;

(S)-6-bromo-2-trifluoromethyl-2H-1-benzopyran-3-carboxylic acid;

(S)-8-chloro-2-trifluoromethyl-2H-1-benzopyran-3-carboxylic acid;

(S)-8-bromo-6-chloro-2-trifluoromethyl-2H-1-benzopyran-3-carboxylic acid;

(S)-6-trifluoromethoxy-2-trifluoromethyl-2H-1-benzopyran-3-carboxylic acid;

(S)-8-fluoro-2-trifluoromethyl-2H-1-benzopyran-3-carboxylic acid;

(S)-5,7-dichloro-2-trifluoromethyl-2H-1-benzopyran-3-carboxylic acid;

(S)-7,8-dichloro-2-trifluoromethyl-2H-1-benzopyran-3-carboxylic acid;

(S)-7-isopropyloxy-2-trifluoromethyl-2H-1-benzopyran-3-carboxylic acid;

(S)-8-phenyl-2-trifluoromethyl-2H-1-benzopyran-3-carboxylic acid;

(S)-7,8-dimethyl-2-trifluoromethyl-2H-1-benzopyran-3-carboxylic acid;

(S)-6,8-bis (1,1-dimethylethyl)-2-trifluoromethyl-2H-1-benzopyran-3-carboxylic acid;

(S)-7-chloro-2-trifluoromethyl-2H-1-benzopyran-3-carboxylic acid;

(S)-7-(1-methylethyl)-2-trifluoromethyl-2H-1-benzopyran-3-carboxylic acid;

(S)-7-phenyl-2-trifluoromethyl-2H-1-benzopyran-3-carboxylic acid;

(S)-6-chloro-7-ethyl-2-trifluoromethyl-2H-1-benzopyran-3-carboxylic acid;

(S)-8-ethyl-2-trifluoromethyl-2H-1-benzopyran-3-carboxylic acid;

(S)-6-chloro-8-ethyl-2-trifluoromethyl-2H-1-benzopyran-3-carboxylic acid;

(S)-6-chloro-7-phenyl-2-trifluoromethyl-2H-1-benzopyran-3-carboxylic acid;

(S)-6,7-dichloro-2-trifluoromethyl-2H-1-benzopyran-3-carboxylic acid;

(S)-6,8-dichloro-2-trifluoromethyl-2H-1-benzopyran-3-carboxylic acid;

(S)-6,8-dibromo-2-trifluoromethyl-2H-1-benzopyran-3-carboxylic acid;

(S)-6,8-dimethoxy-2-trifluoromethyl-2H-1-benzopyran-3-carboxylic acid;

(S)-6-nitro-2-trifluoromethyl-2H-1-benzopyran-3-carboxylic acid;

(S)-6-amino-2-trifluoromethyl-2H-1-benzopyran-3-carboxylic acid;

(S)-ethyl 6-amino-2-trifluoromethyl-2H-1-benzopyran-3-carboxylate;

(S)-6-chloro-8-methyl-2-trifluoromethyl-2H-1-benzopyran-3-carboxylic acid;

(S)-8-chloro-6-methyl-2-trifluoromethyl-2H-1-benzopyran-3-carboxylic acid;

(S)-8-chloro-6-methoxy-2-trifluoromethyl-2H-1-benzopyran-3-carboxylic acid;

(S)-6,8-difluoro-2-trifluoromethyl-2H-1-benzopyran-3-carboxylic acid;
(S)-6-bromo-8-chloro-2-trifluoromethyl-2H-1-benzopyran-3-carboxylic acid;
(S)-8-bromo-6-fluoro-2-trifluoromethyl-2H-1-benzopyran-3-carboxylic acid;
(S)-8-bromo-6-methyl-2-trifluoromethyl-2H-1-benzopyran-3-carboxylic acid;
(S)-8-bromo-5-fluoro-2-trifluoromethyl-2H-1-benzopyran-3-carboxylic acid;
(S)-6-chloro-8-fluoro-2-trifluoromethyl-2H-1-benzopyran-3-carboxylic acid;
(S)-6-bromo-8-methoxy-2-trifluoromethyl-2H-1-benzopyran-3-carboxylic acid;
(S)-7-(N,N-diethylamino)-2-trifluoromethyl-2H-1-benzopyran-3-carboxylic acid;
(S)-6-[[(phenylmethyl)amino]sulfonyl]-2-trifluoromethyl-2H-1-benzopyran-3-carboxylic acid;
(S)-6-[(dimethylamino)sulfonyl]-2-trifluoromethyl-2H-1-benzopyran-3-carboxylic acid;
(S)-6-aminosulfonyl-2-trifluoromethyl-2H-1-benzopyran-3-carboxylic acid;
(S)-6-(methylamino)sulfonyl-2-trifluoromethyl-2H-1-benzopyran-3-carboxylic acid;
(S)-6-[(4-morpholino)sulfonyl]-2-trifluoromethyl-2H-1-benzopyran-3-carboxylic acid;
(S)-6-[(1,1-dimethylethyl)aminosulfonyl]-2-trifluoromethyl-2H-1-benzopyran-3-carboxylic acid;
(S)-6-[(2-methylpropyl)aminosulfonyl]-2-trifluoromethyl-2H-1-benzopyran-3-carboxylic acid;
(S)-6-methylsulfonyl-2-trifluoromethyl-2H-1-benzopyran-3-carboxylic acid;
(S)-8-chloro-6-[[(phenylmethyl)amino]sulfonyl]-2-trifluoromethyl-2H-1-benzopyran-3-carboxylic acid;
(S)-6-N,N-diethylaminosulfonyl-2-trifluoromethyl-2H-1-benzopyran-3-carboxylic acid;
(S)-6-phenylacetyl-2-trifluoromethyl-2H-1-benzopyran-3-carboxylic acid;
(S)-6-(2,2-dimethylpropylcarbonyl)-2-trifluoromethyl-2H-1-benzopyran-3-carboxylic acid;
(S)-6,8-dichloro-7-methoxy-2-trifluoromethyl-2H-1-benzopyran-3-carboxylic acid;
(S)-6-chloro-2-trifluoromethyl-2H-1-benzothiopyran-3-carboxylic acid;
(S)-6-[[(2-furanylmethyl)amino]sulfonyl]-2-(trifluoromethyl)-2H-1-benzopyran-3-carboxylic acid;
(S)-6-[(phenylmethyl)sulfonyl]-2-(trifluoromethyl)-2H-1-benzopyran-3-carboxylic acid;
(S)-6-[[(phenylethyl)amino]sulfonyl]-2-(trifluoromethyl)-2H-1-benzopyran-3-carboxylic acid;
(S)-6-iodo-2-trifluoromethyl-2H-1-benzopyran-3-carboxylic acid;
(S)-6-chloro-8-iodo-2-(trifluoromethyl)-2H-1-benzopyran-3-carboxylic acid;
(S)-8-bromo-6-chloro-2-(trifluoromethyl)-2H-1-benzopyran-3-carboxylic acid;
(S)-6-formyl-2-(trifluoromethyl)-2H-1-benzopyran-3-carboxylic acid;
(S)-6-chloro-8-formyl-2-(trifluoromethyl)-2H-1-benzopyran-3-carboxylic acid;
(S)-6-bromo-7-(1,1-dimethylethyl)-2-(trifluoromethyl)-2H-1-benzopyran-3-carboxylic acid;
(S)-5,6-dichloro-2-(trifluoromethyl)-2H-1-benzopyran-3-carboxylic acid;
(S)-6-cyano-2-(trifluoromethyl)-2H-1-benzopyran-3-carboxylic acid;
(S)-6-hydroxymethyl-2-(trifluoromethyl)-2H-1-benzopyran-3-carboxylic acid;
(S)-6-(difluoromethyl)-2-(trifluoromethyl)-2H-1-benzopyran-3-carboxylic acid;
(S)-2,6-bis(trifluoromethyl)-2H-1-benzopyran-3-carboxylic acid;
(S)-5,6,7-trichloro-2-(trifluoromethyl)-2H-1-benzopyran-3-carboxylic acid;
(S)-6,7,8-trichloro-2-(trifluoromethyl)-2H-1-benzopyran-3-carboxylic acid;
(S)-6-(methylthio)-2-(trifluoromethyl)-2H-1-benzopyran-3-carboxylic acid;
(S)-6-(methylsulfinyl)-2-(trifluoromethyl)-2H-1-benzopyran-3-carboxylic acid;
(S)-5,8-dichloro-2-(trifluoromethyl)-2H-1-benzopyran-3-carboxylic acid;
(S)-6-(pentafluoroethyl)-2-(trifluoromethyl)-2H-1-benzopyran-3-carboxylic acid;
(S)-6-(1,1-dimethylethyl)-2-(trifluoromethyl)-2H-1-benzopyran-3-carboxylic acid;
(S)-2-(trifluoromethyl)-6-[(trifluoromethyl)thio]-2H-1-benzothiopyran-3-carboxylic acid;
(S)-6,8-dichloro-7-methyl-2-(trifluoromethyl)-2H-1-benzopyran-3-carboxylic acid;
(S)-6-chloro-2,7-bis(trifluoromethyl)-2H-1-benzopyran-3-carboxylic acid;
(S)-5-methoxy-2-(trifluoromethyl)-2H-1-benzopyran-3-carboxylic acid;
(S)-6-benzoyl-2-(trifluoromethyl)-2H-1-benzopyran-3-carboxylic acid;
(S)-6-(4-chlorobenzoyl)-2-(trifluoromethyl)-2H-1-benzopyran-3-carboxylic acid;
(S)-6-(4-hydroxybenzoyl)-2-(trifluoromethyl)-2H-1-benzopyran-3-carboxylic acid;
(S)-6-phenoxy-2-(trifluoromethyl)-2H-1-benzopyran-3-carboxylic acid;
(S)-8-chloro-6-(4-chlorophenoxy)-2-(trifluoromethyl)-2H-1-benzopyran-3-carboxylic acid;
(S)-2-(trifluoromethyl)-6-[4-(trifluoromethyl)phenoxy]-2H-1-benzopyran-3-carboxylic acid;
(S)-6-(4-methoxyphenoxy)-2-(trifluoromethyl)-2H-1-benzopyran-3-carboxylic acid;
(S)-6-(3-chloro-4-methoxyphenoxy)-2-(trifluoromethyl)-2H-1-benzopyran-3-carboxylic acid;
(S)-6-(4-chlorophenoxy)-2-(trifluoromethyl)-2H-1-benzopyran-3-carboxylic acid;
(S)-8-chloro-2-(trifluoromethyl)-6-[4-(trifluoromethyl)phenoxy]-2H-1-benzopyran-3-carboxylic acid;
(S)-6-chloro-8-cyano-2-(trifluoromethyl)-2H-1-benzopyran-3-carboxylic acid;
(S)-6-chloro-8-[(hydroxyimino)methyl]-2-(trifluoromethyl)-2H-1-benzopyran-3-carboxylic acid;
(S)-6-chloro-8-(hydroxymethyl)-2-(trifluoromethyl)-2H-1-benzopyran-3-carboxylic acid;
(S)-8-(1H-benzimidazol-2-yl)-6-chloro-2-(trifluoromethyl)-2H-1-benzopyran-3-carboxylic acid;
(S)-7-(1,1-dimethylethyl)-2-(pentafluoroethyl)-2H-1-benzopyran-3-carboxylic acid;
(S)-6-chloro-8-(methoxymethyl)-2-(trifluoromethyl)-2H-1-benzopyran-3-carboxylic acid;
(S)-6-chloro-8-(benzyloxymethyl)-2-(trifluoromethyl)-2H-1-benzopyran-3-carboxylic acid;
(S)-6-chloro-8-ethenyl-2-(trifluoromethyl)-2H-1-benzopyran-3-carboxylic acid;
(S)-6-chloro-8-ethynyl-2-(trifluoromethyl)-2H-1-benzopyran-3-carboxylic acid;
(S)-6-chloro-8-(2-thienyl)-2-(trifluoromethyl)-2H-1-benzopyran-3-carboxylic acid;
(S)-6-chloro-8-(2-furanyl)-2-(trifluoromethyl)-2H-1-benzopyran-3-carboxylic acid;

(S)-6-chloro-8-(5-chloro-1-pentynyl)-2-(trifluoromethyl)-2H-1-benzopyran-3-carboxylic acid;
(S)-6-chloro-8-(1-pentynyl)-2-(trifluoromethyl)-2H-1-benzopyran-3-carboxylic acid;
(S)-6-chloro-8-(phenylethynyl)-2-(trifluoromethyl)-2H-1-benzopyran-3-carboxylic acid;
(S)-6-chloro-8-(3,3-dimethyl-1-butynyl)-2-(trifluoromethyl)-2H-1-benzopyran-3-carboxylic acid;
(S)-6-chloro-8-[(4-chlorophenyl)ethynyl]-2-(trifluoromethyl)-2H-1-benzopyran-3-carboxylic acid;
(S)-6-chloro-8-[(4-methoxyphenyl)ethynyl]-2-(trifluoromethyl)-2H-1-benzopyran-3-carboxylic acid;
(S)-6-(phenylethynyl)-2-(trifluoromethyl)-2H-1-benzopyran-3-carboxylic acid;
(S)-6-chloro-8-(4-chlorophenyl)-2-(trifluoromethyl)-2H-1-benzopyran-3-carboxylic acid;
(S)-6-chloro-8-(3-methoxyphenyl)-2-(trifluoromethyl)-2H-1-benzopyran-3-carboxylic acid;
(S)-6-chloro-8-[(4-methylthio)phenyl]-2-(trifluoromethyl)-2H-1-benzopyran-3-carboxylic acid;
(S)-6-chloro-8-[(4-methylsulfonyl)phenyl]-2-(trifluoromethyl)-2H-1-benzopyran-3-carboxylic acid;
(S)-6-chloro-8-phenyl-2-(trifluoromethyl)-2H-1-benzopyran-3-carboxylic acid;
(S)-6-bromo-8-fluoro-2-(trifluoromethyl)-2H-1-benzopyran-3-carboxylic acid;
(S)-6-(4-fluorophenyl)-2-(trifluoromethyl)-2H-1-benzopyran-3-carboxylic acid;
(S)-6-phenyl-2-(trifluoromethyl)-2H-1-benzopyran-3-carboxylic acid;
(S)-8-chloro-6-fluoro-2-(trifluoromethyl)-2H-1-benzopyran-3-carboxylic acid;
(S)-6,8-diiodo-2-(trifluoromethyl)-2H-1-benzopyran-3-carboxylic acid;
(S)-6-(5-chloro-2-thienyl)-2-(trifluoromethyl)-2H-1-benzopyran-3-carboxylic acid;
(S)-6-(2-thienyl)-2-(trifluoromethyl)-2H-1-benzopyran-3-carboxylic acid;
(S)-6-(4-chlorophenyl)-2-(trifluoromethyl)-2H-1-benzopyran-3-carboxylic acid;
(S)-6-(4-bromophenyl)-2-(trifluoromethyl)-2H-1-benzopyran-3-carboxylic acid;
(S)-6-(ethynyl)-2-(trifluoromethyl)-2H-1-benzopyran-3-carboxylic acid;
(S)-6-methyl-2-(trifluoromethyl)-2H-1-benzopyran-3-carboxylic acid;
(S)-6-chloro-8-(4-methoxyphenyl)-2-trifluoromethyl-2H-1-benzopyran-3-carboxylic acid;
(S)-6-chloro-2-(trifluoromethyl)-4-ethenyl-2H-1-benzopyran-3-carboxylic acid;
(S)-6-chloro-2-(trifluoromethyl)-4-phenyl-2H-1-benzopyran-3-carboxylic acid;
(S)-6-chloro-4-(2-thienyl)-2-(trifluoromethyl)-2H-1-benzopyran-3-carboxylic acid;
(S)-6-(2,2,2-trifluoro-1-hydroxyethyl)-2-(trifluoromethyl)-2H-1-benzopyran-3-carboxylic acid;
(S)-6-methyl-2-(trifluoromethyl)-2H-1-benzothiopyran-3-carboxylic acid;
(S)-6,8-dimethyl-2-(trifluoromethyl)-2H-1-benzothiopyran-3-carboxylic acid;
(S)-6-(1,1-dimethylethyl)-2-(trifluoromethyl)-2H-1-benzothiopyran-3-carboxylic acid;
(S)-7-methyl-2-(trifluoromethyl)-2H-1-benzothiopyran-3-carboxylic acid;
(S)-6,7-dimethyl-2-(trifluoromethyl)-2H-1-benzothiopyran-3-carboxylic acid;
(S)-8-methyl-2-(trifluoromethyl)-2H-1-benzothiopyran-3-carboxylic acid;
(S)-2-(trifluoromethyl)-2H-1-benzothiopyran-3-carboxylic acid;
(S)-6-chloro-7-methyl-2-(trifluoromethyl)-2H-1-benzothiopyran-3-carboxylic acid;
(S)-7-chloro-2-(trifluoromethyl)-2H-1-benzothiopyran-3-carboxylic acid;
(S)-6,7-dichloro-2-(trifluoromethyl)-2H-1-benzothiopyran-3-carboxylic acid;
(S)-2-(trifluoromethyl)-6-[(trifluoromethyl)thio]-2H-1-benzopyran-3-carboxylic acid;
(S)-6,8-dichloro-2-trifluoromethyl-2H-1-benzothiopyran-3-carboxylic acid;
(S)-6-chloro-1,2-dihydro-2-(trifluoromethyl)-3-quinolinecarboxylic acid;
(S)-6,8-dichloro-1,2-dihydro-2-(trifluoromethyl)-3-quinolinecarboxylic acid;
(S)-6,7-difluoro-1,2-dihydro-2-(trifluoromethyl)-3-quinolinecarboxylic acid;
(S)-6-iodo-1,2-dihydro-2-(trifluoromethyl)-3-quinolinecarboxylic acid;
(S)-6-bromo-1,2-dihydro-2-(trifluoromethyl)-3-quinolinecarboxylic acid;
(S)-1,2-dihydro-6-(trifluoromethoxy)-2-(trifluoromethyl)-3-quinolinecarboxylic acid;
(S)-6-(trifluoromethyl)-1,2-dihydro-2-(trifluoromethyl)-3-quinolinecarboxylic acid;
(S)-6-cyano-1,2-dihydro-2-(trifluoromethyl)-3-quinolinecarboxylic acid;
(S)-6-chloro-1,2-dihydro-1-methyl-2-(trifluoromethyl)-3-quinolinecarboxylic acid;
(S)-6-chloro-1,2-dihydro-2-(trifluoromethyl)-1-[[4-(trifluoromethyl)phenyl]methyl]-3-quinolinecarboxylic acid;
(S)-6-chloro-1-[(4-chlorophenyl)methyl]-1,2-dihydro-2-(trifluoromethyl)-3-quinolinecarboxylic acid;
(S)-6-chloro-1,2-dihydro-2-(trifluoromethyl)-1-[[4-(methoxy)phenyl]methyl]-3-quinolinecarboxylic acid;
(S)-6-chloro-1-[(4-cyanophenyl)methyl]-1,2-dihydro-2-(trifluoromethyl)-3-quinolinecarboxylic acid;
(S)-6-chloro-1,2-dihydro-1-[(4-nitrophenyl)methyl]-2-(trifluoromethyl)-3-quinolinecarboxylic acid;
(S)-6-chloro-1,2-dihydro-1-ethyl-2-(trifluoromethyl)-3-quinolinecarboxylic acid;
(S)-6-chloro-2-(triflouromethyl)-1,2-dihydro[1,8]napthyridine-3-carboxylic acid;
(S)-2-trifluoromethyl-2H-naphtho[1,2-b]pyran-3-carboxylic acid;
(S)-2-trifluoromethyl-3H-naptho[2,1-b]pyran-3-carboxylic acid;
(S)-2-trifluoromethyl-2H-naphtho[2,3-b]pyran-3-carboxylic acid; and
(S)-5-(hydroxymethyl)-8-methyl-2-(trifluoromethyl)-2H-pyrano[2,3-c]pyridine-3-carboxylic acid.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to three carbon atoms. The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl" and "lower alkenyl", embrace radicals having "cis" and "trans" orientations, or alternatively, "E" and "Z" orientations. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms. The term "cyanoalkyl" embraces linear or branched alkyl radicals having one to about ten carbon atoms any one of which may be substituted with one cyano radicals. More preferred cyanoalkyl radicals are "lower cyanoalkyl" radicals having one to six carbon atoms and one cyano radical. Even more preferred are lower cyanoalkyl radicals having one to three carbon atoms. Examples of such radicals include cyanomethyl. The terms "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy. The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxy, halo, haloalkyl, nitro, cyano, alkoxy and lower alkylamino. The term "heterocyclyl" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated condensed heterocyclic group containing 1 to 2 oxygen atoms and 1 to 3 nitrogen atoms [e.g. benzoxazolyl, benzoxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]; unsaturated condensed heterocyclic group containing 1 to 2 sulfur atoms and 1 to 3 nitrogen atoms [e.g., benzothiazolyl, benzothiadiazolyl] and the like. The term also embraces radicals where heterocyclic radicals are fused with aryl radicals. Examples of such fused bicyclic radicals include benzofuran, benzothiophene, and the like. Said "heterocyclyl" group may have 1 to 3 substituents such as lower alkyl, hydroxy, oxo, amino and lower alkylamino. Preferred heterocyclic radicals include five to ten membered fused or unfused radicals. More preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Even more preferred are lower alkylsulfonyl radicals having one to three carbon atoms. Examples of such lower alkylsulfonyl radicals include methylsulfonyl, ethylsulfonyl and propylsulfonyl. "Haloalkylsulfonyl" embraces haloalkyl radicals attached to a sulfonyl radical, where haloalkyl is defined as above. More preferred haloalkylsulfonyl radicals are "lower haloalkylsulfonyl" radicals having one to six carbon atoms. Even more preferred are lower haloalkylsulfonyl radicals having one to three carbon atoms. Examples of such lower haloalkylsulfonyl radicals include trifluoromethylsulfonyl. The term "arylalkylsulfonyl" embraces aryl radicals as defined above, attached to an alkylsulfonyl radical. Examples of such radicals include benzylsulfonyl and phenylethylsulfonyl. The term "heterocyclosulfonyl" embraces heterocyclo radicals as defined above, attached to a sulfonyl radical. More preferred heterocyclosulfonyl radicals contain 5–7 membered heterocyclo radicals containing one or two heteroatoms. Examples of such radicals include tetrahydropyrrolylsulfonyl morpholinylsulfonyl and azepinylsulfonyl. The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$). The term "alkylaminosulfonyl" includes "N-alkylaminosulfonyl" and "N,N-dialkylaminosulfonyl" where sulfamyl radicals are substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl. The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-aryl-aminosulfonyl radicals include N-methyl-N-phenylaminosulfonyl and N-ethyl-N-phenylaminosulfonyl. Examples of such N-aryl-aminosulfonyl radicals include N-phenylaminosulfonyl. The term "arylalkylaminosulfonyl" embraces aralkyl radicals as described above, attached to an aminosulfonyl radical. More preferred are lower arylalkylaminosulfonyl radicals having one to three carbon atoms. The term "heterocyclylaminosulfonyl" embraces heterocyclyl radicals as described above, attached to an aminosulfonyl radical. The terms "carboxy" or "carboxyl", whether used alone or with other terms, such as "carboxyalkyl", denotes —CO$_2$H. The term "carboxyalkyl" embraces radicals having a carboxy radical as defined above, attached to an alkyl radical. The term "carbonyl", whether used alone or with other terms, such as "alkylcarbonyl", denotes —(C=O)—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "aroyl" embraces aryl radicals with a carbonyl radical as defined above. Examples of aroyl include benzoyl, naphthoyl, and the like and the aryl in said aroyl may be additionally substituted. The term "alkylcarbonyl" embraces radicals having a carbonyl radical substituted with an alkyl radical. More preferred alkylcarbonyl radicals are "lower alkylcarbonyl" radicals having one to six carbon atoms. Even more preferred are lower alkylcarbonyl radicals having one to three carbon atoms. Examples of such radicals include methylcarbonyl and ethylcarbonyl. The term "haloalkylcarbonyl" embraces radicals having a carbonyl radical substituted with an haloalkyl radical. More preferred haloalkylcarbonyl radicals are "lower haloalkylcarbonyl" radicals having one to six carbon atoms. Even more preferred are lower haloalkylcarbonyl radicals having one to three carbon atoms. Examples of such radicals include trifluoromethylcarbonyl. The term "arylcarbonyl" embraces radicals having a carbonyl radical substituted with an aryl radical. More preferred arylcarbonyl radicals include phenylcarbonyl. The term "heteroarylcarbonyl" embraces radicals having a carbonyl radical substituted with a heteroaryl radical. Even more preferred are 5- or 6-membered heteroarylcarbonyl radicals. The term "arylalkylcarbonyl" embraces radicals having a carbonyl radical substituted with an arylalkyl radical. More preferred radicals are phenyl-C$_1$–C$_3$-alkylcarbonyl, including benzylcarbonyl. The term "heteroarylalkylcarbonyl" embraces radicals having a carbonyl radical substituted with a heteroarylalkyl radical. Even more preferred are lower heteroarylalkylcarbonyl radicals having 5- 6-membered heteroaryl radicals attached to alkyl portions having one to three carbon atoms. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl Even more preferred are lower alkoxycarbonyl radicals having alkoxy portions of one to three carbon atoms. The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$. The terms "N-alkylaminocarbonyl" and "N,N-dialkylaminocarbonyl" denote aminocarbonyl radicals which have been substituted with one alkyl radical and with two alkyl radicals, respectively. More preferred are "lower alkylaminocarbonyl" having lower alkyl radicals as described above attached to an aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "N-cycloalkylaminocarbonyl" denoted aminocarbonyl radicals which have been substituted with at least one cycloalkyl radical. More preferred are "lower cycloalkylaminocarbonyl" having lower cycloalkyl radicals of three to seven carbon atoms, attached to an aminocarbonyl radical. The term "aminoalkyl" embraces alkyl radicals substituted with amino radicals. The term "alkylaminoalkyl" embraces aminoalkyl radicals having the nitrogen atom substituted with an alkyl radical. Even more preferred are lower alkylaminoalkyl radicals having one to three carbon atoms. The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl. The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy. The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, halkoalkyl and haloalkoxy. The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl may be additionally substituted with halo, alkyl, alkoxy, halkoalkyl and haloalkoxy. The terms benzyl and phenylmethyl are interchangeable. The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3$—S—). The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio. The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms. The term "arylsulfinyl" embraces radicals containing an aryl radical, attached to a divalent —S(=O)— atom. Even more preferred are optionally substituted phenylsulfinyl radicals. The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms. The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino or the like. The term "arylamino" denotes amino groups which have been substituted with one or two aryl radicals, such as N-phenylamino. The "arylamino" radicals may be further substituted on the aryl ring portion of the radical. The term "heteroarylamino" denotes amino groups which have been substituted with one or two heteroaryl radicals, such as N-thienylamino. The "heteroarylamino" radicals may be further substituted on the heteroaryl ring portion of the radical. The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical. The terms "N-alkyl-N-arylamino" and "N-aralkyl-N-alkylamino" denote amino groups which have been substituted with one aralkyl and one alkyl radical, or one aryl and one alkyl radical, respectively, to an amino group. The term "arylthio" embraces aryl radicals of six to ten carbon atoms, attached to a divalent sulfur atom. An example of "arylthio" is phenylthio. The term "aralkylthio" embraces aralkyl radicals as described above, attached to a divalent sulfur atom. More preferred are phenyl-$C_1$–$C_3$-alkylthio radicals. An example of "aralkylthio" is benzylthio. The term "aralkylsulfonyl" embraces aralkyl radicals as described above, attached to a divalent sulfonyl radical. More preferred are phenyl-$C_1$–$C_3$-alkylsulfonyl radicals. The term "aryloxy" embraces optionally substituted aryl radicals, as defined above, attached to an oxygen atom. Examples of such radicals include phenoxy. The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The present invention comprises a pharmaceutical composition comprising a therapeutically-effective amount of a compound of Formula I–I" in association with at least one pharmaceutically-acceptable carrier, adjuvant or diluent.

The present invention also comprises a method of treating cyclooxygenase-2 mediated disorders, such as inflammation, in a subject, the method comprising treating the subject having or susceptible to such disorder with a therapeutically-effective amount of a compound of Formula I–I".

Also included in the family of compounds of Formula I–I" are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active base and then separation of the mixture of diastereoisomers by crystallization, followed by liberation of the optically active bases from these salts. Examples of appropriate bases are brucine, strychnine, dehydroabietylamine, quinine, cinchonidine, ephedrine, α-methylbenzylamine, amphetamine, deoxyphedrine, chloramphenicol intermediate, 2-amino-1-butanol, and 1-(1-napthyl) ethylamine. A different process for separation of optical isomers involves the use of a chiral chromatography column optimally chosen to maximize the separation of the enantiomers. Still another available method involves synthesis of covalent diastereoisomeric molecules. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt. Additional methods for resolving optical isomers, known to those skilled in the art may be used, for example, those discussed by J. Jaques et al in *Enantiomers, Racemates, and Resolutions,* John Wiley and Sons, New York (1981).

Also included in the family of compounds of Formula I–I" are the protected acids thereof, such as the esters, hydroxyamino derivatives, amides and sulfonamides. Thus primary and secondary amines can be reacted with the chromene-3-carboxylic acids of Formula I–I" to form amides which can be useful as prodrugs. Preferred amines heterocyclicamines, including optionally substituted aminothiazoles, optionally substituted amino-isoxazoles, and optionally substituted aminopyridines; aniline derivatives; sulfonamides; aminocarboxylic acids; and the like. Additionally, 1-acyldihydroquinolines can behave as prodrugs for the 1H-dihydroquinolines. The esters, hydroxyamino derivatives and sulfonamides can be prepared from the acids by methods known to one skilled in the art.

Also included in the family of compounds of Formula I–I" are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–I" may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I–I" include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I–I".

General Synthetic Procedures

The compounds of the invention can be synthesized according to the following procedures of Schemes 1–16, wherein the $R^1$–$R^6$ substituents are as defined for Formulas I–II, above, except where further noted.

SCHEME 1

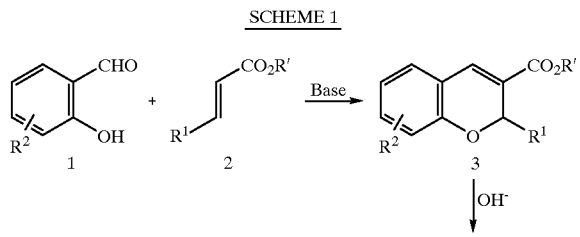

-continued

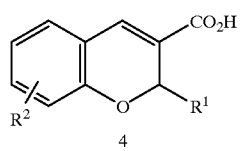

Synthetic Scheme 1 illustrates the general method for the preparation of a wide variety of substituted 2H-1-benzopyran derivatives 3 and 4. In step 1, a representative ortho-hydroxybenzaldehyde (salicylaldehyde) derivative 1 is condensed with an acrylate derivative 2 in the presence of base, such as potassium carbonate in a solvent such as dimethylformamide, to afford the desired 2H-1-benzopyran ester 3. An alternative base-solvent combination for this condensation includes an organic base such as triethylamine and a solvent such as dimethyl sulfoxide. In step 2 the ester is hydrolyzed to the corresponding acid, such as by treatment with aqueous base (sodium hydroxide) in a suitable solvent such as ethanol to afford after acidification the substituted 2H-1-benzopyran-3-carboxylic acid 4.

SCHEME 2

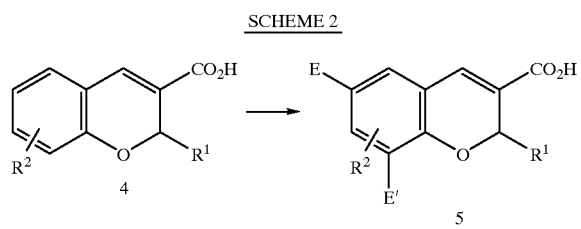

E, E' = halogen, acyl, sulfonyl

Synthetic Scheme 2 shows the general method for functionalizing selected 2H-1-benzopyrans. Treatment of the 2H-1-benzopyran carboxylic acid 4 or ester 3 with an electrophillic agent makes a 6-substituted 2H-1-benzopyran 5. A wide variety of electrophillic agents react selectively with 2H-1-benzopyrans 4 in the 6-position to provide new analogs in high yield. Electrophillic reagents such as halogen (chlorine or bromine) give the 6-halo derivatives. Chlorosulfonic acid reacts to afford the 6-position sulfonyl chloride that can further be converted to a sulfonamide or sulfone. Friedel-Crafts acylation of 4 provides 6-acylated 2H-1-benzopyrans in good to excellent yield. A number of other electrophiles can be used to selectively react with these 2H-1-benzopyrans in a similar manner. A 6-position substituted 2H-1-benzopyran can react with an electrophilic reagent at the 8-position using similar chemistries to that described for electrophilic substitution of the 6-position. This yields an 2H-1-benzopyran which is substituted at both the 6 and 8 positions.

SCHEME 3

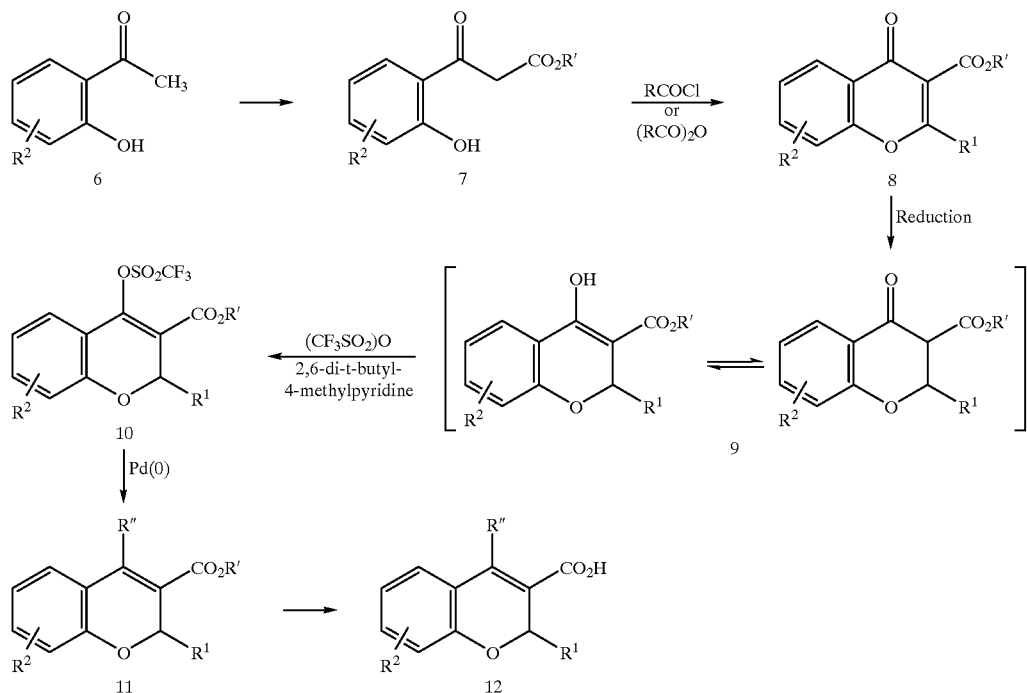

Synthetic Scheme 3 illustrates a second general synthesis of substituted 2H-1-benzopyran-3-carboxylic acids which allows substitution at position 4 of the 2H-1-benzopyran. In this case a commercially or synthetically available subtituted ortho-hydroxy acetophenone 6 is treated with two or more equivalents of a strong base such as lithium bis (trimethylsilyl)amide in a solvent such as tetrahydrofuran (THF), followed by reaction with diethyl carbonate to afford the beta-keto ester 7. Ester 7 is condensed with an acid chloride or anhydride in the presence of a base such as potassium carbonate in a solvent such as toluene with heat to afford 4-oxo-4H-1-benzopyran 8. Reduction of the olefin can be accomplished by a variety of agents including sodium borohydride ($NaBH_4$) in solvent mixtures such as ethanol and tetrahydrofuran (THF), or by use of triethylsilane in a solvent such as trifluoroacetic acid, or by catalytic reduction using palladium on charcoal and hydrogen gas in a solvent such as ethanol to yield the new beta-keto ester 9 (two tautomeric structures shown). Acylation of the oxygen of the ketone enolate in the presence of a base such as 2,6-di-tert-butyl-4-methylpyridine, an acylating agent such as trifluoromethanesulfonic anhydride, and using a solvent such as methylene chloride yields the enol-triflate 10. Triflate 10 can be reduced with reagents such as tri-n-butyltin hydride, lithium chloride and a palladium (0) catalyst such as tetrakis (triphenylphosphine)palladium (0) in a solvent such as tetrahydrofuran to yield 2H-1-benzopyran ester 11 where R″ is hydrogen. The ester 11 can be saponified with a base such as 2.5 N sodium hydroxide in a mixed solvent such as tetrahydrofuran-ethanol-water (7:2:1) to yield the desired substituted 2H-1-benzopyran-3-carboxylic acid.

To incorporate a carbon fragment $R^3$ one can treat triflate 10 with reagents known to undergo "cross-coupling" chemistries such a tributylethyenyltin, lithium chloride and a palladium(0) catalyst such as tetrakis(triphenylphosphine) palladium (0) in a solvent such as tetrahydrofuran to yield 2H-1-benzopyran ester 11 where $R^3$ is a vinyl moiety. The ester 6 can be saponified with a base such as 2.5 N sodium hydroxide in a mixed solvent such as tetrahydrofuran-ethanol-water (7:2:1) to yield the desired 4-vinyl-2H-1-benzopyran-3-carboxylic acid (12, R″=$CH_2CH$—). Similarly triflate 10 can be converted under similar conditions using tri-n-butylphenyltin to 2H-1-benzopyran where $R^3$=phenyl and by hydrolysis of the ester converted to the carboxylic acid 12 where $R^3$=phenyl. Using a similar strategy, substituents which be incorporated as substitutent $R^3$ can be substituted olefins, substituted aromatics, substuted heteroaryl, acetylenes and substituted acetylenes.

SCHEME 4

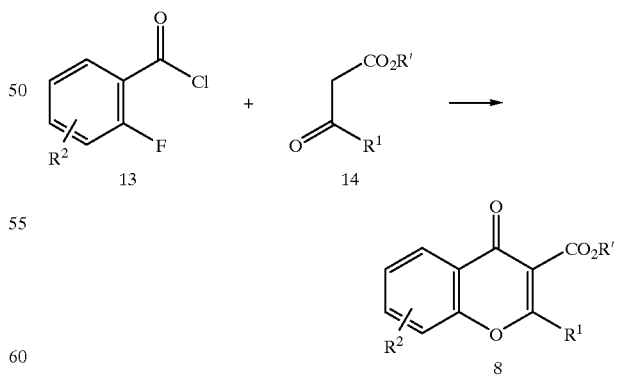

Synthetic Scheme 4 shows an alternative general procedure for the preparation of 4-oxo-4H-1-benzopyran 8. Treatment of an ortho-fluorobenzoyl chloride with an appropriately substituted beta-keto ester 14 with a base such as potassium carbonate in a-solvent such as toluene provides 4-oxo-4H-1-benzopyran 8. 4-Oxo-4H-1-benzopyran 8 can be converted to 2H-1-benzopyran 12 as described in Scheme 3.

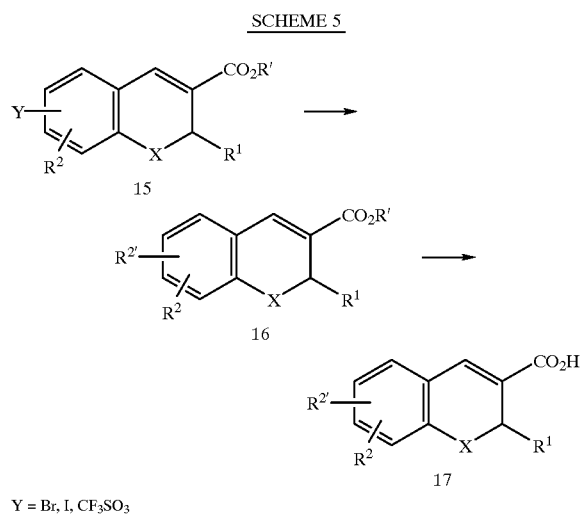

SCHEME 5

Y = Br, I, CF₃SO₃

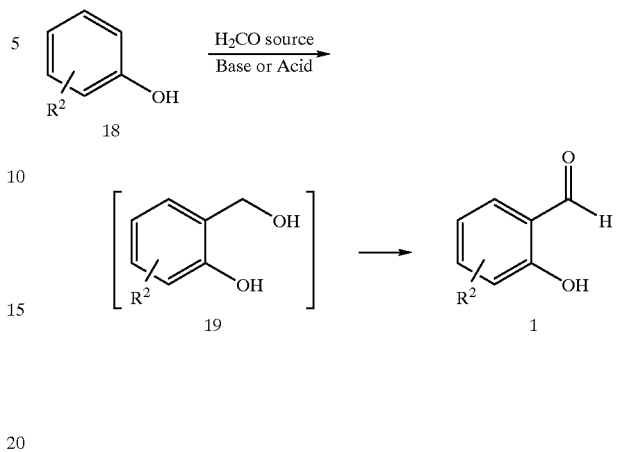

SCHEME 6

Synthetic Scheme 6 shows a general synthetic route for conversion of a commercially or synthetically available substituted phenol into a substituted salicylaldehyde. Several different methods which utilize formaldehyde or a chemically equivalent reagent are described in detail below.

Synthetic Scheme 5 shows a general method for substitution of the aromatic ring of the 2H-1-benzopyran. This can be accomplished through organo-palladium mediated "cross-coupling" chemistries using a palladium (0) catalyst to couple benzopyran 15 at position Y, where Y is iodide, bromide or triflate, with an acetylene, olefin, nitrile, or aryl coupling agent. Substituted acetylenes as the coupling agent will provide the corresponding substituted acetylene. Substituted aryl moieties can be incorporated using arylboronic acids or esters; nitriles can be incorporated by use of zinc (II) cyanide. The resulting ester 16 can be converted to carboxylic acid 17 as described in Scheme 1.

Another approach to substitution of the aryl moiety of the benzopyran 15 is to convert Y, where Y is iodide or bromide, to a perfluoroalkyl moiety. Exemplary of this transformation is the conversion of 15 (Y=iodide) to 16 ($R^2$=pentafluoroethyl) using a potassium pentafluoropropionate and copper (I) iodide in hexamethylphosphoramide (HMPA). The resulting ester 16 can be converted to carboxylic acid 15 as described in Scheme 1.

A similar method adds substitution of the aromatic ring in dihydroquinoline-3-carboxylates. This can be accomplished through organopalladium couplings with aryl iodides, bromides, or triflates and various coupling agents (R. F. Heck, *Palladium Reagents in Organic Synthesis*. Academic Press 1985). When using a suitable palladium catalyst such as tetrakis(triphenyl-phospine)palladium(0) in this reaction, coupling agents such as alkynes provide disubstituted alkynes, phenyl boronic acids afford biphenyl compounds, and cyanides produce arylcyano compounds. A number of other palladium catalysts and coupling reagents could be used to selectively react with appropriately substituted dihydroquinoline-3-carboxylates in a similar manner.

Reaction of an appropriately substituted phenol 18 in basic media with formaldehyde (or chemical equivalent) will yield the corresponding salicylaldehyde 1. The intermediate, ortho-hydroxymethylphenol 19, will under appropriate reaction conditions be oxidized to the salicylaldehyde 1 in situ. The reaction commonly employs ethyl magnesium bromide or magnesium methoxide (one equivalent) as the base, toluene as the solvent, paraformaldehyde (two or more equivalents) as the source of formaldehyde, and employs hexamethylphoramide (HMPA) or N,N,N',N'-tetramethylethylenediamine (TMEDA). (See: Casiraghi, G. et al., J.C.S.Perkin I, 1978, 318–321.)

Alternatively an appropriately substituted phenol 18 may react with formaldehyde under aqueous basic conditions to form the substituted ortho-hydroxybenzyl alcohol 19 (See: a) J. Leroy and C. Wakselman, J. Fluorine Chem., 40, 23–32 (1988). b) A. A. Moshfegh, et al., Helv. Chim. Acta., 65, 1229–1232 (1982)). Commonly used bases include aqueous potassium hydroxide or sodium hydroxide. Formalin (38% formaldehyde in water) is commonly employed as the source of formaldehyde. The resulting ortho-hydroxybenzyl alcohol 19 can be converted to the salicylaldehyde 1 by an oxidizing agent such as manganese (IV) dioxide in a solvent such as methylene chloride or chloroform (See: R -G. Xie, et al., Synthetic Commun. 24, 53–58 (1994)).

An appropriately substituted phenol 18 can be treated under acidic conditions with hexamethylenetetramine (HMTA) to prepare the salicylaldehyde 1 (Duff Reaction; See: Y. Suzuki, and H. Takahashi, Chem. Pharm. Bull., 31, 1751–1753 (1983)). This reaction commonly employs acids such as acetic acid, boric acid, methanesulfonic acid, or trifluoromethanesulfonic acid. The source of formaldehyde commonly used is hexamethylenetetramine.

SCHEME 7

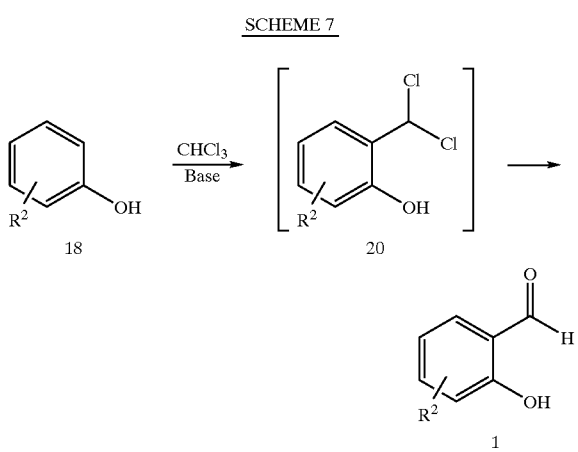

Synthetic Scheme 7 shows the Reimer-Tiemann reaction in which an commercially or synthetically available appropriately substituted phenol 18 will under basic conditions react with chloroform to yield a substituted salicylaldehyde 1 (See: Cragoe, E. J.; Schultz, E. M., U.S. Pat. No. 3,794,734, 1974).

SCHEME 8

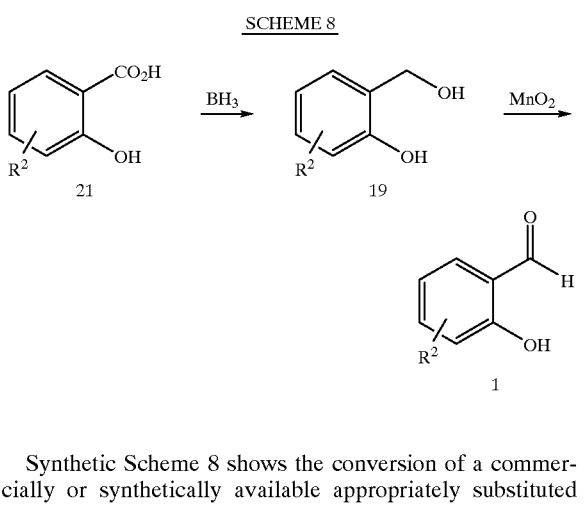

Synthetic Scheme 8 shows the conversion of a commercially or synthetically available appropriately substituted salicylic acid 21 to its respective salicylaldehyde 1 via an intermediate 2-hydroxybenzyl alcohol 19. Reduction of the salicylic acid 21 can be accomplished with a hydride reducing agent such as borane in a solvent such as tetrahydrofuran. Treatment of the intermediate 2-hydroxybenzyl alcohol 19 with an oxidizing agent such as manganese (IV) oxide in a solvent such as methylene chloride or chloroform provides salicylaldehyde 1.

SCHEME 9

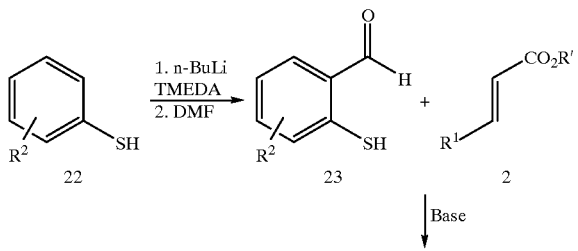

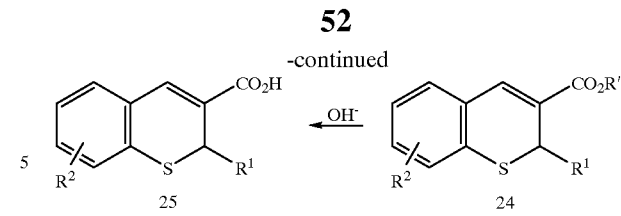

Synthetic Scheme 9 illustrates a general synthetic method for preparation of a wide variety of substituted 2-(trifluoromethyl)-2H-1-benzothiopyran-3-carboxylic acids (25). In step 1, an appropriately commercially or synthetically available substituted thiophenol 22 is ortho-metallated with a base such as n-butyllithium employing TMEDA (N,N,N',N'-tetramethylethylenediamine) followed by treatment with dimethylformamide to provide the 2-mercaptobenzaldehyde 23. Condensation of the 2-mercaptobenzaldehyde 23 with an acrylate 2 in the presence of base provides ester 24 which can be saponified in the presence of aqueous base to afford the substituted 2H-1-benzothiopyran-3-carboxylic acids 25.

SCHEME 10

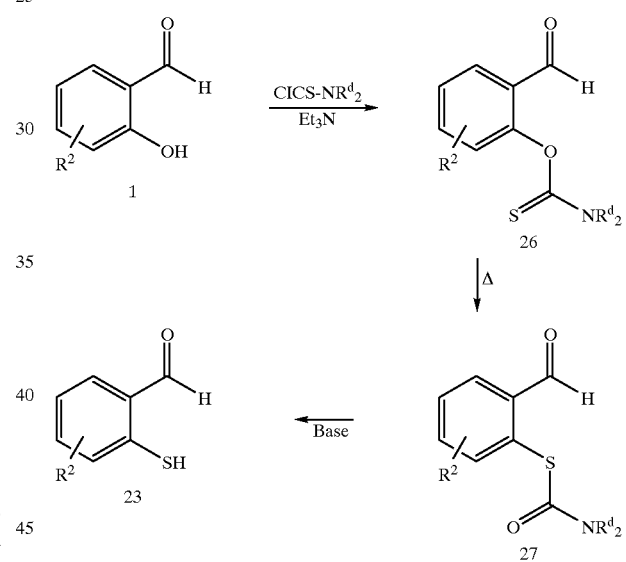

Synthetic Scheme 10 shows a method for preparing a substituted 2-mercaptobenzaldehyde from an appropriate commercially or synthetically available substituted salicylaldehyde. In step 1, the phenolic hydroxyl of salicylaldehyde 1 is converted to the corresponding O-aryl thiocarbamate 26 by acylation with an appropriately substituted thiocarbamoyl chloride such as N,N-dimethylthiocarbamoyl chloride in a solvent such as dimethylformamide using a base such as triethylamine. In Step 2, O-aryl thiocarbamate 26 rearranges to S-aryl thiocarbamate 27 when heated sufficiently such as to 200° C. using either no solvent or a solvent such as N,N-dimethylaniline (See: A. Levai, and P. Sebok, Synth. Commun., 22 1735–1750 (1992)). Hydrolysis of S-aryl thiocarbamate 27 with a base such as 2.5 N sodium hydroxide in a solvent mixture such as tetrahydrofuran and ethanol yields the substituted 2-mercaptobenzaldehyde 23 which can be converted to the substituted 2H-1-benzothiopyran-3-carboxylic acids 25 as described in Scheme 9.

SCHEME 11

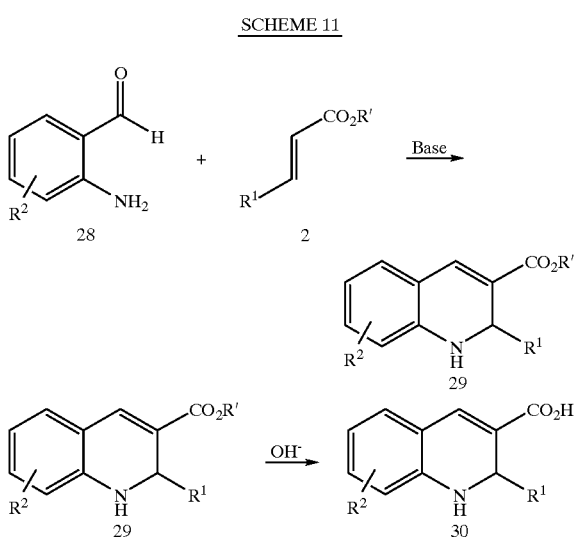

hol 32 was accomplished with a hydride reducing agent such as borane in a solvent such as tetrahydrofuran. Treatment of the desired 2-aminobenzyl alcohol 32 with an oxidizing agent such as manganese(IV)oxide in a solvent such as methylene chloride provides the representative 2-aminobenzaldehydes 28. (C. T. Alabaster, et al. *J. Med. Chem.* 31, 2048–2056 (1988)) The 2-aminobenzaldehydes were converted to the desired dihydroquinoline-3-carbolic acid 30 as described in Scheme 11.

SCHEME 13

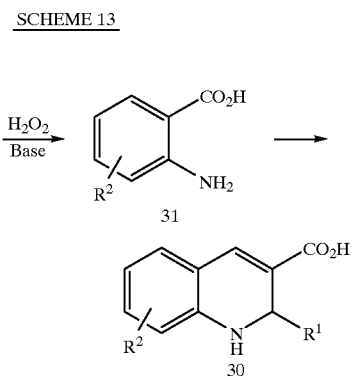

Synthetic Scheme 11 illustrates the general method for the preparation of a wide variety of dihydroquinoline-3-carboxylic acid derivatives 30. $R^2$ represents the aromatic substitution of commercially and synthetically available 2-aminobenzaldeydes 28. The 2-amino-benzaldehyde derivative 28, where $R^2$ represents various substitutions, is condensed with a acrylate derivative 2 in the presence of base such as potassium carbonate, triethylamine, or diazbicyclo[2.2.2]undec-7-ene in solvents such as dimethylformamide to afford the dihydroquinoline-3-carboxylate esters 29. The ester 29 can be saponified to the corresponding acid, such as by treatment with aqueous inorganic base such as 2.5 N sodium hydroxide in a suitable solvent such as ethanol to afford after acidification the desired dihydroquinoline-3-carboxylic acid 30.

Synthetic Scheme 13 illustrates the general method for the preparation of a wide variety of dihydroquinoline-3-carboxylic acid derivatives 30 from isatins 33. $R^2$ represents the aromatic substitution of commercially and synthetically available isatins 33. A representative isatin 33 was treated with basic peroxide generated from hydrogen peroxide and a base such as sodium hydroxide to afford the desired representative 2-aminobenzoic acids 31. (M. S. Newman and M. W. Lougue, *J. Org. Chem.*, 36, 1398–1401 (1971)) The 2-aminobenzoic acids 31 are subsequently converted to the desired dihydroquinoline-3-carboxylic acid derivatives 30 as described in synthetic Scheme 12.

SCHEME 12

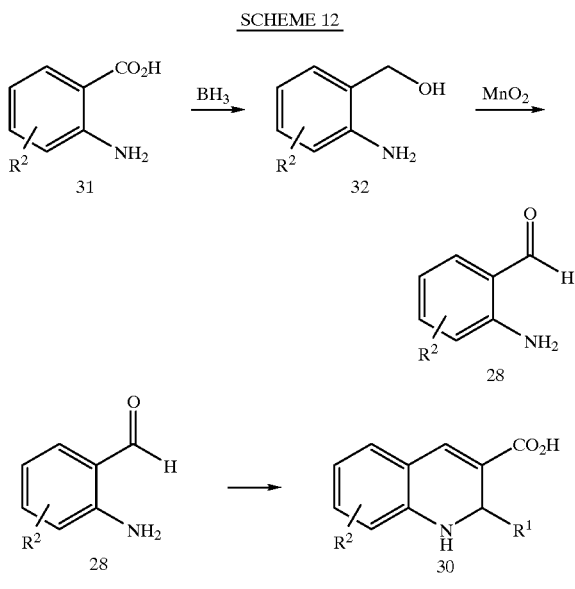

SCHEME 14

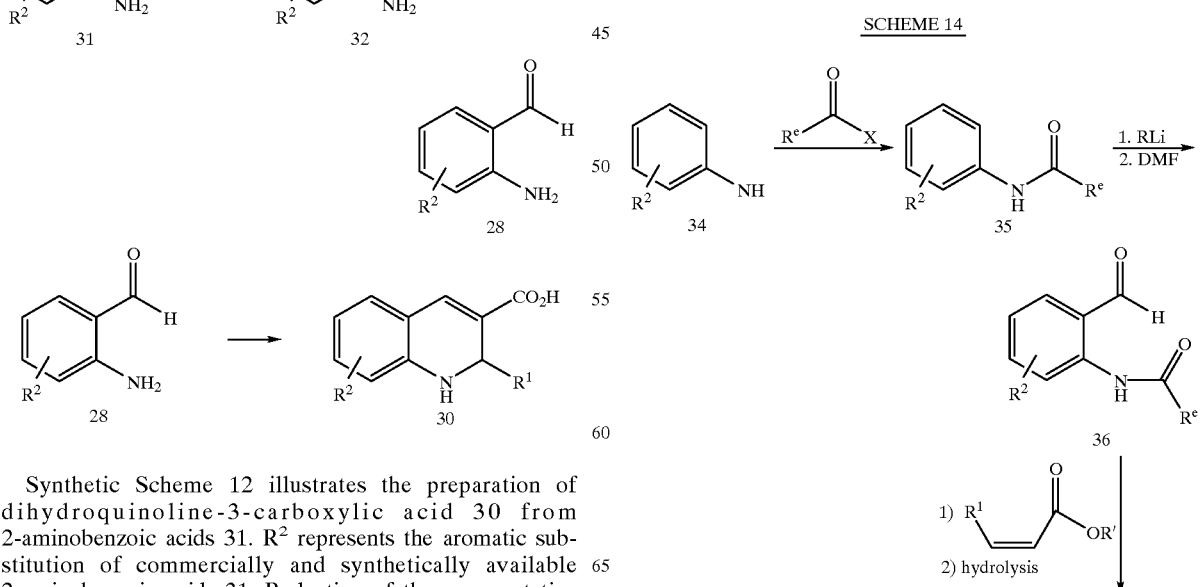

Synthetic Scheme 12 illustrates the preparation of dihydroquinoline-3-carboxylic acid 30 from 2-aminobenzoic acids 31. $R^2$ represents the aromatic substitution of commercially and synthetically available 2-aminobenzoic acids 31. Reduction of the representative 2-aminobenzoic acid 31 to the desired 2-aminobenzyl alco-

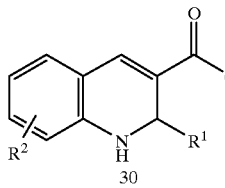

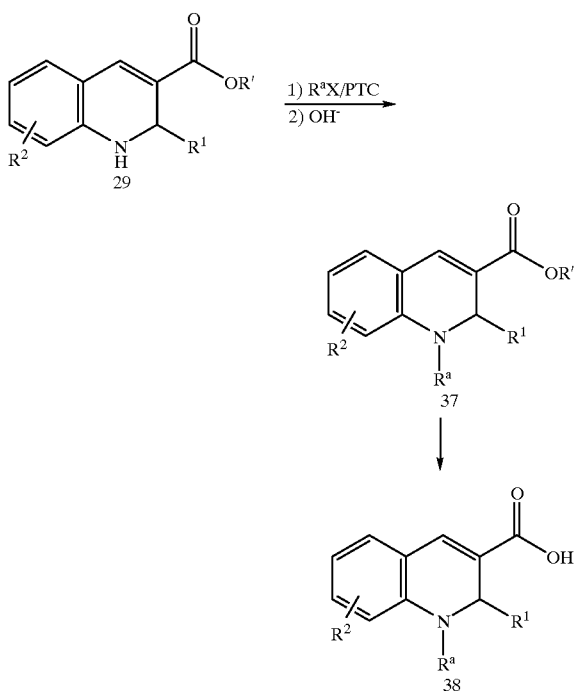

Synthetic Scheme 14 is another general method for the preparation of dihydroquinoline-3-carboxylic acid derivatives 30. In step 1, an appropriate commercially or synthetically available substituted aniline 34 can be treated with an acylating reagent such as pivaloyl chloride yielding an amide 35. The ortho-dianion of amide 35 is prepared by treating amide 35 with organo-lithium bases such as n-butyllithium or tert-butyllithium in tetrahydrofuran at low temperature. The dianion is quenched with dimethylformamide to afford the acylated-2-amino-benzaldehydes 36. (J. Turner, *J. Org. Chem.*, 48, 3401–3408 (1983)) Reaction of these aldehydes in the presence of bases such as lithium hydride with a acrylate followed by work up with aqueous inorganic bases and hydrolysis, such as by treatment with aqueous base (sodium hydroxide) in a suitable solvent such as ethanol affords, after acidification, a dihydroquinoline-3-carboxylic acid 30.

Synthetic Scheme 15 shows a general method for alkylation of the nitrogen of dihydroquinoline-3-carboxylate ester derivatives 29. The step involves treatment of dihydroquinoline-3-carboxylate ester derivatives 29 with alkyl halides such as iodoethane in the presence of phase transfer catalysts such a tetrabutylammonium iodide, and a base such as caustic (50% aqueous sodium hydroxide) in a solvent such as dichloromethane. These conditions afford the N-alkylated dihyrdoquinoline-3-carboxylate esters 37. Saponification of 37 with aqueous base provides N-alkylated-dihyroquinoline-3-carboxylic acid derivatives 38.

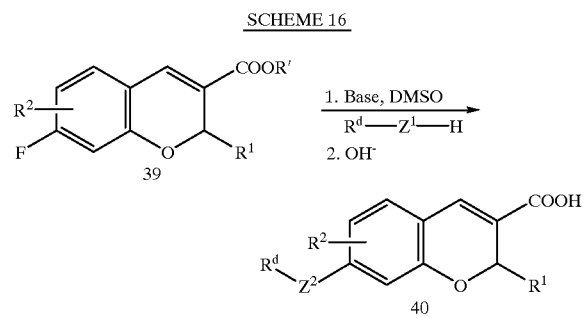

Synthetic Scheme 16 shows a general method for the preparation of a 7-ether ($Z^1$=O) or thioether ($^1$=S) substituted benzopyran-3-carboxylic ester. An appropriately substituted phenol, thiophenol, hydroxy-heterocycle, mercaptoheterocycle, alcohol, or alkylthiol can be condensed under basic conditions using a base such as potassiu carbonate in a solvent such as di ethysulfoxide at te perature above roo te perature such as 100° C., with an appropriately substituted 7-fluorobenzopyran derivative 30 to yield the corresponding ether or thioether. ydrolysis of the ester with an aqueous base such as lithiu hydroxide or sodiu hydroxide in a solvent ixture such as tetrahydrofuran-ethanol-water yields acid hen appropriate a thioether $^2$=S) can be oxidi ed to the sulfoxide $^2$=SO) or sulfone ($Z^2$=$SO_2$) with an oxidant such as OXONE® or m-CPBA either before or after ester hydrolysis. In this chemistry Rd can include aryl, heteroaryl, heterocyclic, alicyclic, branched or linear aliphatic branched or linear perfluoro-aliphatic oiety.

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:
HCl—hydrochloric acid
$MgSO_4$—magnesium sulfate
$Na_2SO_4$—sodium sulfate
DMF—dimethylformamide
THF—tetrahydrofuran
NaOH—sodium hydroxide
EtOH—ethanol
$K_2CO_3$—potassium carbonate
$CDCl_3$—deuterated chloroform
$CD_3OD$—deuterated methanol
$Et_2O$—diethyl ether
EtOAc—ethyl acetate
$NaHCO_3$—sodium bicarbonate
$KHSO_4$—potassium sulfate
$NaBH_4$—sodium borohydride
TMEDA—tetrametylethylenediamine
HMTA—hexamethylenetetraamine
DMSO—dimethyl sulfoxide
HMPA hexamethyl phosphoric triamide
h—hour P₂O₅—phosphorous pentoxide
HOAc—acetic acid
NaOD—deuterated sodium hydroxide
n-BuLi—n-butyllithium
CH₂Cl₂—methylene chloride
TFA—trifluoroacetic acid
OXONE—potassium peroxymonosulfate

EXAMPLE 1

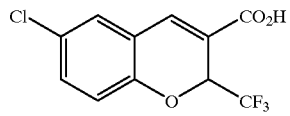

6-Chloro-2-trifluoromethyl-2H-1-benzopyran-3-carboxylic Acid

Step 1. Preparation of ethyl 6-chloro-2-trifluoromethyl-2H-1-benzopyran-3-carboxylate.

A mixture of 5-chlorosalicylaldehyde (20.02 g, 0.128 mole) and ethyl 4,4,4-trifluorocrotonate (23.68 g, 0.14 mole) was dissolved in anhydrous DMF, warmed to 60° C. and treated with anhydrous K₂CO₃ (17.75 g, 0.128 mole). The solution was maintained at 60° C. for 20 hours, cooled to room temperature, and diluted with water. The solution was extracted with ethyl acetate. The combined extracts were washed with brine, dried over anhydrous MgSO₄, filtered and concentrated in vacuo to afford 54.32 g of an oil. The oil was dissolved in 250 mL of methanol and 100 mL of water, whereupon a white solid formed that was isolated by filtration, washed with water and dried in vacuo, to afford the ester as a yellow solid (24.31 g, 62%): mp 62–64° C. $^1$H NMR (CDCl₃/90 MHz) 7.64 (s, 1H), 7.30–7.21 (m, 2H), 6.96 (d, 1H, J=Hz), 5.70 (q, 1H, J=Hz), 4.30 (q, 2H, J=7.2 Hz), 1.35 (t, 3H, J=7.2 Hz).

Step 2. Preparation of 6-chloro-2-trifluoromethyl-2H-1-benzopyran-3-carboxylic Acid.

A solution of the ester from Step 1 (13.02 g, 42 mmole) was dissolved in 200 mL of methanol and 20 mL of water, treated with lithium hydroxide (5.36 g, 0.128 mole) and stirred at room temperature for 16 hours. The reaction mixture was acidified with 1.2 N HCl, whereupon a solid formed that was isolated by filtration. The solid was washed with 200 mL of water and 200 mL of hexanes and dried in vacuo to afford the title compound as a yellow solid (10.00 g, 85%): mp 181–184° C.

EXAMPLE 2

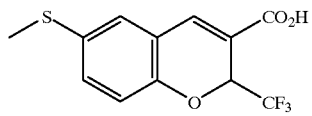

6-(Methylthio)-2-(trifluoromethyl)-2H-1-benzopyran-3-carboxylic Acid

Step 1. Preparation of 5-(methylthio)salicylaldehyde.

Ethyl magnesium bromide (38 mL of a 3.0 M solution in diethyl ether, 113.8 mmole) was chilled with an ice-water bath. To the chilled solution was added a solution of 4-(methylthio)phenol (15.95 g, 113.8 mmole) in diethyl ether (30 mL) over 0.15 hour during which time gas was evolved. The reaction was held at 0° C. for 0.5 hour, at room temperature for 0.5 hour, and the addition funnel replaced with a distillation head. Toluene (250 mL) and the diethyl ether were distilled out of the reactor. The reaction was cooled, toluene (250 mL) and hexamethylphosphoramide (HMPA) (19.8 mL, 20.4 g, 113.8 mmole) were added, and the resulting mixture was stirred for 0.25 hours. The distillation head was replaced with a condenser and paraformaldehyde (8.5 g, 284.4 mmole) was added. The reaction was heated to 90° C. for 3 hours. The reaction mixture was cooled to room temperature, was acidified with 1N HCl and the layers separated. The organic phase was washed with water, and with brine, dried over MgSO₄, filtered, and concentrated in vacuo to yield a solid. This solid was purified by silica chromatography (hexanes-ethyl acetate, 5:1) yielding the salicylaldehyde as a yellow crystalline solid (6.01 g) of suitable purity to be used in the next reaction without further purification.

Step 2. Preparation of Ethyl 6-(methylthio)-2-(trifluoromethyl)-2H-1-benzopyran-3-carboxylate.

5-Methylthiosalicylaldehyde (Step 1) (2.516 g, 14.96 mmole) was added to dimethylformamide (3.5 mL), potassium carbonate (2.27 g, 16.45 mmole) and ethyl 4,4,4-trifluorocrotonate (3.3 mL, 3.8 g, 22.4 mmole). The mixture was heated to 65° C. for 3 h. The reaction was cooled to room temperature, poured into H₂O (50 mL), and extracted with diethyl ether (2×75 mL). The combined ethereal phases were washed with aqueous NaHCO₃ solution (3×50 mL), aqueous 2 N HCl solution (3×50 mL), and brine (3×50 mL), dried over MgSO₄, filtered, diluted with isooctane and partially concentrated in vacuo causing the precipitation of the ethyl ester (2.863 g, 60%) as a yellow powder: mp 87.8–89.6° C. This ester was of suitable purity to use without further purification.

Step 3. Preparation of 6-(methylthio)-2-(trifluoromethyl)-2H-1-benzopyran-3-carboxylic acid.

The ester (Step 2) was hydrolyzed to form the carboxylic acid via a method similar to that described in Example 1, Step 2: mp 166.3–167.9° C. $^1$H NMR (acetone-d₆/300 MHz) 7.87 (s, 1H), 7.43 (d, 1H, J=2.2 Hz), 7.33 (dd, 1H, J=8.5, 2.4 Hz), 6.98 (d, 1H, J=8.5 Hz), 5.79 (q, 1H, J=7.0 Hz), 2.48 (s, 3H). FABLRMS m/z 291 (M+H). ESHRMS m/z 289.0152 (M–H, Calc'd 289.0146). Anal. Calc'd for C₁₂H₉F₃O₃S₁: C, 49.66; H, 3.13; S, 11.05. Found: C, 49.57; H, 3.02; S, 11.37.

EXAMPLE 3

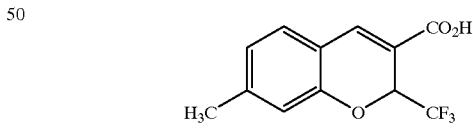

7-Methyl-2-trifluoromethyl-2H-1-benzopyran-3-carboxylic Acid

3-Methylphenol was converted to the title compound by a procedure similar to that described in Example 2: mp 202.1–203.1° C. $^1$H NMR (CDCl₃/300 MHz) 7.84 (s, 1H), 7.12 (d, 1H, J=8.3 Hz), 6.82 (m, 2H), 5.65 (q, 1H, J=6.8 Hz), 2.35 (s, 3H). FABLRMS m/z 259 (M+H). FABHRMS m/z 259.0576 (M+H, Calc'd 259.0582). Anal. Calc'd for C₁₂H₉F₃O₃: C, 55.82; H, 3.51. Found: C, 55.93; H, 3.59.

EXAMPLE 4

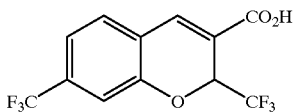

2,7-bis(Trifluoromethyl)-2H-1-benzopyran-3-carboxylic Acid 3-(Trifluoromethyl)phenol was converted to the title compound by a procedure similar to that described in Example 2: mp 190.3–193.5 °C. $^1$H NMR (acetone-$d_6$/300 MHz) 7.98 (5, 1H), 7.73 (d, 1H, J=7.9 Hz), 7.46 (d, 1H, J=7.9 Hz), 7.36 (s, 1H), 5.93 (q, 1H, J=7.1 Hz). FABLRMS m/z 313 (M+H). FABHRMS m/z 313.0267 (M+H, Calc'd 313.0299). Anal. Calc'd for $C_{12}H_6F_6O_3$: C, 46.17; H, 1.94. Found: C, 46.25; H, 2.00.

EXAMPLE 5

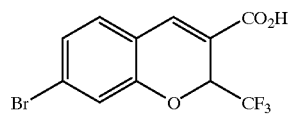

7-Bromo-2-trifluoromethyl-2H-1-benzopyran-3-carboxylic Acid

3-Bromophenol was converted to the title compound by a procedure similar to that described in Example 2: mp 198.4–199.5° C. $^1$H NMR (acetone-$d_6$/300 MHz) 7.89 (s, 1H), 7.43 (d, 1H, J=8.1 Hz), 7.31 (s, 1H), 7.30 (d, 1H, J=8.1 Hz), 5.84 (q, 1H, J=7.1 Hz). FABLRMS m/z 323 (M+H). Anal. Calc'd for $C_{11}H_6BrF_3O_3$: C, 40.90; H, 1.87. Found: C, 41.00; H, 1.85.

EXAMPLE 6

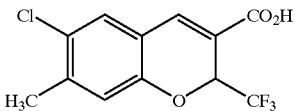

6-Chloro-7-methyl-2-trifluoromethyl-2H-1-benzopyran-3-carboxylic Acid

4-Chloro-3-methylphenol was converted to the title compound by a procedure similar to that described in Example 2: mp 207.5–209.3° C. $^1$H NMR (CDCl$_3$/300 MHz) 7.77 (s, 1H), 7.23 (s, 1H), 6.90 (s, 1H), 5.65 (q, 1H, J=6.8 Hz), 2.37 (s, 3H). FABLRMS m/z 292 (M+H). FABHRMS m/z 299.0287 (M+Li, Calc'd 299.0274). Anal. Calc'd for $C_{12}H_8ClF_3O_3$: C, 49.25; H, 2.76; Cl, 12.11. Found: C, 49.37; H, 2.82; Cl, 12.17.

EXAMPLE 7

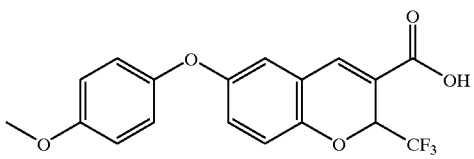

6-(4-Methoxyphenoxy)-2-(trifluoromethyl)-2H-1-benzopyran-3-carboxylic Acid 4-(4-Methoxyphenyl)phenol was converted to the title compound by a procedure similar to that described in Example 2: mp 181.7–182.9° C. $^1$H NMR (acetone-$d_6$/300 MHz) 7.87 (s, 1H), 7.11 (m, 1H), 7.02 (m, 2H), 6.98 (m, 4H), 5.81 (q, 1H, J=7.0 Hz), 3.80 (s, 3H). FABLRMS m/z 365 (M–H). FABHRMS m/z 367.0809 (M+H, Calc'd 367.0793). Anal. Calc'd for $C_{18}H_{13}F_3O_5$: C, 59.02; H, 3.58. Found: C, 59.10; H, 3.61.

EXAMPLE 8

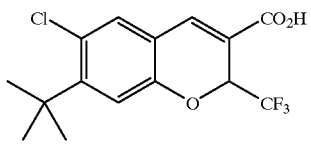

6-Chloro-7-(1,1-dimethylethyl)-2-trifluoromethyl-2H-1-benzopyran-3-carboxylic Acid Step 1. Preparation of 4-tert-butylsalicylaldehyde.

A five liter three-neck round bottom flask equipped with overhead mechanical stirrer and condenser was charged with trifluoroacetic acid (2.4 L). A mixture of 3-tert-butylphenol (412 g, 2.8 mole) and HMTA (424 g, 3.0 mole) was added portion-wise causing an exotherm. With cooling, the temperature was maintained under 80° C. The reaction was heated at 80° C. for one hour, then cooled, and water (2 L) added. After 0.5 hour additional water (4 L) was added and the mixture was extracted with ethyl acetate (6 L). The organic extract was washed with water and brine. The resulting organic phase was divided into 2 L volumes and each diluted with water (1 L), and solid NaHCO$_3$ added until the mixture was neutralized. The organic phases were isolated and combined, dried over MgSO$_4$, filtered and concentrated in vacuo yielding an oil. This oil was distilled at 95° C. (0.8 mm) yielding the desired salicylaldehyde as an oil (272.9 g, 56%) which was of sufficient purity to be used without further purification.

Step 2. Preparation of Ethyl 7-(1,1-dimethylethyl)-2-(trifluoromethyl)-2H-1-benzopyran-3-carboxylate.

A one liter three-neck flask was charged with 4-tert-butylsalicylaldehyde (Step 1) (100.0 g, 0.56 mole), dimethylformamide (110 mL), and potassium carbonate (79.9 g, 0.58 mole) causing the temperature of the mixture to rise to 40° C. Ethyl 4,4,4-trifluorocrotonate (118.0 g, 0.70 mole) in dimethylformamide (110 mL) was added and the mixture heated to 60° C. at which time the reaction temperature rose to 70° C. The reaction was cooled to 60° C., maintained at 60° C. (with added heating) for 8.5 hours and cooled to room temperature. Ethyl acetate (600 mL) and 3 N HCl (600 mL) were added, mixed, and the layers separated. The aqueous phase was extracted with ethyl acetate and the organic phases were combined. The combined organic phases were washed with brine-water (1:1), brine, dried over MgSO$_4$, filtered and concentrated in vacuo, yielding a semi-solid. Hexane (600 mL) was added with mixing and the mixture was filtered. The filtrate was washed with brine, dried over MgSO$_4$, filtered and concentrated in vacuo yielding a solid. This solid was dissolved in hot ethanol (600 mL). Water (190 mL) was added which induced crystallization. Filtration of the mixture and drying of the product provided the desired ester as a crystalline solid (131.3 g, 71%): mp 91.0–94.9° C. This material was of suitable purity to be used in subsequent steps without further purification.

Step 3. Preparation of ethyl 6-chloro-7-(1,1-dimethylethyl)-2-(trifluoromethyl)-2H-1-benzopyran-3-carboxylate.

A one liter three-neck flask equipped with mechanical stirrer and gas inlet tube was charged with the ester (Step 2) (100 g, 0.3 mole) and acetic acid (300 mL). While cooling (water bath) the reaction mixture, chlorine gas (37.6 g, 0.53 mole) was added which caused the temperature to rise to 48° C. After stirring for two hours, the reaction was cooled in an ice-water bath to 15° C. Zinc powder (19.5 g, 0.3 mole) was added in one portion which caused the temperature to rise to 72° C. After cooling to room temperature additional zinc powder (5.0 g, 0.08 mole) was added and the mixture was stirred for 0.5 hour longer. The crude mixture was filtered through diatomaceous earth and was concentrated in vacuo yielding an oil. The oil was dissolved in ethyl acetate (700 mL) washed with brine-water (1:1, 1 L) and brine (0.5 L). The resulting aqueous phase was extracted with ethyl acetate (700 mL). This ethyl acetate phase was washed with brine-water (1:1, 1 L) and brine (0.5 L). The combined organic phases were dried over MgSO$_4$, filtered and concentrated in vacuo yielding the title compound as a yellow oil (116 g, 106%). This material, which contained some entrained ethyl acetate, was of suitable purity to be used in subsequent steps without further purification.

Step 4. Preparation of 6-chloro-7-(1,1-dimethylethyl)-2-(trifluoromethyl)-2H-1-benzopyran-3-carboxylic Acid.

To a solution of the ester (Step 3) (116 g, 0.3 mole) in methanol (500 mL) and tetrahydrofuran (500 mL) in a one liter flask was added aqueous sodium hydroxide (2.5 N, 240 mL, 0.6 mole). After stirring overnight, the pH of the solution was adjusted to 1 with concentrated hydrochloric acid and the solution was extracted with ethyl acetate. The ethyl acetate phase was dried over MgSO$_4$, filtered and concentrated in vacuo yielding a solid. This solid was dissolved in hot ethanol (500 mL). Water (500 mL) was added and upon cooling to room temperature crystals formed which were collected by vacuum filtration. The crystals were washed with ethanol-water (3:7, 3×200 mL) and dried providing the title acid as a crystalline solid (91.6 g, 91%): mp 194.9–196.5° C. $^1$H NMR (acetone-d$_6$/300 MHz) 7.86 (s, 1H), 7.52 (s, 1H), 7.12 (s, 1H), 5.83 (q, 1H, J=7.1 Hz), 1.48 (s, 9H). Anal. Calc'd for C$_{15}$H$_{14}$ClF$_3$O$_3$: C, 53.83; H, 4.22; Cl, 10.59. Found: C, 53.92; H, 4.24; Cl, 10.50.

EXAMPLE 9

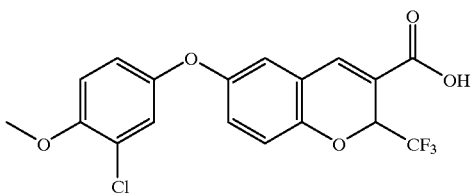

6-(3-Chloro-4-methoxyphenoxy)-2-(trifluoromethyl)-2H-1-benzopyran-3-carboxylic Acid To a stirred solution of chlorine in acetic acid (3.5 mL of 0.24 M solution, 0.84 mmol) was added 6-(4-methoxyphenoxy)-2-(trifluoromethyl)-2H-1-benzopyran-3-carboxylic acid (0.31 g, 0.85 mmol) (Example 7). After 1 hour additional chlorine in acetic acid (1.5 mL of 0.24 M solution, 0.36 mmol) was added. After three additional hours additional chlorine in acetic acid (0.25 ml of 0.25 M solution, 0.06 mmol) was added. After 2.5 hours the reaction was quenched with aqueous 10% sodium bisulfite solution and the resulting mixture extracted with ethyl acetate. The organic phase was washed with water, brine, dried over MgSO$_4$, filtered, and concentrated in vacuo yielding a brown oil. The oil was dissolved in a minimum of hexanes which induced crystallization. Vacuum filtration of the mixture provided the title compound as yellow crystals (0.18 g, 53%): mp 205–207° C. $^1$H NMR (acetone-d$_6$/300 MHz) 7.89 (s, 1H), 6.97–7.18 (m, 6H), 5.83 (q, 1H, J=7.0 Hz), 3.90 (s, 3H). FABLRMS m/z 400 (M+). FABHRMS m/z 399.0249 (M–H, Calc'd 399.0247). Anal. Calc'd for C$_{18}$H$_{12}$ClF$_3$O$_5$: C, 53.95; H, 3.02; Cl, 8.85. Found: C, 53.78; H, 3.08; Cl, 8.98.

EXAMPLE 10

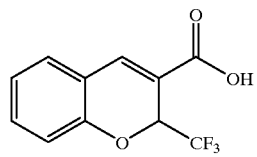

2-Trifluoromethyl-2H-1-benzopyran-3-carboxylic Acid

Step 1. Preparation of Ethyl 2-(trifluoromethyl)-2H-1-benzopyran-3-carboxylate.

The ester was prepared from salicylaldehyde by a procedure similar to the method described in Example 1, Step 1: bp 107° C. 2mm. $^1$HNMR (acetone-d$_6$/300 MHz) 7.89 (s, 1H), 7.52–7.38 (m, 2H), 7.09 (dt, 1 J=1.0, 7.7 Hz), 7.03 (d, 1H, J=8.3 Hz), 5.84 (q, 1H, J=7.3 Hz), 4.39–4.23 (m, 2H), 1.33 (t, 3H, J=7.0 Hz). FABLRMS m/z 273 (M+H). ESHRMS (m/z 273.0720 (M+H Calcd 273.0739)

Step 2. Preparation of 2-(trifluoromethyl)-2H-1-benzopyran-3-carboxylic Acid.

The acid was prepared from the ethyl ester (Step 1) by a procedure similar to the method described in Example 1, Step 2: mp 152.2–153.3° C. $^1$H NMR (acetone-d$_6$/300 MHz) 7.89 (s, 1H), 7.39–7.49 (m, 2H), 7.11–7.01 (m, 2H), 5.81 (q$_{H\text{-}F}$, 1H, J=7.2 Hz). FABHRMS m/z 245.0422 (M+H, Calc'd 245.0426). Anal. Calc'd for C$_{11}$H$_7$F$_3$O$_3$: C, 54.11; H, 2.89. Found: C, 54.22; H, 2.97.

EXAMPLE 11

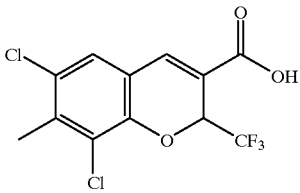

6,8-Dichloro-7-methyl-2-(trifluoromethyl)-2H-1-benzopyran-3-carboxylic Acid

Step 1. Preparation of 3,5-dichloro-4-methylsalicylaldehyde.

2,4-Dichloro-3-methylphenol (25.0 g, 141.2 mmol) was added to methanesulfonic acid (100 mL). With stirring, hexamethylenetetramine (HMTA) (39.8g, 282.4 -mmol) and additional methanesulfonic acid (100 mL) was added portion-wise during which time the reaction began to froth and exotherm. The resulting mixture was heated to 100° C. for 3 hours. The crude ocher colored suspension was cooled to 50° C. and poured over a mechanically stirred mixture of ice-water (2 L). A yellow precipitate was formed which was collected by vacuum filtration. This solid was purified by flash chromatography (silica, hexanes-methylene chloride, 9:10) yielding the salicylaldehyde as a pale yellow powder (6.17 g, 21%; mp 94.0–95.1° C.) of suitable purity to use without further purification.

Step 2. Preparation of ethyl 6,8-dichloro-7-methyl-2-(trifluoromethyl)-2H-1-benzopyran-3-carboxylate.

A mixture of 3,5-dichloro-4-methylsalicylaldehyde (Step 1)(5.94 g, 29.0 mmol) and ethyl 4,4,4-trifluorocrotonate (7.67 g, 45.6 mmol) dissolved in anhydrous DMSO (10 mL) was treated with triethylamine (5.88 g, 58.1 mmol). The reaction was stirred at 85° C. for 49 hours then cooled in ice and filtered to give an orange solid. The solid was dissolved in ethyl acetate (100 mL), washed with 3 N HCl (2×50 mL), saturated $NaHCO_3$, washed with brine, dried over $MgSO_4$, and concentrated in vacuo to give a yellow solid (8.63 g, 84%): mp 117.1–119.5 0C. $^1$H NMR ($CDCl_3$/300 MHz) 7.63 (s, 1H), 7.17 (s, 1H), 5.80 (q, 1H, J=6.6 Hz), 4.33 (m, 2H), 2.48 (s, 3H), 1.35 (t, 3H, J=7.1 Hz).

Step 3. Preparation of 6,8-dichloro-7-methyl-2-(trifluoromethyl)-2H-1-benzopyran-3-carboxylic Acid.

The ester from Step 2 (8.39 g 23.6 mmol) was dissolved in THF (30 mL) and ethanol (20 mL), treated with 2.5 N sodium hydroxide (20 mL, 50 mmol), and stirred at room temperature for 3.5 hours. The reaction mixture was concentrated in vacuo, acidified with 3 N HCl, filtered, and recrystallized from ethanol/water to yield a yellow solid (6.0 g, 78%): mp 229.9–230.9 0C. $^1$H NMR (acetone-$d_6$/300 MHz) 7.90 (s, 1H), 7.58 (s, 1H), 6.00 (q, 1H, J=6.8 Hz), 2.50 (s, 3H). FABLRMS m/z 325 (M−H). FABHRMS m/z 324.9636 (M−H, Calc'd 324.9646). Anal. Calc'd for $C_{12}H_7Cl_2F_3O_3$: C, 44.07; H, 2.16; Cl, 21.68. Found: C, 44.06; H, 2.21; Cl, 21.74.

EXAMPLE 12

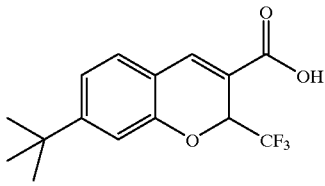

7-(1,1-Dimethylethyl)-2-trifluoromethyl-2H-1-benzopyran-3-carboxylic Acid

Ethyl 7-(1,1-dimethylethyl)-2-(trifluoromethyl)-2H-1-benzopyran-3-carboxylate (Example 8, Step 2) was hydrolyzed to the carboxylic acid via a procedure similar to that described in Example 1, Step 2: mp 165.6–166.8° C. $^1$H NMR (acetone-$d_6$/300 MHz) 7.86 (s, 1H), 7.38 (d, 1H, J=8.1 Hz), 7.15 (dd, 1H, J=1.8 Hz, and J=7.8 Hz), 7.05 (bs, 1H), 5.79 ($q_{H-F}$, 1H, J=7.2 Hz), 1.32 (s, 9H). FABHRMS m/z 301.1033 (M+H, Calc'd 301.1051). Anal. Calc'd for $C_{15}H_{15}F_3O_3$: C, 60.00; H, 5.04. Found: C, 59.80; H, 5.10.

EXAMPLE 13

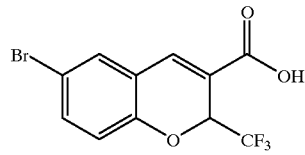

6-Bromo-2-trifluoromethyl-2H-1-benzopyran-3-carboxylic Acid

5-Bromosalicylaldehyde was converted to the title compound by a procedure similar to that described in Example 1: mp 189.6–190.9° C. $^1$H NMR (acetone-$d_6$/300 MHz) 7.89 (s, 1H), 7.70 (d, 1H, J=2.1 Hz), 7.55 (dd, 1H, J=2.4 Hz, and J=8.7 Hz), 7.02 (d, 1H, J=8.7 Hz), 5.86 ($q_{H-F}$, 1H, J=7.2 Hz). FABHRMS m/z 322.9519 (M+H, Calc'd 322.9531). Anal. Calc'd for $C_{11}H_6BrF_3O_3$: C, 40.90; H, 1.87; Br, 24.73. Found: C, 40.87; H, 1.92; Br, 24.80.

EXAMPLE 14

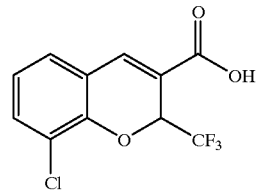

8-Chloro-2-trifluoromethyl-2H-1-benzopyran-3-carboxylic Acid

2-Chlorophenol was converted to the title compound by a procedure similar to that described in Example 2: mp 224.5–225.6° C. $^1$H NMR (acetone-$d_6$/300 MHz) 7.91 (s, 1H), 7.49 (m, 2H), 7.11 (t, 1H, J=7.8 Hz), 5.96 ($q_{H-F}$, 1H, J=7.2 Hz). FABHRMS m/z 279.0027 (M+H, Calc'd 279.0036). Anal. Calc'd for $C_{11}H_6ClF_3O_3$: C, 47.42; H, 2.17. Found: C, 47.33; H, 2.17.

EXAMPLE 15

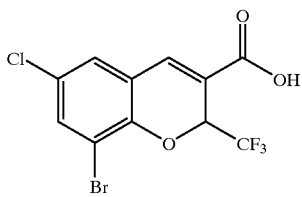

8-Bromo-6-chloro-2-trifluoromethyl-2H-1-benzopyran-3-carboxylic Acid

2-Bromo-4-chlorosalicylaldehyde was converted to the title compound by a similar procedure to that described in Example 1: mp 227.8–228.9° C. $^1$H NMR (acetone-$d_6$/300 MHz) 7.90 (s, 1H), 7.65 (dd, 2H, J=2.4 and J=28.8 Hz), 6.00 ($q_{H-F}$, 1H, J=7.2 Hz). FABHRMS m/z 356.9134 (M+H, Calc'd 356.9141). Anal. Calc'd for $C_{11}H_5BrClF_3O_3$: C, 36.96; H, 1.41. Found: C, 37.05; H, 1.33.

EXAMPLE 16

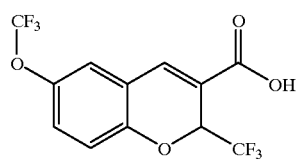

6-Trifluoromethoxy-2-trifluoromethyl-2H-1-benzopyran-3-carboxylic Acid 5-(Trifluoromethoxy)salicylaldehyde was converted to the title compound by a similar procedure to that described in Example 1: mp 118.4–119.5° C. $^1$H NMR (acetone-$d_6$/300 MHz) 7.95 (s, 1H), 7.54 (d, 1H, J=2.1 Hz), 7.39 (dd, 1H, J=2.4 Hz, and J=9.0 Hz), 7.02 (d, 1H, J=9.0 Hz), 5.88 ($q_{H-F}$, 1H, J=7.2 Hz). FABHRMS m/z 329.0228 (M+H, Calc'd 329.0249). Anal. Calc'd for $C_{12}H_6F_6O_4$: C, 43.92; H, 1.84. Found: C, 43.84; H, 1.87.

EXAMPLE 17

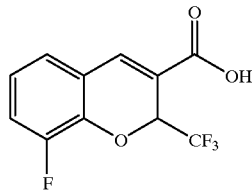

8-Fluoro-2-trifluoromethyl-2H-1-benzopyran-3-carboxylic Acid

3-Fluorosalicylaldehyde was converted to the title compound by a similar procedure to that described in Example 1: mp 197.7–210.1° C. $^1$H NMR (acetone-$d_6$/300 MHz) 7.94 (s, 1H), 7.30 (m, 2H), 7.11 (m 1H), 5.93 ($q_{H-F}$, 1H, J=7.2 Hz). FABHRMS m/z 2 63.0341 (M+H , $C_{11}H_6F_4O_3$ Calc'd 263.0331). Anal. Calc'd for $C_{11}H_6F_4O_3$: C, 50.40; H, 2.31. Found: C, 50.48; H, 2.25.

EXAMPLE 18

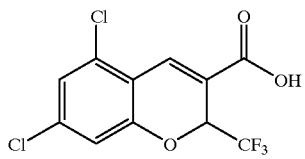

5,7-Dichloro-2-trifluoromethyl-2H-1-benzopyran-3-carboxylic Acid 4,6-Dichlorosalicylaldehyde was converted to the title compound by a similar procedure to that described in Example 1: mp 190.1–191.2° C. $^1$H NMR (acetone-$d_6$/300 MHz) 8.01 (s, 1H), 7.3 (bs, 1H), 7.16 (bs, 1H), 5.94 ($q_{H-F}$, 1H, J=7.2 Hz). FABHRMS m/z 312.9636 (M+H, Calc'd 312.9646). Anal. Calc'd for $C_{11}H_5Cl_2F_3O_3$: C, 42.20; H, 1.61. Found: C, 42.27; H, 1.56.

EXAMPLE 19

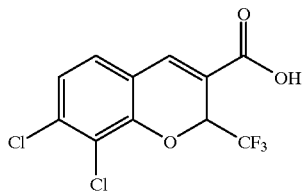

7,8-Dichloro-2-trifluoromethyl-2H-1-benzopyran-3-carboxylic Acid 3,4-Dichlorophenol was converted to the title compound by a procedure similar to that described in Example 2: mp 219.5–220.9° C. $^1$H NMR (acetone-$d_6$/300 MHz) 7.94 (s, 1H), 7.51 (d, 1H, J=8.4 Hz), 7.34 (d, 1H, J=8.4 Hz), 6.02 ($q_{H-F}$, 1H, J=7.2 Hz). FABHRMS m/z 318.9709 (M+Li, $C_{11}H_5Cl_2F_3O_3$ Calc'd 318.9728). Anal. Calc'd for $C_{11}H_5Cl_2F_3O_3$: C, 42.20; H, 1.61. Found: C, 42.15; H, 1.68.

EXAMPLE 20

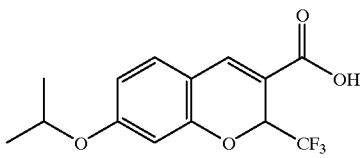

7-Isopropyloxy-2-trifluoromethyl-2H-1-benzopyran-3-carboxylic Acid 2,4-Dihydroxybenzaldehyde was alkylated to prepare 4-(1-methylethyloxy)salicylaldehyde. This salicylaldehyde was converted to the title compound by a similar procedure to that described in Example 1: mp 161–163° C. $^1$H NMR (CD$_3$OD/300 MHz) 7.73 (s, 1H), 7.21 (d, 1H, J=8.5 Hz), 6.57 (dd, 1H, J=8.5, 2.2 Hz). FABHRMS m/z 301.0688 (M–H$^+$, $C_{11}H_{12}F_3O_4$ requires 301.0687). Anal. Calc'd for $C_{11}H_{13}F_3O_4$: C, 55.63; H, 4.34. Found: C, 55.72; H, 4.34.

EXAMPLE 21

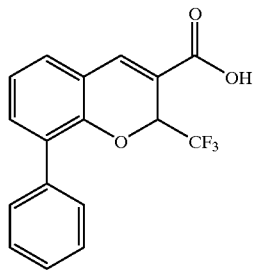

8-Phenyl-2-trifluoromethyl-2H-1-benzopyran-3-carboxylic Acid

2-Phenylphenol was converted to the title compound by a procedure similar to that described in Example 2: mp 171.6–175.0° C. $^1$H NMR (acetone-$d_6$/300 MHz) 7.95 (s, 1H), 7.46 (m, 7H), 7.18 (t, 1H, J=7.5 Hz), 5.81 ($q_{H-F}$, 1H, J=7.2 Hz). FABHRMS m/z 327.0816 (M+Li, Calc'd 327.0820). Anal. Calc'd for $C_{17}H_{11}F_3O_3$: C, 63.76; H, 3.46. Found: C, 63.52; H, 3.55.

EXAMPLE 22

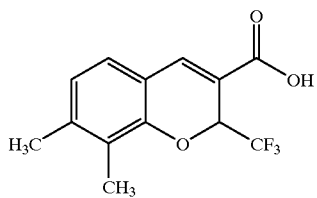

7,8-Dimethyl-2-trifluoromethyl-2H-1-benzopyran-3-carboxylic Acid 2,3-Dimethylphenol was converted to the title compound by a procedure similar to that described in Example 2: mp 245.2–247.3° C. $^1$H NMR (acetone-$d_6$/300 MHz) 7.83 (s, 1H), 7.17 (d, 1H, J=7.8 Hz), 6.89 (d, 1H, J=7.8 Hz), 5.82 ($q_{H-F}$, 1H, J=7.2 Hz), 2.30 (s, 3H), 2.17 (s, 3H). Anal. Calc'd for $C_{13}H_{11}F_3O_3$+1.56% $H_2O$: C, 56.46; H, 4.18. Found: C, 56.46; H, 4.15.

EXAMPLE 23

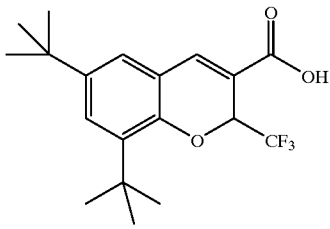

6,8-bis(1,1-Dimethylethyl)-2-trifluoromethyl-2H-1-benzopyran-3-carboxylic Acid 3,5-Di-tert-butylsalicylaldehyde was converted to the title compound by a similar procedure to that described in Example 1: mp 171.6–175.0° C. $^1$H NMR (acetone-$d_6$/300 MHz) 7.65 (s, 1H), 7.34 (d, 1H, J=2.4 Hz), 7.15 (d, 1H, J=2.4 Hz), 6.02 ($q_{H-F}$, 1H, J=7.2 Hz). FABHRMS m/z 363.1743 (M+Li, Calc'd 363.1759). Anal. Calc'd for $C_{19}H_{23}BrF_3O_3$: C, 64.03; H, 6.50. Found: C, 64.13; H, 6.49.

EXAMPLE 24

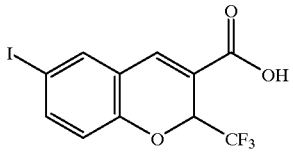

6-Iodo-2-trifluoromethyl-2H-1-benzopyran-3-carboxylic Acid

Step 1: Preparation of 2-hydroxy-5-iodobenzyl Alcohol.

A solution of 5-iodosalicylic acid (25.0 g, 94.6 mmol) in tetrahydrofuran (500 mL) was cooled to 0° C. With vigorous mixing, borane-methyl sulfide complex (15.1 ml of 10 M solution, 151.0 mmol) was added drop-wise over 0.25 hours. The solution was warmed to room temperature and then heated at reflux for 4 h. A white precipitate formed during the reflux. The solution was cooled to room temperature and 10% aqueous hydrochloric acid (100 mL) was added over 15 min and the solution stirred at room temperature for 2 h. The precipitate dissolved and the solvent was concentrated in vacuo to a volume of approximately 200 mL. The solution was poured into ethyl acetate (300 mL) and washed with water (2×200 mL), saturated sodium bicarbonate (2×200 mL), and saturated ammonium chloride (2×200 mL). The organic layer was dried over sodium sulfate and concentrated in vacuo. The 2-hydroxy-5-iodobenzyl alcohol was isolated as a white solid (21.3 g, 85.2 mmol)from hexanes. (90% yield): mp 105–110° C. $^1$H NMR (CDCl$_3$/300 MHz) 8.21 (s, 1H), 7.30–7.33 (M, 2H), 6.57 (d, 1H, J=8.3 Hz), 4.97 (bs, 1H), 4.62 (s, 2H). EIHRMS m/z=249.9492 (M+, Calc'd 249.9491).

Step 2: Preparation of 2-hydroxy-5-iodobenzaldehyde

To a stirred solution of 2-hydroxy-5-iodobenzyl alcohol (43.5 g, 174.0 mmol) in acetone (700 mL) was added 85% activated manganese(IV) oxide (5 micron, 50 g, 494.0 mmol) and the solution stirred at room temperature for 16 hours. The manganese oxide was removed by filtration through diatomaceous earth and the filtrate concentrated in vacuo. The product was purified by flash silica chromatography (0–20% ethyl acetate in hexanes) The 2-hydroxy-5-iodobenzaldehyde was obtained as a greenish-yellow solid (24.3 g, 58%). A small amount of the 2-hydroxy-5-iodobenzaldehyde was recrystallized from methanol/water to afford an analytical sample and the remainder of the compound was used without further purification: mp 99–101° C. $^1$H NMR (CDCl$_3$/300 MHz) 9.83 (s, 1H), 7.79 (d, 1H, J=2.2 Hz), 7.77 (dd, 1H, J=8.7 Hz, J=2.2 Hz), 6.81 (d, 1H, J=8.7 Hz). ESHRMS 246.9229 (M–H Calc'd 246.9256).

Step 3: Preparation of ethyl 6-iodo-2-trifluoromethyl-2H-1-benzopyran-3-carboxylate.

A mixture of 5-iodosalicylaldehyde (16.2 g, 65.3 mmol), ethyl 4,4,4-trifluorocrotonate (22.4 g, 133 mmol) and triethylamine (50 ml, 395 mmol)were combined, stirred at 70° C. for 8 h and then heated at reflux for 48 h. The solution was poured into ethyl acetate (300 mL) and washed with 1N hydrochloric acid (3×200 mL). The aqueous layers were combined and extracted with ethyl acetate (1×100 mL). The combined ethyl acetate extracts were washed with saturated ammonium chloride (2×200 mL), dried over magnesium sulfate and concentrated in vacuo yielding a dark red oil. This oil was purified by flash chromatography using ethyl acetate-hexanes (3:7) yielding a red oil. Crystallization of this oil from hexanes yielded the title compound as light red crystals (8.3 g, 31%): mp 105–106° C. $^1$H NMR (CDCl$_3$/300 MHz) 7.63 (s, 1H), 7.58 (dd, 2H, J=8.6, J=2.1 Hz, 7.54 (d, 1H, J=2.1 Hz), 6.77 (d, 1H, J=8.6 Hz), 5.70 (q, 1H, J=6.7 Hz), 4.20–4.38 (m 2H), 1.35 (t, 3H, J=7.2 Hz). ESHRMS 415.9926 (M+NH$_4^+$ Calc'd 396.9746)

Step 4: Prepartation of 6-iodo-2-(trifluoromethyl)-2H-1-benzopyran-3-carboxylic Acid.

Hydrolysis of the ester (Step 3), using a procedure similar to Example 1, Step 2, yielded the carboxylic acid: mp 168–170° C. $^1$H NMR (CD$_3$OD/300 MHz) 7.57 (s, 1H), 7.70 (d, 1H, J=2.2 Hz), 7.64 (dd, 1H, J=8.5, 2.2 Hz), 6.79 (d, 1H, J=8.5 Hz) 5.78 (q, 1H, J=7.0 Hz). ESHRMS m/z 368.9222 (Calc'd for M–H 368.9235). Anal. Calc'd for C$_{11}$H$_6$F$_3$IO$_3$: C, 35.70; H, 1.63. Found C, 35.67; H, 1.63.

EXAMPLE 25

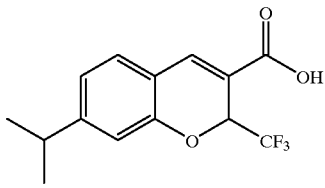

7-(1-Methylethyl)-2-trifluoromethyl-2H-1-benzopyran-3-carboxylic Acid 3-(1-Methylethyl)phenol was converted to the title compound by a procedure similar to that described in Example 2: mp 158.3–159.7° C. $^1$H NMR (acetone-d$_6$/300 MHz) 7.86 (s, 1H), 7.37 (d, 1H, J=7.8 Hz), 7.00 (d, 1H, J=7.8 Hz), 6.91 (s, 1H), 5.78 (q, 1H, J=6.9 Hz), 2.93 (m, 1H), 1.24 (d, 6H, J=6.9 Hz). FABLRMS m/z 287 (M+H). Anal. Calc'd for C$_{14}$H$_{13}$F$_3$O$_3$: C, 58.74; H, 4.58. Found: C, 57.37; H, 4.49.

EXAMPLE 26

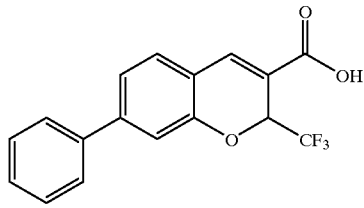

7 enyl-2-trifluoromethyl-2H-1-benzopyran-3-carboxylic Acid

3-Phenylphenol was converted to the title compound by a procedure similar to that described in Example 2: mp 209.4–211.7° C. $^1$H NMR (acetone-d$_6$/300 MHz) 7.94 (s, 1H), 7.74 (m, 2H), 7.47 (m, 5H), 7.33 (s, 1H), 5.86 (q, 1H, J=7.2 Hz). FABLRMS m/z 321 (M+H). Anal. Calc'd for C$_{17}$H$_{11}$F$_3$O$_3$: C, 63.76; H, 3.46. Found: C, 64.17; H, 3.61.

EXAMPLE 27

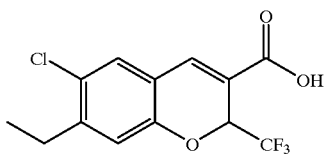

6-Chloro-7-ethyl-2-trifluoromethyl-2H-1-benzopyran-3-carboxylic Acid

4-Chloro-3-ethylphenol was converted to the title compound by a procedure similar to that described in Example 2: mp 170.7–172.1 ° C. $^1$H NMR (CDCl$_3$/300 MHz) 7.78 (s, 1H), 7.26 (s, 1H), 6.90 (s, 1H), 5.67 (q, 1H, J=6.9 Hz), 2.73 (q, 2H, J=7.8 Hz), 1.24 (t, 3H, J=7.8 Hz). FABLRMS m/z 307 (M+H). Anal. Calc'd for C$_{13}$H$_{10}$F$_3$O$_3$: C, 50.92; H, 3.29. Found: C, 51.00; H, 3.33.

EXAMPLE 28

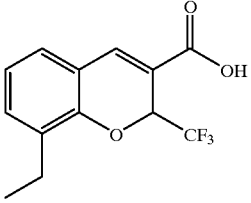

8-Ethyl-2-trifluoromethyl-2H-1-benzopyran-3-carboxylic Acid

2-Ethylphenol was converted to the title compound by a procedure similar to that described in Example 2: mp 185.4–186.8° C. $^1$H NMR (acetone-d$_6$/300 MHz) 7.85 (s, 1H), 7.28 (d, 2H, J=7.5 Hz), 7.00 (t, 1H, J=7.5 Hz), 5.84 (q, 1H, J=7.2 Hz), 2.65 (m, 2H), 1.18 (t, 3H, J=7.5 Hz). FABLRMS m/z 273 (M+H). Anal. Calc'd for C$_{13}$H$_{11}$F$_3$O$_3$: C, 57.36; H, 4.07. Found.: C, 57.15; H, 4.11.

EXAMPLE 29

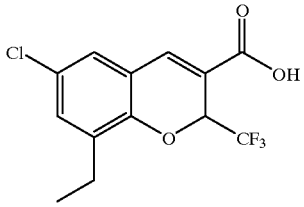

6-Chloro-8-ethyl-2-trifluoromethyl-2H-1-benzopyran-3-carboxylic Acid

8-Ethyl-2-(trifluoromethyl)2H-1-benzopyran-3-carboxylic acid (Example 28) (0.68 g, 2.5 mmol) was dissolved in trimethylphosphate (5 mL) and was treated with sulfuryl chloride (0.35 g, 2.62 mmol) at 0° C. After stirring at 0° C. for 45 minutes and 1 hour at room temperature, the reaction was diluted with cold water (15 mL). The resulting oily mixture was extracted with hexanes-ethyl acetate. The organic phase was washed with brine, dried, and concentrated in vacuo yielding the title compound as a solid (0.9 g, 117%): mp 197.2–199.1° C. $^1$H NMR (acetone-d$_6$/300 MHz) 7.86 (s, 1H), 7.38 (d, 1H, J=2.7 Hz), 7.30 (d, 1H, J=2.4 Hz), 5.88 (q, 1H, J=7.2 Hz), 2.65 (m, 2H), 1.19 (t, 3H, J=7.5 Hz). FABLRMS m/z 307 (M+H). Anal. Calc'd for C$_{13}$H$_{10}$ClF$_3$O$_3$: C, 50.92; H, 3.29. Found: C, 51.00; H, 3.23.

EXAMPLE 30

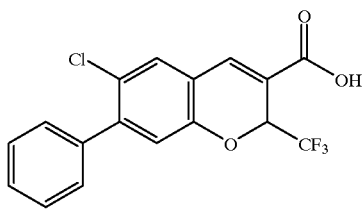

6-Chloro-7-phenyl-2-trifluoromethyl-2H-1-benzopyran-3-carboxylic Acid

7-Phenyl-2-(trifluoromethyl)-2H-1-benzopyran-3-carboxylic acid (Example 26) was converted to the title compound by a procedure similar to that described in Example 29: mp 185.3–187.8° C. $^1$H NMR (acetone-dW/300 MHz) 7.94 (s, 1H), 7.68 (s, 1H), 7.47 (m, 5H), 7.06 (s, 1H), 5.87 (q, 1H, J=6.9 Hz). FABLRMS m/z 355 (M+H). Anal. Calc'd for C$_{17}$H$_{10}$ClF$_3$O$_3$: C, 57.56; H, 2.84. Found: C, 58.27; H, 3.11.

EXAMPLE 31

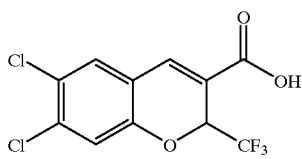

6,7-Dichloro-2-trifluoromethyl-2H-1-benzopyran-3-carboxylic Acid 3,4-Dichlorophenol was converted to the title compound by a procedure similar to that described in Example 2: mp 196.1–198.3° C. $^1$H NMR (acetone-d$_6$/300 MHz) 7.90 (s, 1H), 7.74 (s, 1H), 7.30 (s, 1H), 5.88 (q, 1H, J=6.9 Hz) FABLRMS m/z 314 (M+H). Anal. Calc'd for C$_{11}$H$_5$Cl$_2$F$_3$O$_3$: C, 42.20; H, 1.61. Found: C, 42.31; H, 1.65.

EXAMPLE 32

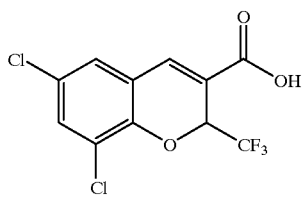

6,8-Dichloro-2-trifluoromethyl-2H-1-benzopyran-3-carboxylic Acid 3,5-Dichlorosalicylaldehyde was converted to the title compound by a procedure similar to that described in Example 11, Steps 2 & 3: mp 212.8–216.8° C. $^1$H NMR (CDCl$_3$/300 MHz) 7.77 (s, 1H), 7.41 (d, 1H, J=2.4 Hz), 7.18 (d, 1H, J=2.2 Hz), 5.82 (q, 1H, J=6.7 Hz). FABLRMS m/z 311 (M–H). FABHRMS m/z 312.9644 (M+H, Calc'd 312.9646). Anal. Calc'd for C$_{11}$H$_5$F$_3$Cl$_2$O$_3$: C, 42.20; H, 1.61. Found: C, 42.50; H, 1.71.

EXAMPLE 33

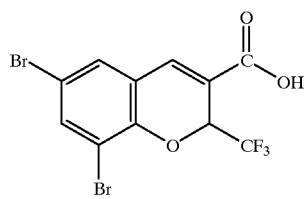

6,8-Dibromo-2-trifluoromethyl-2H-1-benzopyran-3-carboxylic Acid 3,5-Dibromosalicylaldehyde was converted to the title compound by a procedure similar to that described in Example 1: mp 225–226° C. $^1$H NMR (CD$_3$OD/300 MHz) 7.76 (s, 1H), 7.74 (d, 1H, J=2.2 Hz), 7.55 (d, 1H, J=2.2 Hz), 5.91 (q$_{H-F}$, 1H, J=7.2 Hz). FABHRMS m/z 400.8648 (M+H$^+$, Calc'd 400.8636). Anal. Calcd for C$_{11}$H$_5$Br$_2$F$_3$O$_3$: C, 32.87; H, 1.25. Found: C, 33.47; H, 1.38.

EXAMPLE 34

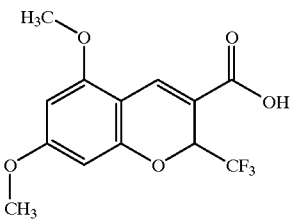

6,8-Dimethoxy-2-trifluoromethyl-2H-1-benzopyran-3-carboxylic Acid 4, 6-Dimethoxysalicylaldehyde was converted to the title compound by a procedure similar to that described in Example 1: mp 215–217° C. $^1$H NMR (CD$_3$OD/300 MHz) 7.95 (s, 1H), 6.18–6.20 (m, 2H), 5.65 (q$_{H-F}$, 1H, J=7.2 Hz), 3.87 (s, 1H), 3.81 (s, 1H). FABHRMS m/z 303.0497 (M–H$^+$, Calc'd 303.0380). Anal. Calc'd for C$_{13}$H$_{11}$F$_3$O$_5$: C, 51.33; H, 3.64. Found: C, 51.19; H, 3.71.

EXAMPLE 35

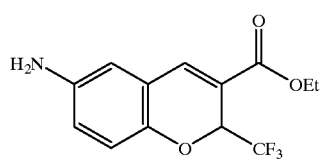

Ethyl 6-amino-2-trifluoromethyl-2H-1-benzopyran-3-carboxylate

Step 1. Preparation of ethyl 6-nitro-2-(trifluoromethyl)-2H-1-benzopyran-3-carboxylate.

A mixture of 5-nitrosalicylaldehyde (4.80g, 28.7 mmol) and ethyl 4,4,4-trifluorocrotonate (6.6 g, 39.4 mol) in anhydrous DMF was warmed to 60° C. and treated with anhydrous $K_2CO_3$ (3.90 g, 28.9 mol). The solution was maintained at 60° C. for 20 hours, cooled to room temperature, diluted with water, and extracted with ethyl acetate. The organic extracts were washed with brine, dried over anhydrous $MgSO_4$, filtered and concentrated in vacuo to afford an oil. The oil was dissolved in diethyl ether (5 mL). Hexanes was added until the solution became cloudy. Upon standing at room temperature overnight the ester was obtained as yellow crystals (0.856 g, 7% yield). This material was of sufficient purity to be used in subsequent steps without further purification. $^1$H NMR ($CDCl_3$/300 MHz) 8.15–8.19 (m, 2H), 7.74 (s, 1H), 7.09 (d, 1H, J=8.9 Hz), 5.81 (q, 1H, J=5.8 Hz), 4.29–4.39 (m, 2H), 1.35 (t, 3H, J=6.0 Hz),
Step 2. Preparation of ethyl 6-amino-2-(trifluoromethyl)-2H-1-benzopyran-3-carboxylate.

The ester (Step 1)(0.345 g, 1.08 mmol) was stirred in ethanol (10.0 mL) with 10% palladium on charcoal (15 mg) with hydrogen at 1 atmosphere for 1 hour. The catalyst was removed by filtration and the solvent removed in vacuo to afford the title compound as an orange-yellow solid (0.298 g, 95%): mp 111–115° C. ($CD_3OD$/300 MHz) 7.69 (s, 1H), 6.69–6.74 (m, 3H), 5.65 ($q_{H-F}$, 1H, J=7.2 Hz), 4.26–4.37 (m, 2H), 1.34 (t, 3H, J=7 Hz). FABHRMS m/z 288.0860 (M+H$^+$, $C_{13}H_{13}F_3NO_3$ requires 288.0847). Anal. Calc'd for $C_{13}H_{12}F_3NO_3$: C, 54.36; H, 4.21; N, 4.88. Found: C, 54.46; H, 4.27; N, 4.83.

EXAMPLE 36

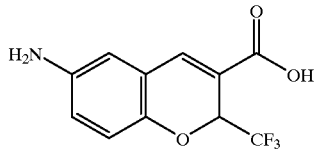

6-Amino-2-trifluoromethyl-2H-1-benzopyran-3-carboxylic Acid

Ethyl 6-amino-2-(trifluoromethyl)-2H-1-benzopyran-3-carboxylate (Example 35, Step 2) was hydrolyzed to the carboxylic acid (title compound) by a procedure similar to that described in Example 1, Step 2: mp 126–133° C. $^1$H NMR ($CD_3OD$/300 MHz) 6.81–6.90 (m, 3H), 5.66 ($q_{H-F}$, 1H, J=7.2 Hz). FABHRMS m/z 260.0535 (M+H$^+$, $C_{11}H_9F_3NO_5$ requires 260.0534).

EXAMPLE 37

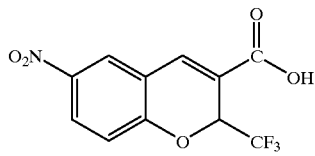

6-Nitro-2-trifluoromethyl-2H-1-benzopyran-3-carboxylic Acid

Ethyl 6-nitro-2-(trifluoromethyl)-2H-1-benzopyran-3-carboxylate (Example 35, Step 1) was hydrolyzed to the carboxylic acid (title compound) by a procedure similar to that described in Example 1, Step 2: mp 187–189° C. $^1$H NMR ($CD_3OD$/300 MHz) 8.34 (d, 1H, J=2.6 Hz), 8.27 (dd, 1H, J=8.7, 2.6 Hz), 7.90 (s, 1H), 7.09 (s, 1H, J=8.7 Hz), 5.81 ($q_{H-F}$, 1H, J=7.2 Hz). EIHRMS m/z 289.0177 (Calc'd 289.0198). Anal. Calc'd for $C_{11}H_6F_3NO_5$: C, 45.69; H, 2.09; N 4.84 Found: C, 45.71; H, 2.08; N 4.75.

EXAMPLE 38

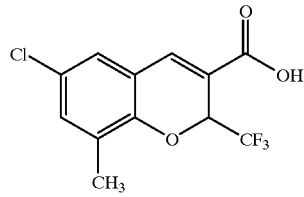

6-Chloro-8-methyl-2-trifluoromethyl-2H-1-benzopyran-3-carboxylic Acid

4-Chloro-2-methylphenol was converted to the title compound by a procedure similar to that described in Example 2: mp 231.9–233.2° C. $^1$H NMR ($CDCl_3$/300 MHz) 7.76 (s, 1H), 7.19 (d, 1H, J=1.8 Hz), 7.09 (d, 1H, J=2.4 Hz), 5.72 (q, 1H, J=6.9 Hz), 2.24 (s, 3H). $^{19}$F NMR ($CDCl_3$/282 MHz) −79.2 (d, J=6.5 Hz). FABLRMS m/z 299 (M+Li). FABHRMS m/z 293.0196 (M+H, Calc'd 293.0192). Anal. Calc'd for $C_{12}H_8ClF_3O_3$: C, 49.25; H, 2.76. Found: C, 49.37; H, 2.86.

EXAMPLE 39

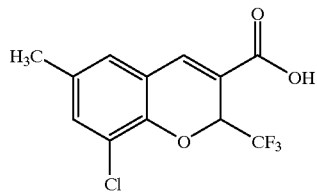

8-Chloro-6-methyl-2-trifluoromethyl-2H-1-benzopyran-3-carboxylic Acid

2-Chloro-4-methylphenol was converted to the title compound by a procedure similar to that described in Example 2: mp 226.4–227.4° C. $^1$H NMR ($CDCl_3$/300 MHz) 7.79 (s, 1H), 7.23 (d, 1H, J=1.4 Hz), 6.97 (d, 1H, J=1.4 Hz), 5.77 (q, 1H, J=6.8 Hz), 2.29 (s, 3H). $^{19}$F NMR ($CDCl_3$/282 MHZ) −79.1 (d, J=7.3 Hz). FABLRMS m/z 291 (M−H). EIHRMS m/z 292.0118 (M+, $C_{12}H_8ClF_3O_3$ Calc'd 292.0114).

EXAMPLE 40

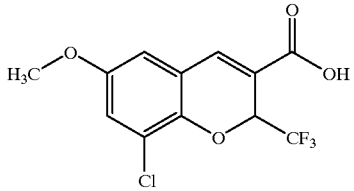

8-Chloro-6-methoxy-2-trifluoromethyl-2H-1-benzopyran-3-carboxylic Acid

2-Chloro-4-methoxyphenol was converted to the title compound by a procedure similar to that described in Example 2: mp 204.5–206.9° C. ¹H NMR (CDCl₃/300 MHz) 7.78 (s, 1H), 6.98 (d, 1H, J=2.8 Hz), 6.71 (d, 1H, J=2.8 Hz), 5.74 (q, 1H, J=6.9 Hz), 3.79 (s, 3H). FABLRMS m/z 326 (M+NH₄). EIHRMS m/z 308.0053 (M+Calc'd 308.0063). Anal. Calc'd for C₁₂H₈ClF₃O₄: C, 46.70; H, 2.61. Found: C, 46.60; H, 2.68.

EXAMPLE 41

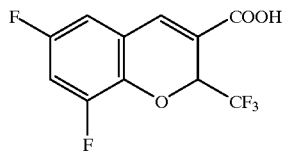

6,8-Difluoro-2-trifluoromethyl-2H-1-benzopyran-3-carboxylic Acid 2,4-Difluorophenol was converted to the title compound by a procedure similar to that described in Example 2: mp 207–211° C. ¹H NMR (CDCl₃) 7.63 (s, 1H), 6.89–6.72 (m, 2H), 5.69 (q, 1H, J=6.7 Hz). Anal. Calc'd for C₁₁H₅O₃F₅: C, 47.16; H, 1.80. Found: C, 47.28; H, 1.87.

EXAMPLE 42

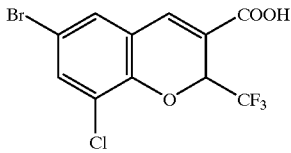

6-Bromo-B-chloro-2-trifluoromethyl-2H-1-benzopyran-3-carboxylic Acid

4-Bromo-2-chlorophenol was converted to the title compound by a procedure similar to that described in Example 2: mp 220.7–221.7° C. ¹H NMR (CDCl₃) 7.58 (s, 1H), 7.44 (d, 1H, J=2.2 Hz), 7.22 (d, 1H, J=2.2 Hz), 5.74 (q, 1H, J=6.8 Hz). Anal. Calc'd for C₁₁H₅O₃F₃BrCl: C, 36.96; H, 1.41. Found: C, 37.03; H, 1.44.

EXAMPLE 43

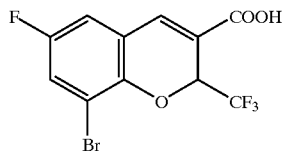

8-Bromo-6-fluoro-2-trifluoromethyl-2H-1-benzopyran-3-carboxylic Acid

2-Bromo-4-fluorophenol was converted to the title compound by a procedure similar to that described in Example 2: mp >300° C. ¹H NMR (CDCl₃) 7.58 (s, 1H), 7.22 (dd, 1H, J=6.3, 3 Hz), 6.88 (dd, 1H, J=6.1, 3.1 Hz), 5.72 (q, 1H, J=6.7 Hz). Anal. Calc'd for C₁₁H₅O₃F₄Br: C, 38.74; H, 1.48. Found: C, 38.82; H, 1.56.

EXAMPLE 44

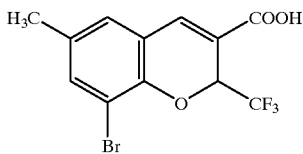

8-Bromo-6-methyl-2-trifluoromethyl-2H-1-benzopyran-3-carboxylic Acid

2-Bromo-4-methylphenol was converted to the title compound by a procedure similar to that described in Example 2: mp 237–238° C. ¹H NMR (CDCl₃) 7.59 (s, 1H), 7.27 (m, 1H), 6.91 (d, 1H, J=1.4 Hz), 5.69 (q, 1H, J=6.9 Hz), 2.20 (s, 3H). Anal. Calc'd for C₁₂H₈O₃F₃Br: C, 42.76; H, 2.39. Found: C, 43.34; H, 2.56.

EXAMPLE 45

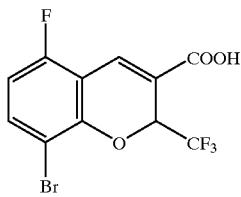

8-Bromo-5-fluoro-2-trifluoromethyl-2H-1-benzopyran-3-carboxylic Acid

2-Bromo-4-fluorophenol was converted to the title compound by a procedure similar to that described in Example 2: mp 221.7–223.3° C. ¹H NMR (CDCl₃) 7.81 (s, 1H), 7.38 (dd, 1H, J=7.3, 5.8 Hz), 6.58 (t, 1H, J=8.9 Hz), 5.71 (q, 1H, J=6.7 Hz). Anal. Calc'd for C₁₁H₅O₃F₄Br: C, 38.74; H, 1.48. Found: C, 38.70; H. 1.54.

EXAMPLE 46

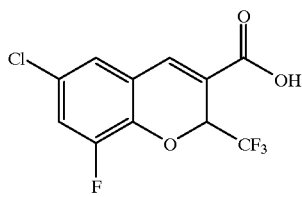

6-Chloro-8-fluoro-2-trifluoromethyl-2H-1-benzopyran-3-carboxylic Acid

4-Chloro-2-fluorophenol was converted to the title compound by a procedure similar to that described in Example 2: mp 190.8–193.0° C. ¹H NMR (CDCl₃/300 MHz) 7.77 (s, 1H), 7.19 (d of d, 1H, J=2.2 and 9.7 Hz), 7.07 (t, 1H, J=1.8 Hz), 5.76 (q, 1H, J=6.7 Hz). FABLRMS m/z 295 (M–H). EIHRMS m/z 295.9876 (M+ Calc'd 295.9863). Anal. Calc'd for C₁₁H₅ClF₄O₃: C, 44.54; H, 1.70. Found: C, 44.36; H, 1.85.

EXAMPLE 47

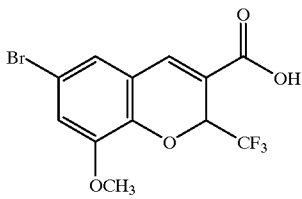

6-Bromo-8-methoxy-2-trifluoromethyl-2H-1-benzopyran-3-carboxylic Acid

4-Bromo-2-methoxysalicylaldehyde was converted to the title compound by a procedure similar to that described in Example 1: mp dec. at 244° C. $^1$H NMR (CD$_3$OD/300 MHz) 7.71 (s, 1H), 7.18 (d, 1H, J=2.2 Hz), 7.11 (d, 1H, J=2.2 Hz), 5.77 (q$_{H-F}$, 1H, J=7.2 Hz), 3.84 (s, 3H). FABLRMS m/z 351 (m-H). Anal. Calc'd for C$_{12}$H$_8$BrF$_3$O$_5$: C, 40.82; H, 2.28. Found: C, 40.83; H, 2.30.

EXAMPLE 48

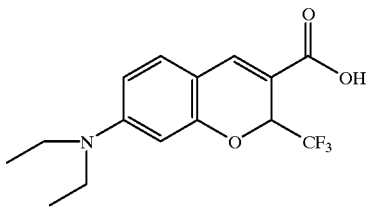

7-(N,N-Diethylamino)-2-trifluoromethyl-2H-1-benzopyran-3-carboxylic Acid 4-(N,N-Diethylamino)salicylaldehyde was converted to the title compound by a procedure similar to that described in Example 1: mp 214.4–215.4° C. $^1$H NMR (CD$_3$OD/300 MHz) 7.67 (s, 1H), 7.06 (d, 1H, J=8.6 Hz), 6.34 (dd, 1H, J=8.6, 2.3 Hz), 5.60 (q$_{H-F}$, 1H, J=7.2 Hz), 3.38 (q, 4H, J=7.1 Hz), 1.16 (t, 6H, J=7.1 Hz). ESLRMS m/z 316 (M+H). FABHRMS m/z 316.1145 (M+H$^+$, Calc'd 316.1161). Anal. Calc'd for C$_{15}$H$_{16}$F$_3$NO$_3$: C, 57.14; H, 5.11; N, 4.44. Found: C, 57.14; H, 5.08; N, 4.44.

EXAMPLE 49

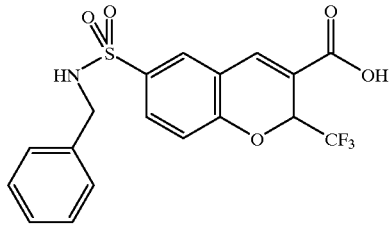

6-[[(Phenylmethyl)amino]sulfonyl]-2-trifluoromethyl-2H-1-benzopyran-3-carboxylic Acid Step 1. Preparation of Ethyl 6-chlorosulfonyl-2-trifluoromethyl-2H-1-benzopyran-3-carboxylate.

Chlorosulfonic acid (50.0 mL) was cooled to 15° C. and ethyl 2-trifluoromethyl-2H-1-benzopyran-3-carboxylate (Example 10, Step 2) (6.21 g, 22.83 mmol) was added. After stirring at −15° C. for 1 hour, the solution was warmed to room temperature and stirred for 16 hours. The solution was added dropwise onto ice (500 mL) with vigorous stirring and extracted with diethyl ether (2×250 mL). The ether layers were combined, washed with water (2×250 mL), saturated sodium bicarbonate (2×250 mL), and brine (2×250 mL). Hexanes (50 mL) were added and the solution was dried over sodium sulfate. The solvent was removed in vacuo to afford the ester as a yellow solid (7.41 g, 87%): mp 97.2–98.4° C. $^1$H NMR (CDCl$_3$, 300 MHz) 7.97 (dd, 1H, J=8.6, 2.2. Hz), 7.92 (d, 1H, J=2.2 Hz), 7.73 (s, 1H), 7.17 (d, 1H, J=2.2 Hz), 5.82 (q$_{H-F}$, 1H, J=7.2 Hz), 4.28–4.39 (m, 2H), 1.35 (t, 3H, J=7.0 Hz). FABLRMS m/z 376 (M+Li$^+$).

Step 2. Preparation of Ethyl 6-[[(phenylmethyl)amino]sulfonyl]-2-trifluoromethyl-2H-1-benzopyran-3-carboxylate.

The sulfonyl chloride from Step 1 (451.0 mg, 1.22 mmol) and benzylamine (600 mg, 5.62 mmol) were mixed in diethyl ether (25 mL) for 1 hour at room temperature. The solution was washed with 1N HCl (2×25 mL), saturated sodium bicarbonate (2×25 mL), and brine (2×25 mL). The solution was dried over sodium sulfate and dried in vacuo. The aminosulfonyl was obtained by crystallization from hexanes (431 mg, 84%): mp 128.2–131.9° C. $^1$H NMR (CDCl$_3$, 300 MHz) 7.76 (dd, 1H, J=8.4, 2.2. Hz), 7.70 (d, 1H, J=2.2 Hz), 7.67 (s, 1H), 7.12–7.30 (m, 5H), 7.05 (d, 1H, J=8.4 Hz), 5.78 (q$_{H-F}$, 1H, J=7.2 Hz), 4.68 (m, 2H), 4.19–4.32 (m, 2H), 1.37 (t, 3H, J=7.0 Hz). FABLRMS m/z 442 (M+H$^+$). FABHRMS m/z 442.0936 (M+H$^+$, C$_{20}$H$_{19}$F$_3$NO$_5$S Calc'd 442.0916).

Step 3. Preparation of 6-[[(phenylmethyl)amino]sulfonyl]-2-trifluoromethyl-2H-1-benzopyran-3-carboxylic Acid.

The acid was converted from the ester (step 2) via the method similar to that described in Example 1, step 2: mp 223.3–224.4° C. $^1$H NMR (CD$_3$OD/300 MHz) 7.31–7.80 (m, 3H), 7.15–7.25 (m, 5H), 7.06 (d, 1H, J=8.3 Hz), 5.87 (q$_{H-F}$, 1H, J=7.2 Hz), 4.11 (s, 2H). FABLRMS m/z 420 (M+Li$^+$). FABHRMS m/z 414.0589 (M+H$^+$ Calc'd 414.0623). Anal. Calc'd for C$_{18}$H$_{14}$F$_3$NO$_5$S: C, 52.30; H, 3.41; N, 3.39. Found: C, 5.16; H, 3.44; N, 3.32.

EXAMPLE 50

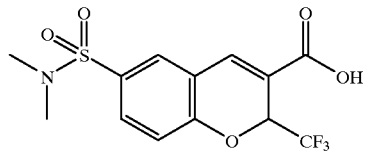

6-[(Dimethylamino)sulfonyl]-2-trifluoromethyl-2H-1-benzopyran-3-carboxylic acid

The title compound was prepared by a similar procedure to that described in Example 49: mp 201.2–202.5° C. $^1$H NMR (CD$_3$OD/300 MHz) 7.90 (s, 1H), 7.82 (d, 1H, J=2.2 Hz), 7.76 (dd, 1H, J=8.6, 2.2 Hz), 7.19 (d, 1H, J=8.6 Hz), 5.91 (q$_{H-F}$, 1H, J=7.2 Hz), 2.70 (s, 6H). FABLRMS m/z 352 (M+H$^+$). FABHRMS m/z 352.0466 (M+H$^+$ Calc'd 352.0467). Anal. Calc'd for C$_{13}$H$_{12}$F$_3$NO$_5$S: C, 44.45; H, 3.44; N, 3.99. Found: C, 4.42; H, 3.45; N, 3.96.

EXAMPLE 51

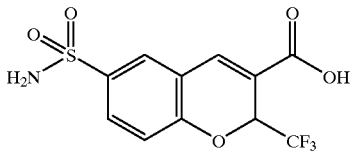

6-Aminosulfonyl-2-trifluoromethyl-2H-1-benzopyran-3-carboxylic Acid

The title compound was prepared by a similar procedure to that described in Example 10 49: mp 187.9–189.8° C. $^1$H NMR (CD$_3$OD/300 MHz) 7.58–7.88 (m, 3H), 7.12 (d, J=8.3 Hz), 5.87 (q$_{H-F}$, 1H, J=7.2 Hz). FABLRMS m/z 324 (M+H$^+$). FABHRMS m/z 324.0156 (M+H$^+$ Calc'd 324.0154). Anal. Calc'd for C$_{11}$H$_8$F$_3$NO$_5$S * 0.74 H$_2$O: C, 39.26; H, 2.84; N, 4.16. Found: C, 39.33; H, 2.82; N, 4.11.

EXAMPLE 52

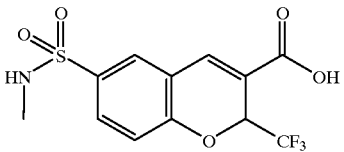

6-(Methylamino)sulfonyl-2-trifluoromethyl-2H-1-benzopyran-3-carboxylic Acid

The title compound was prepared by a similar procedure to that described in Example 49: mp 207.6–208.6° C. $^1$H NMR (CD$_3$OD/300 MHz) 7.83–7.97 (m, 3H), 7.19 (d, 1H, J=8.5 Hz), 5.91 (q$_{H-F}$, 1H, J=7.2 Hz), 3.11 (s, 3H). FABLRMS m/z 338 (M+H$^+$). FABHRMS m/z 338.0331 (M+H$^+$ Calc'd 338.0310). Anal. Calc'd for C$_{12}$H$_{11}$F$_3$NO$_5$S: C, 42.73; H, 2.99; N, 4.15. Found: C, 42.91; H, 3.06; N, 4.04.

EXAMPLE 53

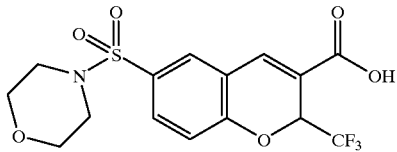

6-[(4-Morpholino)sulfonyl]-2-trifluoromethyl-2H-1-benzopyran-3-carboxylic Acid The title compound was prepared by a similar procedure to that described in Example 49: mp 215.2–219.3° C. $^1$H NMR (CD$_3$OD/300 MHz) 7.88 (S, 1H), 7.81 (d, 1H, J=2.2 Hz), 7.74 (dd, 1H, J=8.6, 2.2 Hz), 5.90 (q$_{H-F}$, 1H, J=7.2 Hz), 3.54–3.70 (m, 4H), 2.94–2.97 (m, 4H). FABLRMS m/z 394 (M+H$^+$). FABHRMS 394.0567 (M+H$^+$, C$_{15}$H$_{15}$F$_3$NO$_6$S Calc'd 394.0572).

EXAMPLE 54

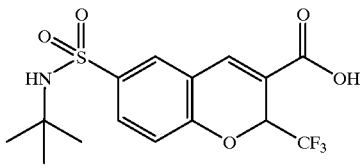

6-[(1,1-Dimethylethyl)aminosulfonyl]-2-trifluoromethyl-2H-1-benzopyran-3-carboxylic Acid The title compound was prepared by a similar procedure to that described in Example 49: mp 229.3–233.5° C. $^1$H NMR (CD$_3$OD/300 MHz) 7.82–7,87 (m, 3H), 7.12 (d, 1H, J=8.6 Hz), 5.87 (q$_{H-F}$, 1H, J=7.2 Hz), 1.18 (s, 9H). FABLRMS m/z 380 (M+H$^+$). Anal. Calc'd for C$_{15}$H$_{16}$F$_3$NO$_5$S: C, 47.49; H, 4.25; N, 3.69. Found: C, 47.95; H, 4.48; N, 3.55.

EXAMPLE 55

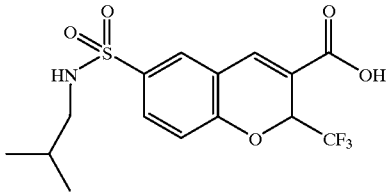

6-[(2-Methylpropyl) aminosulfonyl]-2-trifluoromethyl-2H-1-benzopyran-3-carboxylic Acid The title compound was prepared by a similar procedure to that described in Example 49: mp 190.6–192.4° C. $^1$H NMR (CD$_3$OD/300 MHz) 7.77–7.84 (m, 3H), 7.13 (d, 1H, J=8.4 Hz), 5.86 (q$_{H-F}$, 1H, J=7.2 Hz), 2.64 (d, 2H, J=6.8 Hz), 1.66 (sept, 1H, J=6.6 Hz), 0.84 (d, 6H, J=6.6 Hz). FABLRMS m/z 380 (M+H$^+$). Anal. Calc'd for C$_{15}$H$_{16}$F$_3$NO$_5$S: C, 47.49; H, 4.25; N, 3.69. Found: C, 47.61; H, 3.34; N, 3.55.

EXAMPLE 56

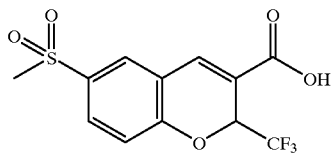

6-Methylsulfonyl-2-trifluoromethyl-2H-1-benzopyran-3-carboxylic Acid

Step 1. Preparation of 6-chlorosulfonyl-2-(trifluoromethyl)-2H-1-benzopyran-3-carboxylic Acid.

To chlorosulfonic acid (50.0 mL) chilled to −15° C. was added 2-(trifluoromethyl)-2H-1-benzopyran-3-carboxylic acid (Example 10) (4.0 g, 16.7 mmol). After stirring at −15° C. for 1 hour, the solution was warmed to room temperature and stirred for 16 hours. The resulting solution was added dropwise over ice (100 mL) with two diethyl ether(2×75 mL) extractions. The diethyl ether layers were combined, washed with water (2×75 mL), and brine (2×75 mL, dried over sodium sulfate and concentrated in vacuo. The resulting solids were triturated with hexane-ethyl acetate (9:1, 100 mL). The 6-chlorosulfonyl-2-trifluoromethyl-2H-1-benzopyran-3-carboxylic acid was isolated as a white solid: mp 169–174. $^1$H NMR (CD$_3$OD/300 MHz) 8.18 (d, 1H, J=2.7 Hz), 8.06 (dd, 1H, J=8.7, 2.7 Hz), 7.93 (s, 1H), 7.28 (d, 1H, J=8.7 Hz), 6.00 (q, 1H, J=6.6 Hz). EIHRMS m/z 324.9977 (M+, Calcd 324.9994).

Step 2. Preparation of 6-methylsulfonyl-2-(trifluoromentyl)-2H-1-benzopyran-3-carboxylic Acid A slurry of the chlorosulfonyl intermediate (Example 49, Step 1)(493 mg, 1.44 mmol), sodium bicarbonate (362 mg, 4.32 mmol), and sodium bisulfite (181 mg, 1.44 mmol) in water (1.5 mL)was heated to 60° C. for 1.5 h, followed by the addition of bromoacetic acid (212 mg, 1.55 mmol). The resulting suspension was heated to reflux, followed by the addition of sodium hydroxide solution (50% NaOH soln., 0.10 mL) and water (3.0 mL). The solution was reluxed for 8 hours, cooled to room temperature, and acidified to pH 1 with 1N aqueous hydrochloric acid. The solution was extracted with ethyl acetate (2×25 mL). The combined ethyl acetate layers were washed with 1N aqueous hydrochloric acid (2×25 mL), water (2×25 mL), and brine (2×25 mL), dried over sodium sulfate, filtered and concentrated in vacuo yielding the title compound as an off white solid. (231 mg, 50% yield): mp 208.3–212.4° C. $^1$H NMR (CD$_3$OD, 300 MHz) 7.97 (d, 1H, 2.2 Hz), 7.91 (1H, dd, J=8.7, 2.2 Hz), 7.19 (d, 1H, J=8.7 Hz), 5.91 (q$_{H-F}$, 1H, J=7.2 Hz), 3.11 (s, 1H) HRLRMS m/z 321 (M−H)FABLRMS m/z 321 (M−H). Anal. Calc'd for C$_{12}$H$_9$F$_3$O$_5$S*0.61 H$_2$O: C, 43.26; H, 3.09. Found: C, 43.24; H, 3.09.

EXAMPLE 57

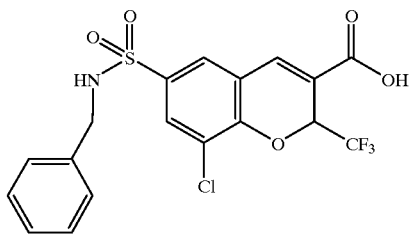

8-Chloro-6-[[(phenylmethyl)amino]sulfonyl]-2-trifluoromethyl-2H-1-benzopyran-3-carboxylic Acid The title compound was prepared by a similar procedure to that described in Example 49: mp 167.0–173.8° C. $^1$H NMR (CD$_3$OD/300 MHz) 7.78 (s, 1H), 7.72 (d, 1H, J=2.0 Hz), 7.64 (d, 1H, J=2.0 Hz). 7.44 (d, 1H), 7.15–7.23 (m, 5H), 6.01 (q$_{H-F}$, 1H, J=7.2 Hz),4.08–4.15 (m, 2H). FABLRMS ml/z 454 (M+Li$^+$). Anal. Calc'd for C$_{16}$H$_{13}$CF$_3$NO$_5$S: C, 48.28; H, 2.93; N, 3.13. Found: C, xx; H, xx; N, xx

EXAMPLE 58

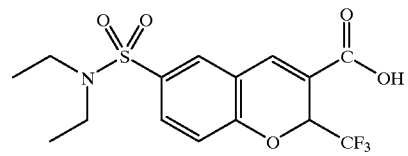

6-N,N-Diethylaminosulfonyl-2-trifluoromethyl-2H-1-benz opyran-3-carboxylic Acid

The title compound was prepared by a similar procedure to that described in Example 49: mp 238–240° C. $^1$H NMR (CD$_3$OD/300 MHz) 7.88 (s, 1H), 7.85 (d, 1H, J=2.2 Hz), 7.79 (dd, 1H, J=8.5, 2.2 Hz), 7.14 (d, 1H, J=8.5 Hz), 5.88 (q$_{H-F}$, 1H, J=7. 2 Hz), 3.24 (q, 2H, J=7.3 Hz), 1.11 (t, 3H, J=7.3 Hz). FABHRMS m/z 380.0763 (M+H$^+$, Calc'd 380.0780). Anal. Calc'd for C$_{15}$H$_{16}$F$_3$NO$_4$S: C, 47.49; H, 4.25; H, 3.69. Found: C, 47.62; H, 4.30; N, 3.72.

EXAMPLE 59

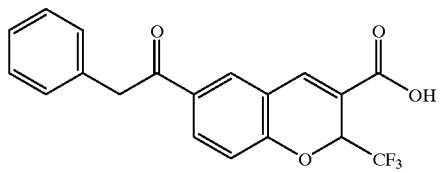

6-Phenylacetyl-2-trifluoromethyl-2H-1-benzopyran-3-carboxylic Acid

Step 1. Preparation of Ethyl 6-phenylacetyl-2-trifluoromethyl-2H-1-benzopyran-3-carboxylate.

2-Trifluoromethyl-2H-1-benzopyran-3-carboxylic acid (Example 10) (1.32 g, 4.85 mmol) was cooled to 0° C. in dichloromethane (50 mL). Aluminum chloride (2.58 g, 19.5 mmol) was added and a dark red solution resulted. A solution of phenylacetyl chloride (1.8 g, 12.1 mmol) in dichloromethane (10.0 mL) was added dropwise over 40 minutes. The solution was warmed to room temperature and stirred for 16 hours. The solution was poured onto ice (200 mL) and extracted with diethyl ether (2×100 mL). The diethyl ether layers were combined, extracted with water (1×100 mL), 1 N HCl (2×100 mL), and saturated sodium bicarbonate (3×100 mL). Hexanes (20 mL) were added and the solution was extracted with brine (1×100 mL). The solution was dried over sodium sulfate and solvent was removed in vacuo. The crude ester was purified by flash chromatography over silica gel (with ethyl acetate as eluant) to afford the ester that was crystllized from diethyl ether/hexanes (830 mg, 44%): mp 136.2–138.0° C. $^1$H NMR (CDCl$_3$/300 MHz) 7.98 (dd, 2H, J=8.4, 2.0 Hz), 7.90 (d, 1H, J=2.0 Hz), 7.29 (s, 1H), 7.22–7.38 (m, 5H), 7.02 (d, 1H, J=8.4 Hz), 5.75 (q$_{H-F}$, 1H, J=7.2 Hz), 4.25 –4.40 (m, 2H), 4.21 (s, 2H), 1.34 (t, 3H, J=7.0 Hz). FABLRMS m/z 391(M+H$^+$).

Step 2. Preparation of 6-phenylacetyl-2-trifluoromethyl-2H-1-benzopyran-3-carboxylic Acid.

The acid was converted from the ester (Step 1) via a method similar to that described in Example 1, step 2: mp 159.0–164.0° C. $^1$H NMR (CD$_3$OD/300 MHz) 8.04–8.16 (m, 3H), 7.87 (s, 1H), 7.05–7.30 (m, 5H), 5.86 (q$_{H-F}$, 1H, J=7.2 Hz), 4.31 (s, 2H). FABLRMS m/z 363 (M+H$^+$). Anal. Calc'd for C$_{19}$H$_{13}$F$_3$O$_4$*0.29 H$_2$O: C, 62.08; H, 3.73. Found: C, 62.04; H, 4.03.

EXAMPLE 60

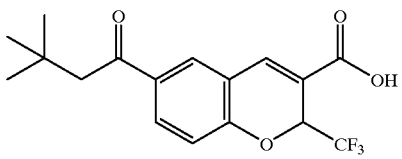

6-(2,2-Dimethylpropylcarbonyl)-2-trifluoromethyl-2H-1-benzopyran-3-carboxylic Acid The title compound was prepared by a similar procedure to that described in Example 59: mp 198–200° C. $^1$H NMR (CD$_3$OD/300 MHz) 7.98–8.06 (m, 2H), 7.88 (s, 1H), 7.07 (d, 1H, J=8.9 Hz), 5.86 (q$_{H\text{-}F}$, 1H, J=7.2 Hz), 2.88 (s, 2H), 1.05 (s, 9H). FABHRMS m/z 343.1175 (M+H$^+$, C$_{17}$H$_{18}$F$_3$O$_4$ requires 343.1157). Anal. Calc'd for C$_{17}$H$_{17}$F$_3$O$_4$: C, 59.65; H, 5.01. Found: C, 59.70; H, 4.97.

EXAMPLE 61

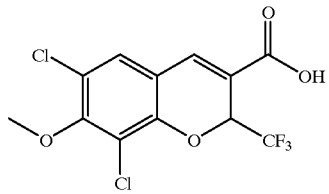

6,8-Dichloro-7-methoxy-2-trifluoromethyl-2H-1-benzopyran-3-carboxylic Acid

Step 1: Preparation of Ethyl 7-methoxy-2-trifluoromethyl-benzopyran-2H-3-carboxylate.

4-Methoxysalicylaldehyde (2.38 g, 15.64 mmol), K$_2$CO$_3$ (2.16 g, 15.64 mmol) and ethyl 4,4,4-trifluorocrotonate (2.8 mL, 3.16 g, 18.77 mmol) were dissolved in DMF (10 mL). The reaction was stirred at room temperature for 24 -hours, diluted with water and extracted with Et$_2$O. The combined Et$_2$O phases were washed with water, dried over MgSO$_4$, filtered and concentrated in vacuo yielding an oil. Trituration with hexanes induced crystallization. Collection of the solid by vacuum filtration yielded the ester as a light brown crystalline solid (1.80 g, 38%): mp 78–80° C. $^1$H NMR (CDCl$_3$/300 MHz) 5 7.69 (s. 1H), 7.14 (d, 1H, J=8.1 Hz), 6.59–6.50 (m, 2H), 5.68 (q, 1H, J=7.1 Hz), 4.39–4.24 (m, 2H), 3.82 (s, 3H), 1.34 (t, 3H, J=7.3 Hz). FABLRMS m/z 303 (M+H). FABHRMS m/z 303.0849 (M+H Calc'd 303.0844). Anal. Calc'd for C$_{14}$H$_{13}$F$_3$O$_4$: C, 55.63; H, 4.34. Found: C, 55.47; H, 4.31.

Step 2. Preparation of Ethyl 6,8-dichloro-7-methoxy-2-trifluoromethyl-benzopyran-2H-3-carboxylate.

Chlorine gas (excess) was added to a stirred solution of the ester (Step 1) (1.35 g, 4.47 mmol) in HOAc (30 mL) until the yellow color persisted. After 20 minutes, the reaction was sparged with nitrogen causing the reaction to become straw colored. Zinc (0.86 g, 13.40 mmol) was added to this solution with vigorous stirring. After 45 minutes, additional zinc (0.86 g, 13.40 mmol) was added and the reaction was stirred overnight. The crude mixture was diluted with EtOH and filtered through diatomaceous earth. The filtrate was concentrated in vacuo yielding a crystalline mass. This solid was dissolved in EtOAc, washed with 2N HCl, brine, dried over MgSO$_4$, filtered and concentrated in vacuo yielding an oil. The oil was dissolved in a minimum of isooctane, inducing crystallization. Vacuum filtration of the suspension yielded tan needles (1.078 g) which were recrystallized from isooctane yielding the dichloro ester as tan crystals (0.71 g, 43%) of suitable purity to use in the next step: mp 113.3–115.1° C. $^1$H NMR (acetone-d$_6$/300 MHz) 7.88 (s, 1H), 7.63 (s, 1H), 6.02 (q, 1H, J=6.8 Hz), 4.38–4.22 (m, 2H), 3.93 (s, 3H), 1.31 (t, 3H, J=7.1 Hz). $^{19}$F NMR (acetone-d$_6$/282 MHz) –80.00 (d, J=7.2 Hz).

Step 3: Preparation of 6,8-dichloro-7-methoxy-2-trifluoromethyl-benzopyran-2H-3-carboxylic Acid.

To a stirred solution of the dichloro ester from Step 2 (0.686 g, 1.848 mmol) in THF (10 mL) and EtOH (3 mL) was added NaOH (0.81 mL of 2.5 M aqueous solution, 2.03 mmol) in one portion. After stirring overnight the reaction was partially concentrated, diluted with H$_2$O and washed with diethyl ether. The resulting aqueous phase was sparged with nitrogen and acidified with 2N HCl solution causing the solution to become turbid. Filtration of this suspension yielded the title compound as a white powder (0.559 g, 88%): mp 195.6–199.1° C. $^1$H NMR (CDCl$_3$/300 MHz) 7.90 (s, 1H), 7.64 (s, 1H), 6.01 (q, 1H, J=6.8 Hz), 3,94 (s, 3H). $^{19}$F NMR (CDCl$_3$/282 MHz) –79.63 (d, J=7.1 Hz). FABL-RMS m/z 349 (M+Li). EIHRMS m/z 341.9681 (M+, Calc'd 341.9673). Anal. Calc'd for C$_{12}$H$_7$Cl$_2$F$_3$O$_4$: C, 42.01; H, 2.06. Found: C, 41.76; H, 2.14.

EXAMPLE 62

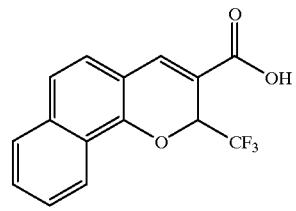

2-Trifluoromethyl-2H-naphtho[1,2-b]pyran-3-carboxylic Acid

Step 1. Preparation of Ethyl 2-trifluoromethyl-3H-naphthopyran-carboxylate.

A mixture of 2-hydroxy-1-naphthaldehyde (8.6 g, 0.050 mol) and ethyl 4,4,4-trifluorocrotonate (9.2 g, 0.055 mol) dissolved in anhydrous dimethylformamide (DMF) and treated with anhydrous K$_2$CO$_3$ (13.8 g, 0.100 mol). The solution was maintained at room temperature for 50 hours and diluted with water. The solution was extracted with ethyl acetate, and the combined extracts were washed with brine, dried over anhydrous MgSO$_4$, filtered and concentrated in vacuo to afford 4.8 g of an oil. The oil was purified by HPLC, eluting with hexanes:ethyl acetate (30:1). The appropriate fractions were concentrated to afford 1.6 g (10%) of the napthopyran ester as a yellow solid.

Step 2. Preparation of 2-trifluoromethyl-3H-naphthopyran-carboxylic Acid.

A solution of the ester from Step 1 (0.8 g, 2.5 mmol) was dissolved in 40 mL of ethanol and 10 mL of tetrahydrofuran, treated with sodium hydroxide (2.5 N, 10 mL, 25 mmol) and stirred at room temperature for 16 hours. The reaction mixture was acidified with 1.0 N HCl, whereupon a solid formed that was isolated by filtration. The solid was washed with 20 mL of water to afford 0.7 g (95%) of the title compound as a yellow solid: mp 245.9–248.6° C. $^1$H NMR (acetone-d$_6$/300 MHz) 8.57 (s, 1H), 8.28 (d, 1H, J=8.7 Hz), 8.03 (d, 1H, J=9.0 Hz), 7.93 (d, 1H, J=8.7), 7.67 (m, 1H), 7.50 (m, 1H), 7.28 (d, 1H, J=9.0), 5.96 (q$_{H\text{-}F}$, 1H, J=7.2 Hz). FABHRMS m/z 295.0561 (M+H, Calc'd 295.0582). Anal. Calc'd for C$_{15}$H$_9$O$_3$F$_3$+3.31% H$_2$O: C, 59.21; H, 3.35. Found: C, 59.17; H, 3.07.

EXAMPLE 63

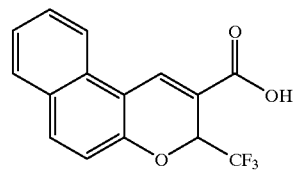

2-Trifluoromethyl-3H-naphtho[2,1-b]pyran-3-carboxylic Acid

2-Hydroxy-napth-1-aldehyde was converted to the title compound by a procedure similar to that described in Example 1: mp 244.7–249.8° C. $^1$H NMR (CDCl$_3$/300 MHz) 8.61 (s, 1H), 8.09 (d, $^1$H, J=8.3 Hz), 7.90 (d, 1H, J=8.9 Hz), 7.82 (d, 1H, J=8.3 Hz), 7.63 (t, 1H, J=8.1 Hz), 7.47 (t, 1H, J=8.1 Hz), 7.23 (d, 1H, J=9.1 Hz), 5.84 (q, 1H, J=6.8 Hz). $^{19}$F NMR (CDCl$_3$/282 MHz) −79.56 (d, J=7.3 Hz). FABLRMS m/z 295 (M+H). FABHRMS m/z 295.0560 (M+H, Calc'd 295.0582). Anal. Calc'd for C$_{15}$H$_9$F$_3$O$_3$: C, 61.23; H, 3.08. Found: C, 60.85; H, 3.12.

EXAMPLE 64

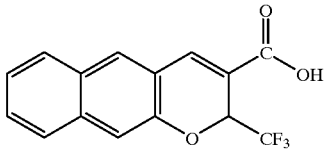

2-Trifluoromethyl-2H-naphtho[2,3-b]pyran-3-carboxylic Acid

3-Hydroxynapthalene-2-carboxylic acid was converted to 3-hydroxynapthalene-2-carboxaldehyde by a similar procedure to that described in Example 24, Steps 1 & 2. The 3-hydroxynapthalene-2-carboxaldehyde was converted to the title compound by a procedure similar to that described in Example 1: mp decompose >300° C. $^1$H NMR (CD$_3$OD/300 MHz) 7.99 (s, 1H), 7.90 (s, 1H), 7.84 (d, 1H, J=8.2 Hz), 7.74 (d, 1H, J=8.2 Hz), 7.50 (t, 1H, J=8.2 Hz), 7.39 (t, 1H, J=8.2 Hz), 7.34 (s, 1H), 5.77 (q, 1H, J=6.6 Hz). EIHRMS m/z 294.0474 (M+, Calc'd 294.0504).

EXAMPLE 65

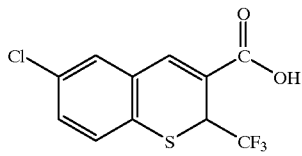

6-Chloro-2-trifluoromethyl-2H-1-benzothiopyran-3-carboxylic Acid

Step 1: Synthesis of 5-chloro-thiosalicylaldehyde.

Tetramethylethylenediamine (TMEDA)(10.44 mL, 8.035 g, 69.15 mmol) was added via syringe to n-BuLi (43.22 mL of 1.6 M in hexanes, 69.15 mmol) and the solution was chilled to 0° C. A solution of 4-chlorothiophenol (5.00 g, 34.57 mmol) in cyclohexane (25 mL) was added with stirring over 1 hour. The resulting tan slurry was stirred overnight at room temperature, chilled to 0° C., and DMF (2.94 mL, 2.78 g, 38.03 mmol) was added via syringe over 2 minutes. The resulting gummy slurry was stirred at room temperature for 30 hours and became a powdery suspension. A mixture of 2 N HCl and ice was added to the reaction mixture until the pH became acidic (pH=1). During this addition, the mixture warmed and became first red and then pale yellow. This mixture was extracted with ethyl acetate. The combined organic layers were washed with brine, dried over MgSO$_4$, filtered and concentrated in vacuo yielding a clear red-brown oil. This oil was triturated with hexanes yielding a red-brown semisolid. This semisolid was purified by plug flash chromatography over silica gel, eluting with 1:1, hexanes:dichloromethane to afford 5-chloro-thiosalicylaldehyde (0.858 g, 14%) as an intensely yellow solid suitable for use without further purification.

Step 2: Preparation of ethyl 6-chloro-2-trifluoromethyl-benzo-1-thiopyran-2-H-3-carboxylate.

5-Chloro-thiosalicylaldehyde (Step 1) (0.84 g, 4.86 mmol) was added to DMF (3 mL) and ethyl 4,4,4-trifluorocrotonate (1.10 mL, 1.22 g). With stirring, K$_2$CO$_3$ (0.67 g, 4.86 mmol) was added causing the reaction to become a deep red. After stirring overnight at room temperature, the reaction was diluted with diethyl ether and washed with water, saturated NaHCO$_3$ solution, aqueous KHSO$_4$ solution (0.25 M), brine, dried over MgSO$_4$, filtered and concentrated in vacuo yielding an oil. The oil was purified by flash chromatography (5:1; hexanes: ethyl acetate) yielding upon concentration ethyl 6-chloro-2-trifluoromethyl-benzo-1-thiopyran-2-H-3-carboxylate as a bright orange solid (0.492 g, 31%): mp 94.6–97.4° C. $^1$H NMR (acetone d$_6$/300 MHz) δ 8.01 (s, 1H), 7.71 (d, 1H, J=2.2 Hz), 7.50 (d, 1H, J=8.5 Hz), 7.44 (d of d, 1H, J=2.3, 8.3 Hz), 5.07 (q, 1H, J=8.5 Hz), 4.42–4.23 (m, 2H), 1.35 (t, 3H, J=7.1 Hz). FABLRMS m/z 329 (M+Li).

Step 3: Preparation of 6-chloro-2-trifluoromethyl-benzo-1-thiopyran-2-H-3-carboxylic Acid.

To a stirred solution of the ester from Step 2 (0.413 g, 1.280 mmol) in THF:EtOH:H$_2$O (7:2:1, mL) was added NaOH solution (0.56 mL of 2.5 N solution, 1.408 mmol) with stirring. After stirring overnight, the reaction was partially concentrated in vacuo to remove the organic solvents, diluted with H$_2$O and washed with several portions of diethyl ether. Acidification of the stirred aqueous phase with concentrated HCl caused precipitation of a flocculent yellow precipitate. Vacuum filtration of the suspension yielded 6-chloro-2-trifluoromethyl-benzo-1-thiopyran-2H-3-carboxylic acid as a yellow powder (0.25 g, 66%): mp 188.8–198.7° C. $^1$H NMR (acetone d$_6$/300 MHz) δ 8.02 (s, 1H), 7.71 (d, 1H, J=2.22 Hz), 7.50 (d, 1H, J=8.5 Hz), 7.44 (d of d, 1H, J=2.2, 8.5 Hz), 5.05 (q, 1H, J=8.6 Hz). $^{19}$F NMR (Acetone d$_6$/282 MHz) d −75.22 (d, J=8.7 Hz). FABLRMS m/z 301 (M+Li); ESLRMS (neg. ion) m/z 293 (M−H).

EXAMPLE 66

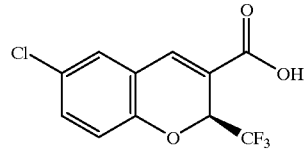

(S)-6-Chloro-2-trifluoromethyl-2H-1-benzopyran-3-carboxylic Acid

To a solution of 6-chloro-2-trifluoromethyl-2H-1-benzopyran-3-carboxylic acid (Example 1, Step 2) (12.00 g, 43.07 mmol) and (S) (−)-α-methylbenzylamine (2.61 g, 21.54 mmol) in methyl-tert-butyl ether (30 mL) was slowly added n-heptane (200 mL) until the mixture became cloudy. The mixture was heated (steam bath) to boiling and set aside for 24 h during which time crystals formed. Filtration of the suspension yielded a crystalline product (5.5 g) which was recrystallized from methyl-tert-butyl ether (30 mL) and n-heptane (200 mL) yielding upon filtration a white solid (3.1 g). This solid was dissolved in EtOAc (100 mL) and washed with 1 N hydrochloric acid (50 mL) and brine (2×50 mL), dried over MgSO$_4$ and concentrated in vacuo yielding a white solid. Recrystallization of this solid from methyl-t-butyl ether/n-heptane yielded the title compound as the highly enriched isomer, a white solid (2.7 g, 45%): mp 126.7–128.9° C. $^1$H NMR (CDCl$_3$/300 MHz) 7.78 (s, 1H), 7.3–7.1 (m, 3H), 6.94 (d, 1H, J=8.7 Hz), 5.66 (q, 1H, J=6.9 Hz). Anal. Calc'd for $C_{11}H_6O3F_3Cl$: C, 47.42; H, 2.17; N, 0.0. Found: C, 47.53; H, 2.14; N, 0.0. This compound was determined to have an optical purity of greater than 90% ee.

Procedure for Determining Optical Purity.

To a solution of the free acid (title compound) (0.005 g, 0.017 mmol) in ethyl acetate (1.5 mL) in a test tube was added (trimethylsilyl)diazomethane (30 μL of 2.0 N solution in hexanes, 60 mmol). The resulting yellow solution was warmed until the solution began to gently boil and then was allowed to cool to room temperature and stand for 0.08 hours. With vigorous mixing, the solution was quenched with aqueous 1 N HCl (1.5 mL). The layers were separated and a sample of the ethyl acetate fraction (0.3 mL) was transferred to a vial, concentrated under a stream of nitrogen, was diluted with hexane (total of 1 mL) and a sample (10 μL) analyzed by chiral chromatography. The HPLC utilized a Daicel ChiralPak AD column eluting with 10% isopropanol-hexane at 0.5 mL/min using a UV detector set at 254 nM.

EXAMPLE 67

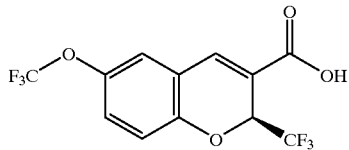

(S)-6-Trifluoromethoxy-2-trifluoromethyl-2H-1-benzopyran-3-carboxylic Acid

To a solution of 6-trifluoromethoxy-2-(trifluoromethyl)-2H-1-benzopyran-3-carboxylic acid (Example 16)(17.72 g, 54.00 mmol) and (−)cinchonidine (7.95 g, 27.04 mmol) in methyl-tert-butyl ether (100 mL) heated on a steam-bath was added n-heptane (200 mL). The mixture was heated on the steam bath to boiling and allowed to cool for 4 h during which time crystals formed. Filtration of the suspension yielded a crystalline solid (18.7 g). This solid was dissolved in 2-butanone (30 mL) followed by the addition of n-heptane (500 mL). After standing for 16 hours, the resulting suspension was filtered yielded a white solid (10.3 g). This solid was dissolved in ethyl acetate (150 mL), washed with 1 N hydrochloric acid (100 mL) and brine (2×50 mL), dried over $MgSO_4$, filtered, and concentrated in vacuo yielding a viscous yellow oil (5.2 g, 59%): $^1$H NMR (acetone-d$_6$/300 MHz) 7.16 (s, 1H), 6.77 (d, 1H, J=2.7 Hz), 6.94 (d, 1H, J=8.7 Hz), 6.64 (m, 1H), 6.39 (d, 1H, J=8.7 Hz) 5.13 (q, 1H, J=7.2 Hz). Anal. Calc'd for $C_{12}H_6O_4F_6$: C, 43.92; H, 1.84; N, 0.0. Found: C, 43.79; H, 1.83; N, 0.0. This compound was determined to have an optical purity of greater than 90% ee. Chiral purity was determined as describe in Example 66.

EXAMPLE 68

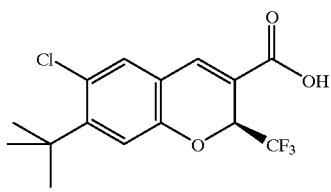

(S)-6-Chloro-7-(1,1-dimethylethyl)-2-(trifluoromethyl)-2H-1-benzopyran-3-carboxylic Acid To a solution of 6-chloro-7-(1,1-dimethylethyl)-2-trifluoromethyl-2H-1-benzopyran-3-carboxylic acid (Example 8) (11.4 g, 34.1 mmol) and (S) (−)-2-amino-3-phenyl-1-propanol (2.57 g, 17.00 mmol) was added n-heptane (200 mL) and the mixture set aside for 16 hours. The resulting suspension was filtered yielding a solid (3.8 g). This solid was recrystallized from 2-butanone (20 mL) and n-heptane (200 mL) yielding upon filtration a white solid (3.0 g). This solid was dissolved in ethyl acetate (100 mL) and washed with 1 N HCl (50 mL) and brine (2×50 mL), dried over $MgSO_4$ and concentrated in vacuo yielding a white solid. This solid was recrystallized from n-heptane yielding the title compound of high optical purity as a crystalline solid (1.7 g, 30%): mp 175.4–176.9° C. $^1$H NMR (acetone-d$_6$/300 MHz) 7.86 (s, 1H), 7.52 (s, 1H), 7.12 (s, 1H), 5.83 (q, 1H, J=7.1 Hz), 1.48 (s, 9H). Anal. Calc'd for $C_{15}H_{14}O_3F_3Cl$: C, 53.83; H, 4.22; N, 0.0; Cl, 10.59. Found: C, 53.78; H, 4.20; N, 0.0; Cl, 10.65. This compound was determined to have an optical purity of greater than 90% ee. Chiral purity was determined as describe in Example 66.

EXAMPLE 69

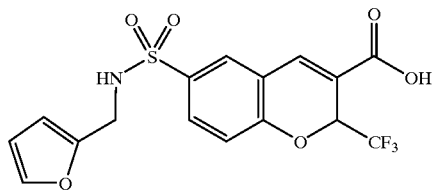

6-([[(2-Furanylmethyl)amino]sulfonyl]-2-(trifluoromethyl)-2H-1-benzopyran-3-carboxylic Acid The title compound was prepared by a similar procedure to that described in Example 49: mp 170–173° C. $^1$H NMR (CD$_3$CD/300 MHz) 7.78 (s, 1H), 7.66–7.76 (m, 2H), 7.18–7.22 (m, 1H), 7.00–7.08 (m, 1H), 6.12–6.18 (m, 1H), 6.02–6.06 (m, 1H), 5.85 (q, 1H, J=7.0 Hz), 4.13 (s, 2H). EIHRMS m/z 403.0332 (M+, Calc'd 403.0337).

EXAMPLE 70

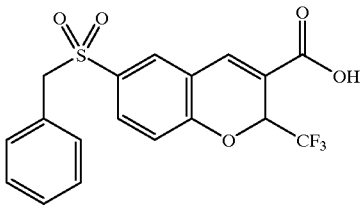

6-[(Phenylmethyl)sulfonyl]-2-(trifluoromethyl)-2H-1-benzopyran-3-carboxylic Acid The 2H-1-benzopyran-3-carboxylic acid was prepared analogously to the procedure described in Example 56: mp 172–176° C. $^1$H NMR (CD$_3$OD/300 MHz)7.73 (s, 1H), 7.43–7.56 (m, 2H), 7.21–7.33 (m, 3H), 7.20–7.21 (m, 3H), 5.88 (q, 1H, J=7.0 Hz), 4.83 (s, 2H). EIHRMS m/z 398.0399 (M+, Calc'd 398.0436).

EXAMPLE 71

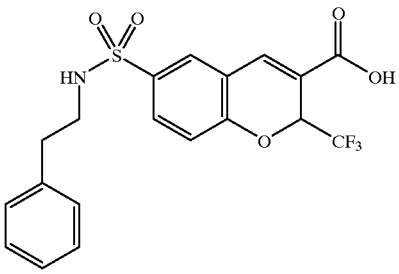

6-[[(Phenylethyl)amino]sulfonyl]-2-(trifluoromethyl)-2H-1-benzopyran-3-carboxylic Acid The 2H-1-benzopyran-3-carboxylic acid was prepared analogously to the procedure described in Example 49: mp 187–190° C. $^1$H NMR (CD$_3$OD/300 MHz) 7.82 (s, 1H), 7.74–7.90 (m, 2H), 7.08–7.29 (m, 6H), 5.89 (q, 1H, J=6.8), 3.12 (t, 2H, J=7.3 Hz), 2.72 (t, J=7.3 Hz). EIHRMS m/z 427.0675 (M+, Calc'd 4 27.0701)

EXAMPLE 72

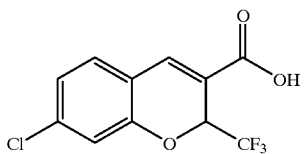

7-Chloro-2-trifluoromethyl-2H-1-benzopyran-3-carboxylic Acid

4-Chlorosalicylic acid was converted to 3-chlorosalicylaldehyde by a procedure similar to that described in Example 24, Steps 1 & 2. The 3-chlorosalicylaldehyde was converted to the title compound by a procedure similar to Example 1: mp 175.2–177.6° C. $^1$H NMR (acetone-d$_6$/300 MHz) 7.90 (5, (H), 7.51 (d, 1H, J=7.8 Hz), 7.12 (m, 2H), 5.86 (q$_{H-F}$, 1H, J=7.2 Hz). FABHRMS m/z 285.0114 (M+Li, Calc'd 285.0118). Anal. Calc7d for C$_{11}$H$_6$ClF$_3$O$_3$: C, 47.42; H, 2.17; Cl, 12.72. Found: C, 47.54; H, 2.37; Cl, 12.85.

EXAMPLE 73

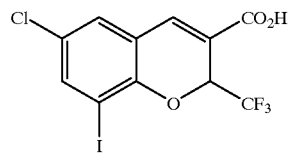

6-Chloro-8-iodo-2-(trifluoromethyl)-2H-1-benzopyran-3-carboxylic Acid

Step 1. Preparation of 3-iodo-5-chlorosalicylaldehyde

N-Iodosuccinimide (144.0 g, 0.641 mole) was added to a solution of 5-chlorosalicyaldehyde (100 g, 0.638 mole) in dimethylformamide (400 mL). The reaction mixture was stirred for two days at room temperature. Additional N-iodosuccinimide (20 g, 0.089 mole) was added and the stirring was continued for an additional two days. The reaction mixture was diluted with ethyl acetate (1 liter), washed with hydrochloric acid (300 mL, 0.1 N), water (300 mL), sodium thiosulfate (300 mL, 5%), and brine (300 mL). It was dried over MgSO$_4$, and was concentrated to dryness to afford the desired aldehyde as a pale yellow solid (162 g, 90%): mp 84.8–86.7° C. $^1$H NMR (CDCl$_3$/300 MHz) 11.67 (s, 1H), 9.71 (s, 1H), 7.92 (d, 1H, J=2.5 Hz), 7.54 (d, 1H, J=2.6 Hz). FABLRMS m/z 281.0 (M–H). ESHRMS m/z 280.8851 (M–H, Calc'd. 280.88630).

Step 2. Preparation of Ethyl 6-chloro-8-iodo-2-(trifluoromethyl)-2H-1-benzopyran-3-carboxylate 5-Chloro-3-iodosalicylaldehyde (20 g, 70.8 mmol), ethyl 4,4,4-trifluorocrotonate (17.85 g, 106 mmol), and triethylamine (14.33 g, 142 mmol) were dissolved in DMSO (200 mL). The reaction mixture was stirred at 90° C. for three days. The reaction mixture was poured into ethyl acetate (800 mL). It was extracted with 10% HCl (2×200 mL), saturated aqueous NaHCO$_3$ (2×200 mL), and water (2×200 mL) The ethyl acetate phase was dried over MgSO$_4$, filtered and evaporated to yield a brown solid. It was then run through a plug of silica with ethyl acetate-hexane (1:20). The solvent was evaporated to give a yellow solid, that was recrystallized in hexane to afford the ester as a white solid (19.61 g, 64%): mp 92.1–93.9° C. $^1$H NMR (CDCl$_3$/300 MHz) 7.71 (d, 1H, J=2.2 Hz), 7.56 (s, 1H), 7.20 (d, 1H, J=2.2 Hz), 5.81 (q, 1H, J=6.7 Hz), 4.37–4.29 (m, 2H), 1.35 (t, 3H, J=7.2 Hz). FABLRMS m/z 431.9 (M–H). EIHRMS m/z 431.9269 (M–H, Calc'd. 431.9237).

Step 3. Preparation of 6-chloro-8-iodo-2-(trifluoromethyl)-2H-1-benzopyran-3-carboxylic Acid.

The ester (Step 2) was converted to the acid by a procedure similar to the method described in Example 1, Step 2: mp 220–223° C. $^1$H NMR (CD$_3$OD/300 MHz) 7.77 (d, 1H, J=2.2 Hz), 7.71 (s, 1H), 7.41 (d, 1H, J=2.2 Hz), 5.87 (q, 1H, J=7.0 Hz). EIHRMS m/z 403.8893 (M–H, Calc'd. 403.8924). Anal. Calc'd for C$_{11}$H$_5$ClF$_3$IO$_3$: C, 32.66; H, 1.25. Found: C, 33.13; H, 1.29.

EXAMPLE 74

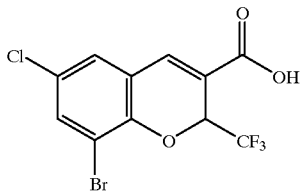

8-Bromo-6-chloro-2-trifluoromethyl-2H-1-benzopyran-3-carboxylic A

Step 1. Preparation of Ethyl 8-bromo-6-chloro-2-trifluoromethyl-2H-1-benzopyran-3-carboxylate A mixture of 3-bromo-5-chlorosalicylaldehyde (1.9 g, 4.2 mmol), potassium carbonate (0.58 g, 4.2 mmol), and ethyl 4,4,4-trifluorocrotonate (0.79 g, 4.7 mmol) was stirred in N,N-dimethylformamide (5 mL) at 95° C. for 18 h. Water (100 mL) was added and the mixture was extracted with ether (3×50 mL). The combined organic extracts were washed with sodium hydroxide (10 mL) and water (2×50 mL). After drying over MgSO$_4$ and concentrating, the mixture filtered through of a pad of silica eluting with ethyl acetate-hexanes (1:4). The eluant was concentrated and a light yellow solid was crystallized from cold hexane (0.43 g, 26%): mp 101.0–102.2 0C. $^1$H NMR (acetone-d$_6$/300 MHz) 7.90 (s, 1H), 7.65 (d, H, J=2.4 Hz), 7.61 (d, H, J=2.4 Hz), 6.03 (q$_{H-F}$, 1H, J=6.9 Hz), 4.34 (m, 2H), 1.33 (t, 3H, J=7.5 Hz). ESHRMS m/z 384.9435 (M–H, Calc'd 384.9454). Anal. Calc'd for C$_{13}$H$_9$BrClF$_3$O$_3$: C, 40.50; H, 2.35. Found: C, 40.61; H, 2.40.

Step 2. Preparation of 8-bromo-6-chloro-2-trifluoromethyl-2H-1-benzopyran-3-carboxylic Acid Ethyl 8-bromo-6-chloro-2-trifluoromethyl-2H-1-benzopyran-3-caboxylate (0.3 g), ethanol (15 mL), tetrahydrofuran (10 mL), and sodium hydroxide solution (10 mL, 2.5 N) were stirred at room temperature for 16 h. Hydrochloric acid (1 N) was added until the mixture was acidic to pH paper. The addition of water (50 mL) caused the formation of a precipitate which was collected by filtration yielding the title compound as a white solid (0.2 g, 72%): mp 227.8–228.9° C. $^1$H NMR (acetone-d$_6$/300 MHz) 7.90 (s, 1H), 7.65 (dd, 2H, J=2.4 and J=28.8 Hz), 6.00 (q$_{H-F}$, 1H, J=7.2 Hz). FABHRMS m/z 356.9134 (M+H, Calc'd 356.9141). Anal. Calc'd for C$_{11}$H$_5$BrClF$_3$O$_3$: C, 36.96; H, 1.41. Found: C, 37.05; H, 1.33.

EXAMPLE 75

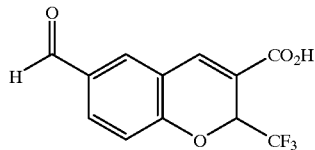

6-Formyl-2-(trifluoromethyl)-2H-1-benzopyran-3-carboxylic Acid

Step 1. Preparation of Ethyl 6-formyl-2-(trifluoromethyl)-2H-1-benzopyran-3-carboxylate.

A 50 mL round bottom flask was charged with 5-formylsalicylaldehyde (3.21 g, 21.39 mmol), ethyl 4,4,4-trifluorocrotonate (3.50 mL, 3.96 g, 23.53 mmol), dimethylformamide (15 mL) and potassium carbonate (2.95 g, 21.39 mmol) and heated to 60° C. for 12 hours. Additional ethyl 4,4,4-trifluorocrotonate (3.50 mL, 3.96 g, 23.53 mmol) was added and the reaction heated for 16 hours at 75° C. After cooling to room temperature, the reaction was partitioned between H$_2$O and diethyl ether. The organic phase was washed with saturated NaHCO$_3$ solution, KHSO$_4$ solution (0.25 M), brine, treated with decolorizing carbon (warmed gently). The resulting black suspension was dried over MgSO$_4$, vacuum filtered through diatomaceous earth, and concentrated in vacuo yielding an orange crystalline mass. This material was recrystallized from hot hexanes yielding the ester (1.51 g, 24%) as orange crystals: mp 84.3–86.2° C. $^1$H NMR (acetone-d$_6$/300 MHz) 9.96 (s, 1H), 8.06 (d, 1H, J=2 Hz), 8.02 (s, 1H), 7.99 (dd, 1H, J=8.5, 2.0 Hz), 7.24 (d, 1H, J=8.5 Hz), 5.99 (q, 1H, J=7.1 Hz), 4.43–4.25 (m, 2H), 1.34 (t, 3H, J=7.3 Hz). FABLRMS m/z 301 (M+H). EIHRMS m/z 300.0605 (M+, Calc'd 300.0609). Anal. Calc'd for C$_{14}$H$_{11}$F$_3$O$_4$: C, 56.01; H, 3.69. Found: C, 56.11; H, 3.73.

Step 2. Preparation of 6-formyl-2-(trifluoromethyl)-2H-1-benzopyran-3-carboxylic Acid.

The ester (Step 1) was converted to the acid via a method similar to that described in Example 1, Step 2: mp 211.3–215.7° C. $^1$H NMR (acetone-d$_6$/300 MHz) 9.97 (s, 1H), 8.07 (d, 1H, J=2.0 Hz), 8.03 (s, 1H), 8.00 (dd, 1H, J=8.3, 2.0 Hz), 7.25 (d, 1H, J=8.5 Hz), 5.98 (q, 1H, J=6.9 Hz). FABLRMS m/z 273 (M+H). EIHRMS m/z 272.0266 (M+, Calc'd 272.0296). Anal. Calc'd for C$_{12}$H$_7$F$_3$O$_4$: C, 52.95; H, 2.59. Found: C, 52.62; H, 2.58.

EXAMPLE 76

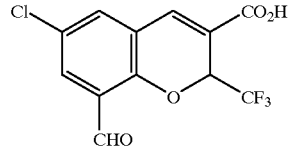

6-Chloro-8-Formyl-2-(trifluoromethyl)-2H-1-benzopyran-3-carboxylic Acid

Step 1. Preparation of 4-chloro-2,6-bis(hydroxymethyl)phenol.

Potassium hydroxide (84.82 g, 1.30 mole) was dissolved in H$_2$O (200 mL) in a two liter 3-neck round bottom flask fitted with thermocouple, mechanical stirrer, and stopper. With stirring, 4-chlorophenol (128.56 g, 1.0 mole) was added with cooling (ice bath) resulting in the temperature rising to 26° C. Formalin (230 mL of 37% aqueous solution, 2.83 mole) was added portion-wise maintaining the temperature below 25° C. The reaction was warmed to 35° C. for 48 hours. To this solution was added aqueous acetic acid (80.0 mL, 84.1 g, 1.40 mole in 800 mL H$_2$O) causing the solution to become turbid. Vacuum filtration of the suspension yielded a tan solid. The solid was stirred with acetone (100 mL) and the insoluble product collected by vacuum filtration. The solution was diluted with hexanes yielding several crops of the diol as fine tan needles (35.0 g, 19%). mp 160.6–163.3° C. $^1$H NMR (acetone-d$_6$5 NaOD, D$_2$O/300 MHz) 6.69 (s, 2H), 4.48 (s, 4H), 7.88 (d, 1H, J=2.6 Hz), 7.75 (d, 1H, J=2.6 Hz), 6.08 (q, 1H, J=6.9 Hz). ESLRMS m/z 206 (M+NH$_4^+$). ESHRMS m/z 187.0131 (M–H, Calc'd 187.0162).

Step 2. Preparation of 5-chloro-3-formyl-salicylaldehyde.

To a stirred suspension of diol (Step 1) (33.0 g, 0.18 mole) in chloroform (1.5 L) in a 2 L round bottom flask was added manganese dioxide (139 g, 1.60 mole) and the resulting suspension heated to a gentle reflux for 10 hours. The reaction was allowed to cool to room temperature, was filtered through diatomaceous earth, concentrated in vacuo, presorbed on silica gel and purified by flash chromatography (hexane/ethyl acetate) yielding the as a mustard colored powder dialdehyde (22.42 g, 67 mp 120.7–122.8° C. This solid was of suitable purity to use in the next step without further purification.

Step 3. Preparation of Ethyl 6-chloro-8-formyl-2-(trifluoromethyl)-2H-1-benzopyran-3-carboxylate.

A stirred solution of the dialdehyde (Step 2)(1.13 g, 6.14 mmol), dimethyl sulfoxide (6 mL), ethyl 4,4,4-trifluorocrotonate (1.37 mL, 1.55g, 9.21 mmoL) and triethylamine (1.71 mL, 1.24g, 12.28 mmol) in a round bottom flask fitted with condenser was heated to 80° C. for 8 h. Upon cooling to room temperature the reaction was diluted with diethyl ether (100 mL) and the resulting mixture washed with aqueous sodium bicarbonate solution (3×75 mL), 1 N HCl solution (3×70 mL), and brine (1×75 mL), dried over $MgSO_4$, filtered and concentrated in vacuo yielding a tan powder. This powder was taken up in hot hexane-ethyl acetate and filtered to remove insoluble matter. Upon cooling of the filtrate, crystallization followed by vacuum filtration yielded the desired ester as tan crystals (0.726 g, 35%): mp 118.1–119.7° C. This material was of suitable purity to use without further purification.

Step 4. Preparation of 6-chloro-8-formyl-2-(trifluoromethyl)-2H-1-benzopyran-3-carboxylic Acid.

To a stirred solution of the ester (Step 3) (0.284 g, 0.849 mmol) in $THF:EtOH:H_2O$ (7:2:1, 5 mL) was added aqueous NaOH solution (0.41 mL of 2.5 M, 1.02 mmol). After stirring 40 hours, the reaction was partially concentrated in vacuo to remove the organic solvents, diluted with $H_2O$, washed with diethyl ether, sparged with nitrogen to remove trace diethyl ether, and acidified with concentrated HCl yielding a suspension. Vacuum filtration of the suspension yielded the title compound as a pale yellow powder (0.160 g, 23%). mp 243.3–252.4° C. $^1H$ NMR (acetone-$d_6$/300 MHz) 10.39 (s, 1H), 7.98 (s, 1H), 7.88 (d, 1H, J=2.6 Hz), 7.75 (d, 1H, J=2.6 Hz), 6.08 (q, 1H, J=6.9 Hz). FABLRMS m/z 307 (M+H). ESHRMS m/z 304.9839 (M–H, Calc'd 304.9828). Anal. Calc'd for $C_{12}H_6C_{11}F_3O_4$: C, 47.01; H, 1.97. Found: C, 46.64; H, 1.86.

EXAMPLE 77

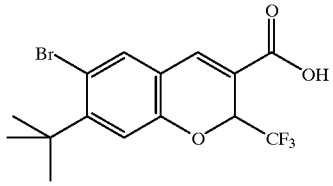

6-Bromo-7-(1,1-dimethylethyl)-2-(trifluoromethyl)-2H-1-benzopyran-3-carboxylic Acid 7-(1,1-Dimethylethyl-2-(trifluoromethyl)-2H-1-benzopyran-3-carboxylic acid (Example 12)(0.6 g, 2 mmol), chloroform (50 mL), iron filings (0.01 g, 0.2 mmol), and bromine (0.48 g, 3.00 mmol) were stirred at reflux for 16 h. The mixture was allowed to cool and was washed with brine (2×50 mL). After drying over $MgSO_4$, the mixture was filtered, concentrated in vacuo, and the residue crystallized from ether-hexanes yielding the title compound as a white solid (0.5 g, 66%): ° p 198.6–199.9° C. $^1H$ NMR (acetone-$d_6$/3(d MHz) 7.85 (s, 1H), 7.72 (s, 1H), 7.13 (H, 1H) 5.83 (q, 1H, J=7.2 Hz), 1.5(s, 9H). Anal. Calc'd for $C_{15}H_{14}O_3F_3Br$: C, 47.52; H, 3.72; N, 21.07. Found: C, 47.42; H. 3.68; N. 21.15.

EXAMPLE 78

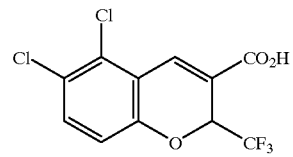

5,6-Dichloro-2-(trifluoromethyl)-2H-1-benzopyran-3-carboxylic Acid 5,6-Dichlorosalicylaldehyde was prepared by the procedure described in Cragoe, E. J.; Schultz, E. M., U.S. Pat. No. 3,794,734, 1974. This salicylaldehyde was converted to the title compound by a similar procedure to that described in Example 1; mp 211.5–213.5° C. $^1H$ NMR (acetone-$d_6$/300 MHz) 8.09 (s, 1H), 7.63 (d, 1H, J=8.9 Hz), 7.12 (d, 1H, J=8.9 Hz), 5.94 (q, 1H, J=7.0 Hz). ESLRMS m/z 311 (M–H). EIHRMS m/z 311.9583 (M+, Calc'd 311.9568). Anal. Calc'd for $C_{11}H_5Cl_2F_3O_3$: C, 42.20; H, 1.61. Found C, 42.33; H, 1.67.

EXAMPLE 79

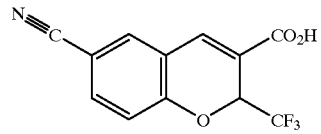

6-Cyano-2-(trifluoromethyl)-2H-1-benzopyran-3-carboxylic Acid

Step 1. Preparation of Ethyl 6-[(hydroxyimino)methyl]-2-(trifluoromethyl)-2H-1-benzopyran-3-carboxylate.

A 50 mL round bottom flask was charged with hydroxylamine HCl (0.255 g, 3.67 mmol), ethyl 6-formyl-2-(trifluoromethyl)-2H-1-benzopyran-3-carboxylate (Example 75, Step 1) (1.00 g, 3.34 mmol), sodium acetate (0.301 g, 3.67 mmol), ethanol (10 mL), and $H_2O$ (2 mL). The reaction was stirred at room temperature for 18 hours, then diluted with $H_2O$ and diethyl ether. The layers were separated and the organic phase washed with $H_2O$, brine, dried over $MgSO_{41}$ filtered, and concentrated in vacuo yielding an orange semi-crystalline mass. Recrystallization of this solid from hot ethyl acetate and isooctane yielded the oxime (0.578 g, 55%): mp 113.0–116.2° C. $^1H$ NMR (acetone-$d_6$/300 MHz) 10.46 (s, ca.1 exch.), 8.11 (s, 2H), 7.92 (s, 1H), 7.72 (d, 1H, J=2 Hz)), 7.68 (dd, 1H, J=8.5, 2.0 Hz), 7.07 (d, 1H, J=8.5 Hz), 5.89 (q, 1H, J=7.1 Hz), 4.43–4.22 (m, 2H), 1.34 9t, 3H, J=7.3 Hz). FABLRMS m/z 316 (M+H). EIHRMS m/z 315.0719 (M+, Calc'd 315.0733). Anal. Calc'd for $C_{14}H_{12}F_3N_{10}O_4$: C, 53.34; H, 3.84; N 4.44. Found: C, 53.85; HI 3.90; N, 4.19.

Step 2. Preparation of Ethyl 6-cyano-2-(trifluoromethyl)-2H-1-benzopyran-3-carboxylate.

To a stirred solution of oxime (Step 1)(0.264 g, 0.840 mmol) in dioxane (4.5 mL) in a 25 mL pear-shaped flask was added trifluoroacetic anhydride (0.130 mL, 0.194 g, 0.924 mmol) and triethylamine (0.140 mL, 0.102 g, 1.008 mmol). The reaction was stirred at room temperature for 12 hours, then heated to 85° C. for 4 hours. After cooling to room temperature, aqueous HCl (50 ml, 1 N HCl) was added, and the resulting mixture extracted with ethyl acetate . The ethyl acetate phase was washed with chilled aqueous HCl (1 N), brine, dried over $Na_2SO_4$, filtered, concentrated in vacuo yielding a pale yellow oil. This oil was resubmitted to similar reaction conditions. After dissolution of the pale yellow oil in dioxane (4.5 mL), trifluoroacetic anhydride (0.130 mL, 0.194 g, 0.924 mmol) and triethylamine (0.140 mL, 0.102 g, 1.008 mmol) were then added. After stirring 3 hours at room temperature, more triethylamine 0.50 mL, 0.36 g, 3.6 mmol) was added and then heated to 85° C. for 3 hours. After cooling to room temperature, aqueous HCl (50 ml, 1 N HCl) was added, and the resulting mixture extracted with ethyl acetate . The ethyl acetate phase was washed with chilled aqueous HCl (1 N), brine, dried over $Na_2SO_4$, filtered, concentrated in vacuo yielding a pale yellow oil. Addition of hexanes induced crystallization followed by vacuum filtration yielded the title compound (0.101g, 40%) as a yellow powder: mp 101.6–106.1° C. $^1H$ NMR (acetone-$d_6$/300 MHz) 7.97 (d, 1H, J=2.2 Hz), 7.95 (s, 1H), 7.82 (dd, 1H, J=8.5, 2.0 Hz), 7.24 (d, 1H, J=8.5 Hz), 6.01 (q, 1H, J=7.1 Hz), 4.38–4.24 (m, 2H), 1.34 (t, 3H, J=7.3 Hz). FABLRMS m/z 298 (M+H). EIHRMS m/z 297.0575 (M+, Calc'd 297.0613).

Step 3. Preparation of 6-cyano-2-(trifluoromethyl)-2H-1-benzopyran-3-carboxylic Acid.

To a stirred solution of the ester (Step 2) (0.077 g, 0.259 mmol) in THF-EtOH-$H_2O$ (7:2:1, 2 mL) in a 5 mL pear-shaped flask was added aqueous NaOH (0.13 mL, 2.5 N solution) in one portion. After stirring for 6 hours at room temperature the solution was partially concentrated in vacuo to remove most of the THF and EtOH. The resulting solution was diluted with $H_2O$ and washed with diethyl ether. The resulting aqueous phase was sparged with nitrogen to remove trace diethyl ether and was acidified with concentrated HCl yielding a sticky suspension. The suspension was extracted with diethyl ether and the ether was dried over $MgSO_4$, filtered and concentrated in vacuo yielding a pale yellow oil. This oil was crystallized from methylene chloride-hexanes yielding the title compound (0.041 g, 59%) as a tan powder: mp 185.1–186.1° C. $^1H$ NMR (acetone-$d_6$/300 MHz) 7.99–7.94 (m, 2H), 7. 3 (dd, 1H, c=8.5, 2.0 Hz), 7.25 (d, 1H, J=8.5 Hz), 5.99 (q, 1H, J=7.0 Hz). FABLRMS m/z 270 (M+H). EIHRMS m/z 269.0316 (M+, Calc'd 269.0300).

EXAMPLE 80

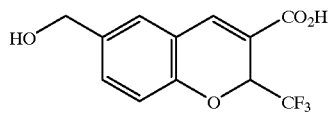

6-Hydroxymethyl-2-(trifluoromethyl)-2H-1-benzopyran-3-carboxylic Acid

To a chilled (ice bath), stirred solution of 6-formyl-2-(trifluoromethyl)-2H-1-benzopyran-3-carboxylic acid (Example 75, Step 2) (0.133 g, 0.489 mmol) in THE (1 mL) and ethanol (1 mL) in a 10 mL round bottom flask was added $NaBH_4$ (0.020 g, 0.528 mmol) in two portions. The reaction was allowed to warm to room temperature and more $NaBH_4$ (0.050 g, 1.322 mmol) was added. The total reaction time was 3 hours. The reaction was quenched with aqueous HCl (1 N solution) and was extracted with chloroform. The organic phase was dried over $MgSO_4$, filtered and concentrated in vacuo yielding a foam. This crude product was purified by flash chromatography (silica gel 60, eluant 1:1, hexane-ethyl Acetate with 2% acetic acid). The product collected from the chromatography was recrystallized from hexanes and ethyl acetate, and collected by vacuum filtration yielding the title compound (0.042 g, 31%) as a very pale yellow powder: mp 177.5–180.8° C. $^1H$ NMR (acetone-$d_6$/300 MHz) 7.89 (s, 1H), 7.44 (s, 1H), 7.41 (d, 1H, J=8.3 Hz), 6.99 (d, 1H, J=8.3 Hz), 5.80 (q, 1H, J=7.3 Hz), 4.59 (s, 2H). FABLRMS m/z 275 (M+H). EIHRMS m/z 274.0417 (M+, Calc'd 274.0453). Anal. Calc'd for $C_{12}H_9F_3O_4$: C, 52.57; H, 3.31. Found: C, 52.43; H, 3.34.

EXAMPLE 81

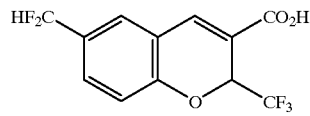

6-(Difluoromethyl)-2-(trifluoromethyl)-2H-1-benzopyran-3-carboxylic Acid

Step 1. Preparation of Ethyl 6-(difluoromethyl)-2-(trifluoromethyl)-2H-1-benzopyran-3-carboxylate.

Ethyl 6-formyl-2-trifluoromethyl-2H-1-benzopyran-3-carboxylate (Example 75, Step 1)(1.672 g, 5.569 mmol) in methylene chloride (1.5 mL) was added to methylene chloride (1.5 mL) and diethylaminosulfur trifluoride (DAST) (0.74 mL, 0.898 g, 5.569 mmol) over 0.07 hours via syringe. After stirring for 20 hours the reaction was poured into aqueous HCl (2.0 N) and the mixture was extracted with diethyl ether. The ethereal phase was washed with dilute aqueous HCl (2.0 N), saturated $NaHCO_3$ solution, brine, dried over $MgSO_4$, filtered and concentrated in vacuo yielding a clear colorless oil. This oil was purified by flash chromatography (Silica gel 60, Eluant (5:1; Hexanes Ethyl Acetate) yielding ethyl 6-difluoromethyl-2-trifluoromethyl-2H-1-benzopyran-3-carboxylate (0.96 g, 54%) as an oil which solidified upon standing. This product was of sufficient purity to be used in the next step without further purification: $^1H$ NMR (acetone-$d_6$/300 MHz) 7.97 (s, 1H), 7.74 (s, 1H), 7.65 (d, 1H, J=8.5 Hz), 7.18 (d, 1H, J=8.5 Hz), 6.90 (t, 1H, J=56.0 Hz), 5.94 (q, 1H, J=7.0 Hz), 4.40–4.25 (m, 2H), 1.34 (t, 3H, J=7.0 Hz).

Step 2. Preparation of 6-(difluoromethyl)-2-(trifluoromethyl)-2H-1-benzopyran-3-carboxylic Acid.

Aqueous NaOH (1.31 mL, 3.277 mmol, 2.5 M solution) was added in one portion to the ester (Step 1) (0.880 g, 2.731 mmol) in THF:EtOH:$H_2O$ (7:2:1, 10 mL). The resulting solution was stirred for 60 hours. The reaction mixture was partially concentrated in vacuo to remove the organic solvents and was diluted with $H_2O$. The resulting aqueous solution was washed with diethyl ether, sparged with nitrogen to remove trace ether, and acidified with concentrated HCl. The resulting oily suspension was extracted with diethyl ether. The combined organic phases were dried over $MgSO_4$, filtered and concentrated in vacuo yielding the title compound (0.483 g, 60%) as an oil which solidified as a white crystalline mass: mp 134.7–136.2° C. $^1H$ NMR (acetone-$d_6$/300 MHz) 7.97 (s, 1H), 7.73 (s, 1H), 7.67 (dd, 1H, J=8.5, 1.0 Hz), 7.17 (d, 1H, J=8.5 Hz), 6.89(t, 1H, J=56.2 Hz), 5.90 (q, 1H, J=7.1 Hz). FAB-ESLRMS m/z 293 (M−H). EIHRMS m/z 293.0235 (M−H, Calc'd 293.0237).

Anal. Calc'd for $C_{12}H_7F_5O_3$: C, 49.00; H, 2.40. Found: C, 48.78; H, 2.21.

EXAMPLE 82

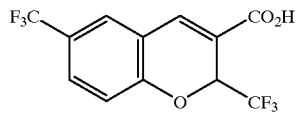

2,6-Bis(trifluoromethyl)-2H-1-benzopyran-3-carboxylic Acid

Step 1. Preparation of Ethyl 2,6-bis(trifluoromethyl)-4-oxo-4H-1-benzopyran-3-carboxylate.

To a stirred solution of ethyl 4,4,4-trifluoroacetoacetate (3.22 mL, 4.06 g, 22.07 mmol) in toluene (100 mL) was added portion-wise sodium hydride (0.971 g, of 60% oil dispersion reagent, 22.07 mmol) causing gas evolution. After gas evolution has subsided, 2-fluoro-5-(trifluoromethyl)benzoyl chloride (5.00 g, 22.07 mmol) was added. The reaction was stirred at room temperature for 24 hours, then heated to 105° C. for 24 hours. After cooling to room temperature, the reaction was diluted with diethyl ether and the resulting solution was washed with $H_2O$ and brine, dried over $MgSO_4$, filtered and concentrated in vacuo yielding a slightly sticky white solid. This solid was triturated with hexanes yielding the desired ester(3.05 g, 39%) as a white powder: mp 116–120.1° C. $^1H$ NMR ($CDCl_3$/300 MHz) 8.52 (d, 2H, J=1.6 Hz), 8.03 (dd, 1H, J=8.9, 2.2 Hz), 7.71 (d, 1H, J=8.9 Hz), 4.48 (q, 2H, J=7.3 Hz), 1.39 (t, 3H, J=7.3 Hz). FABLRMS m/z 355 (M+H). Anal. Calc'd for $C_{14}H_8F_6O_4$: C, 47.45; H, 2.28. Found: C, 47.59; H, 2.43.

Step 2. Preparation of ethyl 2,6-bis(trifluoromethyl)-4-oxo-dihydrobenzopyran-3-carboxylate.

A 250 mL round bottom flask was charged with ethyl 2,6-bis(trifluoromethyl)-benzopyran-4-one-3-carboxylate (Step 1)(2.307 g, 6.513 mmol) and THF (20 mL) yielding a pale yellow solution. Ethanol (20 mL) was added and the reaction chilled in an ice-salt bath. While maintaining the reaction temperature at below 9° C., $NaBH_4$ (0.246 g, 6.513 mmol) was added in two portions and the mixture stirred 1 h. The crude reaction mixture was poured into a vigorously stirred mixture of ice (200 mL) and concentrated HCl (12 N, 5 mL) yielding a precipitate. Vacuum filtration of the resulting suspension yielded the desired keto ester (2.204 g, 87%) as faint pink powder of suitable purity to use in the next step without further purification: mp 71.8–76.9° C. $^1H$ NMR (acetone-$d_6$/300 MHz) 12.71 (br s, 1H exch), 8.01 (d, 1H, J=2.0 Hz), 8.01 (d, 1H, J=2.0 Hz), 7.88 (dd, 1H, J=8.7, 1.8 Hz), 7.31 (d, 1H, J=8.7 Hz), 5.98 (q, 1H, J=6.6 Hz), 4.51–4.28 (m, 2H), 1.35 (t, 3H, J=7.0 Hz). FABLRMS m/z 355 (M–H). ESHRMS m/z 355.0394 (M–H, Calc'd 355.0405). Anal. Calc'd for $C_{14}H_{10}F_6O_4$: C, 47.21; H, 2.83. Found: C, 47.31; H, 2.97.

Step 3. Preparation of Ethyl 2,6-bis(trifluoromethyl)-4-trifluoromethanesulfonate-2H-1-benzopyran-3-carboxylate.

A 50 mL 3-neck Morton flask fitted with addition funnel, 2 stoppers was charged with 2,6-di-tert-butylpyridine (1.576 g, 1.50 mmol), methylene chloride (12 mL), and then via syringe was added trifluoromethanesulfonic anhydride (1.08 mL, 1.80 g, 1.25 mmol). To this solution was added dropwise a solution the keto ester (Step 2) (1.822 g, 5.115 mmol) in methylene chloride (10 mL) over 0.33 h and the reaction stirred for 48 h. The resulting off-white suspension was transferred to a 100 mL round bottom flask and was concentrated in vacuo. The residue was suspended in diethyl ether (50 mL) and vacuum filtered to remove salts. The filtrate was further diluted with diethyl ether (50 mL) and was washed with ice cold HCl solution (2 N), brine, and dried over $Na_2CO_3$, filtered and concentrated in vacuo yielding the desired triflate (1.64 g, 66%) as a tan clumpy powder of suitable purity to use in the next step without further purification.

Step 4. Preparation of Ethyl 2,6-bis(trifluoromethyl)-2H-1-benzopyran-3-carboxylate.

A 25 mL pear flask was charged with LiCl (0.136 g, 3.219 mmol), affixed to a high vacuum line and heated with a heat gun removing superficial water. The flask was allowed to cool to room temperature, and tetrakis(triphenylphosphine) palladium(0) (0.124 g, 0.107 mmol) and THF (2 mL) were added. A reflux condenser was affixed to the flask and the apparatus was purged with nitrogen. A solution of the triflate (Step 3) (0.524 g, 1.073 mmol) in THF (2 mL) and tri-n-butyltin hydride (0.32 mL, 0.34 g, 1.18 mmol) were added sequentially via syringe. The resulting light orange solution was heated to 50° C. with stirring for 1 h, 60° C. for one hour, and 65° C. for one hour. The reaction was allowed to cool to room temperature and was poured into 2 N HCl, stirred, and extracted with hexanes. The hexane phase was dried over $MgSO_4$, filtered and concentrated yielding a light brown oil. The oil was dissolved in hexane and was washed with aqueous ammonium fluoride solution. The resulting hexane phase was dried over $MgSO_4$, filtered and concentrated in vacuo yielding a dull yellow oily solid which solidified as a flaky powder (0.443 g). This solid was purified by flash silica chromatography (eluant: hexanes-methylene chloride, 4:1) yielding ethyl 2,6-di-trifluoromethyl-2H-1-benzopyran-3-carboxylate(0.069 g, 19%) as a white crystalline solid of suitable purity to proceed with the next step.

Step 5. Preparation of 2,6-bis(trifluoromethyl)-2H-1-benzopyran-3-carboxylic Acid.

To a stirred solution of the ester (Step 4) (0.065 g, 0.191 mmol) in THF-EtOH-$H_2O$ (7:2:1, 1 mL) was added NaOH solution (0.084 mL, 0.210 mmol) in one portion at room temperature and allowed to stir overnight. The reaction was partially concentrated in vacuo yielding a pale yellow clear syrup. The syrup was diluted with water (5 mL) and brine (1 mL) and was washed with diethyl ether (3×5 mL). The resulting aqueous phase was sparged with nitrogen to remove trace ether. With stirring, concentrated HCl was added to the aqueous phase causing the formation of a very fine white precipitate. This suspension was extracted with diethyl ether and the ether dried over $Na_2SO_4$, filtered, and concentrated by slow evaporation at atmospheric pressure. The resulting product was recrystallized from hexanes and ethyl acetate yielding the title compound (0.038 g, 64%) as a fine tan powder: mp 143.5–145.2° C. $^1H$ NMR (acetone-$d_6$/300 MHz) 11.97–11.67 (br s, 1H), 8.03 (s, 1H), 7.92 (s, 1H), 7.77 (d, 1H, J=8.5 Hz), 7.26 (d, 1H, J=8.7 Hz), 5.96 (q, 1H, J=7.0 Hz). FABLRMS m/z 311 (M–H). ESHRMS m/z 311.0107 (M–H, Calc'd 311.0143).

EXAMPLE 83

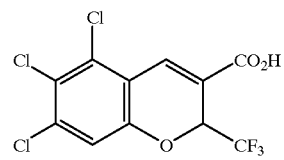

5,6,7-Trichloro-2-(trifluoromethyl)-2H-1-benzopyran-3-carboxylic Acid 3,4,5-Trichlorophenol was converted to 3-ethoxysalicylaldehyde via a procedure similar to that described in Example 11, Step 1. The 4,5,6-trichlrorsalicylaldehyde was converted to the title compound by a procedure similar to that described in Example 1: mp 236.2–239.3° C. $^1$H NMR (acetone-d$_6$/300 MHz) 8.05 (s, 1H), 7.40 (s, 1H), 5.99 (q, 1H, J=7.0 Hz). ESLRMS m/z 345 (M–H). ESHRMS m/z 344.9113 (M–H, Calc'd 344.9100). Anal. Calc'd for $C_{11}H_4Cl_3F_3O_3$+0.89 wt % $H_2O$: C, 37.68; H, 1.25; Cl, 30.33. Found: C, 37.48; H, 1.25; Cl, 30.33.

EXAMPLE 84

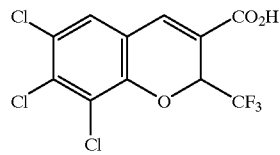

6,7,8-Trichloro-2-(trifluoromethyl)-2H-1-benzopyran-3-carboxylic Acid 2,3,4-Trichlorophenol was converted to 3-ethoxysalicylaldehyde via a procedure similar to that described in Example 11, Step 1. The 3,4,5-trichlrorsalicylaldehyde was converted to the title compound by a procedure similar to that described in Example 1: mp 222.0–225.3° C. $^1$H NMR (acetone-d$_6$/300 MHz) 7.94 (s, 1H), 7.78 (s, 1H), 6.07 (q, 1H, J=7.0 Hz). ESLRMS m/z 345 (M–H). EIHRMS m/z 344.9117 (M–H, Calc'd 344.9100). Anal. Calc'd for $C_{11}H_4Cl_3F_3O_3$+1.56 wt % $H_2O$: C, 37.43; H, 1.32; Cl, 30.13. Found: C, 37.79; H, 0.93; Cl, 29.55.

EXAMPLE 85

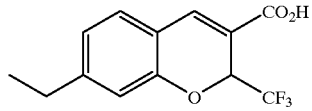

7-Ethyl-2-trifluoromethyl-2H-1-benzopyran-3-carboxylic Acid

3-Ethylphenol was converted to the title compound by a procedure similar to that described in Example 2. : mp 167.0–168.6° C. $^1$H NMR (CDCl$_3$/300 MHz) 7.84 (s, 1H), 7.15 (d, 1H, J=7.5 Hz), 6.84 (m, 2H), 5.66 (q, 1H, J=6.8 Hz), 2.63 (q, 2H, J=7.7 Hz, J=7.7 Hz), 1.24 (t, 3H, J=7.7 Hz). Anal. Calc'd for $C_{13}H_{11}F_3O_3$: C, 57.36; H, 4.07. Found: C, 57.25; H, 4.10.

EXAMPLE 86

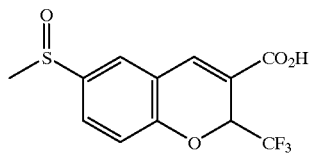

6-(Methylsulfinyl)-2-(trifluoromethyl)-2H-1-benzopyran-3-carboxylic Acid

Step 1. Preparation of Ethyl 6-(methylsulfinyl)-2-(trifluoromethyl)-2H-1-benzopyran-3-carboxylate.

Ethyl 6-(methylthio)-2-(trifluoromethyl)-2H-1-benzopyran-3-carboxylate (Example 2, Step 2) (1.014 g, 3.18 mmol) in methylene chloride was chilled to –50° C. (dry ice acetone). With stirring, meta-chloroperbenzoic acid (0.91 g of 60% reagent, 3.18 mmol) was added and reaction allowed to proceed for 3 hours. Aqueous NaHSO$_3$ solution (40 mL 0.25 M) was poured into the reaction. More methylene chloride was added and the layers mixed, then separated. The organic phase was washed with aqueous NaHSO$_3$ solution, aqueous saturated NaHCO$_3$ solution, brine, dried over MgSO$_4$, filtered and concentrated yielding an oil. The oil was diluted with isooctane (2 mL) and concentrated yielding an oil which upon standing crystallized. Hexanes was added, the solution was heated, and methylene chloride added until partial dissolution occurred. After cooling and standing overnight the suspension was vacuum filtered yielding the sulfoxide substituted ethyl ester (0.753 g, 71%) as white needles: mp 92.2–98.4 0C. This ester was of sufficient purity to be used without further purification.

Step 2. Preparation of 6-(methylsulfinyl)-2-(trifluoromethyl)-2H-1-benzopyran-3-carboxylic Acid.

To a stirred solution of the ester (Step 1) (0.683 g, 2.043 mmol) in THF:EtOH:H$_2$O (7:2:1, 4 mL) was added aqueous NaOH solution (0.98 mL of 2.5 M, 2.45 mmol). After stirring 12 hours, the reaction was partially concentrated in vacuo to remove the organic solvents. The residue was diluted with H$_2$O, washed with diethyl ether, sparged with nitrogen to remove trace diethyl ether, and acidified with concentrated HCl yielding a oily suspension. The suspension was extracted with diethyl ether, and the resulting organic phase dried over MgSO$_4$, filtered, and diluted with hexanes. Upon concentration in vacuo the title acid was obtained as a sticky white powder(0.425 g, 68%): mp 148.3–151.0° C. $^1$H NMR (acetone-d$_6$/300 MHz) 7.99 (s, 1H), 7.82 (s, 1H), 7.78–7.68 (m, 1H), 7.24 (d, 1H, J=8.3 Hz), 5.92 (q, 1H, J=7.1 Hz), 2.73 (s, 3H). FABLRMS m/z 307 (M+H). ESHRMS m/z 305.0098 (M–H, Calc'd 305.0095). Anal. Calc'd for $C_{12}H_9F_3O_4S_1$: C, 47.06; H, 2.96; S, 10.47. Found: C, 46.69; H, 2.86; S, 10.45.

EXAMPLE 87

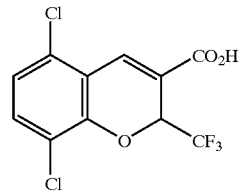

5,8-Dichloro-2-(trifluoromethyl)-2H-1-benzopyran-3-carboxylic Acid 2,5-Dichlorophenol was converted to 3,6-dichlorosalicylaldehyde via a procedure similar to that described in Example 2, Step 1. The 3,6-dichlorosalicylaldehyde was converted to the title compound by a similar procedure to that described in Example 11, Steps 2 & 3: mp 205.7–207.1° C. $^1$H NMR (acetone-d$_6$/300 MHz) 8.02 (s, 1H), 7.53 (d, 1H, J=8.7 Hz), 7.22 (d, 1H, J=8.7 Hz), 6.04 (q, 1H, J=7.1 Hz). FABLRMS m/z 311 (M–H). ESHRMS m/z 310.9506 (M–H, Calc'd 310.9490). Anal. Calc'd for $C_{11}H_5Cl_2F_3O_3$+0.63 wt % $H_2O$: C, 41.94; H, 1.67. Found: C, 41.54; H, 1.27.

EXAMPLE 88

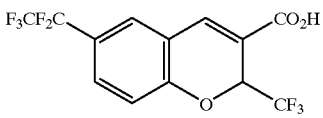

6-(Pentafluoroethyl)-2-(trifluoromethyl)-2H-1-benzopyran-3-carboxylic Acid

Step 1. Preparation of Ethyl 6-(pentafluoroethyl)-2-(trifluoromethyl)-2H-1-benzopyran-3-carboxylate.

Potassium pentafluoropropionate (0.476 g, 2.35 mmol) was dissolved in toluene (6 mL) and DMF (6 mL). The vessel was fitted with a distilling head, and CuI (0.471 g, 2.474 mmol) was added with stirring. The reaction was heated to 120° C., removing the toluene by distillation. Ethyl 6-iodo-2-(trifluoromethyl)-2H-1-benzopyran-3-carboxylate (Example 72, Step 3)(0.469 g, 1.178 mmol) was added and the reaction was heated to 150° C. for 2 hours. The reaction was allowed to cool to room temperature and was partitioned between diethyl ether and $H_2O$. The organic phase was dried over $MgSO_4$, filtered and concentrated in vacuo. The resulting residue was purified by flash chromatography (silica gel 60, eluant: hexanes-ethyl acetate, 8:1) yielding, upon concentration of the solution, the desired ester (0.096 g, 21%) as a tan solid mass of suitable purity to use without further purification: $^1$H NMR (acetone-$d_6$/300 MHz) 8.04 (s, 1H), 7.91 (d, 1H, J=2.2 Hz), 7.74 (dd, 1H, J=8.7, 2.2 Hz), 6.00 (q, 1H, J=7.1 Hz), 4.42–4.24 (m, 2H), 1.34 (t, 3H, J=7.3 Hz).

Step 2. Preparation of 6-(pentafluoroethyl)-2-(trifluoromethyl)-2H-1-benzopyran-3-carboxylic Acid.

To a stirred solution of the ethyl ester (Step 1)(0.090 g, 0.231 mmol) in THF:EtOH:$H_2O$ (7:2:1) (4 mL) was added aqueous NaOH solution (0.11 mL, 2.5 M). After stirring 16 hours, the reaction was partially concentrated in vacuo to remove the organic solvents, diluted with $H_2O$, and washed with diethyl ether. The resulting aqueous phase was acidified with concentrated HCl, extracted with diethyl ether, dried over $MgSO_4$, filtered and concentrated in vacuo yielding an oil. The oil was purified by flash chromatography (silica, hexanes-ethyl acetate, 3:1 with 5% acetic acid). This procedure yielded the title acid (0.020 g, 24%) as a white powder: mp 162.3–164.7° C. $^1$H NMR (acetone-$d_6$/300 MHz) 8.05 (s, 1H), 7.90 (s, 1H), 7.74 (d, 1H, J=8.7 Hz), 7.29 (d, 1H, J=8.7 Hz), 5.97 (q, 1H, J=6.8 Hz). FABLRMS m/z 361 (M−H). ESHRMS m/z 361.0111 (M−H, Calc'd 361.0094).

EXAMPLE 89

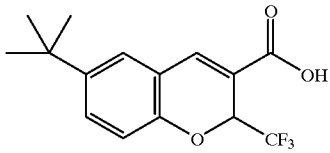

6-(1,1-Dimethylethyl)-2-(trifluoromethyl)-2H-1-benzopyran-3-carboxylic Acid 4-tert-Butylphenol was converted to the title compound by a procedure similar to that described in Example 2: mp 170.6–173.2° C. $^1$H NMR (acetone-$d_6$/300 MHz) 7.89 (s, 1H), 7.5–7.4 (m, 2H), 6.93 (d, 1H, J=8.4 Hz), 5.76 (q, 1H, J=7.2 Hz), 1.3 (s, 9H). Anal. Calc'd for $C_{15}H_{15}O_3F_3$: C, 60.00; H, 5.04. Found: C, 59.93; H, 5.12.

EXAMPLE 90

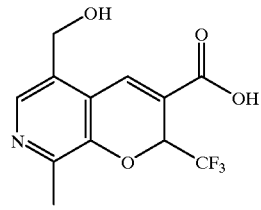

5-(Hydroxymethyl)-8-methyl-2-(trifluoromethyl)-2H-pyrano[2,3-c]pyridine-3-carboxylic Acid 3-Hydroxylmethyl-5-methyl-4-formylpyridine was converted to the title compound by a procedure similar to that described in Example 1: mp 76.1–80.1° C. $^1$H NMR (acetone-$d_6$/300 MHz) 8.15 (s, 2H), 5.93 (q, 1H, J=7.2 Hz), 1.3 (s, 9H) 5.30 (br s, 1H), 4.79 (br s, 1H), 2.41 (s, 3H). ESHRMS m/z 288.0485 (M+H, Calc'd 288.0483).

EXAMPLE 91

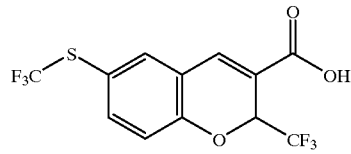

2-(Trifluoromethyl)-6-[(trifluoromethyl)thio]-2H-1-benzopyran-3-carboxylic acid 4-(Trifluoromethoxy)phenol was converted to 5-(trifluoromethoxy)salicylaldehyde via a procedure similar to that described in Example 2, Step 1. The 5-(trifluoromethoxy)salicylaldehyde was converted to the title compound by a similar procedure to that described in Example 11, Steps 2 & 3: mp 139.1–143.2° C. $^1$H NMR (acetone-$d_6$/300 MHz) 7.95 (s, 1H), 7.88 (d, 2H, J=2.4 Hz), 7.71–7.75 (m, 1H), 6.93 (d, 1H, J=8.7 Hz), 5.91 (q, 1H, J=6.9 Hz). Anal. Calc'd for $C_{12}H_6O_3F_3S$: C, 41.87; H, 1.76. Found: C, 41.94; H, 1.84.

EXAMPLE 92

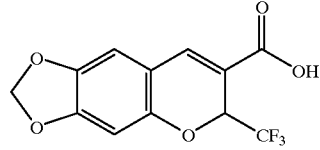

6-(Trifluoromethyl)-6H-1,3-dioxolo[4,5-g][1]benzopyran-7-carboxylic Acid 4-tert-Butylphenol was converted to the title compound by a procedure similar to that described in Example 2: mp 245.8–247.8° C. $^1$H NMR (acetone-$d_6$/300 MHz) 7.77 (s, 1H), 6.95 (s, 1H), 6.12 (s, 1H), 6.05 (d, 2H, J=0.90 Hz), 5.91 (q, 1H, J=7.2 Hz). Anal. Calc'd for $C_{12}H_7O_5F_3$: C, 50.01; H, 2.45. Found: C, 50.02; H, 2.50.

EXAMPLE 93

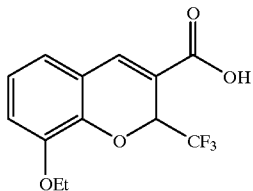

8-Ethoxy-2-trifluoromethyl-2H-1-benzopyran-3-carboxylic Acid

2-Ethoxyphenol was converted to 3-ethoxysalicylaldehyde via a procedure similar to that described in Example 11, Step 1. The 3-ethoxysalicylaldehyde was converted to the title compound by a procedure similar to that described in Example 1: mp 159.4–160.9° C. $^1$H NMR (acetone-$d_6$/300 MHz) 7.86 (s, 1H), 6.97–7.14 (m, 3H), 5.83 ($q_{H-F}$, 1H, J=7.2 Hz), 4.12 (q, 2H, J=7.2 Hz), 1.38 (t, 3H, J=7.2 Hz). FABHRMS m/z 289.0656 (M+H, Calc'd 289.0686). Anal. Calc'd for $C_{13}H_{11}F_3O_4$: C, 54.17; H, 3.85. Found: C, 54.06; H, 3.83.

EXAMPLE 94

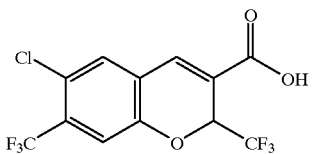

6-Chloro-2,7-bis(trifluoromethyl)-2H-1-benzopyran-3-carboxylic Acid

4-Chloro-3-(trifluoromethyl)phenol was converted to the title compound by a procedure similar to that described in Example 11: mp 180.9–182.4° C. $^1$H NMR (acetone-$d_6$/300 MHz) 7.96 (s, 1H), 7.84 (s, 1H), 7.47 (s, 1H), 5.96 (q, 1H, J=6.8 Hz), 2.50 (s, 3H). FABLRMS m/z 345 (M–H). FABHRMS m/z 344.9767 (M–H, Calc'd 344.9753). Anal. Calc'd for $C_{12}H_5ClF_6O_3$: C, 41.58; H, 1.45; Cl, 10.23. Found: C, 41.57; H, 1.50; Cl, 10.33.

EXAMPLE 95

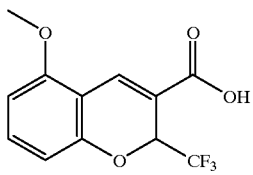

5-Methoxy-2-(trifluoromethyl)-2H-1-benzopyran-3-carboxylic Acid

6-Methoxysalicylaldehyde was converted to the title compound by a similar procedure to that described in Example 11, Steps 2 & 3: mp 204.5–206.7° C. $^1$H NMR (acetone-$d_6$/300 MHz) 8.08 (s, 1H), 7.38 (dd, 1H, J=8.5 Hz 8.3 Hz), 6.74 (d, 1H, J=8.5 Hz), 6.65 (d, 1H, J=8.3 Hz), 5.80 (q, 1H, J=7.2 Hz), 3.94 (s, 3H). FABLRMS m/z 273 (M–H). EIHRMS m/z 274.0444 (M+, Calc'd 274.0453). Anal. Calcd for $C_{12}H_9F_3O_4$: C, 52.57; H, 3.31. Found: C, 52.47; H, 3.34.

EXAMPLE 96

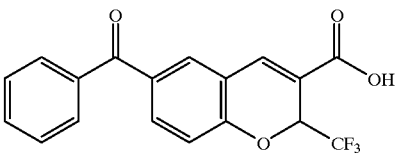

6-Benzoyl-2-(trifluoromethyl)-2H-1-benzopyran-3-carboxylic Acid

Step 1. Preparation of Ethyl 6-benzoyl-2-(trifluoromethyl)-2H-1-benzopyran-3-carboxylate.

Ethyl 2-(trifluoromethyl)-2H-1-benzopyran-3-carboxylate (Example 10, Step 1)(1.59 g, 5.8 mmol) was dissolved in 1,2-dichloroethane (3 mL) and added to a 0° C. suspension of aluminum chloride (2.59 g, 19.4 mmol) in 1,2-dichloroethane (3 mL). A solution of benzoyl chloride (1.01 g, 7.2 mmol) in 1,2-dichloroethane (3 mL) was added and the reaction was heated to 80° C. and stirred for 4 hours. The solution was poured onto 3 N HCl and ice and extracted with ethyl acetate. The ethyl acetate layers were combined, washed with 3N HCl, saturated sodium bicarbonate, brine, dried over $MgSO_4$ and concentrated in vacuo. The crude ester was purified by flash chromatography over silica gel (with 1:9 ethyl acetate/hexane as eluant) to afford the ester as a white crystalline solid (0.26 g, 12%): mp 114.7–116.1 0C. $^1$H NMR ($CDCl_3$/300 MHz) 7.82 (dd, 1H, J=8.5 Hz 2.0 Hz), 7.76 (m, 4H), 7.61 (m, 1H), 7.50 (m, 2H), 7.09 (d, 1H, J=8.7 Hz), 5.79 (q, 1H, J=6.8 Hz), 4.34 (m, 2H), 1.36 (t, 3H, J=7.2 Hz).

Step 2. Preparation of 6-benzoyl-2-trifluoromethyl-2H-1-benzopyran-3-carboxylic Acid.

The ester from Step 1 (0.24 g, 0.64 mmol) was dissolved in THF (2 mL) and ethanol (2 mL), treated with 2.5 N sodium hydroxide (1.5 mL, 3.8 mmol), and stirred at room temperature for 4.3 hours. The reaction mixture was concentrated in vacuo, acidified with 3N HCl yielding a solid. The solid was collected by filtration and was recrystallized from ethanol-water to yield a white solid (0.14 g, 64%): mp 269.8–270.8° C. $^1$H NMR (acetone-$d_6$/300 MHz) 8.04 (s, 1H), 7.99 (d, 1H, J=2.0 Hz), 7.88 (dd, 1H, J=8.5 Hz 2.0 Hz), 7.79 (m, 2H), 7.68 (m, 1H), 7.57 (m, 1H), 7.23 (d, 1H, J=8.6 Hz), 5.98 (q, 1H, J=7.0 Hz). FABLRMS m/z 347 (M–H). ESHRMS m/z 347.0560 (M–H, Calc'd 347.0531). Anal. Calc'd for $C_{18}H_{11}F_3O_4$: C, 62.08; H, 3.18. Found: C, 61.48; H, 3.22.

EXAMPLE 97

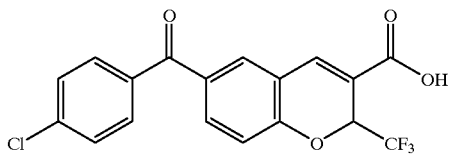

6-(4-Chlorobenzoyl)-2-(trifluoromethyl)-2H-1-benzopyran-3-carboxylic Acid

The 2H-1-benzopyran-3-carboxylic acid was prepared analogous to the procedure described in Example 96: mp 268.3–269.4° C. $^1$H NMR (acetone-d$_6$/300 MHz) 8.03 (s, 1H), 7.99 (d, 1H, J=2.0 Hz), 7.89 (dd, 1H, J=8.5 Hz, 2.0 Hz), 7.81 (d, 2H, J=8.5 Hz), 7.62 (d, 2H, J=8.5 Hz), 7.23 (d, 1H, J=8.5 Hz), 5.98 (q, 1H, J=7.1 Hz). FABLRMS m/z 381 (M−H). ESHRMS m/z 381.0135 (M−H, Calc'd 381.0141). Anal. Calc'd for C$_{18}$H$_{10}$ClF$_3$O$_4$: C, 56.49; H, 2.63; Cl, 9.26. Found: C, 56.35; H, 2.66; Cl, 9.34.

EXAMPLE 98

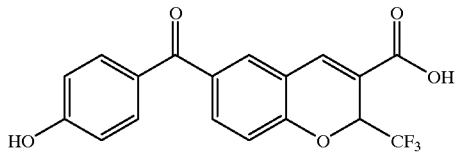

6-(4-Hydroxybenzoyl)-2-(trifluoromethyl)-2H-1-benzopyran-3-carboxylic Acid

The 2H-1-benzopyran-3-carboxylic acid was prepared analogously to the procedure described in Example 96: mp 234.0–239.5° C. $^1$H NMR (acetone-d$_6$/300 MHz) 8.03 (s, 1H), 7.92 (d, 1H, J=2.0 Hz), 7.83 (dd, 1H, J=8.5 Hz 2.0 Hz), 7.74 (d, 2H, J=8.7 Hz), 7.20 (d, 1H, J=8.5 Hz), 7.00 (d, 1H, J=8.7 Hz), 5.94 (q, 1H, J=7.1 Hz). ESHRMS m/z 363.0471 (M−H, Calc'd 363.0480).

EXAMPLE 99

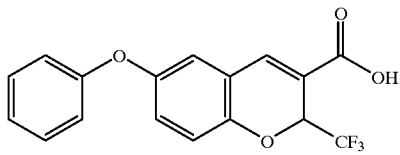

6-Phenoxy-2-(trifluoromethyl)-2H-1-benzopyran-3-carboxylic Acid

4-Phenoxyphenol was converted to 5-phenoxysalicylaldehyde by a similar procedure to that described in Example 2, Step 1. 5-Phenoxysalicylaldehyde was converted into the title compound by a similar procedure to that described in Example 11, Steps 2 & 3: mp 184.9–186.4° C. $^1$H NMR (acetone-d$_6$/300 MHz) 7.90 (s, 1 H)., 7. 39 (m, 2H), 7. 20 (d, 1H, JT=2.0 H z), 7.08 (m, 3H), 7.02 (m, 2H), 5.98 (q, 1H, J=7.2 Hz). FABLRMS m/z 335 (M−H). FABHRMS m/z 337.0663 (M+H, Calc'd 337.0687). Anal. Calc'd for C$_{17}$H$_{11}$F$_3$O$_4$: C, 60.72; H, 3.30. Found: C, 60.62; H, 3.29.

EXAMPLE 100

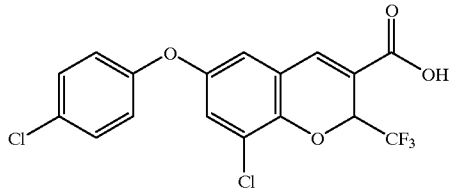

8-Chloro-6-(4-chlorophenoxy)-2-trifluoromethyl)-2H-1-benzopyran-3-carboxylic Acid Step 1. Preparation of 5-phenoxysalicylaldehyde.

Ethyl magnesium bromide (67.5 mL of an approximately 3.0 M solution in diethyl ether, 202.5 mmol) was added to toluene (50 mL). A solution of 4-phenoxyphenol (25.00 g, 134.26 mmol) in diethyl ether (35 mL) was added resulting in the evolution of gas. The reaction was heated to 80° C. causing distillation of the diethyl ether. Toluene (300 mL), HMPA (23.4 mL, 24.059 g, 134.26 mmol), and paraformaldehyde (10.07 g, 335.65 mmol) were added and the reaction was heated to 85° C. for 4 hours. The reaction was cooled to room temperature and was acidified with 2N HCl. The resulting layers were separated and the organic phase collected. The organic phase was washed with brine. The combined aqueous phases were extracted with methylene chloride. The organic phases were combined, dried over MgSO$_4$, filtered and concentrated in vacuo yielding a yellow oil. The oil was purified by silica flash chromatography (hexanes-ethyl acetate, 95:5). Concentration in vacuo of the desired fractions provided the salicylaldehyde as a pale yellow powder (12.0 g, 42%) of suitable purity to use in subsequent steps.

Step 2. Preparation of 3-chloro-5-(4-chlorophenoxy) salicylaldehyde.

To a stirred solution of the salicylaldehyde (Step 1)(0.981 g, 4.58 mmol) in acetic acid (20 mL) was added chlorine gas via a tube until the yellow color of chlorine persisted. After stirring for four hours at room temperature the reaction was sparged with nitrogen and diluted with water (50 mL). The resulting oily suspension was extracted with methylene chloride. The methylene chloride phase was washed with sodium bisulfite solution, dried over MgSO$_4$, filtered and concentrated in vacuo providing the dichlorinated salicylaldehyde as a yellow oil (0.66 g, 51%) of suitable purity for use in subsequent steps without further purification.

Step 3. Preparation of ethyl 8-chloro-6-(4-chlorophenoxy)-2-(trifluoromethyl)-2H-1-benzopyran-3-carboxylate.

A mixture of the dichlorinated salicylaldehyde (Step 2) (0.66 g, 2.3 mmol), triethylamine (0.49 g, 4.8 mmol), ethyl 4,4,4-trifluorocrotonate (0.59 g, 3.5 mmol) in dimethyl sulfoxide (5 mL) was heated to 85° C. for 3.5 hours. The reaction was allowed to cool to room temperature and was diluted with ethyl acetate (50 mL). The resulting mixture was washed with 3 N HCl (50 mL), aqueous potassium carbonate solution (10 weight %, 2×30 mL), and brine. The organic phase was dried over MgSO$_4$, filtered and concentrated in vacuo yielding a brown oil. This oil was purified by flash silica chromatography (hexanes-ethyl acetate, 9:1) providing the substituted 2H-1-benzopyran (0.39 g, 39%) of suitable purity to use in subsequent steps without further purification.

Step 4. Preparation of 8-chloro-6-(4-chlorophenoxy)-2-(trifluoromethyl)-2H-1-benzopyran-3-carboxylic Acid.

To a solution of the substituted 2H-1-benzopyran ethyl ester (Step 3)(0.37 g, 0.85 mmol) in ethanol-THF (4 mL, 1:1) was added sodium hydroxide solution (2 mL of 2.5 N, 5 mmol). After stirring for six hours the mixture was concentrated in vacuo. Acidification of the mixture with 3 N HCl yielded a solid which was collected by vacuum filtration. This solid was recrystallized from ethanol-water yielding the title compound as yellow crystals(0.134 g, 38%): mp 227.8–228.9° C. $^1$H NMR (acetone-d$_6$/300 MHz) 7.93 (s, 1H), 7.42 (d, 2H, J=8.9 Hz), 7.24 (s, 2H), 7.12 (d, 2H, J=8.9 Hz), 5.97 (q, 1H, J=7.1 Hz). FABLRMS m/z 403 (M−H). FABHRMS m/z 405.9790 (M+H, Calc'd 405.9801). Anal. Calc'd for C$_{17}$H$_9$Cl$_2$F$_3$O$_4$+2.33% H$_2$O: C, 49.22; H, 2.45. Found: C, 49.19; H, 2.27.

EXAMPLE 101

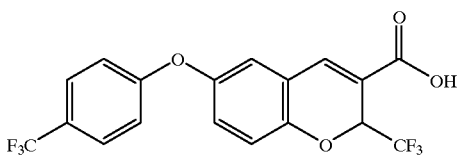

2-(Trifluoromethyl)-6-[4-(trifluoromethyl)phenoxy]-2H-1-benzopyran-3-carboxylic Acid 4-(4-Trifluoromethylphenyl)phenol was converted to 5-(4-trifluoromethylphenyl)salicylaldehyde via a procedure similar to that described in Example 2, Step 1. The 5-(4-trifluoromethylphenyl)salicylaldehyde was converted to the title compound by a similar procedure to that described in Example 11, Steps 2 & 3: mp 153.5–154.4° C. $^1$H NMR (acetone-$d_6$/300 MHz) 7.91 (s, 1H), 7.71 (d, 2H, J=8.9 Hz), 7.33 (s, 1H, J=2.8 Hz), 7.15 (m, 4H), 5.86 (q, 1H, J=7.1 Hz). FABLRMS m/z 403 (M−H). ESHRMS m/z 403.0399 (M−H, Calc'd 403.0405). Anal. Calc'd for $C_{18}H_{10}F_6O_4$: C, 53.48; H, 2.49. Found: C, 53.52; H, 2.55.

EXAMPLE 102

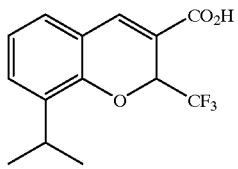

8-(1-Methylethyl)-2-trifluoromethyl-2H-1-benzopyran-3-carboxylic Acid 4-(4-Methoxyphenyl)phenol was converted to the title compound by a procedure similar to that described in Example 2: mp 210.5–211.5° C. $^1$H NMR (acetone-$d_6$/300 MHz) 7.86 (s, 1H), 7.35 (d, 1H, J=7.7 Hz), 7.28 (s, 1H, J=7.5 Hz), 7.04 (t, 1H, J=7.7 Hz), 5.85 (q, 1H, J=7.2 Hz), 3.33 (sept, 1H, J=7.1 Hz), 1.25 (d, 6H, J=7.1 Hz). Anal. Calc'd for $C_{14}H_{13}F_3O_3$: C, 58.74; H, 4.58. Found: C, 58.65; H, 4.60.

EXAMPLE 103

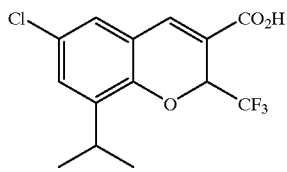

6-Chloro-8-(1-methylethyl)-2-trifluoromethyl-2H-1-benzopyran-3-carboxylic Acid 8-(1-Methylethyl)-2-(trifluoromethyl)-2H-1-benzopyran-3-carboxylic acid (Example 6) was converted to the title compound by a procedure similar to that described in Example 9. mp 185.4–189.2° C. $^1$H NMR (acetone-$d_6$/300 MHz) 7.87 (s, 1H), 7.38 (d, 1H, J=2.4 Hz), 7.34 (d, 1H, J=2.4 Hz), 5.90 (q, 1H, J=7.3 Hz), 3.31 (m, 1H), 1.24 (d, 6H, J=6.8 Hz). Anal. Calc'd for $C_{15}H_{14}ClF_3O_3$: C, 52.43; H, 3.77; Cl, 11.05. Found: C, 52.58; H, 3.79; Cl, 10.96.

EXAMPLE 104

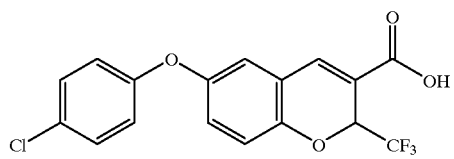

6-(4-Chlorophenoxy)-2-(trifluoromethyl)-2H-1-benzopyran-3-carboxylic Acid

The 2H-1-benzopyran-3-carboxylic acid was prepared from 6-phenoxy-2-(trifluoromethyl)-2H-1-benzopyran-3-carboxylic acid (Example 99) as the starting material by a procedure similar to that described in Example 9: mp 140.5–142.5° C. $^1$H NMR (acetone-$d_6$/300 MHz) 7.90 (s, 1H), 7.39 (d, 2H, J=9.1 Hz), 7.25 (d, 1H, J=2.6 Hz) 7.01–7.15 (m, 4H), 5.85 (q, 1H, J=7.2 Hz). FABLRMS m/z 370 (M+). ESHRMS m/z 369.0130 (M−H, Calc'd 369.0141). Anal. Calc'd for $C_{17}H_{10}ClF_3O_4$+0.96% $H_2O$: C, 54.55; H, 2.80. Found: C, 54.38; H, 2.90.

EXAMPLE 105

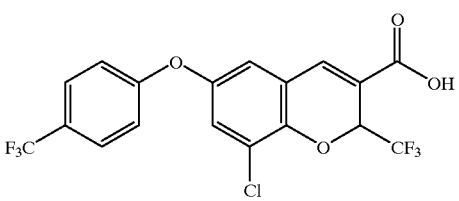

8-Chloro-2-(trifluoromethyl)-6-[4-(trifluoromethyl)phenoxy]-2H-1-benzopyran-3-carboxylic Acid The benzopyran-3-carboxylic acid was prepared using 2-(trifluoromethyl)-6-[4-(trifluoromethyl)phenoxy]-2H-1-benzopyran-3-carboxylic acid (Example 101) as the starting material by a similar procedure to that described in Example 100: mp 223.7–226.0° C. $^1$H NMR (acetone-$d_6$/300 MHz) 7.94 (s, 1H), 7.74 (d, 2H, J=8.5 Hz), 7.35 (m, 2H) 7.25 (d, 2H, J=8.5 Hz), 6.00 (q, 1H, J=7.0 Hz). FABLRMS m/z 437 (M−H). ESHRMS m/z 437.0000 (M−H, Calc'd 437.0015). Anal. Calc'd for $C_{18}H_9ClF_6O_4$: C, 49.28; H, 2.07; Cl, 8.08. Found: C, 49.42; H, 2.12; Cl, 8.17.

EXAMPLE 106

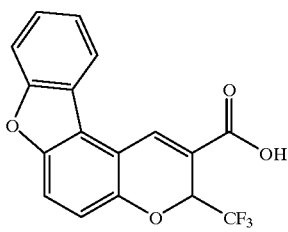

3-(Trifluoromethyl)-3H-benzofuro[3,2-f][1]benzopyran-2-carboxylic Acid

2-Hydroxydibenzofuran was converted to the title compound by a procedure similar to that described in Example 2: mp 253.5–254.6° C. ¹H NMR (acetone-d₆/300 MHz) 8.54 (s, 1H), 8.23 (d, 1H, J=7.5 Hz), 7.71 (s, 1H), 7.62 (m, 1H), 7.50 (m, 1H), 7.23 (d, 1H, J=8.9 Hz), 5.95 (q, 1H, J=7.3 Hz). FABLRMS m/z 333 (M−H). ESHRMS m/z 333.0401 (M−H, Calc'd 333.0375). Anal. Calc'd for $C_{17}H_9F_3O_4$: C, 61.09; H, 2.71. Found: C, 60.95; H, 2.80.

EXAMPLE 107

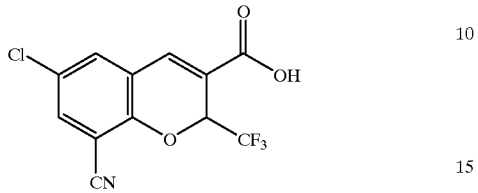

6-Chloro-8-cyano-2-(trifluoromethyl)-2H-1-benzopyran-3-carboxylic Acid

Step 1. Preparation of Ethyl 6-chloro-8-(hydroxyiminomethyl)-2-(trifluoromethyl)-2H-1-benzopyran-3-carboxylate.

Hydroxylamine hydrochloride (1.30 g, 18.7 mmol), sodium acetate (1.50 g, 19.4 mmol), and a mixture of ethanol-water (80:20, 15 mL) were stirred at room temperature for 0.4 hours. The aldehyde (Example 76, Step 3)(3.07 g, 9.0 mmol) was dissolved in a solution of ethanol-water (4:1, 25 mL) and added to this mixture and stirred at 100° C. for 1 hour. The reaction was filtered hot and the filtrate allowed to cool to room temperature. An orange solid crystallized in the filtrate which was collected by vacuum filtration. The solid was dissolved in ethyl acetate and the solution washed with water, brine, dried over MgSO₄, concentrated in vacuo. The resulting solid was recrystallized from ethyl acetate-hexane yielding the oxime as a tan powder (1.50 g, 47%): mp 186.6–187.6° C. ¹H NMR (acetone-d₆/300 MHz) 10.87 (s, 1H), 8.34 (s, 1H), 7.90 (s, 1H), 7.77 (d, 1H, J=2.6 Hz), 7.60 (d, 1H, J=2.6 Hz), 6.02 (q, 1H, J=7.1 Hz), 4.35 (m, 2H), 1.34 (t, 3H, J=7.0 Hz)

Step 2. Preparation of Ethyl 6-chloro-8-cyano-2-trifluoromethyl-2H-1-benzopyran-3-carboxylate.

The oxime from Step 1 (0.61 g, 1.7 mmol) and acetic anhydride (6 mL) were stirred at 140° C. for 6.3 hours. The reaction was poured into water, extracted with ethyl acetate, washed with saturated NaHCO₃, brine, dried over MgSO₄, and concentrated in vacuo to give a brown oil (1.09 g). The oil was purified by flash chromatography (10:1; hexanes: ethyl acetate) yielding upon concentration the title compound as a white solid (0.51 g, 88%): mp 114.6–115.6° C. ¹H NMR (CDCl₃/300 MHz) 7.65 (s, 1H), 7.53 (d, 1H, J=2.4 Hz), 7.44 (d, 1H, J=2.4 Hz), 5.87 (q, 1H, J=6.4 Hz), 4.36 (m, 2H), 1.37 (t, 3H, J=6.5 Hz).

Step 3. Preparation of 6-chloro-8-cyano-2-(trifluoromethyl)-2H-1-benzopyran-3-carboxylic Acid.

The ester from Step 2 (0.51 g 1.5 mmol) was dissolved in THF (5 mL) and ethanol (5 mL), treated with 2.5N sodium hydroxide (1.2 mL, 3.0 mmol), and stirred at room temperature for 1.5 hours. The reaction mixture was concentrated in vacuo, acidified with 3N HCl, extracted with ethyl acetate, washed with water, brine, dried over MgSO₄, concentrated in vacuo, and recrystallized from diethyl ether /hexane to give a white powder (0.10 g, 21%): mp 238.1–239.7° C. ¹H NMR (acetone-d₆/300 MHz) 7.97 (s, 1H), 7.92 (d, 1H, J=2.4 Hz), 7.89 (d, 1H, J=2.4 Hz), 6.14 (q, 1H, J=6.6 Hz). FABLRMS m/z 302 (M−H). ESHRMS m/z 301.9819 (M−H, Calc'd 301.9832). Anal. Calc'd for $C_{12}H_5ClF_3NO_3$: C, 47.47; H, 1.66; N, 4.61. Found: C, 47.41; H, 1.70; N, 4.55.

EXAMPLE 108

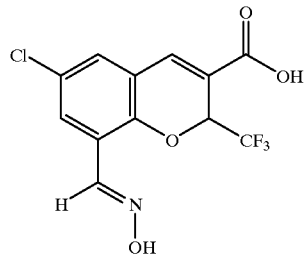

6-Chloro-8-[(hydroxyimino)methyl]-2-(trifluoromethyl)-2H-1-benzopyran-3-carboxylic acid The 2H-1-benzopyran-3-carboxylic acid was prepared from the ethyl ester (Example 107, Step 2) by a method similar to the procedure described in Example 1, Step 2: mp 246.9–247.9° C. ¹H NMR (acetone-d₆/300 MHz) 10.90 (brs, 1H), 8.35 (s, 1H), 7.92 (s, 1H), 7.78 (d, 1H, J=2.6 Hz), 7.61 (d, 1H, J=2.6 Hz), 5.98 (q, 1H, J=7.0 Hz). FABLRMS m/z 320 (M−H). ESHRMS m/z 319.9959 (M−H, Calc'd 319.9937). Anal. Calc'd for $C_{12}H_7ClF_3NO_4$: C, 44.81; H, 2.19; N, 4.35. Found: C, 44.92; H, 2.25; N, 4.26.

EXAMPLE 109

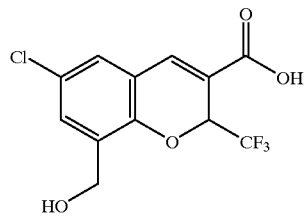

6-Chloro-8-(hydroxymethyl)-2-(trifluoromethyl)-2H-1-benzopyran-3-carboxylic Acid The 2H-1-benzopyran-3-carboxylic acid was prepared by a procedure similar to the method described in Example 80 using the carboxylic acid (Example 76, step 4) as the starting material: mp 174.6–178.9° C. ¹H NMR (acetone-d₆/300 MHz) 7.90 (s, 1H), 7.57 (d, 1H, J=2.6 Hz), 7.47 (d, 1H, J=2.6 Hz), 5.87 (q, 1H, J=7.0 Hz), 4.70 (s, 2H). FABLRMS m/z 309 (M+H). ESHRMS m/z 306.9981 (M−H, Calc'd 306.9985). Anal. Calc'd for $C_{12}H_5ClF_3O_3$ (3.81 wt. % H₂O): C, 47.37; H, 3.08. Found: C, 47.33; H, 2.82.

EXAMPLE 110

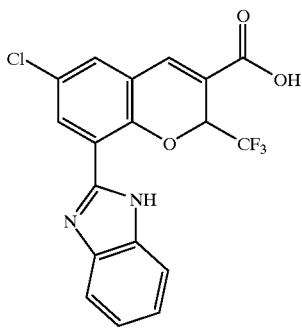

8-(1H-Benzimidazol-2-yl)-6-chloro-2-(trifluoromethyl)-2H-1-benzopyran-3-carboxylic Acid Step 1. Preparation of ethyl 8-(1H-Benzimidazol-2-yl)-6-chloro-2-(trifluoromethyl)-2H-1-benzopyran-3-carboxylate.

A solution of the aldehyde (Example 76, Step 3)(0.33 g, 0.99 mmol) and 1,2-phenylenediamine (0.11 g, 1.02 mmol) in nitrobenzene (20 mL) was heated to 150° C. for 1.8 hours. The reaction mixture was extracted with ethyl acetate, washed with brine, dried over $MgSO_4$, and concentrated in vacuo and purified by flash chromatography over silica gel (with 1:9 ethyl acetate/hexane as eluant) to give the ester as a brown solid (0.18 g, 43%) which was used in the next step without further purification.

Step 2. Preparation of 8-(1H-enzimidazol-2-yl)-6-chloro-2-trifluoromethyl-2H-1-benzopyran-3-carboxylic Acid.

The ester from Step 1 (0.18 g 1.5 mmol) was dissolved in THF (5 mL) and ethanol (5 mL), treated with 2.5 N sodium hydroxide (2.6 mL, 6.5 mmol), and stirred at room temperature for 1.7 hours. The reaction mixture was concentrated in vacuo, acidified with 3 N HCl, filtered and recrystallized from ethanol-water to give a tan solid (0.09 g, 52%): mp>300° C. $^1$H NMR (acetone-$d_6$/300 MHz) 8.59 (d, 1H, J=2.6 Hz), 8.03 (s, 1H), 7.73 (d, 1H, J=2.6 Hz), 7.67 (brs, 2H), 7.28 (m, 2H), 6.13 (q, 1H, J=6.8 Hz). FABLRMS m/z 395 (M−H{$^{37}$Cl}). ESHRMS m/z 393.0262 (M−H, Calc'd 393.0254). Anal. Calc'd for $C_{18}H_{10}ClF_3N_2O_3$ (2.88 wt % $H_2O$): C, 53.19; H, 2.80; N, 6.89. Found: C, 53.22; H, 2.90; N, 6.80.

EXAMPLE 111

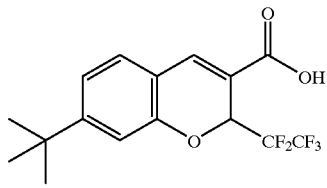

7-(1,1-Dimethylethyl)-2-(pentafluoroethyl)-2H-1-benzopyran-3-carboxylic Acid

Step 1. Preparation of Ethyl 3-hydroxy-4,4,5,5,5-pentafluoropentanoate.

A solution of ethyl 4,4,5,5,5-pentafluoro-3-oxo-pentanoate (41.32 g, 0.18 mole) in diethyl ether (70 mL) was cooled to 0° C. and treated with $NaBH_4$ (7.09 g, 0.19 mole). The reaction was allowed to warm to room temperature and stirred for 2 hours before quenching with 1 N HCl (200 mL). The layers were separated and the aqueous layer was extracted with diethyl ether. The combined organic layers were washed with 1 N HCl, brine, dried over $MgSO_4$, and concentrated in vacuo to give the hydroxy ester as a clear oil (46.40 g) which was used in the next step without further purification.

Step 2. Preparation of Ethyl 4,4,5,5,5-pentafluoro-2-pentenoate.

The hydroxy ester from Step 1 (46.40 g, 0.18 mole) was stirred at 120° C. with $P_2O_5$ (25.59 g, 0.09 mole) for 2.6 hours then vacuum distilled (95 torr, 45–64° C.) to give the ester as a clear oil (13.70 g, 35%)9: H NMR (CDCl$_3$/300 MHz) 6.78 (m, 1H), 6.57 (dt, 1H, J=15.9 Hz 2.0 Hz), 4.30 (q, 2H, J=7.3 Hz), 1.34 (t, 3H, J=7.1 Hz).

Step 3. Preparation of Ethyl 7-(1,1-Dimethylethyl)-2-(pentafluoroethyl)-2H-1-benzopyran-3-carboxylate.

A mixture of 4-tert-butylsalicylaldehyde Example 8, step 1 (1.15 g, 6.4 mmol) and the ethyl ester from Step 2 (1.59 g, 7.3 mmol) was dissolved in anhydrous DMF (4 mL). With stirring, $K_2CO_3$ (1.10 g, 9.0 mmol) was added causing the reaction to become deep red. The reaction was stirred at room temperature for 100 hours, acidified with 3 N HCl, diluted with ethyl acetate and washed with saturated $NaHCO_3$ solution, brine, dried over $MgSO_4$, filtered and concentrated in vacuo yielding a brown oil. This oil was purified by flash chromatography over silica gel, eluting with 10% ethyl acetate/hexanes to afford a yellow oil (1.72 g, 70%): $^1$H NMR (CDCl$_3$/300 MHz) 7.76 (s, 1H), 7.14 (d, 1H, J=8.1 Hz), 7.04 (dd, 1H, J=8.1 Hz 1.8 Hz), 6.94 (s, 1H), 5.92 (dd, 1H, J=22.4 Hz 3.0 Hz), 4.32 (m, 2H), 1.35 (t, 3H, J=7.2 Hz), 1.30 (s, 9H).

Step 4. Preparation of 7-(1,1-Dimethylethyl)-2-(pentafluoroethyl)-2H-1-benzopyran-3-carboxylic Acid.

The ester from Step 3 (1.58 g 4.20 mmol) was dissolved in THF (3 mL) and ethanol (3 mL), treated with 2.5 N sodium hydroxide (2 mL, 5 mmol), and stirred at room temperature for 23.3 hours. The reaction mixture was concentrated in vacuo, acidified with 3 N HCl yielding a suspension. The solid was collected by filtration and was recrystallized from ethanol-water to yield a yellow solid (0.76 g, 52%): mp 171.0–173.5° C. $^1$H NMR (acetone-$d_6$/300 MHz) 7.93 (s, 1H), 7.39 (d, 1H, J=8.1 Hz), 7.18 (dd, 1H, J=8.1 Hz 1.8 Hz), 7.02 (s, 1H), 6.01 (dd, 1H, J=23.1 Hz 3.2 Hz), 1.32 (s, 9H). FABLRMS m/z 351 (M+H). EIHRMS m/z 350.0945 (M+, Calc'd 350.0941). Anal. Calc'd for $C_{16}H_{11}F_5O_3$: C, 54.86; H, 4.32. Found: C, 54.88; H, 4.32.

EXAMPLE 112

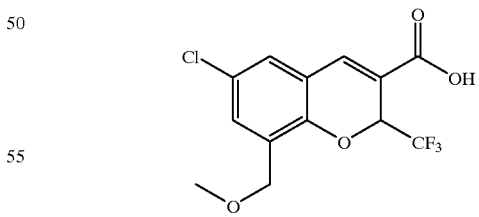

6-Chloro-8-(methoxymethyl)-2-(trifluoromethyl)-2H-1-benzopyran-3-carboxylic Acid Step 1. Preparation of Ethyl 6-chloro-8-(hydroxymethyl)-2-(trifluoromethyl)-2H-1-benzopyran-3-carboxylate.

A suspension of the aldehyde (Example 75, Step 1)(4.78 g, 14.3 mmol) was cooled to 0° C. and treated with $NaBH_4$ (0.33 g, 4.8 mmol). The solution was stirred for 10 minutes then quenched with 3N HCl, extracted with ethyl acetate, washed with saturated NaHCO$_3$, brine, dried over MgSO$_4$, and concentrated in vacuo to give a brown solid which was filtered through a plug of silica gel to give the alcohol as a brown solid (3.60 g, 75%). $^1$H NMR (CDCl$_3$/300 MHz) 7.66 (s, 1H), 7.41 (d, 1H, J=2.4 Hz), 7.17 (d, 1H, J=2.4 Hz), 5.75 (q, 1H, J=6.8 Hz), 4.71 (s, 2H), 4.33 (m, 2H), 1.85 (brs, 1H), 1.36 (t, 3H, J=7.1). This solid was used in the next step without further purification.

Step 2. Preparation of Ethyl 6-chloro-8-(methoxymethyl)-2-(trifluoromethyl)-2H-1-benzopyran-3-carboxylate.

The alcohol from Step 1 (0.44 g, 1.3 mmol), silver triflate (0.36 g, 1.4 mmol) and 2,6-di-tert-butylpyridine (0.37 g, 1.9 mmol) were dissolved in methylene chloride (3 mL) cooled to 0° C. and treated with methyl iodide (0.40 g, 2.8 mmol). The reaction was allowed to warm and stirred at room temperature for 4.6 hours. The reaction was filtered through diatomaceous earth and the filtrate was washed with 3N HCl, saturated NaHCO$_3$, brine, dried over MgSO$_4$, and concentrated in vacuo yielding a brown oil. This oil was purified by flash chromatography over silica gel, eluting with 10% ethyl acetate-hexanes to afford the substituted 2H-1-benzopyran (0.19 g, 41%) as a white oily solid suitable ESHRMS m/z 321.0141 (M–H, Calc'd 321.0141). Anal. Calc'd for C$_{13}$H$_{10}$ClF$_3$O$_4$: C, 48.39; H, 3.12. Found: C, 48.45; H, 3.11.

EXAMPLE 113

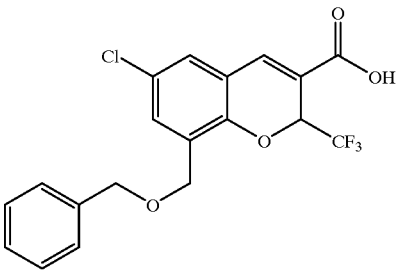

6-Chloro-8-(benzyloxymethyl)-2-(trifluoromethyl)-2H-1-benzopyran-3-carboxylic Acid The 2H-1-benzopyran-3-carboxylic acid was prepared by a procedure similar to the method described in Example 112: mp 133.8–135.4° C. $^1$H NMR (acetone-d$_6$/300 MHz) 7.90 (s, 1H), 7.54 (d, 1H, J=2.6), 7.51 (d, 1H, J=2.4 Hz), 7.42 (m, 5H), 5.91 (q, 1H, J=7.1 Hz), 4.68 (s, 2H), 4.63 (s, 2H). FABLRMS m/z 399 (M+H). ESHRMS m/z 397.0454 (M–H, Calc'd 397.0461). Anal. Calc'd for C$_{19}$H$_{13}$ClF$_3$O$_4$: C, 57.23; H, 3.54; Cl, 8.89. Found: C, 57.34; H, 3.63; Cl, 8.77.

EXAMPLE 114

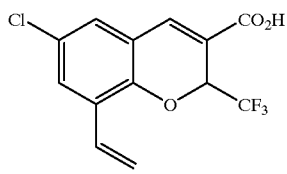

6-Chloro-8-ethenyl-2-(trifluoromethyl)-2H-1-benzopyran-3-carboxylic Acid

Step 1. Preparation of Ethenyl-6-chloro-8-ethenyl-2-(trifluoromethyl)-2H-1-benzopyran-3-carboxylate.

In a 100 mL round bottomed flask under N$_2$, ethyl 8-bromo-6-chloro-2-trifluoromethyl-2H-benzopyran-3-carboxylate (Example 74, Step 1)(2.21 g, 5.73 mmol) was dissolved in toluene (30 mL of anhydrous reagent).

Tetrakis(triphenylphosphine)palladium(0) (0.132 g, 0.115 mmol) was added, followed by tributylethyenylstannane (2.0 g, 6.31 mmol). The resulting solution was heated to reflux for 5 hours. The reaction mixture was allowed to cool to room temperature, was poured into 50 mL of 20% ammonium fluoride solution and stirred for one hour. Diethyl ether (100 mL) was added and the mixture was washed with water (2×50 mL). The organic phase was dried over MgSO$_4$, filtered, and evaporated to yield a yellow oil. The crude material was purified by flash chromatography (0.5% ethyl acetate in hexanes) to afford the ester as a yellow solid (0.86 g, 45%): mp 75.9–77.2° C. $^1$H NMR (CDCl$_3$/300 MHz) 7.64 (s, 1H), 7.45 (d, 1H, J=2.5 Hz), 7.12 (d, 1H, J=2.6 Hz), 6.92 (dd, 1H, J=17.7 Hz, 11.3 Hz), 5.81 (d, 1H, J=17.7 Hz), 5.76 (q, 1H, J=6.8 Hz), 5.41 (d, 2H, J=11.1 Hz), 4.36–4.29 (m, 2H), 1.36 (t, 3H, J=7.3 Hz). FABLRMS m/z 350.1 (M+NH$_4^+$). ESHRMS m/z 350.0796 (M+NH$_4^+$, Calc'd. 350.0771). Anal. Calc'd. for C$_{15}$H$_{12}$ClF$_3$O$_3$+4.07% H$_2$O: C, 51.95; H, 3.94. Found: C, 51.67; H, 3.69.

Step 2. Preparation of 6-chloro-8-ethenyl-2-(trifluoromethyl)-2H-1-benzopyran-3-carboxylic Acid.

The ester (Step 1) (0.350 g, 1.05 mmol) was dissolved in a solution of THF:ethanol:water(7:2:1; 10 mL), was treated with sodium hydroxide (0.46 mL, 1.05 mmol of a 2.5 N solution), and stirred at room temperature for 18 hours. The solvent was removed in vacuo and the residue was dissolved in water (10 mL). Diethyl ether (10 mL) was added and the mixture acidified with concentrated HCR. The layers were separated, and the aqueous phase was extracted with diethyl ether (2×10 mL). The organic phases were combined, dried over MgSO$_4$, filtered, and evaporated to yield a yellow solid, which was recrystallized in diethyl ether-hexane to afford the title compound as a yellow solid (0.288 g, 90%): mp 183.2–185.8° C. $^1$H NMR (CDCl$_3$/300 MHz) 7.77 (s, 1H), 7.49 (d, 1H, J=2.2 Hz), 7.16 (d, 1H, J=2.4 Hz), 6.93 (dd, 1H, J=11.3, 17.7 Hz), 5.82 (d, 1H, J=17.7 Hz), 5.74 (q, 1H, J=6.9 Hz), 5.43 (d, 1H, J=11.1 Hz). FABLRMS m/z 303 (M–H). ESHRMS m/z 303.0014 (M–H, Calc'd. 303.003582). Anal. Calc'd. for C$_{13}$H$_8$ClF$_3$O$_3$+1.58% H$_2$O: C, 50.44; H, 2.78. Found: C, 50.42; H, 2.65.

EXAMPLE 115

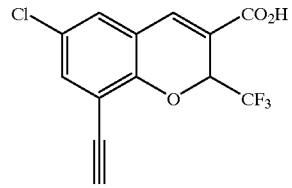

6-Chloro-8-ethynyl-2-(trifluoromethyl)-2H-1-benzopyran-3-carboxylic Acid

The 2H-1-benzopyran-3-carboxylic acid was prepared by a procedure similar to the method described in Example 114: mp 186.2–189.0° C. $^1$H NMR (acetone-d$_6$/300 MHz) 7.87 (s, 1H), 7.60 (d, 1H, J=2.4 Hz), 7.51 (d, 1H, J=2.4 Hz), 5.95 (q, 1H, J=7.0 Hz), 4.02 (s, 1H). FABLRMS m/z 301 (M–H). ESHRMS m/z 300.9875 (M–H, Calc'd 300.9879). Anal. Calc'd. for C$_{13}$H$_6$ClF$_3$O$_3$: C, 51.59; H, 2.00; Cl, 11.71. Found: C, 51.26; H, 2.06; Cl, 11.40.

EXAMPLE 116

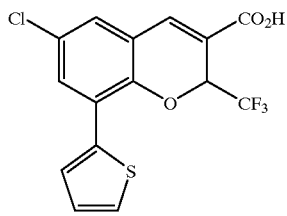

6-Chloro-8-(2-thienyl)-2-(trifluoromethyl)-2H-1-benzopyran-3-carboxylic Acid

The 2H-1-benzopyran-3-carboxylic acid was prepared by a procedure similar to the method described in Example 114: mp 257.5–258.8° C. $^1$H NMR (acetone-$d_6$/300 MHz) 7.91 (s, 1H), 7.79 (d, 1H, J=2.4 Hz), 7.74–7.72 (m, 1H), 7.62–7.61 (m, 1H), 7.51 (d, 1H, J=2.4 Hz), 7.19–7.16 (m, 1H), 6.04 (q, 1H, J=7.1 Hz). FABLRMS m/z 359 (M−H). ESHRMS m/z 358.9747 (M−H, Calc'd. 358.9756). Anal. Calc'd. for $C_{15}H_8ClF_3O_3S$: C, 49.94; H, 2.24; Cl, 9.83; S, 8.89. Found: C, 50.26; H, 2.45; Cl, 9.72; S, 9.00.

EXAMPLE 117

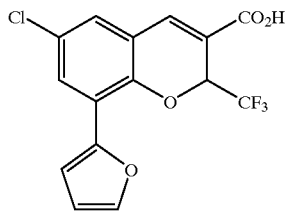

6-Chloro-8-(2-furanyl)-2-(trifluoromethyl)-2H-1-benzopyran-3-carboxylic Acid

The 2H-1-benzopyran-3-carboxylic acid was prepared by a procedure similar to the method described in Example 114: mp 171.5–173.3° C. $^1$H NMR (acetone-$d_6$/300 MHz) 7.93 (s, 1H), 7.82 (d, 1H, J=2.6 Hz), 7.72–7.71 (m, 1H), 7.50 (d, 1H, J=2.6 Hz), 7.16 (d, 1H, J=2.4 Hz), 6.65–6.63 (m, 1H), 6.11 (q, 1H, J=7.1 Hz). FABLRMS m/z 343 (M−H). ESHRMS m/z 342.9995 (M−H, Calc'd. 342.9985). Anal. Calc'd. for $C_{15}H_8ClF_3O_4$+1.31% $H_2O$: C, 51.59; H, 2.46; Cl, 10.15. Found: C, 51.57; H, 2.33; Cl, 10.14.

EXAMPLE 118

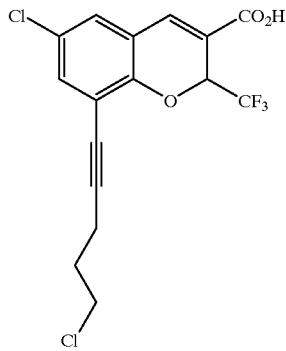

6-Chloro-8-(5-chloro-1-pentynyl)-2-(trifluoromethyl)-2H-1-benzopyran-3-carboxylic Acid Step 1. Preparation of Ethyl 6-chloro-8-(5-chloro-1-pentynyl)-2-(trifluoromethyl)-2H-1-benzopyran-3-carboxylate.

Ethyl 6-chloro-8-iodo-2-trifluoromethyl-2H-1-benzopyran-3-carboxylate (Example 73, Step 2) (1.50 g, 3.47 mmol), tetrakis-(triphenylphosphine)palladium(0) (0.2 g, 0.174 mmol), copper(I)iodide (0.066 g, 0.347 mmol), and triethylamine (1.05 g, 10.4 mmol) were dissolved in toluene (50 mL). 5-Chloro-1-pentyne (0.53 g, 5.20 mmol) was added via syringe and the mixture stirred for 18 hours at room temperature. The reaction was diluted with diethyl ether (50 mL), extracted with 0.5 N HCl (2×25 mL), and water (2×25 mL). The organic phase was dried over $MgSO_4$, filtered, and evaporated to yield an orange oil. The crude material was purified by flash chromatography in 2% ethyl acetate in hexane. Recrystallization from hexane afforded the ester as a white solid (0.96 g, 68%): mp 84.8–85.9° C. $^1$H NMR (CDCl$_3$/300 MHz) 7.61 (s, 1H), 7.33 (d, 1H, J=2.6 Hz), 7.14 (d, 1H, J=2.6 Hz), 5.79 (q, 1H, J=6.7 Hz), 4.37–4.29 (m, 2H), 3.75 (t, 2H, J=6.7 Hz), 2.67 (t, 2H, J=6.7 Hz), 2.11–2.03 (m, 2H,), 1.35 (t, 3H, J=7.2 Hz). FABLRMS m/z 424.1 (M+NH$_4^+$). ESHRMS m/z 424.0694 (M+NH$_4^+$, Calc'd. 424.0694). Anal. Calc'd. for $C_{18}H_{15}Cl_2F_3O_3$: C, 53.09; H, 3.71;, Cl, 17.41. Found: C, 53.02; H, 3.90; Cl, 17.63.

Step 2. Preparation of 6-chloro-8-(5-chloro-1-pentynyl)-2-(trifluoromethyl)-2H-1-benzopyran-3-carboxylic Acid.

The ester (Step 1) (0.500 g, 1.23 mmol) was dissolved in THF-ethanol-water(7:2:1; 10 mL). It was treated with sodium hydroxide (0.49 mL, 1.23 mmol of a 2.5 N solution), and stirred at room temperature for 18 hours. The solvent was evaporated and the residue was dissolved in water (10 mL). Diethyl ether (10 mL) was added and the mixture acidified with concentrated HCl. The organic layer was separated, and the aqueous phase was extracted with diethyl ether (2×10 mL). The combined extracts were dried over $MgSO_4$, filtered, and evaporated to yield a yellow solid, which was recrystallized in diethyl ether-hexane to afford the title compound as a yellow solid (0.371 g, 80%): mp 154.4–156.4° C. $^1$H NMR (acetone-$d_6$/300 MHz) 7.88 (s, 1H), 7.53 (d, 1H, J=2.4 Hz), 7.44 (d, 1H, J=2.4 Hz), 5.94 (q, 1H, J=7.1 Hz), 3.83 (t, 2H, J=6.5 Hz), 2.68 (t, 2H, J=6.8 Hz), 2.12–2.04 (m, 2H). ESLRMS m/z 377 (M−H). ESHRMS m/z 376.9930 (M−H, Calc'd. 376.9959). Anal. Calc'd. for $C_{16}H_{11}Cl_2F_3O_3$+1.18% $H_2O$: C, 50.08; H, 3.02; Cl, 18.48. Found: C, 50.11; H, 2.73; Cl, 18.28.

EXAMPLE 119

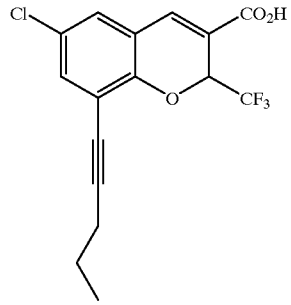

6-Chloro-8-(1-pentynyl)-2-(trifluoromethyl)-2H-1-benzopyran-3-carboxylic Acid

The 2H-1-benzopyran-3-carboxylic acid was prepared by a procedure similar to the method described in Example 118: mp 168.1–171.2° C. $^1$H NMR (CDCl$_3$/300 MHz) 7.75 (s, 1H), 7.37 (d, 1H, J=2.6 Hz), 7.15 (d, 1H, J=2.4 Hz), 5.77 (1, 1H, J=6.7 Hz), 2.44 (t, 2H, J=6.9 Hz), 1.68–1.61 (m, 2H), 1.07 (t, 3H, J=7.25 Hz. FABLRMS m/z 345 (M+H). ESHRMS m/z 343.0373 (M–H, Calc'd. 343.0349). Anal. Calc'd. for $C_{16}H_{12}ClF_3O_3$+0.69% $H_2O$: C, 55.36; H, 3.56. Found: C, 55.21; H, 3.62.

EXAMPLE 120

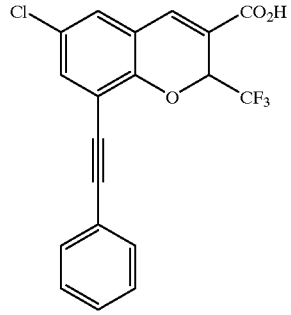

6-Chloro-8-(phenylethynyl)-2-(trifluoromethyl)-2H-1-benzopyran-3-carboxylic Acid The 2H-1-benzopyran-3-carboxylic acid was prepared by a procedure similar to the method described in Example 118: mp 190.1–192.1° C. $^1$H NMR (CDCl$_3$/300 MHz) 7.92 (s, 1H), 7.61–7.57 (m, 4H), 7.47–7.44 (m, 3H), 6.01 (q, 1H, J=7.0 Hz). ESLRMS m/z 377 (M–H). ESHRMS m/z 377.0167 (M–H, Calc'd. 377.0192). Anal. Calc'd. for $C_{19}H_{10}ClF_3O_3$: C, 60.26; H, 2.66; Cl, 9.36. Found: C, 60.09; H, 2.73; Cl, 9.09.

EXAMPLE 121

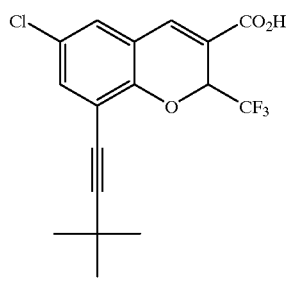

6-Chloro-8-(3,3-dimethyl-1-butynyl)-2-(trifluoromethyl)-2H-1-benzopyran-3-carboxylic Acid The 2H-1-benzopyran-3-carboxylic acid was prepared by a procedure similar to the method described in Example 118: mp 218.3–222.4° C. $^1$H NMR (acetone-d$_6$/300 MHz) 7.87 (s, 1H), 7.51 (d, 1H, J=2.4 Hz), 7.38 (d, 1H, J=2.6 Hz), 5.92 (q, 1H, J=6.9 Hz), 1.32 (s, 9H). FABLRMS m/z 359 (M+H). ESHRMS m/z 357.0490 (M–H, Calc'd. 357.0505). Anal. Calc'd. for $C_{17}H_{14}ClF_3O_3$: C, 56.92; H, 3.93; Cl, 9.88. Found: C, 56.63; H, 3.94; Cl, 10.03.

EXAMPLE 122

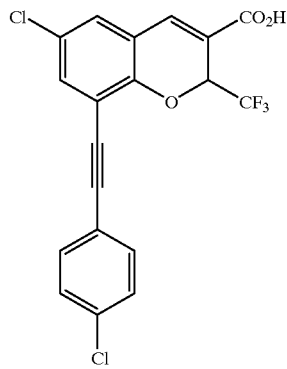

6-Chloro-8-[(4-chlorophenyl)ethynyl]-2-(trifluoromethyl)-2H-1-benzopyran-3-carboxylic Acid The 2H-1-benzopyran-3-carboxylic acid was prepared by a procedure similar to the method described in Example 118: mp 210.4–211.4° C. $^1$H NMR (CDCl$_3$/300 MHz) 7.75 (s, 1H), 7.48–7.43 (m, 3H), 7.36 (s, 1H), 7.33 (s, 1H), 7.22 (d, 1H, J=2.6 Hz), 5.82 (q, 1H, J=6.6 Hz). FABLRMS m/z 411 (M–H). ESHRMS m/z 410.9802 (M–H, Calc'd. 410.980259). Anal. Calc'd. for $C_{20}H_{12}Cl_2F_3O_3$: C, 55.23; H, 2.20; Cl, 17.16. Found: C, 55.22; H, 2.07; Cl, 17.39.

EXAMPLE 123

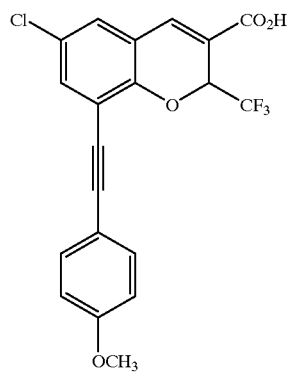

6-Chloro-8-[(4-methoxyphenyl)ethynyl]-2-(trifluoromethyl)-2H-1-benzopyran-3-carboxylic Acid The 2H-1-benzopyran-3-carboxylic acid was prepared by a procedure similar to the method described in Example 118: mp 217.7–218.7° C. $^1$H NMR (CDCl$_3$/300 MHz) 7.75 (s, 1H), 7.51–7.47 (m, 3H), 7.18 (d, 1H, J=2.4 Hz), 6.91–6.88 (m, 2H), 5.82 (1, 1H, J=6.7 Hz). ESLRMS m/z 407 (M–H). ESHRMS m/z 407.0293 (M–H, Calc'd 407.0298). Anal. Calc'd for C$_{20}$H$_{12}$ClF$_3$O$_4$: C, 58.77; H, 2.96; Cl, 8.67. Found: C, 58.68; H, 2.85; Cl, 9.15.

EXAMPLE 124

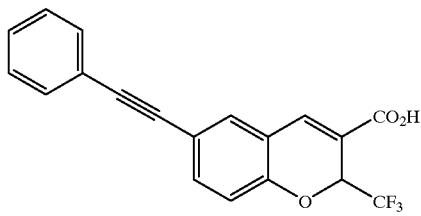

6-(Phenylethynyl)-2-(trifluoromethyl)-2H-1-benzopyran-3-carboxylic Acid

The 2H-1-benzopyran-3-carboxylic acid was prepared by a procedure similar to the method described in Example 118 using ethyl 6-iodo-2-(trifluoromethyl)-2H-1-benzopyran-3-carboxylate (Example 24, Step 3) as the starting material: mp 240.1–241.3° C. $^1$H NMR (acetone-d$_6$/300 MHz) 7.94 (s, 1H), 7.70–7.69 (m, 1H), 7.61–7.53 (m, 3H), 7.44–7.41 (m, 3H), 7.10 (d, 1H, J=7.1 Hz). ESHRMS m/z 343.0550 (M–H, Calc'd. 343.0582). Anal. Calc'd for C$_{19}$H$_{11}$F$_3$O$_3$: C, 66.29; H, 3.22. Found: C, 66.26; H, 3.29.

EXAMPLE 125

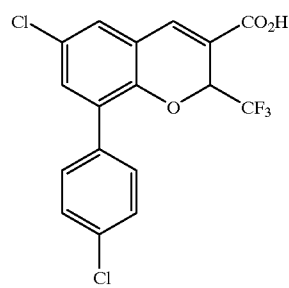

6-Chloro-8-(4-chlorophenyl)-2-(trifluoromethyl)-2H-1-benzopyran-3-carboxylic Acid Step 1. Preparation of Ethyl 6-chloro-8-(4-chlorophenyl)-2-(trifluoromethyl)-2H-1-benzopyran-3-carboxylate.

Ethyl 6-chloro-8-iodo-2-(trifluoromethyl)-2H-1-benzopyran-3-carboxylate (Example 73, Step 2) (1.3 g, 3.02 mmol), potassium carbonate (1.25 g, 9.06 mmol), 4-chorophenylboronic acid (0.52 g, 3.33 mmol), and tetrakis(triphenylphosphine)palladium(0) (0.174 g, 0,151 mmol) were added to toluene (30 mL) and the resulting solution was heated to reflux for 18 hours. After cooling to room temperature the reaction mixture was poured into ethyl acetate (50 mL). It was washed with 1 N HCl (2×25 mL), saturated aqueous sodium bicarbonate (2×25 mL), and water (2×25 mL). The organic phase was dried over MgSO$_4$, filtered, and concentrated in vacuo to yield a brown oil. The crude material was purified by flash chromatography using 1% ethyl acetate in hexane yielding a white solid. Recrystallization from hexane afforded the ester as a white solid (0.79 g, 64%): mp 114.2–115.9° C. $^1$H NMR (CDCl$_3$/300 MHz) 7.69 (s, 1H), 7.41 (s, 4H), 7.30 (d, 1H, J=2.4 Hz), 7.22 (d, 1H, J=2.6 Hz), 5.70 (q, 1H, J=6.9 Hz), 4.37–4.29 (m, 2H), 1.35 (t, 3H, J=7.1 Hz). ESLRMS m/z 434 (M+NH$_4^+$). FABHRMS m/z 434.0574 (M+NH$_4^+$, Calc'd. 434.0538). Anal. Calc'd. for C$_{19}$H$_{13}$Cl$_2$F$_3$O$_3$: C, 54.70; H, 3.14; Cl, 17.00. Found: C, 54.79; H, 3.18; Cl, 16.65.

Step 2. Preparation of 6-chloro-8-(4-chlorophenyl)-2-(trifluoromethyl)-2H-1-benzopyran-3-carboxylic Acid.

The ester from Step 1 (0.500 g, 1.20 mmol) was dissolved in a solution of THF:ethanol:water (7:2:1; 10 mL), treated with sodium hydroxide (0.48 mL, 1.20 mmol of a 2.5 N solution), and stirred at room temperature for 18 hours. The solvent was removed in vacuo and the residue was dissolved in water (10 mL). Diethyl ether (10 mL) was added and the mixture acidified with concentrated HCl. The organic layer was separated, and the aqueous phase was extracted with diethyl ether (2×10 mL). The combined extracts were dried over MgSO$_4$, filtered, and evaporated to yield a white solid, which was recrystallized in diethyl ether-hexane to afford the title compound as a white solid (0.40 g, 86%): mp 205.5–207.3° C. $^1$H NMR (CDCl$_3$/300 MHz) 7.81 (s, 1H), 7.42(s, 4H), 7.34 (d, 1H, J=2.4 Hz), 7.25 (s, 1H), 5.69 (q, 1H, J=6.8 Hz). FABLRMS m/z 387 (M–H). ESHRMS m/z 386.9788 (M–H, Calc'd. 386.980259). Anal. Calc'd. for C$_{17}$H$_9$Cl$_2$F$_3$O$_3$: C, 52.47; H, 2.33; Cl, 18.22. Found: C, 52.38; H, 2.47; Cl, 18.20.

EXAMPLE 126

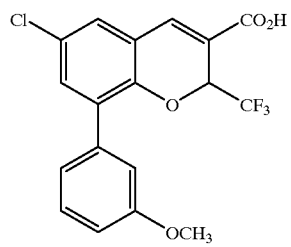

6-Chloro-8-(3-methoxyphenyl)-2-(trifluoromethyl)-2H-1-benzopyran-3-carboxylic Acid Step 1. Preparation of Ethyl 6-chloro-8-(3-methoxyphenyl)-2-(trifluoromethyl)-2H-1-benzopyran-3-carboxylate.

In a 100 mL round bottomed flask under nitrogen, ethyl 6-chloro-8-iodo-2-(trifluoromethyl)-2H-1-benzopyran-3-carboxylate (Example 73, Step 2)(1.00 g, 2.31 mmol) and 3-methoxyphenylboronic acid (0.369 g, 2.43 mmol) were dissolved in 1-propanol (50 mL). The mixture was stirred at room temperature for 0.5 hours, allowing for the solids to dissolve. The resulting solution was treated with palladium (II) acetate (0.016 g, 0.0693 mmol), triphenylphosphine (0.055 g, 0.208 mmol), sodium carbonate (0.294 g, 2.77 mmol), and deionized water (10 mL). The reaction mixture was heated to reflux for 3 hours. After cooling to room temperature the mixture was extracted with ethyl acetate (1×150 mL, 2×25 mL). The combined organic phases were washed with saturated aqueous $NaHCO_3$ (50 mL) and brine (2×50 mL), dried over $MgSO_4$, filtered, and concentrated in vacuo to yield a yellow oil. The crude material was purified by flash chromatography in 0.5% ethyl acetate in hexane yielding a white solid. The solid was recrystallized from hexane yielding the desired ester as a white solid (0.60 g, 63%): mp 93.7–95.1° C. $^1$H NMR ($CDCl_3$/300 MHz) 7.69 (s, 1H), 7.35–7.32 (m, 2H), 7.22 (d, 1H, J=2.6 Hz), 7.05–7.03 (m, 2H), 6.96–6.93 (m, 1H), 5.72 (q, 1H, J=6.7 Hz), 4.34–4.31 (m, 2H), 1.35 (t, 3H, J=7.1 Hz). FABLRMS m/z 413 (M+H). ESHRMS m/z 413.0765 (M+H, Calc'd. 413.076747). Anal. Calc'd. for $C_{20}H_{16}ClF_3O_4$: C, 58.19; H, 3.91; Cl, 8.59. Found: C, 58.33; H, 4.10; Cl, 8.61.

Step 2. Preparation of 6-chloro-8-(3-methoxyphenyl)-2-(trifluoromethyl)-2H-1-benzopyran-3-carboxylic Acid.

The ester from Step 1 (0.300 g, 0.727 mmol) was dissolved in THF-ethanol-water (7:2:1, 10 mL). It was treated with sodium hydroxide (0.29 mL of a 2.5 N solution, 0.727 mmol), and stirred at room temperature for 18 hours. The solvent was evaporated and the residue was dissolved in water (10 mL). Ether (10 mL) was added, followed by a few drops of concentrated HCN. The ether layer was separated, and the aqueous phase was extracted with ether (2×10 mL). The ether extracts were combined, dried over $MgSO_4$, filtered, and concentrated in vacuo to yield a white solid, which was recrystallized in diethyl ether-hexane to afford the title compound as a white solid (0.23 g, 81%): mp 173.1–177.4° C. $^1$H NMR ($CDCl_3$/300 MHz) 7.81 (s, 1H), 7.39–7.37 (m, 2H), 7.05–7.04 (m, 2H), 6.97–6.94 (m, 1H), 5.71 (q, 1H, J=6.7 Hz), 3.85 (s, 3H). ESHRMS m/z 383.0278 (M–H, Calc'd. 383.029796). Anal. Calc'd. for $C_{18}H_{12}ClF_3O_4$: C, 56.20; H, 3.14; Cl, 9.21. Found: C, 55.90; H, 3.11; Cl, 9.48.

EXAMPLE 127

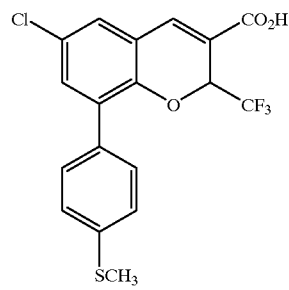

6-Chloro-8-[(4-methylthio)phenyl]-2-(trifluoromethyl)-2H-1-benzopyran-3-carboxylic Acid The 2H-1-benzopyran-3-carboxylic acid was prepared by a procedure similar to the method described in Example 126: mp 211.4–212.5° C. $^1$H NMR (acetone-d/300 MHz) 7.94 (s, 1H), 7.57 (d, 1H, J=2.6 Hz), 7.53–7.50 (m, 2H), 7.45 (d, 1H, J=2.6 Hz), 7.39–7.36 (m, 2H), 5.87 (q, 1H, J=7.1 Hz), 2.55 (s, 3H). ESHRMS m/z 399.0051 (M–H, Calc'd. 399.0069). Anal. Calc'd. for $C_{18}H_{12}ClF_3O_3S$: C, 53.94; H, 3.02; Cl, 8.84; S, 8.00. Found: C, 53.86; H, 2.82; Cl, 8.91; S, 8.21.

EXAMPLE 128

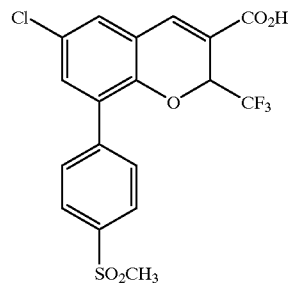

6-Chloro-8-[(4-methylsulfonyl)phenyl]-2-(trifluoromethyl)-2H-1-benzopyran-3-carboxylic Acid Step 1. Preparation of Ethyl-6-chloro-8-[(4-methylsulfonyl)phenyl]-2-(trifluoromethyl)-2H-1-benzopyran-3-carboxylate.

Oxone™ (1.44 g, 2.34 mmol) was dissolved in $H_2O$ (10 mL) and then chilled to 5° C. A solution of ethyl 6-chloro-8-[(4-methylthio)phenyl]-2-(trifluoromethyl)-2H-1-benzopyran-3-carboxylate (Example 127, ethyl ester)(0.5 g, 1.17 mmol)in methanol (20 mL) was slowly added to the reaction mixture and the solution was stirred at room temperature for 5 hours. The methanol was then removed in vacuo. The remaining solution was extracted with methylene chloride (2×50 mL). The combined organic layers were dried over $MgSO_4$, filtered, and evaporated to yield a yellow solid. This solid was recrystallized in ether-hexane to afford the sulfone as a white solid (0.46 g, 84%): mp 139.2–146.2° C. $^1$H NMR ($CDCl_3$/300 MHz) 8.03(s, 1H), 8.00 (s, 1H), 7.70 (d, 2H, J=2.4 Hz), 7.28 (d, 1H, J=2.6 Hz), 5.71 (q, 1H, J=6.9 Hz), 4.35–4.32 (m, 2H), 3.11(s, 3H), 1.35 (t, 3H, J=7.2 Hz). FABLRMS m/z 467 (M+Li). ESHRMS m/z 478.0707 (M+$NH_4^+$, Calc'd. 478.070281). Anal. Calc'd. for $C_{20}H_{16}ClF_3O_5S$: C, 52.12; H, 3.50; Cl, 7.69. Found: C, 52.17; H, 3.36; Cl, 7.77.

Step 2. Preparation of 6-chloro-8-[(4-methylsulfonyl)phenyl]-2-(trifluoromethyl)-2H-1-benzopyran-3-carboxylic Acid.

The sulfone from Step 1 (0.300 g, 0.651 mmol) was dissolved in a solution of THF:ethanol:water (7:2:1; 10 mL). It was treated with sodium hydroxide (0.26 mL, 0.651 mmol of a 2.5 N solution), and stirred at room temperature for 18 hours. The solvent was removed in vacuo and the residue was dissolved in water (10 mL). Diethyl ether (10 mL) was and the mixture acidified with concentrated HCl. The organic layer was separated, and the aqueous phase was extracted with diethyl ether (2×10 mL). The combined organic extracts were dried over $MgSO_4$, filtered, and evaporated to yield a white solid. Recrystallization of this solid in ether-hexane afforded the title compound as a white solid (0.20 g, 73%): mp 286.5–287.8° C. $^1$H NMR (acetone-$d_6$/300 MHz) 8.07 (d, 2H, J=6.7 Hz), 7.97 (s, 1H), 7.84 (d, 2H, J=6.7 Hz), 7.67 (d, 1H, J=2.6 Hz), 7.55 (d, 1H, J=2.6 Hz), 5.92 (q, 1H, J=7.1 Hz), 3.20 (s, 1H). ESHRMS m/z 430.9947 (M–H, Calc'd. 430.996782). Anal. Calc'd. for $C_{18}H_{12}ClF_3O$, S: C, 49.95; H, 2.80; Cl, 8.19. Found: C, 50.04; H, 2.80; Cl, 8.25.

EXAMPLE 129

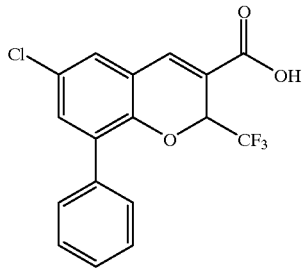

6-Chloro-8-phenyl-2-(trifluoromethyl)-2H-1-benzopyran-3-carboxylic Acid

Step 1. Preparation of Ethyl 6-chloro-8-phenyl-2-(trifluoromethyl)-2H-1-benzopyran-3-carboxylate.

A mixture of ethyl 6-chloro-8-bromo-2-(trifluoromethyl)-2H-1-benzopyran-3-carboxylate(Example 74, Step 1)(2.0 g, 5.2 mmol), tetrakis(triphenylphosphine) palladium(0) (2.15 g, 1.7 mmol), triphenylphosphine (0.013 g, 0.05 mmol), and tributylphenyltin (1.9 mL, 5.7 mmol) in toluene (60 mL) was heated to 110° C. for 3 days. The reaction mixture was allowed to cool to room temperature and filtered through a plug of silica gel eluting with 25% ethyl acetate in hexanes. The filtrate was concentrated in vacuo and then purified by flash chromatography (silica gel, ethyl acetate-hexanes, 1:9). The fractions containing desired product were combined and concentrated in vacuo. To remove the remaining tin impurities the mixture was taken up in THF (10 mL) and aqueous ammonium fluoride solution (10 wt %, 20 mL) and stirred at room temperature for 2 hours. The solution was extracted with ethyl acetate. The extracts were combined, dried over $MgSO_{41}$ filtered, and concentrated in vacuo to afford the ester as an oil (1.30 g, 65%). $^1$H NMR(CDCl$_3$/300 MHz) 7.67 (s, 1H),7.47–7.36 (m, 5H), 7.31 (d, 1H, J=2.6 Hz), 7.18 (d, 1H, J=2.4 Hz), 5.69 (q, 1H, J=6.8 Hz), 4.30 (m, 2H), 1.33 (t, 3H, J=7.1 Hz). $^{19}$F NMR (CDCl$_3$/282 MHz) d –78.27 (d, J=7.2 Hz). FABLRMS m/z 383 (M+H). ESHRMS m/z 400.0937 (M+NH$_4$, Calc'd 400.0927).

Step 2. Preparation of 6-chloro-8-phenyl-2-trifluoromethyl-2H-1-benzopyran-3-carboxylic Acid.

A solution of the ester from step 1 (1.0 g, 2.6 mmol) was dissolved in THF (5 mL) and methanol (5 mL) was treated with a 2.5 N NaOH solution (4.0 mL, 10.4 mmol). The resulting mixture was stirred at room temperature for 18 hours. The solvent was removed in vacuo, and the residue taken up in ethyl acetate and acidified with 3 N HCl. The solution was extracted with ethyl acetate. The extracts were combined, dried over $MgSO_4$, filtered, and concentrated in vacuo yielding a yellow solid. Recrystallization from ethyl acetate-hexanes afforded the title compound as a pale yellow solid (0.42 g, 46%): mp 196.3–197.7° C. $^1$H NMR (CDCl$_3$/300 MHz) d 7.65 (s, 1H), 7.40–7.23 (m, 6H), 7.15 (s, 1H), 5.63 (q, 1H, J=6.5 Hz), 3.35 (broad s, 1H). $^{19}$F NMR (CDCl$_3$/282 MHz)d –78.71 (d, J=5.8 Hz). FABLRMS m/z 355 (M+H). ESHRMS m/z 353.0198 (M–H, Calc'd 353.0192).

EXAMPLE 130

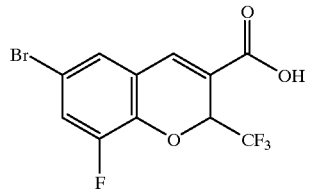

6-Bromo-8-fluoro-2-(trifluoromethyl)-2H-1-benzopyran-3-carboxylic Acid

4-Bromo-2-fluorophenol was converted to the title compound by a procedure similar to that described in Example 2: mp 206–208° C. $^1$H NMR (CD$_3$OD/300 MHz) 7.78 (s, 1H), 7.36–7.48 (m, 2H), 5.87 (q, 1H, J=6.8 Hz). EIHRMS m/z 339.9349 (Calc'd 339.9358). Anal. Calc'd for $C_{11}H_5BrF_4O_3$: C 38.74, H 1.48; Found C 38.97, H, 1.60.

EXAMPLE 131

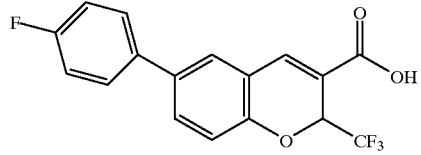

6-(4-Fluorophenyl)-2-(trifluoromethyl)-2H-1-benzopyran-3-carboxylic Acid

The 2H-1-benzopyran-3-carboxylic acid was prepared by a procedure similar to the method described in Example 125 using ethyl 6-iodo-2-(trifluoromethyl)-2H-1-benzopyran-3-carboxylate (Example 24, Step 3) as the starting material: mp 207–210° C. $^1$H NMR (CD$_3$OD/300 MHz) 7.87 (s, 1H), 7.54–7.64 (m, 4H), 7.10–7.20 (m, 2H), 7.03 (d, 1H, J=9.4 Hz), 5.77 (q, 1H, J=7.0 Hz). EIHRMS m/z 338.0573 (Calc'd 338.0566) Anal. Calc'd for $C_{11}H_6F_3IO_3$+1.25% $H_2O$: C, 59.62; H, 3.08. Found C, 59.61; H, 3.09.

EXAMPLE 132

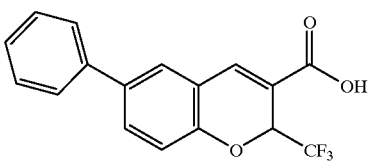

6-Phenyl-2-(trifluoromethyl)-2H-1-benzopyran-3-carboxylic Acid

The 2H-1-benzopyran-3-carboxylic acid was prepared by a procedure similar to the method described in Example 125 using ethyl 6-iodo-2-(trifluoromethyl)-2H-1-benzopyran-3-carboxylate (Example 24, Step 3) as the starting material: mp 197–198° C. $^1$H NMR (CD$_3$OD/300 MHz) 7.87 (s, 1H), 7.28–7.64 (m, 7H), 7.03 (d, 1H, J=6.8 Hz), 5.76 (q, 1H, J=247.0 Hz). EIHRMS m/z 320.0604 (M+, Calc'd 320.0660). Anal. Calc'd for C$_{17}$H$_{11}$F$_3$O$_3$: C, 63.75; H 3.46. Found C, 63.56; H, 3.46.

EXAMPLE 133

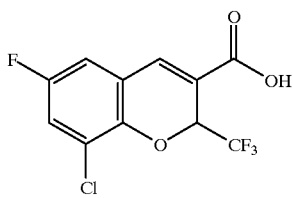

8-Chloro-6-fluoro-2-(trifluoromethyl)-2H-1-benzopyran-3-carboxylic Acid

2-Chloro-4-fluorophenol was converted to the title compound by a procedure similar to that described in Example 2: mp 240–241° C. $^1$H NMR (CD$_3$OD/300 MHz) 7.77 (s, 1H), 7.26 (dd, 1H, J=8.3, 2.9), 7.14 (dd, 1H, J=8.1, 2.9), 5.87 (q, 1H, J=6.8 Hz). EIHRMS m/z 295.9836 (Calc'd 295.9863). Anal. Calc'd for C$_{11}$H$_5$ClF$_4$O$_3$: C, 44.54; H, 1.70. Found C, 44.70; H, 1.73.

EXAMPLE 134

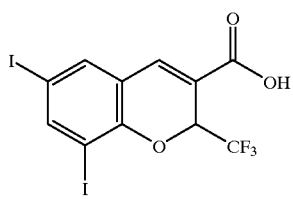

6,8-Diiodo-2-(trifluoromethyl)-2H-1-benzopyran-3-carboxylic Acid

The 2H-1-benzopyran-3-carboxylic acid was prepared by a procedure similar to the method described in Example 1: mp 243–244° C. $^1$H NMR (CD$_3$OD/300 MHz) 8.07 (d, 1H, J=2.0 Hz), 7.71 (s, 1H), 7.70 (d, 1H, J=2.0 Hz), 5.89 (q, 1H, J=6.8 Hz). ESHRMS m/z 494.8174 (Calc'd for M–H 494.8202) Anal. Calc'd for C$_{11}$H$_5$F$_3$I$_2$O$_3$: C, 26.64; H, 1.02. Found C, 26.75; H, 1.06.

EXAMPLE 135

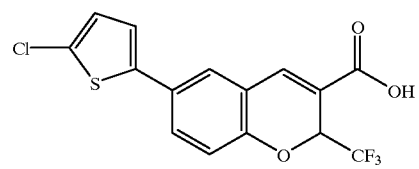

6-(5-Chloro-2-thienyl)-2-(trifluoromethyl)-2H-1-benzopyran-3-carboxylic Acid

The 2H-1-benzopyran-3-carboxylic acid was prepared by a procedure similar to the method described in Example 125 using ethyl 6-iodo-2-(trifluoromethyl)-2H-1-benzopyran-3-carboxylate (Example 72, Step 3) as the starting material: mp 205–206° C. $^1$H NMR (CD$_3$OD/300 MHz) 7.83 (s, 1H), 7.50–7.58 (m, 2H), 7.14 (d, 1H, J=4.0 Hz), 7.00 (d, 1H, J=8.86 Hz), 6.93 (d, 1H, J=4.0 Hz), 5.77 (q, 1H, J=7.0 Hz). EIHRMS m/z 359.9810 (M+, Calc'd 359.9835). Anal. Calc'd for C$_{15}$H$_8$ClF$_3$O$_3$S: C, 49.94; H 2.24. Found C, 50.14; H, 2.29.

EXAMPLE 136

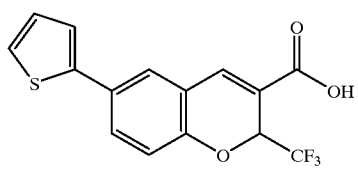

6-(2-thienyl)-2-(trifluoromethyl)-2H-1-benzopyran-3-carboxylic Acid

The 2H-1-benzopyran-3-carboxylic acid was prepared by a procedure similar to the method described in Example 125 using ethyl 6-iodo-2-(trifluoromethyl)-2H-1-benzopyran-3-carboxylate (Example 24, Step 3) as the starting material: mp 209–212° C. $^1$H NMR (CD$_3$OD/300 MHz) 7.83 (s, 1H), 7.58–7.62 (m, 2H), 7.30–7.38 (m, 2H), 6.80–7.09 (m, 2H), 5,76 (q, 1H, J=7.0 Hz) FABHRMS m/z 325.0153 (Calc'd for M–H 325.0146).

EXAMPLE 137

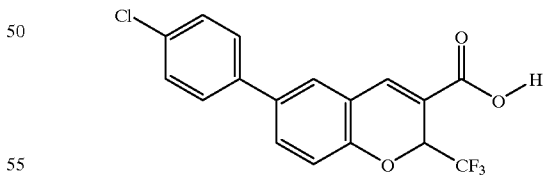

6-(4-Chlorophenyl)-2-(trifluoromethyl)-2H-1-benzopyran-3-carboxylic Acid

The 2H-1-benzopyran-3-carboxylic acid was prepared by a procedure similar to the method described in Example 125 using ethyl 6-iodo-2-(trifluoromethyl)-2H-1-benzopyran-3-carboxylate (Example 24, Step 3) as the starting material: mp 212–213° C. $^1$H NMR (CD$_3$OD/300 MHz) 7.89 (s, 1H), 7.56–7.66 (m, 4H), 7.40–7.48 (m, 2H), 7.04–7.10 (m, 1H), 5.77 (q, 1H, J=7.0 Hz). ESHRMS m/z 353.0190 (Calc'd for

EXAMPLE 138

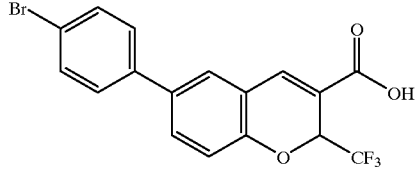

6-(4-Bromophenyl)-2-(trifluoromethyl)-2H-1-benzopyran-3-carboxylic Acid

The 2H-1benzopyran-3-carboxylic acid was prepared by a procedure similar to the method described in Example 126: using ethyl 6-iodo-2-(trifluoromethyl)-2H-1-benzopyran-3-carboxylate (Example 24, Step 3) as the starting material: mp 215–216° C. $^1$H NMR (CD$_3$OD/300 MHz)7.89 (s, 1H), 7.06–7.71 (m, 6H), 7.04–7.06 (m, 1H), 5.78 (q, 1H, J=6.8 Hz). ESHRMS ml/z 396.9681 (Calc'd for M–H 396.9687).

EXAMPLE 139

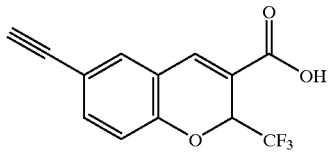

6-(Ethynyl)-2-(trifluoromethyl)-2H-1-benzopyran-3-carboxylic Acid

The 2H-1-benzopyran-3-carboxylic acid was prepared by a procedure similar to the method described in Example 118 using ethyl 6-iodo-2-(trifluoromethyl)-2H-1-benzopyran-3-carboxylate (Example 24, Step 3) as the starting material: mp 198–200° C. $^1$H NMR (CD$_3$OD/300 MHz) 7.80 (s, 1H), 7.47 (dd, 1H, J=8.5, 2.0 Hz), 7.41 (d, 1H, J=2.0 Hz), 6.97 (d, 1H, J=8.5 Hz), 5.71 (q, 1H, J=6.8 Hz), 3.06 (s, 1H). ESHRMS m/z 267.0271 (Calc'd for M–H 267.0269) Anal. Calc'd for C$_{13}$H$_7$F$_3$O$_3$+1.06% H$_2$O: C, 57.60; H, 2.72. Found C, 57.59; H, 2.62.

EXAMPLE 140

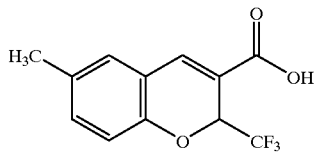

6-Methyl-2-(trifluoromethyl)-2H-1-benzopyran-3-carboxylic Acid

4-Methylsalicylaldehyde was converted to the title compound by a procedure similar to that described in Example 1: mp 191.8–193.0° C. $^1$H NMR (acetone-d$_6$/300 MHz) 7.80 (s, 1H), 7.72–7.73 (m, 2H), 6.90 (d, 1H, J=8.4 Hz), 5.91 (q, 1H, J=7.2 Hz). Anal. Calc'd for C$_{12}$H$_9$O$_3$F$_3$: C, 55.82; H, 3.51. Found: C, 55.89; H, 3.49.

EXAMPLE 141

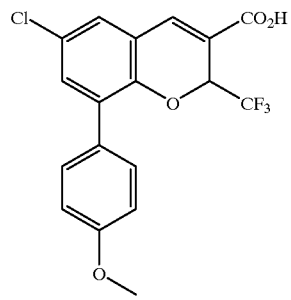

6-Chloro-8-(4-methoxyphenyl)-2-trifluoromethyl-2H-1-benzopyran-3-carboxylic Acid The 2H-1-benzopyran-3-carboxylic acid was prepared by a procedure similar to the method described in Example 126: mp 194.0–196.0° C. $^1$H NMR (CDCl$_3$/300 MHz) 7.81 (s, 1H), 7.44 (s, 1H), 7.41 (s, 1H), 7.34 (d, 1H, J=2.4 Hz),7.21 (d, 1H, J=2.4 Hz), 6.99 (s, 1H), 6.96 (s, 1H), 5.69 (q, 1H, J=6.7 Hz), 3.86 (s, 3H). FABLRMS m/z 402.2 (M+NH$_4$). ESHRMS m/z 383.0267 (M–H, Calc'd. 383.029796). Anal. Calc'd. for C$_{18}$H$_{12}$ClF$_3$O$_4$: C, 56.20; H, 3.14; Cl, 9.21. Found: C, 56.08; H, 3.11; Cl, 9.13.

EXAMPLE 142

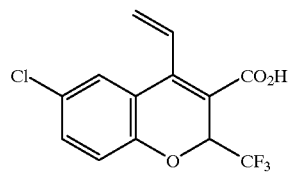

6-Chloro-2-(trifluoromethyl)-4-ethenyl-2H-1-benzopyran-3-carboxylic Acid

Step 1: Preparation of Ethyl 3-(5-chloro-2-hydroxyphenyl)-3-oxo-propionate

A solution of lithium hexamethyldisilazide (800 mL of 1.0 M solution in THF, 800.0 mmol) was chilled to −78° C. under a nitrogen atmosphere. A solution of 5-chloro-2-hydroxyacetophenone (45.493 g, 266.67 mmol) in THF (130 mL) was added dropwise to the stirred solution over 0.5 hour. The reaction was held at −78° C. for 1 hour, warmed to −10° C. for 2 hours, warmed to 0° C. for 1 hour, then cooled to −78° C. Diethyl carbonate (35.54 mL, 34.65 g, 29.34 mmol) was added via syringe in one portion. The temperature was maintained at −78° C. for 0.5 hour, warmed to room temperature over 0.5 hour, and stirred for 3 hours. The crude reaction mixture was carefully poured over a mixture of rapidly stirred ice (1200 mL)/conc HCl (222 mL). The layers were separated and the aqueous phase was extracted with ethyl acetate. The combined organic phase was washed with brine, dried over Na$_2$SO$_4$, filtered and concentrated in vacuo yielding an oil that began to crystallize. Hexanes (150 mL) was added and crystallization proceeded. The crystalline product was collected by vacuum filtration to afford the title compound (29.04 g, 45%) as tan crystalline needles: mp 71.8–73.1° C. $^1$H NMR (CDCl$_3$/300 MHz) 7.63 (d, 1H, J=2.4 Hz), 7.45 (dd, 1H, J=8.9, 2.6), 6.98 (d, 1H, J=8.9 Hz), 4.25 (q, 2H, J=7.3 Hz), 3.98 (s, 2H), 1.29 (t, 3H, 7.3 Hz). FABLRMS m/z 249 (M+Li). EIHRMS m/z 242.0346 (M+, Calc'd 242.0346). Anal. Calc'd for $C_{11}H_{11}ClO_4$: C, 54.45; H, 4.57. Found: C, 54.48; H, 4.62.
Step 2. Preparation of Ethyl 2-(trifluoromethyl)-6-chloro-4-oxo-4H-1-benzopyran-3-carboxylate.

The keto-ester (Step 1) (19.2 g, 79.1 mmol), was added to trifluoroacetic anhydride (67.2 mL, 49.9 g, 475.8 mmol), potassium carbonate (44 g, 318 mmol) and toluene (400 mL). This suspension was stirred at room temperature for 36 hours, then heated to reflux for 4 hours. After cooling to room temperature, the suspension was poured over rapidly stirred (mechanical stirrer) ice (300 mL) and aqueous HCl (12 N, 50 mL). The resulting organic phase was separated from the clear mixture, was washed with water (5×500 mL), brine (1×500 mL), dried over $MgSO_4$, filtered and concentrated in vacuo yielding tan solid which was dried under high vacuum. This sample was partially dissolved in heptane (100 mL) and ethyl acetate (12 mL) with heating on a steam bath, was filtered to remove insoluble material. The filtrate was allowed to cool to room temperature yielding the desired 4-oxo-4H-1-benzopyran as a fluffy tan solid (14.17 g, 56%): mp 106.7–108.6° C. This material was of suitable purity to use in the next step without further purification.
Step 3. Preparation of Ethyl 2-(trifluoromethyl)-4-oxo-dihydro-1-benzopyran-3-carboxylate.

A stirred, chilled (0° C.) solution of the ketone (Step 2) (6.92 g, 21.58 mmol) in tetrahydrofuran (40 mL) and ethanol (50 mL) was treated portion-wise with sodium borohydride ($NaBH_4$, 0.41 g, 10.79 mmol). After 3 h additional sodium borohydride (0.30 g, 7.93 mmol) was added portion-wise over 1 hour. The reaction was poured into rapidly stirred cold aqueous HCl (15 mL of 12 N HCl diluted to 300 mL). During the addition a precipitate formed, that was collected by vacuum filtration and dried under high vacuum yielding the desired substituted 4-oxo-dihydro-1-benzopyran as a white powder (6.92 g, 99%): mp 80.2–84.9° C. $^1H$ NMR ($CDCl_3$/300 MHz) 12.60 (br s, 1H), 7.69 (d, 1H, J=2.6 Hz), 7.34 (dd, 1H, J=2,6, 8.7 Hz), 6.93 (d, 1H, J=8.7 Hz), 5.59 (q, 1H, 6.6 Hz), 4.46–4.23 (m, 2H), 1.35 (t, 3H, J=7.0 Hz). FABLRMS m/z 329 (M+Li). EIHRMS m/z 322.0213 (M+, Calc'd 322.0220). Anal. Calc'd for $Cl_3H_{10}C_{11}F_3O_4$ with 3.57% water: C, 46.67; H, 3.41. Found: C, 46.62; H, 3.14.
Step 4. Preparation of Ethyl 6-chloro-4-(trifluoromethanesulfonoxy)-2-(trifluoromethyl)-2H-1-benzopyran-3-carboxylate.

A 50 mL Morton flask fitted with septa and addition funnel was charged with 2,6-di-tert-butylpyridine (1.782 g, 8.679 mmol), methylene chloride (15 mL), and trifluoromethanesulfonic anhydride (1.22 mL, 2.04 g, 7.23 mmol) followed by the dropwise addition of the chroman-4-one (Step 3)(2.145 g, 5.786 mmol) in methylene chloride (12 mL) over 0.33 hour. After stirring for 16 h at room temperature, the reaction was concentrated in vacuo and diluted with diethyl ether (50 mL) yielding a suspension. The suspension was vacuum filtered and the filtrate washed with cold 2 N HCl and brine, dried over $MgSO_4$, filtered and concentrated in vacuo yielding the desired triflate as a light yellow powder (1.45 g, 55%) of suitable purity to use without further purification: mp 79.2–80.4° C. $^1H$ NMR ($CDCl_3$/300 MHz) 7.40 9s, 1H), 7.37 (d, 1H, J=2.4 Hz), 7.02–6.99 (m, 1H), 5.92 (q, 1H, J=6.6 Hz), 4.47–4.32 (m, 2H), 1.39 (t, 3H, J=7.2 Hz).
Step 5. Preparation of Ethyl 6-chloro-4-ethenyl-2-(trifluoromethyl)-2H-1-benzopyran-3-carboxylate.

Ethyl 6-chloro-4-trifluoromethanesulfoxy-2-(trifluoromethyl)-2H-1-benzopyran-3-carboxylate (Step 4) (1.50 g, 3.30 mmol) was dissolved in anhydrous THF (40 mL)in a 100 mL round bottomed flask under nitrogen. Tetrakis(triphenylphosphine)palladium(0) (0.267 g, 0.231 mmol) and lithium chloride (0.140 g, 3.3 mmol) were added, followed by tributylethenylstannane (1.15 g, 3.6 mmol). The resulting solution was heated to reflux for 18 hours. GCMS analysis indicated the starting material had been consumed. The reaction mixture was allowed to cool to room temperature and was poured into 20% ammonium fluoride solution (50 mL). After stirring for one hour, diethyl ether (100 mL) was added and the mixture was washed with water (2×50 mL). The organic phase was dried over $MgSO_4$, filtered, and concentrated in vacuo yielding a brown oil. The crude material was purified by flash column chromatography (hexane) to afford the ester as a yellow oil, which crystallized upon standing (0.760 g, 69%): mp 51.9–53.2° C. $^1H$ NMR ($CDCl_3$/300 MHz) 7.46 (d, 1H, J=2.4 Hz), 7.28–7.14 (m, 2H), 6.96 (d, 1H, J=8.7 Hz), 5.77–5.71 (m, 2H), 5.38 (dd, J=1.2, 17.9 Hz), 4.32–4.26 (m, 2H), 1.33 (t, 2H, J=7.1 Hz). FABLRMS m/z 333.2 (M+H). ESHRMS m/z 333.0510 (M+H, Calc'd. 333.050532). Anal. Calc'd for $C_{15}H_{12}ClF_3O_3$ (1.14 wt % $H_2O$): C, 53.53; H, 3.72; Cl, 10.53. Found: C, 53.46; H, 3.42; Cl, 10.70.
Step 6. Preparation of 6-chloro-4-ethenyl-2-trifluoromethyl-2H-1-benzopyran-3-carboxylic Acid.

The ester from Step 5 (0.300 g, 0.902 mmol) was dissolved in a $THF-EtOH-H_2O$ mixture (10 mL, 7:2:1) and treated with sodium hydroxide (0.360 mL, 0.902 mmol of a 2.5 N solution). This solution was stirred at room temperature for 18 hours. The solvent was evaporated and the residue was dissolved in water (10 mL). Diethyl ether (10 mL was added and the mixture acidified by the addition of concentrated HCl. The organic layer was separated, and the aqueous phase was extracted with diethyl ether (2×10 mL). The ether extracts were combined, dried over $MgSO_4$, filtered, and concentrated in vacuo yielding a yellow solid, which was recrystallized in diethyl ether-hexane to afford the title compound as a white solid (0.163 g, 59%): mp 143.0–145.0° C. 1H NMR ($CDCl_3$/300 MHz 7.49 (d, 1H, J=2.6 Hz), 7.33–7.17 (m, 2H), 6.99 (d, 1H, J=8.5 Hz), 5.82–5.72 (m, 2H), 5.42 (d, 1H, J=17.9 Hz). ESHRMS m/z 303.00207 (M–H, Calc'd. 303.003582). Anal. Calc'd for $C_{13}H_8ClF_3O_3$ (1.10 wt % $H_2O$): C, 50.69; H, 2.74; Cl, 11.51. Found: C, 50.57; H, 2.37; Cl, 11.75.

EXAMPLE 143

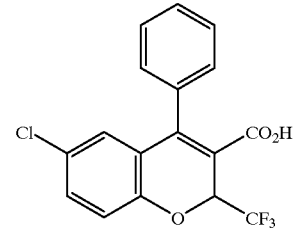

6-Chloro-2-(trifluoromethyl)-4-phenyl-2H-1-benzopyran-3-carboxylic Acid

The 2H-1-benzopyran-3-carboxylic acid was prepared from ethyl 6-chloro-4-(trifluoromethanesulfonoxy)-2-(trifluoromethyl)-2H-1-benzopyran-3-carboxylate (Example 142, Step 4) using a procedure similar to that described in Example 142, Steps 5–6: mp 225.5–226.6° C. 1H NMR (DMSO-$d_6$/300 MHz). 7.46–7.39 (m, 4H), 7.20–7.13 (m, 3H), 6.52 (d, 1H, J=2.42 Hz), 6.12(q, 1H, J=7.1 Hz). FABLRMS m/z 355.1 (M+H). ESHRMS m/z 353.0215 (M–H, Calc'd. 353.019232). Anal. Calc'd. for $C_{17}H_{10}ClF_3O_3$: C, 57.56; H, 2.84; Cl, 10.17. Found: C, 57.18; H, 2.66; Cl, 10.17.

EXAMPLE 144

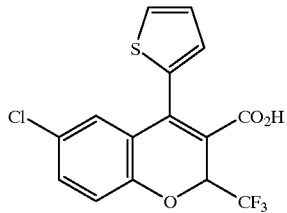

6-Chloro-4-(2-thienyl)-2-(trifluoromethyl)-2H-1-benzopyran-3-carboxylic Acid

The 2H-1-benzopyran-3-carboxylic acid was prepared from ethyl 6-chloro-4-(trifluoromethanesulfonoxy)-2-(trifluoromethyl)-2H-1-benzopyran-3-carboxylate (Example 142, Step 4) using a procedure similar to that described in Example 142, Steps 5–6: mp 200.8–206.7° C. $^1$H NMR (CDCl$_3$/300 MHz) 7.52(dd, 1H, J=1.21, 5.04 Hz), 7.28 (dd, 1H, J=2.42, 8.67 Hz), 7.15 (dd, 1H, J=1.21, 3.42 Hz), 6.98–6.93 (m, 2H), 5.83 (q, 1H, J=6.9 Hz). FABLRMS m/z 378 (M+NH$_4$). Anal. Calc'd. for $C_{15}H_8ClF_3O_3S$: C, 49.94; H, 2.24; Cl, 9.83; S, 8.89. Found: C, 50.02; H, 1.98; Cl, 9.34; S, 8.89.

EXAMPLE 145

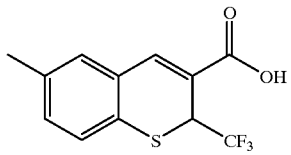

6-Methyl-2-(trifluoromethyl)-2H-1-benzothiopyran-3-carboxylic Acid

Step 1. Preparation of 5-methyl-2-mercaptobenzaldehyde.

Tetramethylethylenediamine (TMEDA)(12.6 mL, 83.5 mmol) was added via syringe to n-BuLi (33 mL of 1.6 M in hexanes, 82.5 mmol) and the solution was chilled to 0° C. A solution of p-thiocresol (4.53 g, 36.5 mmol) in cyclohexane (40 mL) was added with stirring over 5 minutes. The resulting tan slurry was stirred overnight at room temperature, chilled to 0° C., and DMF (4.0 mL, 3.77 g, 51.6 mmol) was added via syringe over 2 minutes. The resulting gummy slurry was stirred at room temperature for 1.3 hours. The reaction mixture was added to 3 N HCl (150 mL). This mixture was extracted with ethyl acetate. The combined organic layers were washed with brine, dried over MgSO$_4$, filtered and concentrated in vacuo yielding a brown oil. This oil was purified by flash chromatography over silica gel, eluting with 10% ethyl acetate-hexanes to afford 5-methyl-2-mercaptobenzaldehyde (4.47 g, 69%) as an intensely yellow solid suitable for use without further purification.

Step 2. Preparation of Ethyl 6-methyl-2-(trifluoromethyl)-2H-1-benzothiopyran-3-carboxylate.

The 5-methyl-2-mercaptobenzaldehyde (Step 1) (3.25 g, 21.3 mmol) was added to DMF (5 mL) and ethyl 4,4,4-trifluorocrotonate (4.32 g, 25.7 mmol). With stirring, K$_2$CO$_3$ (3.78 g, 27.3 -mmol) was added causing the reaction to become a deep red. The reaction was stirred at room temperature for 20 hours, acidified with 3N HCl, diluted with ethyl acetate and washed with water, saturated NaHCO$_3$ solution, brine, dried over MgSO$_{41}$ filtered and concentrated in vacuo yielding an oil. The oil was crystallized from diethyl ether-petroleum ether to give ethyl 6-methyl-2-(trifluoromethyl)-2H-1-benzothiopyran-3-carboxylate as a light yellow solid (4.47 g, 69%): mp 93.1–94.7° C. $^1$H NMR (acetone-d6/300 MHz) 7.94 (s, 1H), 7.41 (s, 1H), 7.31 (d, 1H, J=7.9 Hz), 7.25 (d, 1H, J=7.9 Hz), 4.96 (q, 1H, J=8.5 Hz), 4.33 (m, 2H), 2.34 (s, 3H), 1.35 (t, 3H, J=7.0 Hz). FABLRMS m/z 309 (M+Li).

Step 3. Preparation of 6-methyl-2-(trifluoromethyl)-2H-1-benzothiopyran-3-carboxylic Acid.

The ester from Step 2 (0.55 g 1.8 mmol) was dissolved in THF (1.5 mL) and ethanol (1.5 mL), treated with 2.5 N sodium hydroxide (1.5 mL, 3.8 mmol), and stirred at room temperature for 88 hours. The reaction mixture was concentrated in vacuo, acidified with 3 N HCl, filtered, and recrystallized from diethyl ether/petroleum ether to yield the title compound as a yellow solid (0.14 g, 28%): mp 180.8–184.2° C. $^1$H NMR (acetone-d$_6$/300 MHz) 7.95 (s, 1H), 7.42 (s, 1H), 7.31 (d, 1H, J=8.1 Hz), 7.25 (d, 1H, J=8.1 Hz), 4.94 (q, 1H, J=8.7 Hz), 2.34 (s, 3H). FABLRMS m/z 281 (M+Li). EIHRMS m/z 274.0250 (M+, Calc'd 274.0275). Anal. Calc'd for $C_{12}H_9F_3O_2S$: C, 52.55; H, 3.31. Found: C, 52.54; H, 3.35.

EXAMPLE 146

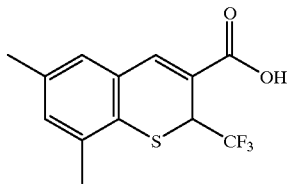

6,8-Dimethyl-2-(trifluoromethyl)-2H-1-benzothiopyran-3-carboxylic Acid

The 2H-1-benzothiopyran-3-carboxylic acid was prepared by a procedure similar to the method described in Example 145: mp 220–225° C. (dec). $^1$H NMR (acetone-d$_6$/300 MHz) 11.5 (brs, 1H), 7.94 (s, 1H), 7.26 (s, 1H) 7.14 (s, 1H), 4.98 (q, 1H, J=8.7 Hz), 2.34 (s, 3H), 2.31 (s, 3H). FABLRMS m/z 295 (M+Li). EIHRMS m/z 288.0431 (M+, Calc'd 288.0432). Anal. Calc'd for $C_{13}H_{11}F_3O_2S$: C, 54.16; H, 3.85. Found: C, 54.10; H, 3.91.

EXAMPLE 147

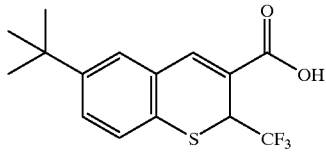

6-(1,1-Dimethylethyl)-2-(trifluoromethyl)-2H-1-benzothiopyran-3-carboxylic Acid

The 2H-1-benzothiopyran-3-carboxylic acid was prepared by a procedure similar to the method described in Example 145: mp 183.8–184.6° C. $^1$H NMR (acetone-d6/

300 MHz) 8.04 (s, 1H), 7.68 (d, 1H, J=2.2 Hz), 7.46 (dd, 1H, J=8.3 Hz 2.2 Hz), 7.37 (d, 1H, J=8.3 Hz), 4.94 (q, 1H, J=8.7 Hz), 1.34 (s, 9H). FABLRMS m/z 334 (M+NH$_4$). ESHRMS m/z 334.1087 300 MHz) 7.52(dd, 1H, J=1.21, 5.04 Hz), 7.28 (dd, 1H, J=2.42, 8.67 Hz), 7.15 (dd, 1H, J=1.21, 3.42 Hz), 6.98–6.93 (m, 2H), 5.83 (q, 1H, J=6.9 Hz) FABLRMS m/z 378 (M+NH$_4$). Anal. Calc'd. for C$_{15}$H$_8$ClF$_3$O$_3$S: C, 49.94; H, 2.24; Cl, 9.83; S, 8.89. Found: C, 50.02; H, 1.98; Cl, 9.34; S, 8.89.(M+NH$_4$, Calc'd 334.1089). Anal. Calc'd for C$_{15}$H$_{15}$F$_3$O$_2$S: C, 56.95; H, 4.78. Found: C, 57.03; H, 4.83.

EXAMPLE 148

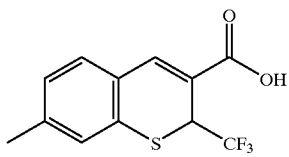

7-Methyl-2-(trifluoromethyl)-2H-1-benzothiopyran-3-carboxylic Acid

The 2H-1-benzothiopyran-3-carboxylic acid was prepared by a procedure similar to the method described in Example 145: mp 186.6–191.9° C. $^1$H NMR (acetone-d6/300 MHz) 7.96 (s, 1H), 7.49 (dd, 1H, J=7.6 Hz 2.82 Hz), 7.27 (s, 1H), 7.14 (d, 1H, J=7.6 Hz), 4.96 (q, 1H, J=5.3 Hz), 2.36 (s, 3H). ESHRMS m/z 273.0204 (M–H, Calc'd 273.0197). Anal. Calc'd for C$_{12}$H$_9$F$_3$O$_2$S (3.32 wt % H$_2$O): C, 50.81; H, 3.57. Found: C, 50.79; H, 3.44.

EXAMPLE 149

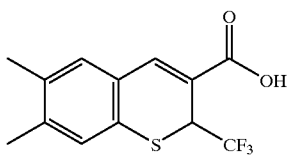

6,7-Dimethyl-2-(trifluoromethyl)-2H-1-benzothiopyran-3-carboxylic Acid

The 2H-1-benzothiopyran-3-carboxylic acid was prepared by a procedure similar to the method described in Example 145: mp 235–237° C. $^1$H NMR (acetone-d6/300 MHz) 7.90 (s, 1H), 7.33 (s, 1H), 7.19 (s, 1H), 4.91 (q, 1H, J=8.7 Hz), 2.28 (s, 3H), 2.26 (s, 3H). FABLRMS m/z 295 (M+Li). EIHRMS m/z 288.0439 (M+, Calc'd 288.0432). Anal. Calc'd for C$_{13}$H$_{11}$F$_3$O$_2$S: C, 54.16; H, 3.85. Found: C, 54.13; H, 3.85.

EXAMPLE 150

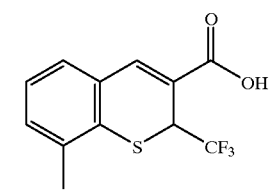

8-Methyl-2-(trifluoromethyl)-2H-1-benzothiopyran-3-carboxylic Acid

The 2H-1-benzothiopyran-3-carboxylic acid was prepared by a procedure similar to the method described in Example 145: mp 224–225° C. $^1$H NMR (acetone-d$_6$/300 MHz) 11.60 (br s, 1H), 8.00 (s, 1H), 7.44 (d, 1H, J=6.7 Hz), 7.31 (d, 1H, J=6.8 Hz), 7.21 (m, 1H), 5.05 (q, 1H, J=8.5 Hz), 2.38 (s, 3H). FABLRMS m/z 292 (M+NH$_4$). ESHRMS m/z 292.0591 (M+NH$_4$, Calc'd 292.0619). Anal. Calc'd for C$_{12}$H$_9$F$_3$O$_2$S: C, 52.55; H, 3.31. Found: C, 52.63; H, 3.38.

EXAMPLE 151

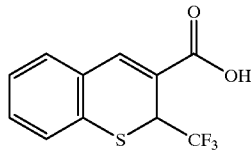

2-(Trifluoromethyl)-2H-1-benzothiopyran-3-carboxylic Acid

The 2H-1-benzothiopyran-3-carboxylic acid was prepared by a procedure similar to the method described in Example 145: mp 187–190° C. $^1$H NMR (acetone-d6/300 MHz) 8.01 (s, 1H), 7.60 (d, 1H, J=7.5 Hz), 7.45 (m, 2H), 7.31 (m, 1H), 4.98 (q, 1H, J=8.7 Hz). ESHRMS m/z 259.0070 (M–H, Calc'd 259.0041). Anal. Calc'd for C$_{11}$H$_7$F$_3$O$_2$S: C, 50.77; H, 2.71. Found: C, 50.75; H, 2.78.

EXAMPLE 152

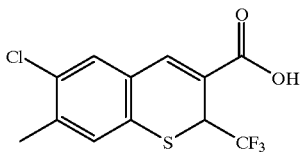

6-Chloro-7-methyl-2-(trifluoromethyl)-2H-1-benzothiopyran-3-carboxylic Acid

Step 1. Preparation of N,N-dimethyl-O-(4-chloro-2-formyl-5-methylphenyl)thiocarbamate.

A mixture of 5-chloro-4-methylsalicylaldehyde (12.96 g, 76.0 mmol) and triethylamine (11.58 g, 114.4 mmol) was dissolved in anhydrous DMF (15 mL) treated with N,N-dimethylthiocarbamoyl chloride (11.25 g, 91.0 mmol) and stirred at room temperature for 16 hours. The reaction was treated with 3 N HCl (50 mL) and filtered to give an orange solid. The solid was dissolved in ethyl acetate washed with 3 N HCl, water, brine, dried over anhydrous MgSO$_4$, filtered and concentrated in vacuo to afford a brown solid (16.79 g) which was recrystallized from diethyl ether/hexane to give the O-aryl thiocarbamate as a tan solid (4.92 g, 25%): $^1$H NMR (acetone-d6/300 MHz) 9.96 (s, 1H), 7.80 (s, 1H), 7.19 (s, 1H), 3.46 (s, 3H), 3.42 (s, 3H), 2.43 (s, 3H).

Step 2. Preparation of N,N-dimethyl-S-(4-chloro-2-formyl-5-methylphenyl)thiocarbamate.

The O-aryl thiocarbamate (Step 1) (4.92 g, 19.1 mmol) was dissolved in N,N-dimethylaniline (25 mL) and immersed in and stirred at 200° C. for 1.5 hours. The reaction mixture was cooled to room temperature and poured into a mixture of 3 N HCl (200 mL) and ice. Filtration gave a brown semisolid which was dissolved in ethyl acetate, washed with 3 N HCl, brine, dried over anhydrous MgSO$_4$, filtered and concentrated in vacuo to afford the S-arylthiocarbamate as a brown oil (3.80 g, 77%) which was used in the next step without further purification.

Step 3. Preparation of Ethyl 6-chloro-7-methyl-2-(trifluoromethyl)-2H-1-benzothiopyran-3-carboxylate.

The S-arylthiocarbamate (Step 2) (3.80 g, 14.7 mmol) was dissolved in THF (10 mL) and ethanol (10 mL), treated with 2.5 N sodium hydroxide (16.5 mL, 34.2 mmol), and stirred at room temperature for 0.9 hours. The reaction was diluted with diethyl ether and washed with 3 N HCl, brine, dried over $MgSO_4$, filtered and concentrated in vacuo to yield the crude substituted 2-mercaptobenzaldehyde as a brown oil (2.82 g). This oil was added to DMF (10 mL) and ethyl 4,4,4-trifluorocrotonate (3.89 g, 23.1 mmol). With stirring, $K_2CO_3$ (3.23 g, 23.4 mmol) was added causing the reaction to become a deep red. The reaction was stirred at room temperature for 14.5 hours, acidified with 3 N HCl, extracted with ethyl acetate. The resulting organic phase was washed with brine, dried over $MgSO_4$, filtered and concentrated in vacuo to give a yellow solid (6.36 g) which was used in the next step without further purification.

Step 4. Preparation of 6-chloro-7-methyl-2-(trifluoromethyl)-2H-1-benzothiopyran-3-carboxylic Acid The ester from Step 3 (2.02 g, 6.0 mmol) was dissolved in THF (10 mL) and ethanol (10 mL), treated with 2.5 N sodium hydroxide (5.5 mL, 13.8 mmol), and stirred at room temperature for 4.8 hours. The reaction mixture was concentrated in vacuo, acidified with 3 N HCl yielding a suspension. The solid was collected by filtration and was recrystallized from ethanol-water to yield the title compound as a yellow solid (0.20 g, 11%): mp 240.5–241.7° C. $^1H$ NMR (acetone-$d_6$/300 MHz) 7.99 (s, 1H), 7.67 (s, 1H), 7.43 (s, 1H), 4.99 (q, 1H, J=8.5 Hz), 2.39 (s, 3H). FABLRMS m/z 307 (M−H). FABHRMS m/z 306.9831 (M−H, Calc'd 306.9807). Anal. Calc'd for $C_{12}H_8ClF_3O_2S$: C, 46.69; H, 2.61; Cl, 11.48. Found: C, 46.78; H, 2.61; Cl, 11.41.

EXAMPLE 153

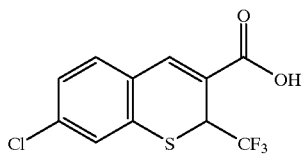

7-Chloro-2-(trifluoromethyl)-2H-1-benzothiopyran-3-carboxylic Acid

The 2H-1-benzothiopyran-3-carboxylic acid was prepared by a procedure similar to the method described in Example 152: mp 225.7–227.3° C. $^1H$ NMR (acetone-d6/300 MHz) 8.02 (s, 1H), 7.63 (d, 1H, J=8.3 Hz), 7.54 (d, 1H, J=2.0 Hz), 7.36 (dd, 1H, J=8.3 Hz 2.0 Hz), 5.04 (q, 1H, J=8.5 Hz). ESHRMS m/z 292.9646 (M−H, Calc'd 292.9651).

EXAMPLE 154

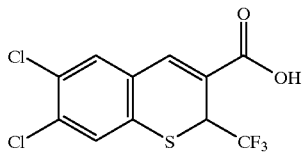

6,7-Dichloro-2-(trifluoromethyl)-2H-1-benzothiopyran-3-carboxylic Acid

The 2H-1-benzothiopyran-3-carboxylic acid was prepared by a procedure similar to the method described in Example 152: mp 262.5–263.5° C. $^1H$ NMR (acetone-d6/300 MHz) 8.04 (s, 1H), 7.90 (s, 1H), 7.74 (s, 1H), 5.09 (q, 1H, J=8.5 Hz). ESHRMS m/z 326.9242 (M−H, Calc'd 326.9261).

EXAMPLE 155

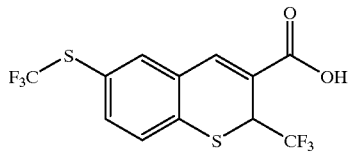

2-(Trifluoromethyl)-6-[(trifluoromethyl)thio]-2H-1-benzothiopyran-3-carboxylic Acid The 2H-1-benzothiopyran-3-carboxylic acid was prepared by a procedure similar to the method described in Example 152: mp 129.3–132.4° C. $^1H$ NMR (acetone-$d_6$/300 MHz) 8.10 (s, 2H), 8.00 (s, 2H), 7.71 (d, 2H, J=8.1 Hz), 7.65 (d, 2H, J=8.1 Hz), 5.09 (q, 1H, J=8.5 Hz). ESHRMS m/z 358.9630 (M−H, Calc'd 358.9635).

EXAMPLE 156

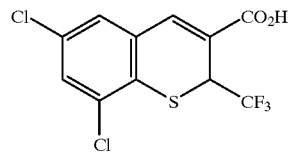

6,8-Dichloro-2-trifluoromethyl-2H-1-benzothiopyran-3-carboxylic Acid

The 2H-1-benzothiopyran-3-carboxylic acid was prepared by a procedure similar to the method described in Example 152: mp 217.9–220.3° C. H NMR (acetone-d6/300 MHz) 12.50–11.20 (br s, 1H exch.), 8.06 (s, 1H), 7.75 (d, 1H, J=2.0 Hz), 7.64 (d, 1H, J=2.2 Hz), 5.23 (q, 1H, J=8.5 Hz). ESLRMS m/z 327 (M−H). ESHRMS m/z 326.9272 (M−H, Calc'd 326.9261).

EXAMPLE 157

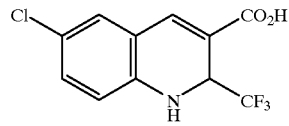

6-Chloro-1,2-dihydro-2-(trifluoromethyl)-3-quinolinecarboxylic Acid

Step 1. Preparation of 2-amino-5-chlorobenzaldehyde.

2-Amino-5-chlorobenzyl alcohol (4.8 g, 30 mmol) and activated manganese (IV) oxide (21 g, 240 mmol) were refluxed in chloroform (100 mL) for 1 hour. The contents were allowed to cool, filtered through diatomaceous earth and concentrated in vacuo to afford the 2-amino-5-chlorobenzaldehyde as a dark solid (4.14 g, 81%): mp 74–76° C. $^1H$ NMR ($CDCl_3$, 300 MHz) 9.80 (s, 1H), 7.42 (s, 1H), 7.23 (d, 1H, J=7.0 Hz), 6.60 (d, 1H, J=7.0 Hz).

Step 2. Preparation of Ethyl 6-chloro-1,2-dihydro-2-(trifluoromethyl)-3-quinolinecarboxylate.

The 2-amino-5-chlorobenzaldehyde from Step 1 (15.0 g, 96 mmol), anhydrous potassium carbonate (27.6 g, 200 mmol), and ethyl 4,4,4-trifluorocrotonate (34 mL, 200 mmol) were mixed in anhydrous dimethyformamide (60 mL) and heated at 100° C. for 7 hours. The contents were allowed to cool and partitioned between ethyl acetate (200 mL) and water (200 mL). The aqueous layer was extracted with ethyl acetate (1×100 mL). The ethyl acetate extracts were combined and washed with brine (1×200 mL), dried over $MgSO_4$, and concentrated in vacuo leaving a dark oil which solidified upon standing. The solid was purified by flash chromatography (silica gel; ethyl acetate-hexanes, 1:9). Fractions containing the desired product were combined, concentrated in vacuo and the residue recrystallized from ethyl acetate-hexanes to afford the ethyl 6-chloro-1,2-dihydro-2-(trifluoromethyl)-3-quinolinecarboxylate as a yellow solid (16.36 g, 56%): mp 132.6–134.2° C. $^1$H NMR ($CDCl_3$, 300 MHz) 7.61 (s, 1H), 7.10 (m, 2H), 6.55 (d, 1H, J=8.0 Hz), 5.10 (q, 1H, J=6.0 Hz), 4.55 (brs, 1H), 4.23 (m, 2H), 1.32 (t, 3H, J=7.0 Hz). FABHRMS m/z 306.0468 ($M+H^+$, Calc'd 306.0509). Anal. Calc'd for $C_{13}H_{11}NO_2F_3Cl$: C, 51.08; H, 3.63; N, 4.58. Found: C, 50.81; H, 3.49; N, 4.72.

Step 3. Preparation of 6-chloro-1,2-dihydro-2-(trifluoromethyl)-3-quinolinecarboxylic Acid.

The ester from Step 2 (1.7 g, 5.6 mmol) and 2.5 N sodium hydroxide (4.4 mL, 11 mmol) were mixed in tetrahydrofuran (25 mL), methanol (10 mL), and water (25 mL). After stirring overnight, contents were concentrated in vacuo to remove the THF and methanol. The aqueous solution remaining was extracted with diethyl ether (2×100 mL). The resulting aqueous layer was acidified with 2 N HCl causing the precipitation of an oil. The oil was purified by flash chromatography on silica gel, eluting with ethyl acetate-hexanes (1:1). Fractions containing the desired product were combined, and concentrated in vacuo. The residue was triturated with dichloromethane, and filtered to afford the 6-chloro-1,2-dihydro-2-(trifluoromethyl)-3-quinolinecarboxylic acid as a yellow solid (0.645 g, 41%): mp 187.8–188.8° C. $^1$H NMR (acetone-$d_6$, 300 MHz) 7.69 (s, 1H), 7.36 (s, 1H), 7.15 (d, 1H, J=8.0 Hz), 6.83 (d, 1H, J=8.0 Hz), 6.60 (brs, 1H), 5.20 (m, 1H). ESHRMS m/z 276.0040 (M–H,Calc'd 276.0039). Anal. Calc'd for $C_{11}H_7NO_2F_3Cl+2.6\%$ $H_2O$: C, 46.39; H, 2.98; N, 4.92. Found: C, 45.99; H, 2.54; N. 4.85.

EXAMPLE 158

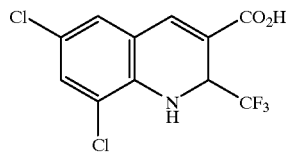

6,8-Dichloro-1,2-dihydro-2-(trifluoromethyl)-3-quinolinecarboxylic Acid

The 1,2-dihydro-3-quinolinecarboxylic acid was prepared by a procedure similar to that described in Example 157: mp 223.4–225.7° C. $^1$H NMR (acetone-$d_6$, 300 MHz) 7.82 (s, 1H), 7.40 (m, 2H), 6.53 (brs, 1H), 5.40 (m, 1H). ESHRMS m/z 309.9657 (M–H, Calc'd 309.9649). Anal. Calc'd for $C_{11}H_6NO_2F_3Cl_2$: C, 42.34; H, 1.94; N, 4.49. Found: C, 42.20; H, 1.74; N, 4.52.

EXAMPLE 159

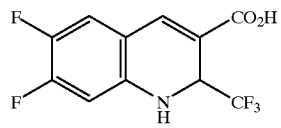

6,7-Difluoro-1,2-dihydro-2-(trifluoromethyl)-3-quinolinecarboxylic Acid

The 1,2-dihydro-3-quinolinecarboxylic acid was prepared by a procedure similar to that described in Example 157: mp 186.6–188.9 C. $^1$H NMR (acetone-$d_6$, 300 MHz) 7.79 (s, 1H), 7.32 (m, 1H), 6.71 (m, 1H), 6.64 (brs, 1H), 5.21 (m, 1H). ESHRMS m/z 278.0262 (M–H, Calc'd 278.0240). Anal. Calc'd for $C_{11}H_6NO_2F$, +1.58% $H_2O$: C, 46.58; H, 2.31; N, 4.94. Found: C, 46.20; H, 2.07; N, 4.54.

EXAMPLE 160

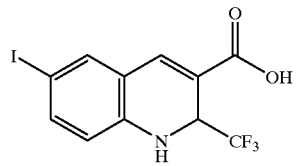

6-Iodo-1,2-dihydro-2-(trifluoromethyl)-3-quinolinecarboxylic Acid

Step 1. Preparation of Ethyl 6-iodo-1,2-dihydro-2-(trifluoromethyl)-3-quinolinecarboxylate.

A mixture of 5-iodo-2-aminobenzaldehyde (24.0 g, 96.7 mmol), diazbicyclo[2.2.2]-undec-7-ene (32.2 g, 212.0 mmol), and ethyl 4,4,4-trifluorocrotonate (35.7 g, 212.0 mmol) in 1,3-dimethyl-3,4,5,6-tetrahydro-2(1H)-pyrimidinone (48 mL) was heated at 60° C. for 8 hours. The solution was cooled to room temperature and the solution poured into ethyl acetate-hexanes (1:1, 500 mL). The solution was extracted with 2.5 N aqueous hydrochloric acid (2×200 mL), saturated aqueous ammonium chloride (2×200 mL), dried over sodium sulfate, filtered and concentrated in vacuo. The resulting dark yellow oil was dissolved in hexanes (100 mL) and fine yellow crystals formed upon standing. Vacuum filtration of this suspension yielded ethyl 6-iodo-1,2-dihydro-2-(trifluoromethyl)-3-quinolinecarboxylate as fine yellow crystals (19.3 g, 50% yield): mp 137–138° C. $^1$H NMR ($CDCl_3$, 300 MHz) 7.62 (s, 1H), 7.36–7.48 (m, 2H), 6.43 (d, J=8.2 Hz), 5.36 (brs, 1H), 5.11 (q, 1H, J=7.1 Hz), 4.25 –4.35 (m, 2H), 1.34 (t, 3H, J=7.0 Hz). ESHRMS m/z 395.9716 (M–H, Calc'd 395.9708).

Step 2. Preparation of 6-iodo-1,2-dihydro-2-(trifluoromethyl)-3-quinolinecarboxylic Acid Hydrolysis of the ester (Step 1) was performed by a procedure similar to that described in Example 157, Step 3, yielding the carboxylic acid. mp 188–192° C. $^1$H NMR ($CD_3OD$/300 MHz) 7.668 (s, 1H), 7.46 (d, 1H, J=2.2 Hz), 7.39 (dd, 1H, J=8.4, 2.2 Hz), 6.52 (d, 1H, J=8.4 Hz), 5.01 (q, 1H, J=7.5 Hz). ESHRMS m/z 367.9401 (M, Calc'd 367.9395).

EXAMPLE 161

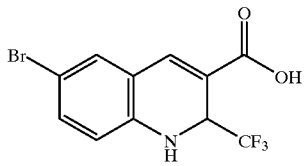

6-Bromo-1,2-dihydro-2-(trifluoromethyl)-3-quinolinecarboxylic Acid

The 1,2-dihydro-3-quinolinecarboxylic acid was prepared by a procedure similar to that described in Example 160: mp 185–186° C. $^1$H NMR (CD$_3$OD/300 MHz) 7.68 (s, 1H), 7.31 (d, 1H, J=2.2 Hz), 7.23 (dd, 1H, J=8.7, 2.2 Hz), 6.64 (d, 1H, J=8.7 Hz), 5.01 (q, 1H, J=7.5 Hz). EIHRMS m/z 319.9519 (M, Calc'd 319.9534). Anal. Calc'd for C$_{11}$H$_7$BrF$_3$NO$_2$: C, 41.02; H, 2.19; N, 4.35; Found: C, 41.27, H, 2.23, N, 4.26.

EXAMPLE 162

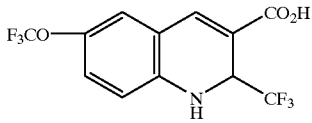

1,2-Dihydro-6-(trifluoromethoxy)-2-(trifluoromethyl)-3-quinolinecarboxylic Acid Step 1. Preparation of 2-amino-5-(trifluoromethoxy)benzoic Acid.

5-(Trifluoromethoxy)isatin (15.0 g, 65 mmol) and potassium hydroxide pellets (4 g) were mixed in water (35 mL) and cooled to 0° C. With vigorous stirring, a solution of 30% aqueous hydrogen peroxide (11.7 g), potassium hydroxide pellets (5.8 g), and water (80 mL) was added drop-wise keeping the temperature below 10° C. After stirring 1 hour at 0° C., glacial acetic acid (22 mL) was added drop-wise, causing foaming and formation of a precipitate. The contents were stirred overnight and filtered to afford the 2-amino-5-trifluoromethoxybenzoic acid as an amber solid (12.5 g, 87%). A small amount was recrystallized from ethyl acetate-hexanes to afford amber needles for an analytical sample and the remaining compound was used without further purification: mp 142.5–144.2° C. $^1$H NMR (CDCl$_3$, 300 MHz) 7.98 (s, 1H), 7.18 (d, 1H, J=8.0 Hz) 6.62 (d, 1H, J=8.0 Hz), 6.40 (brs, 2H). Anal. Calc'd for CBH$_6$NO$_3$F$_3$: C, 43.45; H, 2.73; N, 6.33. Found: C, 43.40; H, 2.65; N, 6.35.

Step 2. Preparation of 2-amino-5-(trifluoromethoxy)benzyl Alcohol.

The 2-amino-5-trifluoromethoxybenzoic acid (2.0 g, 9.0 mmol) in tetrahydrofuran (20 mL) was added dropwise to borane methyl sulfide complex (1.5 mL, 15.0 mmol) in tetrahydrofuran (5 mL). The reaction was refluxed overnight and allowed to cool. A solution of 30% aqueous hydrogen peroxide (0.5 mL), 2.5 N sodium hydroxide (0.5 mL) and water (10 mL) was added drop-wise and the reaction stirred 0.5 hours. After diluting with diethyl ether (50 mL), the organic layer was washed with 0.1 M aqueous sodium meta-bisulfite (2×10 mL) and 2.5 N aqueous sodium hydroxide (2×10 mL). The organic layer was diluted further with hexanes (50 mL) and washed with brine (2×20 mL), dried over anhydrous Na$_2$SO$_4$, and concentrated in vacuo leaving an amber oil (1.9 g) which solidified. The solid was recrystallized from ethyl acetate-hexanes to afford the 2-amino-5-trifluoromethoxybenzyl alcohol as a light amber solid (1.44 g, 77%): mp 75.9–77.6° C. $^1$H NMR (CDCl$_3$, 300 MHz) 7.00 (m, 2H), 6.65 (d, 1H, J=8.0 Hz), 4.05 (s, 2H), 3.25 (brs, 3H). ESHRMS m/z 208.0592 (M+H$^+$, Calc'd 208.0585). Anal. Calc'd for C$_8$H$_8$NO$_2$F$_3$: C, 46.39; H, 3.89; N, 6.76. Found: C, 46.61; H, 3.79; N, 6.71.

Step 3. Preparation of 2-amino-5-(trifluoromethoxy)benzaldehyde.

The 2-amino-5-trifluoromethoxybenzyl alcohol from Step 2 (9.7 g, 47 mmol) and manganese (IV) oxide (21 g, 240 mmol) were refluxed in chloroform (200 mL) for 1 hour. The contents were allowed to cool and filtered. The filtrate was concentrated in vacuo leaving an amber oil (8.2 g) which solidified. The oil was distilled (bulb to bulb apparatus) at 50 C (0.1 mm) to afford a yellow solid (7.2 g). The solid was recrystallized from hexanes to afford the desired 2-amino-5-(trifluoromethoxy)-benzaldehyde as yellow crystals (4.4 g, 46%): mp. 42–44° C. $^1$H NMR (CDCl$_3$, 300 MHz) 9.81 (s, 1H), 7.36 (s, 1H), 7.20 (d, 1H, J=9.0 Hz), 6.64 (d, 1H, J=9.0 Hz). EIHRMS m/z 205.0328 (M+, Calc'd 205.0350).

Step 4. Preparation of Ethyl 1,2-dihydro-6-(trifluoromethoxy)-2(trifluoromethyl)-3-quinolinecarboxylate.

The 2-amino-5-(trifluoromethoxy)benzaldehyde from Step 3 (5.3 g, 26 mmol), anhydrous potassium carbonate (6.9 g, 50 mmol), and ethyl 4,4,4-trifluorocrotonate (7.7 mL, 50 mmol) were mixed in anhydrous dimethylformamide (50 mL) and heated at 90° C. for 6 hours. The reaction was allowed to cool to room temperature and was partitioned between ethyl acetate (200 mL) and water (200 mL). The aqueous layer was extracted with more ethyl acetate (100 mL). The ethyl acetate extracts were combined and washed with brine (200 mL), dried over MgSO$_4$, and concentrated in vacuo yielding an oil (9.6 g). The oil was purified by flash chromatography on silica gel, eluting with ethyl acetate-hexanes (1:1). Fractions containing the desired product were combined, concentrated in vacuo, and the residue recrystallized from ethyl acetate-hexanes to afford the ethyl 1,2-dihydro-6-(trifluoromethoxy)-2-(trifluoromethyl)-3-quinolinecarboxylate as a yellow solid (4.05 g, 32%): mp. 123–125° C. $^1$H NMR (CDCl$_3$, 300 MHz) 7.65 (s, 1H), 7.02 (m, 2H), 6.60 (m, 1H), 5.10 (m, 1H), 4.60 (brs, 1H), 4.28 (m, 2H), 1.32 (t, 3H, J=7.0 Hz). ESHRMS m/z 356.0698 (M–H, Calc'd 356.0721). Anal. Calc'd for C$_{14}$H$_{11}$NO$_3$F$_6$: C, 47.34; H, 3.12; N, 3.94. Found: C, 47.37; H, 3.04; N, 3.93.

Step 5. Preparation of 1,2-dihydro-6-(trifluoromethoxy)-2-(trifluoromethyl)-3-quinolinecarboxylic Acid.

The ethyl 1,2-dihydro-6-(trifluoromethoxy)-2(trifluoromethyl)-3-quinolinecarboxylate from Step 4 (880 mg, 2.5 mmol) and 2.5 N aqueous sodium hydroxide (2 mL) were mixed in methanol (15 mL) and water (15 mL). The solution was heated on a steam bath for 2 hours. The reaction was allowed to cool to room temperature and was extracted with diethyl ether (50 mL). The aqueous layer was acidified (pH=1) with 3 N HCl and extracted with ethyl acetate (2×50 mL).

The combined ethyl acetate extracts were dried over MgSO$_4$ and concentrated in vacuo leaving an oil. The oil was crystallized from cold dichloromethane-hexanes to afford the 1,2-dihydro-6-(trifluoromethoxy)-2-(trifluoromethyl)-3-quinolinecarboxylic acid as yellow needles (0.727 g, 89%): mp 127.7–128.9° C. $^1$H NMR (CDCl$_3$, 300 MHz) 7.80 (s, 1H), 7.05 (m, 2H), 6.62 (d, 1H, J=8.0 Hz), 5.13 (m, 1H), 4.62 (brs, 1H). ESHRMS m/z 326.0252 (M–H, Calc'd 326.0252). Anal. Calc'd for C$_{12}$H$_7$NO$_3$F$_6$: C, 44.05; H, 2.16; N, 4.28. Found: C, 43.89; H, 2.04; N, 4.24.

EXAMPLE 163

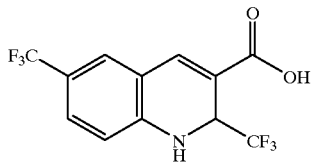

6-(Trifluoromethyl)-1,2-dihydro-2-(trifluoromethyl)-3-quinolinecarboxylic Acid

Step 1. Preparation of N-(4-trifluoromethylphenyl)-2,2-dimethylpropanamide.

A solution of dichloromethane (200 mL), 4-aminobenzotrifluoride (32.0 g, 199 mmol) and triethylamine (40 g, 396 mmol) was cooled to 0° C. under a dry nitrogen atmosphere. Trimethylacetyl chloride (32.9 g, 273 mmol) was added drop-wise over 2 hours, maintaining the temperature below 10° C. After the addition, the contents were allowed to warm to room temperature for 2 hours. The reaction was washed with water (2×200 mL), saturated ammonium chloride solution (2×200 mL), dried over sodium sulfate and filtered. The solvent was removed in vacuo to afford a white solid, N-(4-trifluoromethylphenyl)-2,2-dimethylpropanamide (48.0 g, 98%): mp 157–159° C. $^1$H NMR (CDCl$_3$/300 MHz) 7.61 (ab, 4H, J=8.7, Av=28.6 Hz), 7.47 (br s, 1H), 1.33 (s, 9H). ESHRMS m/z 246.1123 (M+H$^+$, Calc'd 246.1106). Anal. Calc'd for $C_{12}H_{14}F_3NO$: C, 58.77; H, 5.75; N, 5.71. Found: C, 58.28; H, 5.79; N, 5.65.

Step 2. Preparation of N-[2-formyl-4-(trifluoromethyl)phenyl]-2,2-dimethyl Propanamide.

A 1 liter three neck round bottom flask equipped with equalizing addition funnel, magnetic stirer and temperature monitoring device was charged with N-(4-trifluromethylphenyl)-2,2-dimethyl propanamide (10.13 g, 41.4 mmol) and anhydrous tetrahydrafuran (150 mL). The reaction was chilled to −78° C. under nitrogen followed by slow addition of n-butyllithium (50 ml, 2.5 M in hexanes, 124 mmol) over 0.5 hours, such that the temperature of the reaction did not rise above −65° C. The contents were held at −78° C. for one hour, 0° C. for two hours, then chilled back to −78° C. Excess N,N-dimethylformamide (100 mL, 1.37 mol) was added. The contents were warmed to room temperature and stirred for two hours. Aqueous 1 N HCl was added to the reaction until the pH reached 1. The reaction was washed with water (2×200 mL), saturated ammonium chloride solution (2×200 mL), dried over sodium sulfate and filtered. The filtrate was concentrated in vacuo to afford a yellow solid. The product was purified by flash chromatography (silica gel, 10% ethyl acetate, 90% hexanes) to yield, upon concentration of the appropriate fractions, N-(2-formyl-4-trifluoromethylphenyl)-2,2-dimethylpropanamide as a solid (7.36 g, 65%): mp 69–73° C. $^1$H NMR (CDCl$_3$/300 MHz) 11.5 (br s, 1H), 9.99 (s, 1H), 8.67 (d, 1H, J=8.8 Hz), 7.94 (d, 1H, J=1.6 Hz), 7.83 (m, 1H,), 1.37 (s, 9H). ESHRMS m/z 274.1060 (M+H$^+$, Calc'd 274.1055). Anal. Calc'd for $C_{13}H_{14}F_3NO_2$: C, 57.14; H, 5.16; N, 5.13. Found: C, 57.15; H, 5.43; N, 5.01.

Step 3. Preparation of Ethyl 6-(trifluoromethyl)-1,2-dihydro-2-(trifluoromethyl)-3-quinolinecarboxylate.

To a suspension of N-(2-formyl-4-(trifluoromethylphenyl)-2,2-dimethyl propanamide (Step 2) (921 mg, 3.7 mol) and lithium hydride (115 mg, 14.5 mmol) in dimethyl sulfoxide (10 mL) was added ethyl 4,4,4-trifluorocrotonate (2.83 g, 16.8 mmol) and the contents warmed to 30° C. for 4 hours. After the addition of ethyl acetate (50 mL), the reaction was washed with water (2×30 mL), saturated ammonium chloride solution (2×30 mL), dried over sodium sulfate and filtered. The filtrate was concentrated in vacuo to afford a yellow solid. The product was purified by flash chromatography (silica gel, eluant: ethyl acetate-hexanes, 1:9) to yield, upon concentration of the appropriate fractions, ethyl 6-trifluoromethyl-1,2-dihydro-2-(trifluoromethyl)-3-quinolinecarboxylate as a yellow solid (65 mg, 5%): mp 138–139° C. $^1$H NMR (CDCl$_3$/300 MHz) 7.67 (s, 1H), 7.26 (s, 1H), 7.04 (d, 1H, J=6.6 Hz), 6.62 (m, 1H,), 5.14 (m, 1H), 4.60 (brs, 1H), 4.32 (m, 2H), 1.35 (t, 3H, J=7.0 Hz). ESHRMS m/z 338.0592 (M−H, Calc'd 338.0616). Anal. Calc'd for $C_{13}H_{11}F_3NO_2$: C, 49.57; H, 3.27; N, 4.13; Found: C, 49.23; H, 2.81; N, 3.93.

Step 4. Preparation of Ethyl 6-trifluoromethyl-1,2-dihydro-2-(trifluoromethyl)-3-quinolinecarboxylic Acid.

Ethyl 6-trifluoromethyl-1,2-dihydro-2-(trifluoromethyl)-3-quinolinecarboxylate from Step 3 (45 mg, 0.13 mmol) was suspended in methanol-tetrahydrofuran-water (10 mL, 7:2:1). Lithium hydroxide (24 mg, 0.52 mmol) was added, and the mixture was gently heated to reflux for two hours. The reaction was cooled to room temperature and 1 N HCl added until pH=1. The organic solvent was removed in vauco to afford a suspension of a crude yellow solid. Diethyl ether (20 mL) was added, and the solution was washed with water (2×20 mL), saturated ammonium sulfate (2×20 mL), dried over sodium sulfate and filtered. The filtrate was concentrated in vacuo to yield 6-trifluoromethyl-1,2-dihydro-2-(trifluoromethyl)-3-quinolinecarboxylic acid as a yellow solid, (0.041 g, 0.132 mmol, 99%): mp 150–156° C. $^1$H NMR (CD$_3$OD/300 MHz) 7.78 (s, 1H), 7.48 (s, 1H), 7.40 (m, 1H), 6.81 (m, 1H), 5.17 (m, 1H). ESHRMS m/z 310.0307 (M−H, Calc'd 310.0303).

EXAMPLE 164

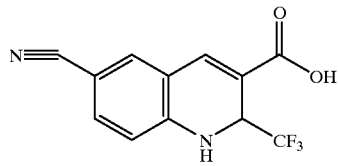

6-Cyano-1,2-dihydro-2-(trifluoromethyl)-3-quinolinecarboxylic Acid

Step 1. Preparation of Ethyl 6-cyano-1,2-dihydro-2-(trifluoromethyl)-3-quinolinecarboxylate.

N,N-Dimethylformamide (5 mL) was degassed with nitrogen for thirty minutes in a three neck round bottom flask equipped with a condenser, temperature monitoring, nitrogen purge and heating mantle. Ethyl 6-iodo-1,2-dihydro-2-(trifluoromethyl)-3-quinolinecarboxylate (Example 158) (0.522 g, 1.32 mmol) and zinc cyanide (0.102 g, 0.792 mmol) were added to the N,N-dimethylformamide and stirred vigorously for ten minutes. Tetrakis(triphenylphosphine)palladium(0) (0.068 g, 0.53 mmol) was added and the contents gently warmed to 80° C. for 2 hours under a nitrogen atmosphere. Ethyl acetate (20 mL) was added, followed by extraction with aqueous 2 N ammonium hydroxide (2×10 mL), water (2×10 mL), saturated ammonium chloride (2×10 mL), dried over sodium sulfate and solvent removed in vacuo to yield a yellow solid. The product was purified by flash chromatography (silica gel, ethyl acetate-hexanes, 3:1) to yield, upon concentration of the appropriate fractions, ethyl 6-cyano-1,2-dihydro-2-(trifluoromethyl)-3-quinolinecarboxylate as a yellow solid (188 mg, 48%): mp 211–212° C. $^1$H NMR (CDCl$_3$/300 MHz) 7.68 (s, 1H), 7.43 (m, 2H), 6.69 (d, 1H, J=8.3 Hz), 5.22 (m, 1H), 4.98 (br s, 1H), 1.30 (m, 2H), 1.36 (t, 3H, J=7.1 Hz). EIHRMS m/z 314.1147 (M+NH$_4^+$, Calc'd 314.1116). Anal. Calc'd for C$_{14}$H$_{11}$F$_3$N$_2$O$_2$: C, 56.76; H, 3.74; N, 9.46. Found: C, 56.44; H, 4.03; N, 9.29.

Step 2. Preparation of 6-cyano-1,2-dihydro-2-(trifluoromethyl)-3-quinolinecarboxylic Acid.

To a suspension of ethyl 6-cyano-1,2-dihydro-2-(trifluoromethyl)-3-quinolinecarboxylate (140 mg, 0.45 mmol) in methanol-tetrahydrofuran-water (10 mL, 7:2:1) was added lithium hydroxide (76 mg, 0.91 mmol) and the mixture gently heated to reflux for two hours. The contents were cooled to room temperature and 1 N aqueous hydrochloric acid added until pH=1. The organic solvent was removed in vacuo to afford a suspension of crude yellow solid. Diethyl ether (20 mL) was added, and the solution was washed with water (2×20 mL), saturated ammonium sulfate (2×20 mL), dried over sodium sulfate and filtered. The filtrate was concentrated in vacuo to yield 6-cyano-1,2-dihydro-2-(trifluoromethyl)-3-quinolinecarboxylic acid as a yellow solid, (116 mg, 95%): mp 238–240° C. $^1$H NMR (CD$_3$OD/300 MHz) 7.75 (g, 1H), 7.56 (m, 1H), 7.43 (m, 1H), 6.79 (d, 1H, J=8.5 Hz) 5.19 (q, 1H, J=7.1 Hz). EIHRMS m/z 267.0405 (M–H, Calc'd 267.0381). Anal. Calc'd for C$_{14}$H$_{11}$F$_3$N$_2$O$_2$: C, 53.74; H, 2.63; N, 10.45. Found: C, 53.99; H, 2.89; N, 10.19.

EXAMPLE 165

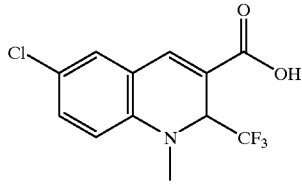

6-Chloro-1,2-dihydro-1-methyl-2-(trifluoromethyl)-3-quinolinecarboxylic Acid

Step 1. Preparation of Ethyl 6-chloro-1,2-dihydro-1-methyl-2-(trifluoromethyl)-3-quinolinecarboxylate.

Ethyl 6-chloro-1,2-dihydro-2-(trifluoromethyl)-3-quinolinecarboxylate (Example 157, Step 2) (1.28 g, 4.21 mmol), tetrabutylammonium iodide (0.36 g, 0.92 mmol) and aqueous NaOH (50%, 2 mL) were stirred vigorously in methylene chloride (40 mL). Dimethyl sulfate (2.12 g, 16.84 mmol) was added to the dark orange mixture via syringe over 2 hours. Hexane (5 mL) was added, and the solution was washed with water (2×20 mL), saturated ammonium chloride solution (2×20 mL), dried over sodium sulfate and filtered. The filtrate was concentrated in vacuo to afford the crude ester as a yellow solid. The solid was purified by flash chromatography (silica gel, 50 g; ethyl acetate-hexanes, 1:19) to yield, upon concentration of the appropriate fractions, ethyl 6-chloro-1,2-dihydro-1-methyl-2-(trifluoromethyl)-3-quinoline-carboxylate (1.2 g, 90% yield): mp 118–120° C. $^1$H NMR (CD$_3$D/300 MHz) 7.71 (s, 1H), 7.30–7.26 (m, 2H), 6.77–6.74 (m, 1H), 5.12 (q, 1H, J=6.8 Hz), 4.44–4.22 (m, 2H), 3.18 (s, 3H), 1.35 (t, 3H, J=7.0 Hz). EIHRMS m/z 320.0701 (M–H, Calc'd 320.0665) Anal. Calc'd for C$_{14}$H$_{13}$F$_3$NO$_2$Cl: C, 52.60; H, 4.10; N, 4.38. Found: C, 52.57; H, 4.14; N, 4.32.

Step 2. Preparation of 6-chloro-1,2-dihydro-1-methyl-2-(trifluoromethyl)-3-quinolinecarboxylic Acid Ethyl 6-chloro-1,2-dihydro-1-methyl-2-(trifluoromethyl)-3-quinolinecarboxylate(1.21 g, 3.78 mmol) was suspended in methanol-tetrahydrofuran-water (20 mL, 7:2:1). Lithium hydroxide (0.262 g, 6.24 mmol) was added, and the mixture was gently heated to reflux for two hours. The reaction was cooled to room temperature and 1 N HCl added until pH=1. The organic solvent was removed in vauco to afford a suspension of crude yellow solid. Diethyl ether (20 mL) was added, and the resulting solution was washed with water (2×20 mL), saturated ammonium chloride (2×20 mL), dried over sodium sulfate and filtered. The filtrate was concentrated in vacuo to afford the product as a yellow solid, 6-chloro-1,2-dihydro-1-methyl-2-(trifluoromethyl)-3-quinoline-carboxylic acid. (1.08 g, 98% yield): mp 208–209° C. $^1$H NMR (CD$_3$OD/300 MHz) 7.69 (d, 1H, J=2.5 Hz), 7.28–7.24 (m, 2H), 6.73 (dd, 1H, J=9.5, 2.5 Hz), 5.13 (q, 1H, J=7.0), 3.16 (s, 3H). Anal. Calc'd for C$_{12}$H$_9$F$_3$NO$_2$Cl: C, 49.42; H, 3.11; N, 4.80; Cl, 12.16. Found: C, 49.88; H, 3.29; N, 4.59; Cl, 12.42.

EXAMPLE 166

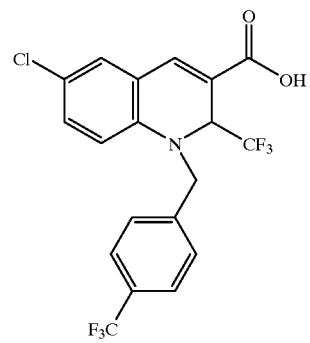

6-Chloro-1,2-dihydro-2-(trifluoromethyl)-1-[[4-(trifluoromethyl)phenyl]methyl]-3-quinolinecarboxylic Acid The 1,2-dihydro-3-quinolinecarboxylic acid was prepared by a procedure similar to that described in Example 165: mp 229–231° C. $^1$H NMR (CD$_3$OD/300 MHz) 7.77 (s, 1H), 7.58 (d, 2H, J=8.0 Hz), 7.39 (d, 2H, J=8.0 Hz), 7.30 (d, 1H, J=2.4), 7.13 (dd, 1H, J=8.9, 2.4 Hz), 6.75 (d, 1H, J=8.9 Hz), 5.27 (q, 1H, J=7.0 Hz), 4.90 (ab, 2H, J=16.7 Hz, Δv=95.2 Hz). EIHRMS m/z 434.0401 (Calc'd for M–H 434.0383) Anal. Calc'd for C$_{19}$H$_{14}$F$_6$NO$_2$Cl: C, 52.13; H, 3.22; N, 3.22; Found: C, 52.36; H, 2.91; N, 3.21.

EXAMPLE 167

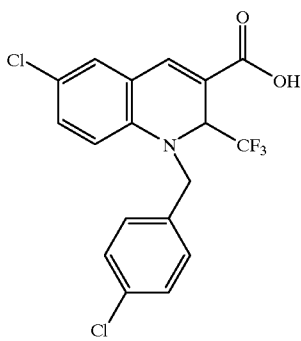

6-Chloro-1-[(4-chlorophenyl)methyl]-1,2-dihydro-2-(trifluoromethyl)-3-quinolinecarboxylic Acid The 1,2-dihydro-3-quinolinecarboxylic acid was prepared by a procedure similar to that described in Example 165: mp 250–253° C. $^1$H NMR (CD$_3$OD/300 MHz) 7.74 (s, 1H), 7.32–7.13 (m, 6H), 6.76 (d, 1H, J=8.7 Hz), 5.22 (q, 1H, J=7.0 Hz), 4.81 (ab, 2H, J=16.3 Hz, Av=54.7 Hz). ESHRMS m/z 400.0105 (M–H, Calc'd 400.0119).

EXAMPLE 168

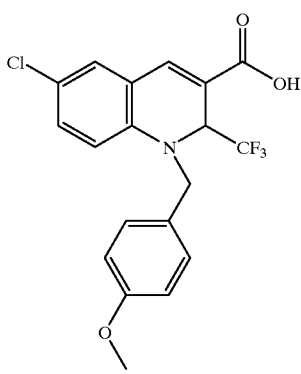

6-Chloro-1,2-dihydro-2-(trifluoromethyl)-1-[[4-(methoxy)phenyl]methyl]-3-quinolinecarboxylic Acid The 1,2-dihydro-3-quinolinecarboxylic acid was prepared by a procedure similar to that described in Example 165: mp 196–197° C. $^1$H NMR (CD$_3$OD/300 MHz) 7.71 (s, 1H), 7.27–7.26 (m, 1H), 7.18–7.12 (m, 3H), 6.85–6.81 (m, 3H), 5.16 (q, 1H, J=7.1 Hz), 4.69 (ab, 2H, J=15.3 Hz, Δv=111.8 Hz), 3.73 (s, 3H). ESHRMS m/z 396.0625 (M–H, Calc'd 396.0614). Anal. Calc'd for C$_{19}$H$_{14}$F$_6$NO$_2$Cl: C, 52.13; H, 3.22; N, 3.22. Found: C, 52.36; H, 2.91; N, 3.21.

EXAMPLE 169

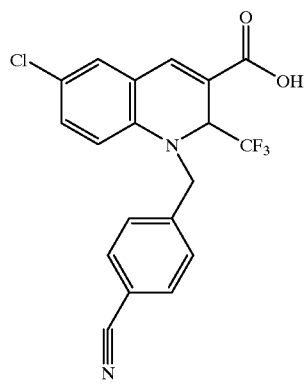

6-Chloro-1-[(4-cyanophenyl)methyl]-1,2-dihydro-2-(trifluoromethyl)-3-quinolinecarboxylic Acid The 1,2-dihydro-3-quinolinecarboxylic acid was prepared by a procedure similar to that described in Example 165: mp 258–260° C. $^1$H NMR (CD$_3$OD/300 MHz) 7.78 (s, 1H), 7.66 (d, 2H, J=8.2 Hz), 7.41 (d, 2H, J=8.2 Hz), 7.33 (d, 1H, J=2.7 Hz), 7.15 (dd, 1H, J=8.7, 2.7 Hz), 6.71 (d, 1H, J=8.7 Hz), 5.31 (q, 1H, J=7.0 Hz), 4.94 (ab, 2H, J=17.1, Δv=91.8 Hz). ESHRMS m/z 391.0443 (M–H, Calc'd 391.0461). Anal. Calc'd for C$_{19}$H$_{12}$F$_3$N$_2$O$_2$Cl+0.53% H$_7$O: C, 57.79; H, 3.55; N, 7.09; Found: C, 57.26; H, 3.17; N, 6.78.

EXAMPLE 170

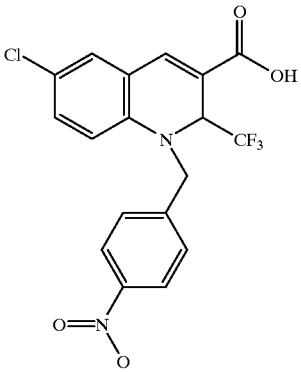

6-Chloro-1,2-dihydro-1-[(4-nitrophenyl)methyl]-2-(trifluoromethyl)-3-quinolinecarboxylic Acid The 1,2-dihydro-3-quinolinecarboxylic acid was prepared by a procedure similar to that described in Example 165: mp 225–228° C. $^1$H NMR (CD$_3$OD-3% TFA/300 MHz) 8.14 (d, 2H, J=8.8 Hz), 7.77 (s, 1H), 7.42 (d, 2H, J=8.8 Hz), 7.29 (d, 1H, J=2.4 Hz), 7.11 (dd, 1H, J=8.9, 2.4 Hz), 6.67 (d, 1H, J=8.9 Hz), 5.27 (q, 1H, J=6.8 Hz), 4.93 (ab, 2H, J=17.2 Hz, Δv=95.0 Hz). ESHRMS m/z 411.0327 (M–H, Calc'd 411.0359).

EXAMPLE 171

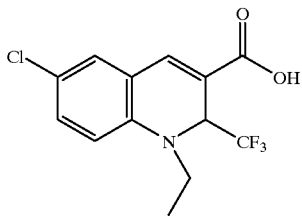

6-Chloro-1,2-dihydro-1-ethyl-2-(trifluoromethyl)-3-quinolinecarboxylic Acid

The 1,2-dihydro-3-quinolinecarboxylic acid was prepared by a procedure similar to that described in Example 165: mp 201–202° C. $^1$H NMR (CD$_3$OD/300 MHz)7.67 (s, 1H), 7.25–7.22 (m, 2H), 6.86 (d, 1H, J=8.7 Hz), 5.21 (q, 1H, J=7.0 Hz), 3.81–3.71 (m, 1H), 3.47–3.39 (m, 1H), 1.20 (t, 3H, J=7.2 Hz). ESHRMS m/z 304.0360 (M−H, Calc'd 304.0352).

EXAMPLE 172

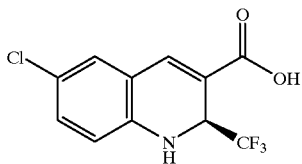

(S)-6-chloro-1,2-dihydro-2-(trifluoromethyl)-3-quinolinecarboxylic Acid

To a solution of 6-chloro-1,2-dihydro-2-(trifluoromethyl)-3-quinolinecarboxylic acid (Example 157) (6.75 g, 24.3 mmol) in ethyl acetate (25 mL) was added (S)-(−)-α-methylbenzylamine (1.50 g, 12.2 mmol). To the resulting solution was added hexanes (50 mL) with mixing. Stirring was discontinued and the reaction held static at room temperature for 16 hours during which time yellow crystals formed. The crystals were collected and washed with ethyl acetate-hexanes (100 mL, 1:2). The resulting yellow solid (932 mg) was dissolved in ethyl acetate (20 mL) and extracted with 1 N HCl (3×10 mL). The organic layer was dried over sodium sulfate and solvent removed at reduced pressure. The (s)-6-chloro-1,2-dihydro-2-(trifluoromethyl)-3-quinolinecarboxylic acid was obtained as a yellow solid (648 mg, 10% yield). mp 173–176° C. $^1$H NMR (acetone-d, 300 MHz) 7.80 (s, 1H), 7.35(d, 1H, J=2.2 Hz), 7.18 (d, 1H, J=8.0, J=2.2 Hz), 6.86 (d, 1H, J=8.0 Hz), 6.60 (brs, 1H), 5.20 (m, 1H). Anal. Calc'd. for $C_{11}H_7NO_2F_3Cl$ C, 47.40 H, 2.54; N, 5.40. Found C, 47.49; H, 2.60; N, 4.98. The compound was determined to have an optical purity greater than 90% ee. Optical purity was determined by HPLC as described in Example 66.

EXAMPLE 173

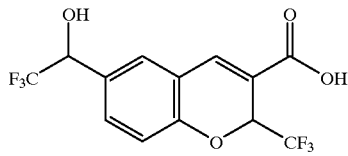

6-(2,2,2-Trifluoro-1-hydroxyethyl)-2-(trifluoromethyl)-2H-1-benzopyran-3-carboxylic Acid Step 1. Preparation of Ethyl 6-(1-hydroxy-2,2,2-trifluoroethyl)-2-(trifluoromethyl)-2H-1-benzopyran-3-carboxylate.

The aldehyde (Example 75, Step 1)(0.89 g, 3.0 mmol) was cooled to 0° C. and treated with a 0.5 M solution of trimethyl(trifluoromethyl)silane (8.4 mL, 4.2 mmol) and four drops of a 1.0M solution of tetrabutylammonium fluoride was added. The reaction was allowed to warm to room temperature and stirred for 21.1 hours. The reaction was quenched with 3 N HCl, extracted with ethyl acetate, washed with water, brine, dried over MgSO$_4$, and concentrated in vacua to give a brown oil (1.02 g). This oil was purified by flash chromatography over silica gel, eluting with 10% ethyl acetate/hexanes to afford a brown oil (0.77 g, 58%): $^1$H NMR (CDCl$_3$/300 MHz) 7.72 (d, 1H, J=3.4 Hz), 7.34 (m, 2H), 6.99 (d, 1H, J=8.5 Hz), 5.71 (q, 1H, J=6.8 Hz), 4.83 (q, 1H, J=6.4 Hz), 4.33 (m, 2H), 1.35 (t, 3H, J=7.1 Hz), 0.11 (s, 9H). FABLRMS m/z 443 (M+H).

Step 2. Preparation of 6-(1-hydroxy-2,2,2-trifluoroethyl)-2-trifluoromethyl-2H-1-benzopyran-3-carboxylic Acid.

The ester from Step 1 (0.15g 0.34 mmol) was dissolved in THF (2 mL) and ethanol (2 mL), treated with 2.5 N NaOH (1 mL, 2.5 mmol), and stirred at room temperature for 18.6 hours. The reaction mixture was concentrated in vacuo, acidified with 3 N HCl, extracted with ethyl acetate, washed with 3 N HCl, brine, dried over MgSO$_4$, and concentrated in vacuo to give a yellow oil which was recrystallized from ethyl acetate/hexane to yield a white solid (0.03 g, 25%): mp 114–120° C. $^1$H NMR (acetone-d$_6$/300 MHz) 7.94 (s, 1H), 7.65 (s, 1H), 7.60 (dd, 1H, J=8.2 Hz 2.0 Hz), 7.11 (d, 1H, J=8.3 Hz), 5.87 (q, 1H, J=7.0 Hz), 5.24 (q, 1H, J=7.0 Hz). FABLRMS m/z 341 (M−H). ESHRMS m/z 341.0241 (M−H, Calc'd 341.0249).

EXAMPLE 174

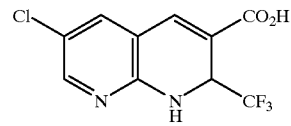

6-Chloro-2-(triflouromethyl)-1,2-dihydro[1,8]napthyridine-3-carboxylic Acid

Step 1. Preparation of N-[5-chloropyridin-2-yl]-2,2-dimethylpropanamide.

To 2-amino-5-chloropyridine (10.0 g, 0.078 mol) (Aldrich) and triethylamine (12 mL, 0.086 mol) in methylene chloride (200 mL), at 0° C., was added dropwise trimethylacetyl chloride in methylene chloride (15 mL). The reaction was allowed to warm to room temperature while stirring overnight. The resulting mixture was washed with water, brine, and was dried over MgSO$_4$ and filtered. Concentration of the filtrate in vacuo provided a colorless oil (19.2 g). The oil was dissolved in hexanes and cooled causing the precipitation of a solid. The solid was collected by filtration affording the amide as a white solid (14.96 g, 90%): mp 51.4 –53.4° C. H NMR (CDCl$_3$/300 MHz) 8.25–8.15(m, 2H), 8.00 (br s, 1H), 7.68–7.60 (m, 1H), 1.28 (s, 9H). Anal. Calc'd for C$_{10}$H$_{13}$N$_2$OCl: C, 56.47; H, 6.16; N, 13.17 Found: C, 56.72; H, 6.34; N, 12.88.

Step 2. Preparation of N-[5-chloro-3-formylpyridin-2-yl]-2,2-dimethylpropanamide.

To a chilled (–78° C.), stirred solution of the amide (Step 1) (5.0 g, 0.024 mole) in tetrahydrofuran (100 mL) was added t-butyl lithium (1.7M in pentane, 32.4 mL, 0.055 mole) dropwise. Dimethylformamide (2.3 mL, 0.03 mole) was added dropwise at –78° C. over 3 hours and the mixture allowed to warm room temperature. The reaction was quenched with ice water (200 mL) and extracted with ethyl acetate. The resulting organic phase was dried over MgSO$_4$ and was concentrated in vacuo to a volume of 20 mL. A white solid precipitated which was collected by filtration yielding the formylated product (3.24 g, 56%): mp 168.7–170.8° C. $^1$H NMR (CDCl$_3$/300 MHz) 10.60(br s, 1H), 9.88 (s, 1H), 8.57 (s, 1H), 8.00 (s, 1H), 1.28 (s, 9H). Anal. Calc'd for C$_{11}$H$_{13}$N$_2$O$_2$Cl: C, 54.89; H, 5.44; N, 11.64 Found: C, 54.87; H, 5.42; N, 11.40.

Step 3. Preparation 2-amino-5-chloro-3-formylpyridine.

The product of Step 2 (2.7 g, 11 mmol) and 3 N HCl (50 mL) were heated at reflux for 2 hours. The reaction was allowed to cool to room temperature and was concentrated in vacuo yielding a light yellow solid (2.1 g). The solid was partitioned between ethyl acetate and 2.5 N NaOH solution. The ethyl acetate layer was dried over MgSO$_4$ and concentrated in vacuo providing a solid (1.7 g). The solid was recrystallized from ethyl acetate to give the desired substituted pyridine as yellow needles (1.2 g, 68%): mp 176.1–177.3 C. H NMR (CDCl$_3$/300 MHz) 9.80 (s, 1H), 8.21 (s, 1H), 7.75 (s, 1H), 6.75 (br s, 2H). Anal. Calc'd for CHNOCl: C, 46.03; H, 3.22; N, 17.89 Found: C, 45.90; H, 3.24; N, 17.80.

Step 4. Preparation of Ethyl 6-chloro-2-(triflouromethyl)-1,2-dihydro[1,8]napthyridine-3-carboxylate.

The substituted pyridine from Step 3 (1.7 g, 11 mmol), anhydrous potassium carbonate (3.0 g, 22 mmol), and ethyl 4,4,4-trifluorocrotonate (3.3 mL, 22 mmol) were mixed in anhydrous dimethylformamide (20 mL) and heated at 80° C. for 2 hours. The reaction was allowed to cool to room temperature and was partitioned between ethyl acetate (100 mL) and water (100 mL). The aqueous layer was extracted with more ethyl acetate (100 mL). The combined organic extracts were washed with brine (100 mL), dried over MgSO$_4$, and concentrated in vacuo yielding a waxy amber solid The solid was triturated with diethyl ether providing the ester as a yellow solid (613 mg, 18%). A small amount was recrystallized from ethyl acetate for analytical data: mp 180.1–181.9° C. $^1$H NMR (CDCl$_3$/300 MHz) 7.99 (s, 1H), 7.61 (s, 1H), 7.39 (s, 1H), 6.00 (br s, 1H), 5.33–5.20 (m, 1H), 4.40–4.23 (m, 2H), 1.40–1.30 (m, 3H). Anal. Calc'd for C$_{12}$H$_{10}$N$_2$O$_2$F$_3$Cl: C, 47.00; H, 3.29; N, 9.13 Found: C, 46.83; H, 3.03; N, 9.18.

Step 5. Preparation of 6-chloro-2-(trifluoromethyl)-1,2-dihydro[1,8]napthyridine-3-carboxylic Acid.

The ester from Step 4 (1.3 g, 4.4 mmol) and 2.5 N sodium hydroxide solution (3.5 mL, 9 mmol) were mixed in tetrahydrofuran (25 mL), methanol (10 mL), and water (25 mL). The mixture was heated at 50° C. for 4 hours, allowed to cool to room temperature, and was concentrated in vacuo to remove the tetrahydrofuran and methanol. The resulting aqueous solution was washed with diethyl ether (2×100 mL). The aqueous phase was acidified with 3 N HCl causing the precipitation of a yellow solid (1.1 g). The solid was triturated with ethanol-acetone and collected by vacuum filtration providing the title compound as a yellow solid (276 mg, 23%): mp 287.4–288.4 C. H NMR (acetone-d$_6$/300 MHz) 11.50 (br s, 1H), 8.03 (s, 1H), 7.83 (s, 1H), 7.75 (s, 1H), 7.28 (br s, 1H), 5.42–5.30 (m, 1H). Anal. Calc'd for C$_{10}$H$_6$N$_2$O$_2$F$_3$Cl: C, 43.11; H, 2.17; N, 10.05 Found: C, 42.88; H, 2.03; N, 10.06.

EXAMPLE 175

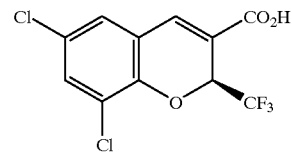

(S)-6,8-Dichloro-2-(trifluoromethyl)-2H-1-benzopyran-3-carboxylic Acid 6,8-Dichloro-2-(trifluoromethyl)-2H-1-benzopyran-3-carboxylic acid (Example 32) (300 g, 1.04 mol) was added to ethyl acetate (750 mL). The mixture was stirred for 5 minutes, warmed to 70° C. and held at this temperature for 5 minutes. The resulting solution was cooled to 50° C. and (s)-(–)-α-methylbenzylamine (58 g, 0.48 mol)was added. Heptane (1880 mL) was added and the mixture stirred for 0.5 hour, then stirring was discontinued. The reaction was allowed to cool to 22° C. and stand for 8 hours. The salt crystallized during this time and was collected by vacuum filtration. The solid was washed with ethyl acetate-heptane (1:3, 2×50 mL). The solid obtained was dried at 40° C. under vacuum (20 mm) for 24 hours to give the salt(35 g, 16%).

A three-neck 2 L round bottom flask was purged with nitrogen and was charged with deionized water (750 mL) and the salt (103 g, 0.24 mole; This material was obtained using a similar procedure to that described above). To the resulting stirred suspension was added concentrated HCl (37 mL) drop-wise over 0.5 hours with good stirring below 20° C. causing the free carboxylic acid to precipitate. After stirring for 2 hours, the suspension was vacuum filtered and the solid washed with deionized water (5×50 mL; until the washings were neutral). The solid was dried at 40° C. under vacuum (20 mm) for 12 hours yielding the title compound as a solid (74 g, 100%): mp 166.0–168.4° C. 1H NMR (acetone-d$_6$/300 MHz) 7.94 (s, 1H), 7.60 (s, 2H), 6.04 (q, 1H, J=6.8 Hz). ESHRMS m/z 310.9489 (M–H, Calc'd 310.9450). This compound was determined to have an optical purity of greater than 90% ee. The optical purity was determined by the method described in Example 66.

EXAMPLE 176

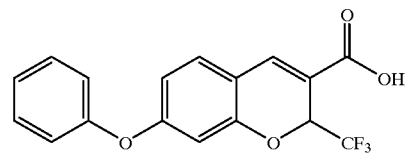

7-Phenoxy-2-(trifluoromethyl)-2H-1-benzopyran-3-carboxylic Acid

3-Phenoxyphenol was converted to the title compound by a procedure similar to that described in Example 2: mp 180.0–181.0° C. $^1$H NMR (acetone-d$_6$/300 MHz) 7.87 (s, 1H), 7.47 (m, 3H), 7.26 (dt, 1H, J=7.6 Hz, 1.4 Hz), 7.15 (d, 2H, J=7.7 Hz), 6.68 (dd, 1H, J=8.5 Hz 2.3 Hz), 6.58 (s, 1H), 5.81 (q, 1H, J=7.1 Hz). $^{19}$F NMR (acetone-d$_6$/282 MHz) −79.5 (d, J=7.2 Hz). FABLRMS m/z 335 (M−H). ESHRMS m/z 335.0542 (M−H, Calc'd 335.0531). Anal. Calc'd for C$_{17}$H$_{11}$F$_3$O$_4$: C, 60.72; H, 3.30. Found: C, 60.55; H, 3.29.

EXAMPLE 177

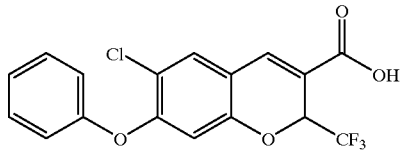

6-Chloro-7-phenoxy-2-(trifluoromethyl)-2H-1-benzopyran-3-carboxylic Acid

3-Phenoxyphenol was converted to the title compound by a procedure similar to that described in Example 100: mp 220.2–221.8° C. $^1$H NMR (acetone-d$_6$/300 MHz) 7.91 (s, 1H), 7.72 (s, 1H), 7.50 (m, 2H), 7.28 (t, 1H, J=7.5 Hz), 7.15 (d, 2H, J=7.7 Hz), 6.53 (s, 1H), 5.81 (q, 1H, J=7.1 Hz). $^{19}$F NMR (acetone-d$_6$/282 MHz) −79.4 (d, J=7.2 Hz). FABLRMS m/z 369 (M−H). ESHRMS m/z 369.0157 (M−H, Calc'd 369.0141). Anal. Calc'd for C$_{17}$H$_{10}$ClF$_3$O$_4$: C, 55.08; H, 2.72; Cl, 9.56. Found: C, 54.94; H, 2.60; Cl, 9.84.

EXAMPLE 178

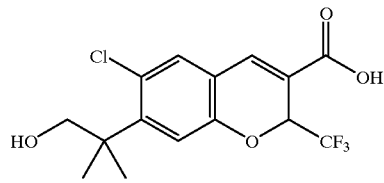

6-Chloro-7-(2-hydroxy-1,1-dimethylethyl)-2-(trifluoromethyl)-2H-1-benzopyran-3-carboxylic Acid Step 1. Preparation of Methyl 3-methoxyphenylacetate.

Trimethylsilyl chloride (182 g, 1.68 mol) was added dropwise to a solution of 3-methoxyphenylacetic acid (127 g, 0.77 mol) in methanol (1.0 L) over 1.1 hours. The reaction was stirred at room temperature for 17.25 hours, concentrated in vacuo, dissolved in ethyl acetate, dried over MgSO$_4$, and concentrated in vacuo, to give a brown oil (133 g, 97%): $^1$H NMR (CDCl$_3$/300 MHz) 7.24 (t, 1H, J=7.5 Hz), 6.83 (m, 3H), 3.80 (s, 3H), 3.69 (s, 3H), 3.60 (s, 2H).

Step 2. Preparation of Methyl 2-(3-methoxyphenyl)-2-methylpropionate.

A 2L flask was charged with a 60% dispersion of sodium hydride in mineral oil (48.7 g, 1.22 mol) and THF (0.4 L). A solution of the ester from Step 1 (73.2 g, 0.41 mol) in THF (0.2 L) was added over one hour and the reaction was stirred for an additional 2.67 hours. The reaction was cooled in ice and treated with methyl iodide (136.8 g, 0.96 mol) over a period of 0.67 hours, and then stirred at room temperature for 14.75 hours. The reaction was poured into a mixture of 3N HCl (0.3 L) and ice (0.8 L), extracted with ethyl acetate (0.8 L), washed with 10% NaHSO$_3$, water, brine, dried over MgSO$_4$ and concentrated in vacuo, to give a brown oil which was distilled under vacuum (2.2 mm Hg, 97–112° C.) to give a clear oil (50.9 g, 60%): $^1$H NMR (CDCl$_3$/300 MHz) 7.25 (t, 1H, J=8.0 Hz), 6.89 (m, 2H), 6.81 (dd, 1H, J=8.0 Hz, 2.6 Hz), 3.81 (s, 3H), 3.66 (s, 3H), 1.57 (s, 6H).

Step 3. Preparation of Methyl 2-(3-hydroxyphenyl)-2-methylpropionate.

The ester from Step 2 (29.1 g, 140 mmol) was dissolved in CH$_2$Cl$_2$ (170 mL) and cooled to −65° C. The reaction was treated with a 1.0 M solution of boron tribromide in CH$_2$Cl$_2$ (180 mL, 180 mmol). The reaction was stirred at −65° C. for 1.6 hours, then the cooling bath was removed and the reaction was warmed to room temperature. The reaction was added to ice water and the layers were separated. The organic layer was concentrated in vacuo, dissolved in ethyl acetate, washed with saturated NaHCO$_3$, brine, dried over MgSO$_4$ and concentrated in vacuo, to give methyl 2-(3-hydroxyphenyl)-2-methylpropionate as a brown oil (10.6 g, 42%): $^1$H NMR (CDCl$_3$/300 MHz) 7.19 (m, 1H), 6.90 (d, 1H, J=7.9 Hz), 6.84 (m, 1H), 6.75 (d, 1H, J=8.1 Hz), 3.66 (s, 3H), 1.56 (s, 6H). The saturated NaHCO$_3$ layer was acidified with concentrated HCl, extracted with ethyl acetate, washed with brine, dried over MgSO$_4$ and concentrated in vacuo, to give 2-(3-hydroxyphenyl)-2-methylpropionic acid as a brown oil (15.8 g, 42%): $^1$H NMR (CDCl$_3$/300 MHz) 7.20 (m, 1H), 6.97 (dd, 1H, J=7.9 Hz, 0.8 Hz), 6.88 (m, 1H), 6.75 (dd, 1H, J=8.1 Hz, 0.8 Hz), 1.57 (s, 6H).

Step 4. Preparation of 2-(3-hydroxyphenyl)-2-methylpropionic Acid.

The ester (Step 3) was hydrolyzed to the carboxylic acid via a method similar to that described in Example 1, Step 2: $^1$H NMR (CDCl$_3$/300 MHz) 7.20 (m, 1H), 6.97 (dd, 1H, J=7.9 Hz, 0.8 Hz), 6.88 (m, 1H), 6.75 (dd, 1H, J=8.1 Hz, 0.8 Hz), 1.57 (s, 6H).

Step 5. Preparation of 3-(2-hydroxy-1,1-dimethylethyl)phenol.

The carboxylic acid obtained from several lots obtained from Step 3 and Step 4 (31.6 g, 175 mmol) was dissolved in THF (150 mL), cooled to 0° C., and treated with borane methyl sulfide complex (33 mL, 348 mmol). The reaction was warmed to room temperature and stirred for 7.5 hours. The reaction was added to 3N HCl, extracted with ethyl acetate, washed with brine, dried over MgSO$_4$ and concentrated in vacuo, to give a brown oil (18.6 g, 64%): $^1$H NMR (CDCl$_3$/300 MHz) 7.21 (m, 1H), 6.96 (d, 1H, J=7.9 Hz), 6.86 (t, 1H, J=2.0 Hz), 6.71 (dd, 1H, J=7.8 Hz, 2.4 Hz), 3.60 (s, 2H), 1.31 (s, 6H).

Step 6. Preparation of 4-(2-hydroxy-1,1-dimethylethyl)salicylaldehyde.

The phenol (Step 5) was converted to the salicylaldehyde via a method similar to that described in Example 2, Step 1: mp 80.4–81.9° C. $^1$H NMR (CDCl$_3$/300 MHz) 11.00 (s, 1H), 9.87 (s, 1H), 7.51 (d, 1H, J=8.3 Hz), 7.08 (dd, 1H, J=8.3 Hz, 1.4 Hz), 7.02 (d, 1H, J=1.4 Hz), 3.66 (s, 2H), 1.34 (s, 6H).

Step 7. Preparation of Ethyl 6-chloro-7-(2-acetoxy-1,1-dimethylethyl)-2-(trifluoromethyl)-2H-1-benzopyran-3-carboxylate.

The salicylaldehyde (Step 6) was chlorinated via a method similar to that described in Example 9 yielding 5-chloro-4-(2-acetoxy-1,1-dimethylethyl)salicylaldehyde. This salicylaldehyde was converted to the substituted ethyl 2H-1-benzopyran-3-carboxylate via a method similar to that described in Example 1, Step 1: $^1$H NMR (CDCl$_3$/300 MHz) 7.63 (s, 1H), 7.22 (s, 1H), 7.02 (s, 1H), 5.70 (q, 1H, J=6.8 Hz), 4.46 (s, 2H), 4.32 (m, 2H), 1.97 (s, 3H), 1.49 (s, 6H), 1.36 (t, 3H, J=7.0 Hz). $^{19}$F NMR (CDCl$_3$/282 MHz) −78.8 (d, J=6.5 Hz).

Step 8. Preparation of 6-chloro-7-(2-hydroxy-1,1-dimethylethyl)-2-(trifluoromethyl)-2H-1-benzopyran-3-carboxylic Acid.

The ester obtained from Step 7 was hydrolyzed to the carboxylic acid via a method similar to that described in Example 1, Step 2: mp 203.8–205.4° C. $^1$H NMR (acetone-$d_6$/300 MHz) 7.87 (s, 1H), 7.50 (s, 1H), 7.21 (s, 1H), 5.83 (q, 1H, J=7.0 Hz), 3.90 (s, 2H), 1.46 (s, 6H). $^{19}$F NMR (acetone-$d_6$/282 MHz) −79.4 (d, J=7.2 Hz). ESHRMS m/z 349.0443 (M−H, Calc'd 349.0454). Anal. Calc'd for $C_{15}H_{14}ClF_3O_4$: C, 51.37; H, 4.02; Cl, 10.11. Found: C, 51.24; H, 4.02; Cl, 10.45.

EXAMPLE 179

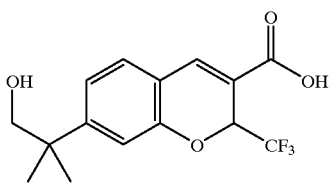

7 (2-Hydroxy-1,1-dimethylethyl)-2-(trifluoromethyl)-2H-1-benzopyran-3-carboxylic Acid The salicylaldehyde from Example 178, Step 6 was converted to the title compound via a procedure similar to that described in Example 11, Steps 2 and 3: mp 228.9–230.0° C. $^1$H NMR (acetone-$d_6$/300 MHz) 7.86 (s, 1H), 7.37 (d, 1H, J=8.1 Hz), 7.17 (dd, 1H, J=8.1 Hz, 1.6 Hz), 7.08 (s, 1H), 5.81 (q, 1H, J=7.2 Hz), 3.60 (s, 2H), 1.30 (s, 6H). $^{19}$F NMR (acetone-$d_6$/282 MHz) −79.5 (d, J=7.2 Hz). ESHRMS m/z 315.0843 (M−H, Calc'd 315.0844). Anal. Calc'd for $C_{17}H_{10}ClF_3O_4$: C, 56.96; H, 4.78. Found: C, 56.91; H, 4.85.

EXAMPLE 180

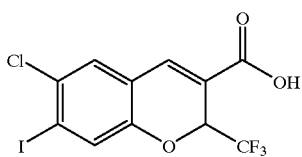

6-Chloro-7-iodo-2-(trifluoromethyl)-2H-1-benzopyran-3-carboxylic Acid 3-iodophenol was converted to the title compound by a procedure similar to that described in Example 100: mp 224.9–225.9° C. $^1$H NMR (acetone-$d_6$/300 MHz) 7.92 (s, 1H), 7.72 (s, 1H), 7.68 (5, 1H), S. 91 (q, 1H, J=7.0 Hz). $^{19}$F NMR (acetone-$d_6$/282 MHz) −79.3 (d, J=7.2 Hz). FABLRMS m/z 403 (M−H). ESHRMS m/z 402.8836 (M−H, Calc'd 402.8846). Anal. Calc'd for $C_{11}H_5ClF_3IO_3$: C, 32.66; H, 1.25; Cl, 8.76. Found: C, 32.65; H, 0.97; Cl, 8.39.

EXAMPLE 181

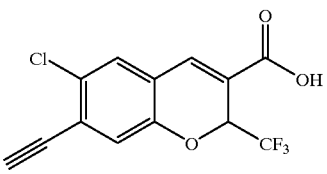

6-Chloro-7-ethynyl-2-(trifluoromethyl)-2H-1-benzopyran-3-carboxylic Acid

The title compound was prepared from ethyl 6-chloro-7-iodo-2-(trifluoromethyl)-2H-1-benzopyran-3-carboxylate (Example 180) via a procedure similar to that described in Example 118: mp>300° C. $^1$H NMR (acetone-$d_6$/300 MHz) 7.91 (s, 1H), 7.68 (s, 1H), 7.24 (s, 1H), 5.90 (q, 1H, J=7.0 Hz), 4.23 (s, 1H). $^{19}$F NMR (acetone-$d_6$/282 MHz) −79.3 (d, J=6.5 Hz). FABLRMS m/z 301 (M−H). ESHRMS m/z 300.9884 (M−H, Calc'd 300.9879). Anal. Calc'd for $C_{13}H_6ClF_3O_3$: C, 51.59; H, 2.00; Cl, 11.71. Found: C, 51.63; H, 2.04; Cl, 11.84.

EXAMPLE 182

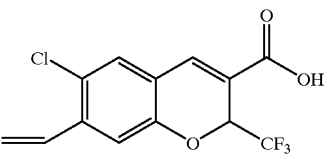

6-Chloro-7-ethenyl-2-(trifluoromethyl)-2H-1-benzopyran-3-carboxylic Acid

The title compound was prepared from ethyl 6-chloro-7-iodo-2-(trifluoromethyl)-2H-1-benzopyran-3-carboxylate (Example 180) via a procedure similar to that described in Example 114: mp>200° C. with decomposition. $^1$H NMR (acetone-$d_6$/300 MHz) 7.89 (s, 1H), 7.59 (s, 1H), 7.37 (s, 1H), 7.07 (dd, 1H, J=17.5 Hz, 11.1 Hz), 6.07 (d, 1H, J=17.3 Hz), 5.87 (q, 1H, J=7.0 Hz), 5.57 (d, 1H, J=11.1 Hz). $^{19}$F NMR (acetone-$d_6$/282 MHz) −79.2 (d, J=7.2 Hz). FABLRMS m/z 303 (M−H). ESHRMS m/z 303.0030 (M−H, Calc'd 303.0036). Anal. Calc'd for $C_{13}H_8ClF_3O_3$: C, 51.25; H, 2.65; Cl, 11.64. Found: C, 51.41; H, 2.66; Cl, 11.68.

EXAMPLE 183

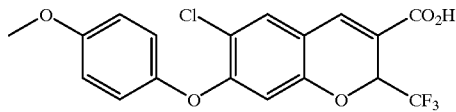

6-Chloro-7-(4-methoxyphenoxy)-2-(trifluoromethyl)-2H-1-benzopyran-3-carboxylic Acid Step 1. Preparation of 5-chloro-4-fluorosalicylaldehyde.

4-Chloro-3-fluorophenol (Avocado product #16029) was converted to the salicylaldehyde via a method similar to that described in Example 2, Step 1: mp 102.7–103.7° C. $^1$H NMR (CDCl$_3$/300 MHz) 11.22 (d, 1H, J=1.6 Hz), 9.80 (s, 1H), 7.63 (d, 1H, J=7.9 Hz), 6.77 (d, 1H, J=10.3 Hz). $^{19}$F NMR (CDCl$_3$/282 MHz) −100.3 (t).

Step 2. Preparation of ethyl 6-chloro-7-fluoro-2-(trifluoromethyl)-2H-1-benzopyran-3-carboxylate.

The salicylaldehyde (Step 1) was converted to the substituted ethyl 2H-1-benzopyran-3-carboxylate via a method similar to that described in Example 11 (Steps 2,3), Step 2: mp 97.6–98.6° C. $^1$H NMR (CDCl$_3$/300 MHz) 7.63 (s, 1H), 7.29 (d, 1H, J=9.7 Hz), 6.84 (d, 1H, J=9.3 Hz), 5.69 (q, 1H, J=6.6 Hz), 4.32 (m, 2H), 1.35 (t, 3H, J=7.0 Hz). $^{19}$F NMR (CDCl$_3$/282 MHz) −78.8 (d, J=6.5 Hz), −106.7 (t, J=8.7 Hz).

Step 3. Preparation of Ethyl 6-chloro-7-(4-methoxyphenoxy)-2-(trifluoromethyl)-2H-1-benzopyran-3-carboxylate.

A 50 mL flask was charged with the substituted ethyl 2H-1-benzopyran-3-carboxylate from Step 2 (1.44 g, 4.43 mmol), 4-methoxyphenol (0.62g, 4.99 mmol), K$_2$CO$_3$ (0.84 g, 6.07 mmol), and DMSO (10 mL). The reaction was stirred at 105° C. for 18 hours, poured into water extracted with ethyl acetate, washed with water, brine, dried over MgSO$_4$ and concentrated in vacuo, to give a brown oil which was passed through a column of silica gel with 5% ethyl acetate/hexanes to give a yellow solid (0.78 g, 41%): mp 115.8–117.0° C. $^1$H NMR (CDCl$_3$/300 MHz) 7.66 (s, 1H), 7.32 (s, 1H), 7.04 (d, 2H, J=9.3 Hz), 6.98 (d, 2H, J=9.1 Hz), 6.38 (s, 1H), 5.65 (q, 1H, J=6.8 Hz), 4.33 (m, 2H), 3.86 (s, 3H), 1.37 (t, 3H, J=7.2 Hz). $^{19}$F NMR (CDCl$_3$/282 MHz) −78.9 (d, J=6.5 Hz).

Step 4. Preparation of 6-chloro-7-(4-methoxyphenoxy)-2-(trifluoromethyl)-2H-1-benzopyran-3-carboxylic Acid.

The ester (Step 3) was hydrolyzed to the carboxylic acid via a method similar to that described in Example 1, Step 2: mp 213.2–214.3° C. $^1$H NMR (acetone-d$_6$/300 MHz) 7.90 (s, 1H), 7.70 (s, 1H), 7.13 (d, 2H, J=9.3 Hz), 7.09 (d, 2H, J=8.9 Hz), 6.42 (s, 1H), 5.83 (q, 1H, J=7.0 Hz), 3.87 (s, 3H). $^{19}$F NMR (acetone-d$_6$/282 MHz) −79.5 (d, J=7.2 Hz). FABLRMS m/z 401 (M+H). ESHRMS m/z 418.0799 (M+NH$_4$, Calc'd 418.0669). Anal. Calc'd for C$_{18}$H$_{12}$ClF$_3$O$_5$: C, 53.95; H, 3.02; Cl, 8.85. Found: C, 54.17; H, 3.03; Cl, 8.91.

EXAMPLE 184

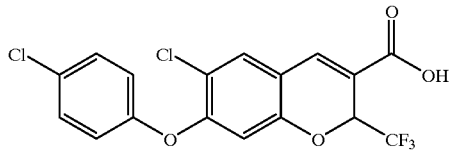

6-Chloro-7-(4-chlorophenoxy)-2-(trifluoromethyl)-2H-1-benzopyran-3-carboxylic Acid The title compound was prepared from 4-chlorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 205.4–206.5° C. $^1$H NMR (acetone-d$_6$/300 MHz) 7.93 (s, 1H), 7.75 (s, 1H), 7.50 (d, 2H, J=8.9 Hz), 7.19 (d, 2H, J=8.9 Hz), 6.69 (s, 1H), 5.87 (q, 1H, J=7.0 Hz). $^{19}$F NMR (acetone-d$_6$/282 MHz) −79.4 (d, J=7.2 Hz). FABLRMS m/z 403 (M−H). ESHRMS m/z 402.9773 (M−H, Calc'd 402.9752). Anal. Calc'd for C$_{17}$H$_9$Cl$_2$F$_3$O$_4$: C, 50.40; H, 2.24; Cl, 17.50. Found: C, 50.02; H, 1.98; Cl, 17.79.

EXAMPLE 185

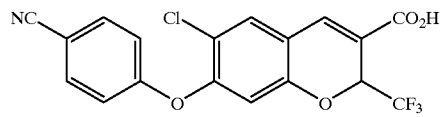

6-Chloro-7-(4-cyanophenoxy)-2-(trifluoromethyl)-2H-1-benzopyran-3-carboxylic Acid The title compound was prepared from 4-cyanophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 212.5–215.7° C. $^1$H NMR (acetone-d$_6$/300 MHz) 7.96 (s, 1H), 7.90 (d, 2H, J=8.9 Hz), 7.81 (s, 1H), 7.27 (d, 2H, J=8.9 Hz), 6.96 (s, 1H), 5.90 (q, 1H, J=7.0 Hz). $^{19}$F NMR (acetone-d$_6$/282 MHz) −79.4 (d, J=7.2 Hz). FABLRMS m/z 396 (M+H). ESHRMS m/z 413.0544 (M+NH$_4$, Calc'd 413.0516). Anal. Calc'd for C$_{18}$H$_9$ClF$_3$NO$_4$: C, 54.63; H, 2.29; N, 3.54; Cl, 8.96. Found: C, 54.40; H, 2.18; N 3.30; Cl, 9.20.

EXAMPLE 186

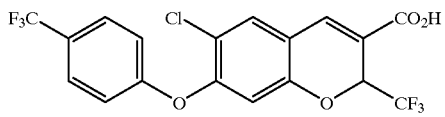

6-Chloro-2-(trifluoromethyl)-7-[4-(trifluoromethyl)phenoxy]-2H-1-benzopyran-3-carboxylic Acid The title compound was prepared from 4-(trifluoromethyl)phenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 230.9–232.0° C. $^1$H NMR (acetone-d$_6$/300 MHz) 7.93 (s, 1H), 7.77 (m, 3H), 7.27 (d, 2H, J=8.7 Hz), 6.86 (s, 1H), 5.87 (q, 1H, J=7.0 Hz). $^{19}$F NMR (acetone-d$_6$/282 MHz) −62.8 (s, 3F), −79.4 (d, 3F, J=7.2 Hz). ESLRMS m/z 437 (M−H). ESHRMS m/z 437.0008 (M−H, Calc'd 437.0015). Anal. Calc'd for C$_{18}$H$_9$ClF$_6$O$_4$: C, 49.28; H, 2.07; Cl, 8.08. Found: C, 49.25; H, 2.08; Cl, 8.24.

EXAMPLE 187

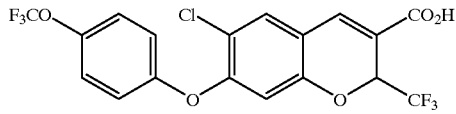

6-Chloro-2-(trifluoromethyl)-7-[4-(trifluoromethoxy)phenoxy]-2H-1-benzopyran-3-carboxylic Acid The title compound was prepared from 4-(trifluoromethoxy)phenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 198.0–199.2° C. $^1$H NMR (acetone-d$_6$/300 MHz) 7.91 (s, 1H), 7.73 (s, 1H), 7.43 (d, 2H, J=9.1 Hz), 7.25 (d, 2H, J=9.1 Hz), 6.70 (s, 1H), 5.82 (q, 1H, J=7.0 Hz). $^{19}$F NMR (acetone-$d_6$/282 MHz) −59.4 (s, 3F), −79.4 (d, 3F, J=7.2 Hz). ESLRMS m/z 453 (M−H). ESHRMS m/z 452.9950 (M−H, Calc'd 452.9964). Anal. Calc'd for $C_{18}H_9ClF_6O_5$: C, 47.55; H, 2.00; Cl, 7.80. Found: C, 47.47; H, 1.89; Cl, 8.02.

EXAMPLE 188

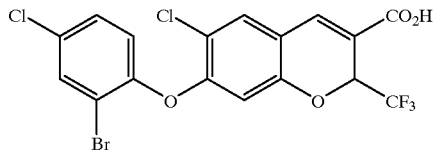

7-(2-Bromo-4-chlorophenoxy)-6-chloro-2-(trifluoromethyl)-2H-1-benzopyran-3-carboxylic Acid The title compound was prepared from 2-bromo-4-chlorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 223.6–225.6° C. $^1$H NMR (acetone-$d_6$/300 MHz) 7.89 (s, 1H), 7.83 (d, 1H, J=2.6 Hz), 7.73 (s, 1H), 7.52 (dd, 1H, J=8.7 Hz, 2.4 Hz), 7.25 (d, 1H, J=8.9 Hz), 6.55 (s, 1H), 5.83 (q, 1H, J=7.0 Hz). $^{19}$F NMR (acetone-$d_6$/282 MHz) −79.4 (d, J=7.2 Hz) FABLRMS m/z 481 (M−H). ESHRMS m/z 480.8856 (M−H, Calc'd 480.8857). Anal. Calc'd for $C_{17}H_8BrCl_2F_3O_4$: C, 42.18; H, 1.67; Br, 16.51; Cl, 14.65. Found: C, 42.15; H, 1.54; Br, 16.56; Cl, 14.39.

EXAMPLE 189

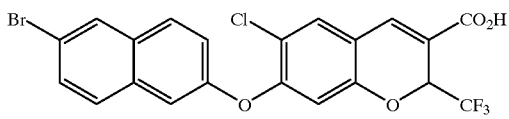

7-[(6-Bromo-2-naphthalenyl)oxy]-6-chloro-2-(trifluoromethyl)-2H-1-benzopyran-3-carboxylic Acid The title compound was prepared from 6-bromo-2-napthol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 252.6–254.8° C. $^1$H NMR (acetone-$d_6$/300 MHz) 8.19 (s, 1H), 8.04 (d, 1H, J=9.1 Hz), 7.93 (s, 1H), 7.87 (d, 1H, J=8.9 Hz), 7.75 (s, 1H), 7.65 (d, 1H, J=8.8 Hz), 7.55 (s, 1H), 7.43 (d, 1H, J=9.1 Hz), 6.72 (s, 1H), 5.83 (q, 1H, J=7.0 Hz). $^{19}$F NMR (acetone-$d_6$/282 MHz) −79.4 (d, J=6.5 Hz). FABLRMS m/z 497 (M−H). ESHRMS m/z 496.9421 (M−H, Calc'd 496.9403). Anal. Calc'd for $C_{21}H_{11}BrClF_3O_4$ with 1.75 wt % $H_2O$: C, 49.60; H, 2.38; Br, 15.71; Cl, 6.97. Found: C, 49.55; H, 2.03; Br, 15.56; Cl, 7.22.

EXAMPLE 190

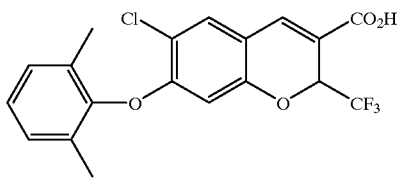

6-Chloro-7-(2,6-dimethylphenoxy)-2-(trifluoromethyl)-2H-1-benzopyran-3-carboxylic Acid The title compound was prepared from 2,6-dimethylphenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 252.7–258.6° C. $^1$H NMR (acetone-$d_6$/300 MHz) 7.88 (s, 1H), 7.71 (s, 1H), 7.22 (m, 3H), 6.04 (s, 1H), 5.77 (q, 1H, J=7.0 Hz), 2.13 (s, 6H). $^{19}$F NMR (acetone-$d_6$/282 MHz) −79.6 (d, J=7.2 Hz). FABLRMS m/z 397 (M−H). ESHRMS m/z 397.0450 (M−H, Calc'd 397.0454). Anal. Calc'd for $C_{19}H_{14}ClF_3O_4$: C, 57.23; H, 3.54; Cl, 8.89. Found: C, 57.21; H, 3.56; Cl, 8.98.

EXAMPLE 191

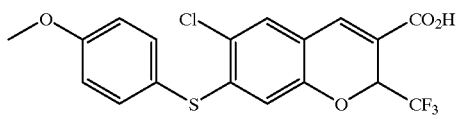

6-Chloro-7-[(4-methoxyphenyl)thio]-2-(trifluoromethyl)-2H-1-benzopyran-3-carboxylic Acid The title compound was prepared from 4-methoxybenzenethiol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 239.4–242.3° C. $^1$H NMR (acetone-$d_6$/300 MHz) 7.84 (s, 1H), 7.55 (m, 3H), 7.16 (d, 2H, J=8.7 Hz), 6.20 (s, 1H), 5.75 (q, 1H, J=7.0 Hz), 3.90 (s, 3H). $^{19}$F NMR (acetone-$d_6$/282 MHz) −79.4 (d, J=6.5 Hz) ESLRMS m/z 415 (M−H). ESHRMS m/z 415.0005 (M−H, Calc'd 415.0019). Anal. Calc'd for $C_{18}H_{12}ClF_3O_4S$: C, 51.87; H, 2.90; Cl, 8.51; S, 7.69. Found: C, 51.76; H, 2.83; Cl 8.55; S, 7.77.

EXAMPLE 192

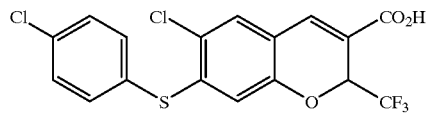

6-Chloro-7-[(4-chlorophenyl)thio]-2-(trifluoromethyl)-2H-1-benzopyran-3-carboxylic Acid The title compound was prepared from 4-chlorobenzenethiol and ethyl 6-chloro-7-fluoro-2-

(trifluoromethyl)-2H-1-benzopyran-3-carboxylate (Example 183, Step 2) via a procedure similar to that described in Example 183, Steps 3 and 4: mp 251.7–253.3° C. $^1$H NMR (acetone-$d_6$/300 MHz) 7.86 (s, 1H), 7.62 (m, 5H), 6.39 (s, 1H), 5.78 (q, 1H, J=7.0 Hz). $^{19}$F NMR (acetone-$d_6$/282 MHz) −79.4 (d, J=6.5 Hz). ESLRMS m/z 419 (M−H). ESHRMS m/z 418.9559 (M−H, Calc'd 418.9523). Anal. Calc'd for $C_{17}H_9Cl_2F_3O_3S$: C, 48.47; H, 2.15; Cl, 16.83; S, 7.61. Found: C, 48.38; H, 2.12; Cl, 17.09; S, 7.75.

EXAMPLE 193

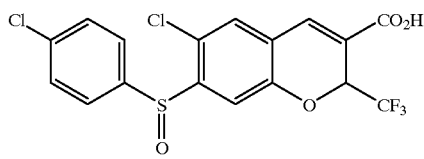

6-Chloro-7-[(4-chlorophenyl)sulfinyl]-2-(trifluoromethyl)-2H-1-benzopyran-3-carboxylic Acid Following a procedure similar to that described in Example 128, ethyl 6-chloro-7-[(4-chlorophenyl)thio]-2-(trifluoromethyl)-2H-1-benzopyran-3-carboxylate (Example 192) was treated with OXONE® yielding the products labeled Example 193 and Example 194: mp 213.8–217.4° C. $^1$H NMR (acetone-$d_6$/300 MHz) 7.91 (s, 1H), 7.83 (d, 2H, J=8.7 Hz), 7.62 (m, 4H), 5.98 (q, 1H, J=6.8 Hz). $^{19}$F NMR (acetone-$d_6$/282 MHz) −79.3 (d, J=7.2 Hz) ESLRMS m/z 435 (M−H). ESHRMS m/z 434.9470 (M−H, Calc'd 434.9472). Anal. Calc'd for $C_{17}H_9Cl_2F_3O_4S$: C, 46.70; H, 2.07; Cl, 16.22; S, 7.33. Found: C, 46.80; H, 2.28; Cl, 16.75; S, 7.39.

EXAMPLE 194

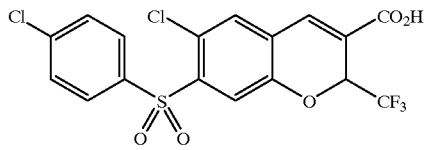

6-Chloro-7-[(4-chlorophenyl)sulfonyl]-2-(trifluoromethyl)-2H-1-benzopyran-3-carboxylic Acid mp 240.4–241.5° C. $^1$H NMR (acetone-$d_6$/300 MHz) 8.04 (d, 2H, J=8.9 Hz), 7.92 (s, 2H), 7.75 (s, 1H), 7.72 (d, 2H, J=8.7 Hz), 6.02 (q, 1H, J=6.8 Hz). $^{19}$F NMR (acetone-$d_6$/282 MHz) −79.2 (d, J=7.4 Hz). ESLRMS m/z 451 (M−H). ESHRMS m/z 450.9409 (M−H, Calc'd 450.9422). Anal. Calc'd for $C_{17}H_9Cl_2F_3O_5S$: C, 45.05; H, 2.00; Cl, 15.64. Found: C, 45.35; H, 2.05; Cl, 16.01.

EXAMPLE 195

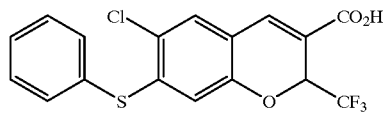

6-Chloro-7-(phenylthio)-2-(trifluoromethyl)-2H-1-benzopyran-3-carboxylic Acid

The title compound was prepared from benzenethiol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 271.7–274.4° C. $^1$H NMR (acetone-$d_6$/300 MHz) 7.86 (s, 1H), 7.60 (m, 6H), 6.29 (s, 1H), 5.74 (q, 1H, J=7.0 Hz). $^{19}$F NMR (acetone-$d_6$/282 MHz) −79.4 (d, J=7.2 Hz). FABLRMS m/z 385 (M−H). ESHRMS m/z 384.9904 (M−H, Calc'd 384.9913). Anal. Calc'd for $C_{17}H_{10}ClF_3O_3S$: C, 52.79; H, 2.61; Cl, 9.17; S, 8.29. Found: C, 52.80; H, 2.49; Cl, 9.71; S, 8.37.

EXAMPLE 196

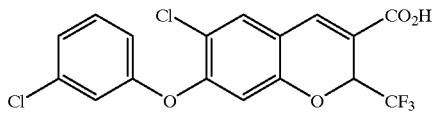

6-Chloro-7-(3-chlorophenoxy)-2-(trifluoromethyl)-2H-1-benzopyran-3-carboxylic Acid The title compound was prepared from 3-chlorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 174.1–176.1° C. $^1$H NMR (acetone-$d_6$/300 MHz) 7.91 (s, 1H), 7.73 (s, 1H), 7.48 (m, 1H), 7.29 (d, 1H, J=7.5 Hz), 7.17 (d, 1H, J=2.0 Hz), 7.08 (d, 1H, J=8.3 Hz), 6.73 (s, 1H), 5.85 (q, 1H, J=7.0 Hz). $^{19}$F NMR (acetone-$d_6$/282 MHz) −79.4 (d, J=6.5 Hz) FABLRMS m/z 403 (M−H). ESHRMS m/z 402.9752 (M−H, Calc'd 402.9729). Anal. Calc'd for $C_{17}H_9Cl_2F_3O_4$: C, 50.40; H, 2.24; Cl, 17.50. Found: C, 50.18; H, 2.00; Cl, 17.26.

EXAMPLE 197

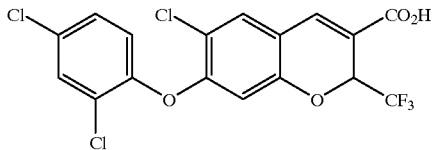

6-Chloro-7-(2,4-dichlorophenoxy)-2-(trifluoromethyl)-2H-1-benzopyran-3-carboxylic Acid The title compound was prepared from 2,4-dichlorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 233.0–234.0° C. $^1$H NMR (acetone-$d_6$/300 MHz) 7.90 (s, 1H), 7.73 (s, 1H), 7.69 (d, 1H, J=2.6 Hz), 7.47 (dd, TH, J=8.7 Hz, 2.6 Hz), 7.28 (d, 1H, J=8.7 Hz), 6.57 (1, 1H), 5.81 (q, 1H, J=7.0 Hz). $^{19}$F NMR (acetone-$d_6$/282 MHz) −79.4 (d, J=6.5 Hz). FABLRMS m/z 437 (M−H). ESHRMS m/z 436.9379 (M−H, Calc'd 436.9362). Anal. Calc'd for $C_{17}H_8Cl_3F_3O_4$: C, 46.45; H, 1.83; Cl, 24.19. Found: C, 46.38; H, 1.59; Cl, 24.46.

EXAMPLE 198

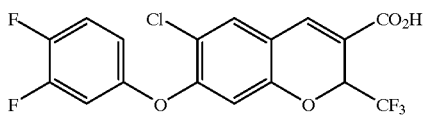

6-Chloro-7-(3,4-difluorophenoxy)-2-(trifluoromethyl)-2H-1-benzopyran-3-carboxylic Acid The title compound was prepared from 3,4-difluorobenzenethiol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 191.9–193.1° C. $^1$H NMR (acetone-$d_6$/300 MHz) 7.90 (s, 1H), 7.72 (d, 1H, J=3.0 Hz), 7.45 (q, 1H, J=9.1 Hz), 7.21 (m, 1H), 7.00 (m, 1H), 6.70 (d, 1H, J=2.6 Hz), 5.84 (q, 1H, J=7.0 Hz). $^{19}$F NMR (acetone-$d_6$/282 MHz) −79.4 (d, 3F, J=6.5 Hz), −136.4 (m, 1F), −145.1 (m, 1F). FABLRMS m/z 405 (M−H). ESHRMS m/z 404.9923 (M−H, Calc'd 404.9953). Anal. Calc'd for $C_{17}H_8ClF_5O_4$: C, 50.21; H, 1.98; Cl, 8.72. Found: C, 50.14; H, 1.73; Cl, 8.93.

EXAMPLE 199

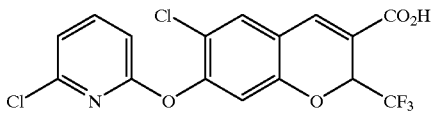

6-Chloro-7-[(6-chloro-2-pyridinyl)oxy]-2-(trifluoromethyl)-2H-1-benzopyran-3-carboxylic Acid The title compound was prepared from 6-chloro-2-pyridinol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 226.4–227.4° C. $^1$H NMR (acetone-$d_6$/300 MHz) 7.99 (m, 1H), 7.96 (s, 1H), 7.75 (s, 1H), 7.30 (d, 1H, J=7.7 Hz), 7.16 (d, 1H, J=8.0 Hz), 7.10 (s, 1H), 5.90 (q, 1H, J=7.0 Hz). $^{19}$F NMR (acetone-$d_6$/282 MHz) −79.3 (d, J=7.2 Hz). FABLRMS m/z 404 (M−H). ESHRMS m/z 405.9853 (M+H, Calc'd 405.9861). Anal. Calc'd for $C_{16}H_8Cl_2F_3NO_4$: C, 47.32; H, 1.99; N, 3.45; Cl, 17.46. Found: C, 47.26; H, 1.93; N, 3.35; Cl, 17.19.

Example 200

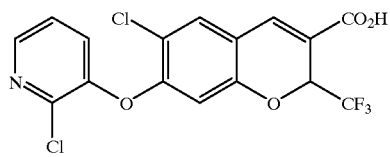

6-Chloro-7-[(2-chloro-3-pyridinyl)oxy]-2-(trifluoromethyl)-2H-1-benzopyran-3-carboxylic Acid The title compound was prepared from 2-chloro-3-pyridinol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 213.4–216.2° C. $^1$H NMR (acetone-$d_6$/300 MHz) 8.33 (m, 1H), 7.91 (s, 1H), 7.76 (s, 1H), 7.64 (m, 1H), 7.53 (m, 1H), 6.67 (s, 1H), 5.85 (q, 1H, J=7.0 Hz). $^{19}$F NMR (acetone-$d_6$/282 MHz) −79.4 (d, J=7.2 Hz). ESHRMS m/z 405.9890 (M+H, Calc'd 405.9861). Anal. Calc'd for $C_{16}H_8Cl_2F_3NO_4$: C, 47.32; H, 1.99; N, 3.45; Cl, 17.46. Found: C, 47.36; H, 1.98; N, 3.40; Cl, 17.14.

EXAMPLE 201

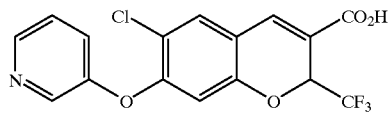

6-Chloro-7-[3-pyridinyloxy]-2-(trifluoromethyl)-2H-1-benzopyran-3-carboxylic Acid The title compound was prepared from 3-hydroxypyridine and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 237.8–238.8° C. $^1$H NMR (DMSO-$d_6$/300 MHz) 13.3 (br s, 1H), 8.42 (m, 2H), 7.87 (s, 1H), 7.83 (s, 1H), 7.48 (m, 2H), 6.72 (s, 1H), 5.93 (q, 1H, J=7.2 Hz). $^9$F NMR (DMSO-$d_6$/282 MHz) −77.8 (d, J=7.2 Hz). FABLRMS m/z 372 (M+H). ESHRMS m/z 370.0083 (M−H, Calc'd 370.0094). Anal. Calc'd for $C_{16}H_9ClF_3NO_4$: C, 51.70; H, 2.44; N, 3.77; Cl, 9.54. Found: C, 51.49; H, 2.47; N, 3.70; Cl, 9.69.

EXAMPLE 202

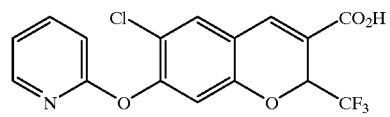

6-Chloro-7-[2-pyridinyloxy]-2-(trifluoromethyl)-2H-1-benzopyran-3-carboxylic Acid The title compound was prepared from 2-hydroxypyridine and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 234.2–235.4° C. $^1$H NMR (acetone-$d_6$/300 MHz) 8.14 (dd, 1H, J=4.8 Hz, 1.4 Hz), 7.92 (m, 2H), 7.70 (s, 1H), 7.14 (m, 2H), 6.99 (s, 1H), 5.88 (q, 1H, J=7.0 Hz). $^{19}$F NMR (acetone-d$_6$/282 MHz) −79.4 (d, J=7.2 Hz). ESLRMS m/z 372 (M+H). ESHRMS m/z 372.0252 (M+H, Calc'd 372.0250). Anal. Calc'd for C$_{16}$H$_9$ClF$_3$NO$_4$: C, 51.70; H, 2.44; N, 3.77; Cl, 9.54. Found: C, 51.70; H, 2.44; N, 3.71; Cl, 9.65.

EXAMPLE 203

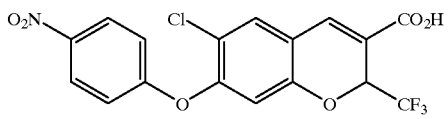

6-Chloro-7-(4-nitrophenoxy)-2-(trifluoromethyl)-2H-1-benzopyran-3-carboxylic Acid The title compound was prepared from 4-nitrophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 246.4–248.3° C. $^1$H NMR (acetone-d$_6$/300 MHz) 8.34 (d, 2H, J=9.3 Hz), 7.96 (s, 1H), 7.82 (s, 1H), 7.29 (d, 2H, J=9.3 Hz), 7.02 (s, 1H), 5.90 (q, 1H, J=7.0 Hz). $^{19}$F NMR (acetone-d$_6$/282 MHz) −79.3 (d, J=7.2 Hz). ESLRMS m/z 433 (M+NH$_4$). ESHRMS m/z 433.0463 (M+NH$_4$, Calc'd 433.0414). Anal. Calc'd for C$_{17}$H$_9$ClF$_3$NO$_6$: C, 49.12; H, 2.18; N, 3.37; Cl, 8.53. Found: C, 48.94; H, 2.05; N, 3.32; Cl, 8.72.

EXAMPLE 204

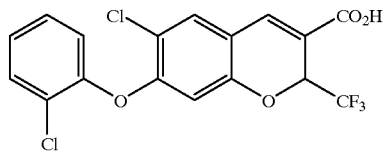

6-Chloro-7-(2-chlorophenoxy)-2-(trifluoromethyl)-2H-1-benzopyran-3-carboxylic Acid The title compound was prepared from 2-chlorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 199.0–199.1° C. $^1$H NMR (acetone-d$_6$/300 MHz) 7.94 (s, 1H), 7.76 (s, 1H), 7.65 (m, 1H), 7.51 (m, 1H), 7.38 (m, 1H), 7.32 (m, 1H), 6.44 (s, 1H), 5.85 (q, 1H, J=7.0 Hz). $^{19}$F NMR (acetone-d$_6$/282 MHz) −79.5 (d, J=6.5 Hz). ESHRMS m/z 402.9752 (M−H, Calc'd 402.9751). Anal. Calc'd for C$_{17}$H$_9$Cl$_2$F$_3$O$_4$: C, 50.40; H, 2.24; Cl, 17.50. Found: C, 50.42; H, 2.12; Cl, 17.72.

EXAMPLE 205

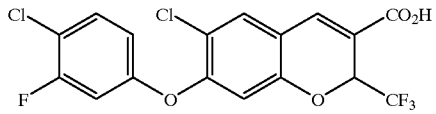

6-Chloro-7-(4-chloro-3-fluorophenoxy)-2-(trifluoromethyl)-2H-1-benzopyran-3-carboxylic Acid The title compound was prepared from 4-chloro-3-fluorophenol and ethyl 6-chloro-7-fluoro-2-(trifluoromethyl)-2H-1-benzopyran-3-carboxylate (Example 183, Step 2) via a procedure similar to that described in Example 183, Steps 3 and 4: mp 206.8–207.4° C. $^1$H NMR (acetone-d$_6$/300 MHz) 7.92 (s, 1H), 7.74 (s, 1H), 7.59 (m, 1H), 7.16 (m, 1H), 6.99 (m, 1H), 6.83 (s, 1H), 5.86 (q, 1H, J=7.0 Hz). $^{19}$F NMR (acetone-d$_6$/282 MHz) −79.4 (d, 3F, J=6.5 Hz), −113.8 (m, 1F). Anal. Calc'd for C$_{17}$H$_8$Cl$_2$F$_4$O$_4$: C, 48.25; H, 1.91; Cl, 16.76. Found: C, 48.20; H, 1.97; Cl, 16.92.

EXAMPLE 206

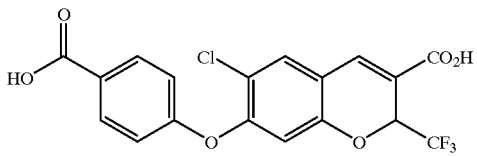

7-(4-Carboxyphenoxy)-6-chloro-2-(trifluoromethyl)-2H-1-benzopyran-3-carboxylic Acid The title compound was prepared from 4-hydroxybenzoic acid and ethyl 6-chloro-7-fluoro-2-(trifluoromethyl)-2H-1-benzopyran-3-carboxylate (Example 183, Step 2) via a procedure similar to that described in Example 183, Steps 3 and 4. (Note: In the step similar to step 3, an additional equivalent of potassium carbonate was added.) mp>300° C. $^1$H NMR (acetone-d$_6$/300 MHz) 8.16 (d, 2H, J=8.9 Hz), 7.96 (s, 1H), 7.79 (s, 1H), 7.20 (d, 2H, J=8.9 Hz), 6.87 (s, 1H), 5.90 (q, 1H, J=7.0 Hz). $^{19}$F NMR (acetone-d$_6$/282 MHz) −79.4 (d, J=7.2 Hz). ESHRMS m/z 413.0006 (M−H, Calc'd 413.0040). Anal. Calc'd for C$_{18}$H$_{10}$ClF$_3$O$_6$: C, 52.13; H, 2.43. Found: C, 51.81; H, 2.31.

EXAMPLE 207

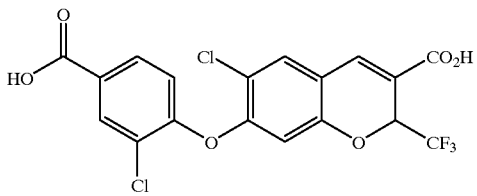

7-(4-Carboxy-2-chloro-phenoxy)-6-chloro-2-(trifluoromethyl)-2H-1-benzopyran-3-carboxylic Acid The title compound was prepared from 3-chloro-4-hydroxybenzoic acid and ethyl 6-chloro-7-fluoro-2-(trifluoromethyl)-2H-1-benzopyran-3-carboxylate (Example 183, Step 2) via a procedure similar to that described in Example 183, Steps 3 and 4. (Note: In the step similar to Example 183, Step 3, an additional equivalent of potassium carbonate was added.) mp >300° C. $^1$H NMR (acetone-d$_6$/300 MHz) 8.18 (d, 1H, J=2.0 Hz), 8.03 (dd, 1H, J=8.5 Hz 2.0 Hz), 7.93 (s, 1H), 7.78 (s, 1H), 7.23 (d, 1H, J=8.7 Hz), 6.77 (s, 1H), 5.87 (q, 1H, J=7.0 Hz). $^{19}$F NMR (acetone-d$_6$/282 MHz) −79.4 (d, J=6.5 Hz). ESHRMS m/z 446.9625 (M−H, Calc'd 446.9650). Anal. Calc'd for C$_{18}$H$_9$Cl$_2$F$_3$O$_6$: C, 48.13; H, 2.02 ; Cl, 15.79. Found: C, 47.96; H, 1.90; Cl, 15.65.

EXAMPLE 208

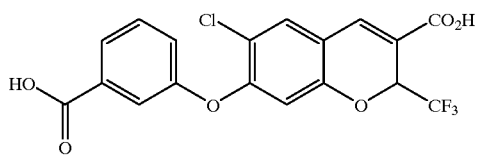

7-(3-Carboxyphenoxy)-6-chloro-2-(trifluoromethyl)-2H-1-benzopyran-3-carboxylic Acid The title compound was prepared from 3-hydroxybenzoic acid and ethyl 6-chloro-7-fluoro-2-(trifluoromethyl)-2H-1-benzopyran-3-carboxylate (Example 183, Step 2) via a procedure similar to that described in Example 183, Steps 3 and 4. (Note: In the step similar to step 3, an additional equivalent of potassium carbonate was added.) mp 288.1–289.2° C. $^1$H NMR (acetone-$d_6$/300 MHz) 7.92 (m, 2H), 7.75 (s, 1H), 7.68 (d, 1H, J=1.4 Hz), 7.62 (t, 1H, J=7.9 Hz), 7.41 (m, 1H), 6.72 (s, 1H), 5.85 (q, 1H, J=7.0 Hz). $^{19}$F NMR (acetone-$d_6$/282 MHz) −79.4 (d, J=6.5 Hz) ESHRMS m/z 413.0027 (M−H, Calc'd 413.0040). Anal. Calc'd for $C_{18}H_{10}ClF_3O_6$: C, 52.13; H, 2.43; Cl, 8.55. Found: C, 51.88; H, 2.48; Cl, 8.65.

EXAMPLE 209

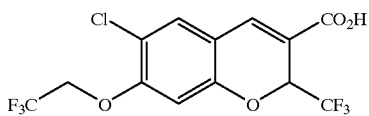

6-Chloro-7-(2,2,2-trifluoroethoxy)-2-(trifluoromethyl)-2H-1-benzopyran-3-carboxylic Acid Step 1. Preparation of Ethyl 6-Chloro-7-(2,2,2-trifluoroethoxy)-2-(trifluoromethyl)-2H-1-benzopyran-3-carboxylate.

A solution of 2,2,2-trifluoroethanol(1.3 g, 13 mmol) in 1,4-dioxane (2 mL) was added to a slurry of NaH (0.5 g, 13 mmol) in 1,4-dioxane (2 mL). The reaction was stirred for 10 minutes then a solution of 6-chloro-7-fluoro-2-(trifluoromethyl)-2H-1-benzopyran-3-carboxylate (1.61 g, 5.0 mmol) in 1,4-dioxane (5 mL) was added and the reaction was heated to 85° C. for 22 hours. The reaction mixture was acidified with 3N HCl, extracted with ethyl acetate, washed with saturated NaHCO$_3$, brine, dried over MgSO$_4$ and concentrated in vacuo, to give a brown oil which was passed through a column of silica gel with 10% ethyl acetate/hexanes to give a white solid (0.37 g, 18%): $^1$H NMR (CDCl$_3$/300 MHz) 7.62 (s, 1H), 7.28 (s, 1H), 6.58 (s, 1H), 5.69 (q, 1H, J=6.6 Hz), 4.42 (m, 2H), 4.31 (m, 2H), 1.34 (t, 3H, J=7.1 Hz). $^{19}$F NMR (CDCl$_3$/282 MHz) −74.2 (t, 3F, J=8.0 Hz), −78.9 (d, 3F, J=6.5 Hz).

Step 2. Preparation of 6-Chloro-7-(2,2,2-trifluoroethoxy)-2-(trifluoromethyl)-2H-1-benzopyran-3-carboxylic Acid.

The ester (Step 1) was hydrolyzed to the carboxylic acid via a method similar to that described in Example 1, Step 2: mp 174.4–176.0° C. $^1$H NMR (acetone-$d_6$/300 MHz) 7.86 (s, 1H), 7.62 (s, 1H), 7.00 (s, 1H), 5.86 (q, 1H, J=7.0 Hz), 4.90 (m, 2H). $^{19}$F NMR (acetone-$d_6$/282 MHz) −75.1 (t, 3F, J=8.7 Hz), −79.5 (d, 3F, J=7.2 Hz). FABLRMS m/z 375 (M−H). ESHRMS m/z 374.9880 (M−H, Calc'd 374.9859).

EXAMPLE 210

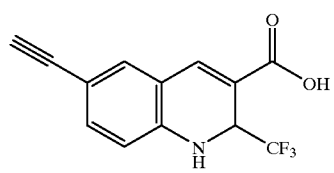

1,2-Dihydro-6-ethynyl-2-(trifluoromethyl)-3-quinolinecarboxylic Acid

Step 1. Preparation of Ethyl 6-trimethylsilylethynyl-1,2-dihydro-2-(trifluoromethyl)-3-quinolinecarboxylate.

The ethyl 6-iodo-1,2-dihydro-2-(trifluoromethyl)-3-quinolinecarboxylate (Example 160, Step 1)(750 mg, 1.89 mmol), trimethylsilylacetylene (925 mg, 9.44 mmol), dichlorobis(triphenylphosphine)palladium(II) (35 mg, 0.05 mmol), copper(I)iodide (9.5 mg, 0.05 mmol), and triethylamine (953 mg, 9.44 mmol) were mixed at room temperature for 2 h in acetonitrile (10 mL). The resulting black heterogeneous mixture was poured into ethyl acetate(50 mL) and extracted with water (2×25 mL), 1 N aqueous hydrochloric acid (25 mL), and saturated aqueous ammonium chloride (2×25 mL). The organic layer was dried over sodium sulfate and solvent removed at reduce pressure. The product was purified by flash chromatography (0–25% ethyl acetate/hexanes, silica gel). A black semisolid was isolated which upon trituration with hexanes afforded ethyl 6-trimethylsilylethynyl-1,2-dihydro-2-(trifluoromethyl)-3-quinolinecarboxylate as a yellow solid(267 mg, 38%): mp 117–119° C. $^1$H NMR (CDCl$_3$, 300 MHz) 7.65 (s, 1H), 7.24–7.32 (m, 2H), 6.55 (d, 1H, J=8.0 Hz), 5.08–5.18 (m, 1H), 4.66 (brs, 1H), 4.24–4.64 (m, 2H), 1.34 (t, 3H, J=7.1 Hz) 0.22 (s, 9H). ESHRMS m/z 368.1306 (Calc'd for M+H 368.1293).

Step 2: Preparation of 1,2-dihydro-6-ethynyl-2-(trifluoromethyl)-3-quinolinecarboxylic Acid.

Hydrolysis of the ester and the trimethylsilyl moiety of ethyl 6-trimethylsilylethynyl-1,2-dihydro-2-(trifluoromethyl)-3-quinolinecarboxylate (Step 1) was performed by a procedure similar to that described in Example 157, Step 3, yielding the title compound: mp 259–268° C. $^1$H NMR (CD$_3$OD, 300 MHz) 7.69 (s, 1H), 7.21–7.28 (m, 2H), 6.65 (d, 1H, J=8.4 Hz), 5.11 (q, 1H, J=7.3 Hz). ESHRMS m/z 268.0580 (Calc'd for M+H 268.0586).

EXAMPLE 211

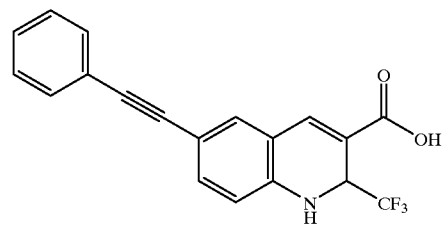

1,2-Dihydro-6-(phenylethynyl)-2-(trifluoromethyl)-3-quinolinecarboxylic Acid Ethyl 6-iodo-1,2-dihydro-2-(trifluoromethyl)-3-quinolinecarboxylate (Example 160, Step 1) was converted to the title compound by a procedure similar to that described in Example 210: mp 218–219° C. $^1$H NMR (CDCl$_3$/DMSO-d$_6$ (19:1), 400 MHz) 7.56 (s, 1H), 7.35 (d, 1H, J=8.5 Hz), 7.18–7.24 (m, 6H), 6.57 (d, 1H, J=8.5 Hz), 5.93 (bs, 1H), 5.03–5.05 (m, 1H). FABHRMS m/z 344.0898 (Calc'd for M+H 344.0901).

EXAMPLE 212

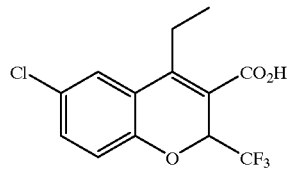

6-Chloro-4-ethyl-2-trifluoromethyl-2H-1-benzopyran-3-carboxylic Acid

Step 1. Preparation of ethyl-6-chloro-4-ethyl-2-trifluoromethyl-2H-1-benzopyran-3-carboxylate.

Ethyl-6-chloro-4-ethenyl-2-trifluoromethyl-2H-1-benzopyran-3-carboxylate (Example 142,Step 5) (0.433 g, 1.30 mmol) was dissolved in methanol (10 mL). Palladium(5 wt % on activated carbon)(0.150 g) was slowly added. The reaction vessel was charged with hydrogen (25 psi) and was stirred for 25 minutes. Gas chromatographic analysis indicated that the reaction was complete. The reaction mixture was filtered through Celite and evaporated to yield a orange oil. The oil was purified by flash column chromatography(100% hexanes) to yield the desired product as a yellow oil (0.282 g, 65%): $^1$H NMR (CDCl$_3$/300 MHz) 7.43 (d, 1H, J=2.4 Hz), 7.25 (dd, 1H, J=2.4, 8.7 Hz), 6.92(d, 1H, J=8.7 Hz), 5.75 (q, 1H, J=7.0 Hz), 4.38–4.24 (m, 2H), 3.05–2.95 (m, 2H), 1.35 (t, 3H, J=7.2 Hz), 1.25, (t, 3H, J=7.6 Hz).

Step 2. Preparation of 6-chloro-4-ethyl-2-trifluoromethyl-2H-1-benzopyran-3-carboxylic Acid.

The ester from Step 1 (0.282 g, 0.842 mmol) was dissolved in a THF-EtOH-H$_2$O mixture (10 mL, 7:2:1). The resulting solution was treated with aqueous sodium hydroxide (0.340 mL, 0.842 mmol of a 2.5 N solution) and was stirred at room temperature for 18 hours. The solvent was removed in vacuo and the residue was dissolved in water (10 mL). Diethyl ether (10 mL) was added and the resulting mixture acidified by the addition of a few drops of concentrated HCR. The diethyl ether layer was separated, and the aqueous phase was extracted with additional ether(2×10 mL). The ether extracts were combined, dried over MgSO$_4$, filtered, and evaporated to yield a clear oil. Addition of hexane (10 mL) resulted in the formation of a white precipitate which was collected by vacuum filtration to afford the title compound (0.064 g, 25%)as a white powder: mp 170.9–172.1° C. $^1$H NMR (CDCl$_3$/300 MHz) 7.47 (d, 1H, J=2.4 Hz), 7.30 (dd, 1H, J=2.4, 8.7 Hz), 6.96 (d, 1H, J=8.7 Hz), 5.76 (q, 1H, J=7.0 Hz), 3.08 (q, 2H, J=7.6 Hz), 1.27 (t, 3H, J=7.5 Hz). FABLRMS m/z 305.2 (M–H).ESHRMS m/z 305.0185 (M–H, Calc'd. 305.0192). Anal. Calc'd for C$_{13}$H$_8$ClF$_3$O$_3$: C, 50.92; H, 3.29; Cl, 11.56. Found: C, 50.68; H, 3.18; Cl, 11.64.

Biological Evaluation

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, Laboratory Models for Testing NSAIDs, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

TABLE I

| Example | RAT PAW EDEMA % Inhibition 30 mg/g body weight | ANALGESIA % Inhibition 30 mg/g body weight |
| --- | --- | --- |
| 1 | 57 | 58 |
| 8 | 43 | 36 |
| 12 | 30 | 37 |
| 16 | 48 | 34 |
| 24 | 29 | 25 |
| 31 | 39* | 37* |
| 32 | 59* | 73* |
| 38 | 47 | 55 |
| 39 | 18 | 8 |
| 46 | 59 | 67 |
| 65 | 43 | 32 |
| 79 | 45 | 53 |
| 81 | 36 | 44 |
| 83 | 56 | 65 |
| 84 | 44 | 24 |
| 105 | 75 | 69 |
| 115 | 52 | 62 |
| 139 | 42 | 41 |
| 156 | 54 | 66 |
| 157 | 44* | 36* |
| 158 | 45* | 55* |
| 161 | 53 | 56 |
| 165 | 30* | 33* |
| 172 | 57 | 67 |
| 177 | 59* | 61* |
| 188 | 57 | 69 |

*- @ 10 mpk

Evaluation of COX-1 and COX-2 Activity in vitro

The compounds of this invention exhibited inhibition in vitro of COX-2. The COX-2 inhibition activity of the compounds of this invention illustrated in the Examples was determined by the following methods.

a. Preparation of Recombinant COX Baculoviruses

Recombinant COX-1 and COX-2 were prepared as described by Gierse et al, [J. Biochem., 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (Baculovirus Expression Vectors: A Laboratory Manual (1992)). Recombinant baculoviruses were isolated by transfecting 4 μg of baculovirus transfer vector DNA into SF9 insect cells (2×10$^8$) along with 200 ng of linearized baculovirus plasmid DNA by the calcium phosphate method. See M. D. Summers and G. E. Smith, A Manual of Methods for Baculovirus Vectors and Insect Cell Culture Procedures, Texas Agric. Exp. Station Bull. 1555 (1987). Recombinant viruses were purified by three rounds of plaque purification and high titer ($10^7$–$10^8$ pfu/mL) stocks of virus were prepared. For large scale production, SF9 insect cells were infected in 10 liter fermentors ($0.5 \times 10^6$/mL) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX-1 and Cox-2 Activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

c. Fast Assay for COX-1 and COX-2 Activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (0.05 M Potassium phosphate, pH 7.5, 2 μM phenol, 1 μM heme, 300 μM epinephrine) with the addition of 20 μl of 100 μM arachidonic acid (10 μM). Compounds were pre-incubated with the enzyme for 10 minutes at 25° C. prior to the addition of arachidonic acid. Any reaction between the arachidonic acid and the enzyme was stopped after two minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II.

| Example | COX-2* $IC_{50}$ μM | COX-1* $IC_{50}$ μM | COX-2 $IC_{50}$ μM | COX-1 $IC_{50}$ μM |
|---|---|---|---|---|
| 1 | 0.3 | 45 | | |
| 2 | <0.1 | 78 | <0.1 | 5.0 |
| 6 | <0.1 | >100 | | |
| 7 | 0.1 | 16 | <0.1 | 1.0 |
| 8 | <0.1 | 61 | <0.1 | 21 |
| 9 | <0.1 | 1.4 | <0.1 | <0.1 |
| 12 | 7 | 55 | | |
| 13 | .3 | >100 | | |
| 14 | >100 | >100 | | |
| 15 | >0.1 | 11 | 133.6 | 44 |
| 16 | <0.1 | 24 | 1.4 | 51 |
| 18 | 12 | >100 | | |
| 21 | 11 | 3.5 | | |
| 22 | >100 | >100 | | |
| 23 | 7 | >100 | 24 | >100 |
| 25 | >100 | 78 | | |
| 26 | >100 | 20 | | |
| 27 | 67 | >100 | | |
| 29 | <0.1 | >100 | | |
| 30 | <0.1 | 1.2 | 16 | 3.8 |
| 31 | <0.1 | 94 | | |
| 32 | 0.3 | 31 | 0.3 | 0.7 |
| 33 | <0.1 | 5.7 | 8.2 | 28 |
| 35 | 2.2 | 8.9 | 1.7 | 11 |
| 38 | 0.2 | 6.2 | 25.7 | 57 |
| 39 | 0.2 | 45 | 1.3 | >100 |
| 40 | <0.1 | 24 | 74 | 43 |
| 42 | <0.1 | 2.3 | <0.1 | 11 |
| 43 | 99 | 85 | | |
| 44 | 0.3 | 72 | 21 | >100 |
| 45 | 0.2 | 47 | 46 | >100 |
| 46 | 0.2 | 24 | 74 | 43 |
| 47 | 1.9 | 31 | 1.7 | >100 |
| 49 | 24 | >100 | 31 | >100 |
| 50 | 79 | >100 | | |
| 52 | 20 | >100 | | |
| 53 | 8 | 13 | 6 | >100 |
| 54 | 19 | >100 | | |
| 55 | 46 | >100 | 53 | >100 |
| 56 | 12 | >100 | 29 | >100 |
| 57 | 21 | 10 | 21 | >100 |
| 59 | 43 | >100 | | |
| 63 | 1.4 | >100 | | |
| 65 | <0.1 | 1.0 | | |
| 66 | 82 | 38 | <0.1 | 16.9 |
| 67 | <0.1 | 30 | <0.1 | 6.7 |
| 81 | <0.1 | 10.5 | <0.1 | 1.6 |
| 82 | <0.1 | 16 | <0.1 | 5.6 |
| 83 | <0.1 | 9.6 | <0.1 | 1.4 |
| 84 | 0.1 | 25 | <0.1 | 2.8 |
| 88 | <0.1 | 12.4 | <0.1 | 6.4 |
| 91 | <0.1 | 23 | 0.2 | 36 |
| 96 | 0.2 | >100 | 0.3 | 100 |
| 97 | 0.2 | 78 | 0.1 | 25 |
| 98 | 2.0 | >100 | 1.5 | 19 |
| 99 | 0.2 | 36 | <0.1 | 23 |
| 101 | <0.1 | 18 | <0.1 | 16 |
| 103 | 36 | 61 | | |
| 104 | <0.1 | 24 | <0.1 | 8.2 |
| 105 | 0.3 | 4.5 | 0.2 | 0.1 |
| 106 | 0.2 | 21 | <0.1 | 5.7 |
| 114 | <0.1 | <0.1 | <0.1 | <0.1 |
| 115 | <0.1 | <0.1 | <0.1 | <0.1 |
| 116 | <0.1 | <0.1 | <0.1 | <0.1 |
| 120 | <0.1 | 98 | <0.1 | 33 |
| 125 | <0.1 | 0.2 | <0.1 | <0.1 |
| 129 | 0.2 | 2.6 | <0.1 | 0.3 |
| 138 | 0.3 | 42.5 | <0.1 | 11.1 |
| 152 | <0.1 | 74 | <0.1 | 10 |
| 154 | 0.5 | 68.5 | <0.1 | 37 |
| 155 | <0.1 | 1.6 | <0.1 | <0.1 |
| 156 | <0.1 | 0.8 | <0.1 | 0.1 |
| 176 | <0.1 | <0.1 | 2.0 | 3.3 |
| 177 | <0.1 | <0.1 | <0.1 | 0.3 |
| 178 | 8.4 | >100 | 14.7 | >100 |
| 179 | 15.6 | >100 | 16.0 | >100 |
| 180 | <0.1 | 43.4 | <0.1 | >100 |
| 181 | 1.5 | >100 | >100 | >100 |
| 182 | <0.1 | >100 | >100 | >100 |
| 183 | <0.1 | 0.1 | <0.1 | 4.1 |
| 184 | <0.1 | <0.1 | <0.1 | 1.3 |
| 185 | <0.1 | 68.4 | <0.1 | >100 |
| 186 | <0.1 | 10.6 | 3.4 | 32.8 |
| 187 | 2.9 | 48.9 | 33.7 | >100 |
| 188 | <0.1 | 1.3 | <0.1 | 3.7 |
| 189 | <0.1 | 56.2 | 1.2 | 44.8 |
| 190 | 0.5 | 0.5 | 0.5 | 37.4 |
| 191 | <0.1 | 39.7 | 42.2 | >100 |
| 192 | <0.1 | 5.9 | 1.4 | 12.3 |
| 193 | 1.2 | >100 | >100 | >100 |
| 195 | <0.1 | 0.6 | <0.1 | 2.6 |
| 196 | <0.1 | 10.1 | 9.5 | 30.3 |
| 197 | <0.1 | 0.2 | <0.1 | 0.4 |
| 198 | <0.1 | 3.8 | <0.1 | 12.4 |
| 199 | <0.1 | >100 | | |

TABLE II.-continued

| Example | COX-2* IC$_{50}$ µM | COX-1* IC$_{50}$ µM | COX-2 IC$_{50}$ µM | COX-1 IC$_{50}$ µM |
|---|---|---|---|---|
| 200 | <0.1 | 1.6 | <0.1 | 28.5 |
| 201 | <0.1 | 9.4 | 0.1 | 63.8 |
| 202 |  |  | <0.1 | 42.8 |
| 203 | <0.1 | 78.1 |  |  |
| 209 | 0.2 | >100 | >100 | >100 |
| 210 | 1.7 | 88.8 | 10.0 | >100 |
| 211 | 1.9 | 1.7 | 2.4 | 3.8 |

*fast assay

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, pulmonary, mucosally, intravascularly, intraperitoneally, subcutaneously, intramuscularly or topically.

The phrase "co-therapy" (or "combination-therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds which are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

For pulmonary administration, the pharmaceutical composition may be administered in the form of an aerosol or with an inhaler including dry powder aerosol.

All mentioned references are incorporated by reference as if here written. The priority applications (Ser. No. 60/044,485, filed Apr. 21, 1997 and Ser. No. 09/062,537, filed Apr. 17, 1998) are also incorporated by reference.

Although this invention has been described with respect to specific embodiments, the details of these embodiments are not to be construed as limitations.

What is claimed is:

1. A compound of Formula I″

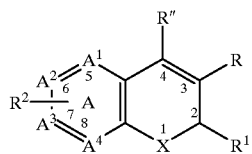

wherein X is selected from S, $CR^cR^b$ and $NR^a$;

wherein $R^a$ is selected from hydrido, $C_1$–$C_3$-alkyl, (optionally substituted phenyl)-$C_1$–$C_3$-alkyl, acyl and carboxy-$C_1$–$C_6$-alkyl;

wherein each of $R^b$ and $R^c$ is independently selected from hydrido, $C_1$–$C_3$-alkyl , phenyl-$C_1$–$C_3$-alkyl, $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; or wherein $CR^bR^c$ forms a 3–6 membered cycloalkyl ring;

wherein R is selected from carboxyl, aminocarbonyl, $C_1$–$C_6$-alkylsulfonylaminocarbonyl and $C_1$–$C_6$-alkoxycarbonyl;

wherein R″ is selected from hydrido, phenyl, thienyl, $C_1$–$C_6$-alkyl and $C_2$–$C_6$-alkenyl;

wherein $R^1$ is selected from $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl;

wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_1$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkyloxy, heteroaryl-$C_1$–$C_6$-alkyloxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, Cl-C.-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl-$C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are independently selected from carbon and nitrogen with the proviso that at least two of $A^1$, $A^2$, $A^3$ and $A^4$ are carbon;

or wherein $R^2$ together with ring A forms a radical selected from naphthyl, quinolyl, isoquinolyl, quinolizinyl, quinoxalinyl and dibenzofuryl;

or an isomer or pharmaceutically acceptable salt thereof.

2. A compound of claim 1 wherein X is selected from S, $CR^cR^b$ and $NR^a$; wherein $R^a$ is selected from hydrido, $C_1$–$C_3$-alkyl, (optionally substituted phenyl)-$C_1$–$C_3$-alkyl, acyl and carboxy-$C_1$–$C_6$-alkyl; wherein each of $R^b$ and $R^c$ is independently selected from hydrido, $C_1$–$C_3$-alkyl, phenyl-$C_1$–$C_3$-alkyl, $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; or wherein $CR^bR^c$ forms a cyclopropyl ring; wherein R is selected from carboxyl, aminocarbonyl, $C_1$–$C_6$-alkylsulfonylaminocarbonyl and $C_1$–$C_6$-alkoxycarbonyl; wherein R″ is selected from hydrido, phenyl, thienyl, $C_1$–$C_4$-alkyl and $C_2$–$C_4$-alkenyl; wherein $R^1$ is selected from $C_1$–$C_3$-perfluoroalkyl, chloro, $C_1$–$C_6$-alkylthio, $C_1$–$C_6$-alkoxy, nitro, cyano and cyano-$C_1$–$C_3$-alkyl; wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, aryl-$C_1$–$C_3$-alkyl, aryl-$C_2$–$C_6$-alkynyl, aryl-$C_2$–$C_6$-alkenyl, $C_1$–$C_6$-alkoxy, methylenedioxy, $C_1$–$C_6$-alkylthio, $C_1$–$C_6$-alkylsulfinyl, aryloxy, arylthio, arylsulfinyl, heteroaryloxy, $C_1$–$C_6$-alkoxy-$C_1$–$C_6$-alkyl, aryl-$C_1$–$C_6$-alkyloxy, heteroaryl-$C_1$–$C_6$-alkyloxy, aryl-$C_1$–$C_6$-alkoxy-$C_1$–$C_6$-alkyl, $C_1$–$C_6$-haloalkyl, $C_1$–$C_6$-haloalkoxy, $C_1$–$C_6$-haloalkylthio, $C_1$–$C_6$-haloalkylsulfinyl, $C_1$–$C_6$-haloalkylsulfonyl, $C_1$–$C_3$-(haloalkyl-$C_1$–$C_3$-hydroxyalkyl, $C_1$–$C_6$-hydroxyalkyl, hydroxyimino-$C_1$–$C_6$-alkyl, $C_1$–$C_6$-alkylamino, arylamino, aryl-$C_1$–$C_6$-alkylamino, heteroarylamino, heteroaryl-$C_1$–$C_6$-alkylamino, nitro, cyano, amino, aminosulfonyl, $C_1$–$C_6$-alkylaminosulfonyl, arylaminosulfonyl, heteroarylaminosulfonyl, aryl-$C_1$–$C_6$-alkylaminosulfonyl, heteroaryl-$C_1$–$C_6$-alkylaminosulfonyl, heterocyclylsulfonyl, $C_1$–$C_6$-alkylsulfonyl, aryl-$C_1$–$C_6$-alkylsulfonyl, optionally substituted aryl, optionally substituted heteroaryl, aryl-$C_1$–$C_6$-alkylcarbonyl, heteroaryl- $C_1$–$C_6$-alkylcarbonyl, heteroarylcarbonyl, arylcarbonyl, aminocarbonyl, $C_1$–$C_6$-alkoxycarbonyl, formyl, $C_1$–$C_6$-haloalkylcarbonyl and $C_1$–$C_6$-alkylcarbonyl; and wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl or quinolyl radical; or an isomer or pharmaceutically acceptable salt thereof.

3. A compound of claim 2 wherein X is selected from S and $NR^a$; wherein $R^a$ is selected from hydrido, $C_1$–$C_3$-alkyl and (optionally substituted phenyl)methyl; wherein R is carboxyl; wherein R" is selected from hydrido, $C_1$–$C_3$-alkyl and $C_2$–$C_3$-alkenyl; wherein $R^1$ is selected from $C_1$–$C_3$-perfluoroalkyl; wherein $R^2$ is one or more radicals independently selected from hydrido, halo, $C_1$–$C_6$-alkyl, $C_2$–$C_6$-alkenyl, $C_2$–$C_6$-alkynyl, halo-$C_2$–$C_6$-alkynyl, optionally substituted phenyl-$C_1$–$C_6$-alkyl, optionally substituted phenyl-$C_2$–$C_6$-alkynyl, phenyl-$C_2$–$C_6$-alkenyl, $C_1$–$C_3$-alkoxy, methylenedioxy, $C_1$–$C_3$-alkoxy-$C_1$–$C_3$-alkyl, $C_1$–$C_3$-alkylthio, $C_1$–$C_3$-alkylsulfinyl, optionally substituted phenyloxy, optionally substituted phenylthio, optionally substituted phenylsulfinyl, $C_1$–$C_3$-haloalkyl-$C_1$–$C_3$-hydroxyalkyl, phenyl-$C_1$–$C_3$-alkyloxy-$C_1$–$C_3$-alkyl, $C_1$–$C_3$-haloalkyl, $C_1$–$C_3$-haloalkoxy, $C_1$–$C_3$-haloalkylthio, $C_1$–$C_3$-hydroxyalkyl, $C_1$–$C_3$-alkoxy-$C_1$–$C_3$-alkyl, hydroxyimino-$C_1$–$C_3$-alkyl, $C_1$–$C_6$-alkylamino, nitro, cyano, amino, aminosulfonyl, N-alkylaminosulfonyl, N-arylaminosulfonyl, N-heteroarylaminosulfonyl, N-(phenyl-$C_1$–$C_6$-alkyl)aminosulfonyl, N-(heteroaryl-$C_1$–$C_6$-alkyl)aminosulfonyl, phenyl-$C_1$–$C_3$-alkylsulfonyl, 5- to 8-membered heterocyclylsulfonyl, $C_1$–$C_6$-alkylsulfonyl, optionally substituted phenyl, optionally substituted 5- to 9-membered heteroaryl, phenyl-$C_1$–$C_6$-alkylcarbonyl, phenylcarbonyl, 4-chlorophenylcarbonyl, 4-hydroxyphenylcarbonyl, 4-trifluoromethylphenylcarbonyl, 4-methoxyphenylcarbonyl, aminocarbonyl, formyl, and $C_1$–$C_6$-alkylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, benzofurylphenyl, or quinolyl radical; or an isomer or pharmaceutically acceptable salt thereof.

4. A compound of claim 3 wherein X is selected from S and $NR^a$; wherein $R^a$ is selected from hydrido, methyl, ethyl, (4-trifluoromethyl)benzyl, (4-chloromethyl)benzyl, (4-methoxy)benzyl, and (4-cyano)benzyl, (4-nitro)benzyl; wherein R is carboxyl; wherein R" is selected from hydrido, ethyl and ethenyl; wherein $R^1$ is selected from trifluoromethyl and pentafluoroethyl; wherein $R^2$ is one or more radicals independently selected from hydrido, chloro, bromo, fluoro, iodo, methyl, tert-butyl, ethenyl, ethynyl, 5-chloro-1-pentynyl, 1-pentynyl, 3,3-dimethyl-1-butynyl, benzyl, phenylethyl, phenyl-ethynyl, 4-chlorophenyl-ethynyl, 4-methoxyphenyl-ethynyl, phenylethenyl, methoxy, methylthio, methylsulfinyl, phenyloxy, phenylthio, phenylsulfinyl, methylenedioxy, benzyloxymethyl, trifluoromethyl, difluoromethyl, pentafluoroethyl, trifluoromethoxy, trifluoromethylthio, hydroxymethyl, hydroxy-trifluoroethyl, methoxymethyl, hydroxyiminomethyl, N-methylamino, nitro, cyano, amino, aminosulfonyl, N-methylaminosulfonyl, N-phenylaminosulfonyl, N-furylaminosulfonyl, N-(benzyl)aminosulfonyl, N-(furylmethyl)aminosulfonyl, benzylsulfonyl, phenylethylaminosulfonyl, furylsulfonyl, methylsulfonyl, phenyl, phenyl substituted with one or more radicals selected from chloro, fluoro, bromo, methoxy, methylthio and methylsulfonyl, benzimidazolyl, thienyl, thienyl substituted with chloro, furyl, furyl substituted with chloro, benzylcarbonyl, optionally substituted phenylcarbonyl, aminocarbonyl, formyl and methylcarbonyl; wherein the A ring atoms $A^1$, $A^2$, $A^3$ and $A^4$ are independently selected from carbon and nitrogen with the proviso that at least three of $A^1$, $A^2$, $A^3$ and $A^4$ are carbon; or wherein $R^2$ together with ring A forms a naphthyl, or quinolyl radical; or an isomer or pharmaceutically acceptable salt thereof.

5. A compound of claim 4 selected from compounds, and their isomers and pharmaceutically-acceptable salts, of the group consisting of
1,2-dihydro-6-ethynyl-2-((trifluoromethyl))-3-quinolinecarboxylic acid; and
1,2-dihydro-6-phenylethynyl-2-(trifluoromethyl)-3-quinolinecarboxylic acid.

6. A compound of Formula IIc

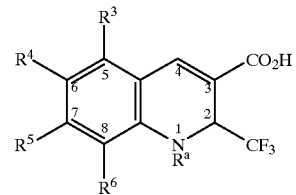

IIc wherein $R^a$ is selected from hydrido and lower aralkyl; wherein $R^3$ is selected from hydrido, lower alkyl, lower hydroxyalkyl, lower alkoxy and halo;
wherein $R^4$ is selected from hydrido, halo, lower alkyl, lower alkylthio, lower haloalkyl, amino, aminosulfonyl, lower alkylsulfonyl, lower alkylsulfinyl, lower alkoxyalkyl, lower alkylcarbonyl, formyl, cyano, lower haloalkylthio, substituted or unsubstituted phenylcarbonyl, lower haloalkoxy, lower alkoxy, lower alkynyl, phenyl-lower alkynyl, lower aralkylcarbonyl, lower dialkylaminosulfonyl, lower alkylaminosulfonyl, lower aralkylaminosulfonyl, lower heteroaralkylaminosulfonyl, 5- or 6-membered heteroaryl, lower hydroxyalkyl, optionally substituted phenyl and 5- or 6-membered nitrogen containing heterocyclosulfonyl;
wherein $R^5$ is selected from hydrido, lower alkyl, halo, lower haloalkyl, lower alkoxy, and phenyl; and wherein $R^6$ is selected from hydrido, halo, cyano, hydroxyiminomethyl, lower hydroxyalkyl, lower alkynyl, phenylalkynyl, lower alkyl, lower alkoxy, formyl and phenyl; or an isomer or pharmaceutically acceptable salt thereof.

7. Compound of claim 6 wherein $R^4$ is selected from chloro, methyl, tert-butyl, methylthio, trifluoromethyl, difluoromethyl, pentafluoromethyl, trifluoromethylthio, trifluoromethoxy, ethynyl, phenylethynyl, substituted or unsubstituted phenylcarbonyl, and substituted or unsubstituted phenyl; wherein $R^5$ is selected from hydrido, methyl, tert-butyl, chloro; and wherein $R^6$ is selected from hydrido, chloro, thienyl, hydroxyiminomethyl, substituted or unsubstituted phenylethynyl, and substituted or unsubstituted phenyl; or an isomer or pharmaceutically acceptable salt thereof.

8. Compound of claim 7 wherein $R^3$ is hydrido or chloro; wherein $R^4$ is selected from ethynyl, and optionally substituted phenylethynyl; or an isomer or pharmaceutically acceptable salt thereof.

9. A method of treating a cyclooxygenase-2 mediated disorder in a subject, said method comprising treating the subject having or susceptible to said disorder with a therapeutically-effective amount of a compound of claims 1–8; or a pharmaceutically-acceptable salt thereof.

10. The method of claim 9 wherein the cyclooxygenase-2 mediated disorder is inflammation.

11. The method of claim 9 wherein the cyclooxygenase-2 mediated disorder is arthritis.

12. The method of claim 9 wherein the cyclooxygenase-2 mediated disorder is pain.

13. The method of claim 9, wherein the cyclooxygenase-2 mediated disorder is cancer.

14. A pharmaceutical composition comprising a therapeutically-effective amount of a compound, said compound selected from a family of compounds of claims 1–8; or a pharmaceutically-acceptable salt thereof.

* * * * *